United States Patent [19]
Strieter et al.

[11] Patent Number: 5,871,723
[45] Date of Patent: Feb. 16, 1999

[54] CXC CHEMOKINES AS REGULATORS OF ANGIOGENESIS

[75] Inventors: Robert M. Strieter; Peter J. Polverini; Steven L. Kunkel, all of Ann Arbor, Mich.

[73] Assignee: The Regent of the University of Michigan, Ann Arbor, Mich.

[21] Appl. No.: 468,819

[22] Filed: Jun. 6, 1995

[51] Int. Cl.⁶ .................................................. A61K 38/19
[52] U.S. Cl. ................................. 424/85.1; 514/2; 514/8; 514/12
[58] Field of Search ................................ 424/85.1; 514/2, 514/8, 12

[56] References Cited

U.S. PATENT DOCUMENTS 5,459,128  10/1995  Rollins et al. .............................. 514/8
5,739,103   4/1998  Rollins et al. .............................. 514/8

*Primary Examiner*—Garnette D. Draper
*Attorney, Agent, or Firm*—Arnold, White & Durkee

[57] ABSTRACT

Disclosed are various discoveries concerning the angiogenic and angiostatic properties of the CXC chemokines, including the finding that the ELR motif controls the ability of these molecules to induce angiogenesis. Aspects of the invention include, for example, the identification of IP-10, MIG and certain IL-8 analogues as angiostatic agents, and their use in inhibiting angiogenesis in various systems.

29 Claims, 71 Drawing Sheets

CXC CHEMOKINES AS REGULATORS OF ANGIOGENESIS

The U.S. Government owns rights in the present invention pursuant to grant numbers HL50057, HL39926 and HL31693 from the National Institutes of Health.

BACKGROUND OF THE INVENTION

1. Field of the Invention

The present invention relates generally to the field of cytokines. More particularly, it concerns CXC chemokines, CXC chemokine analogues, and methods of using such chemokines, for example, in modulating angiogenic and angiostatic responses.

2. Description of the Related Art

Cytokines are, generally, small protein or polypeptide-based molecules that modulate the activity of certain cell types following binding to cell surface receptors. The CXC (α) chemokines are one group of cytokines, so named due to the conserved Cys Xaa Cys sequence element located towards their N-terminus. The CXC chemokine family includes interleukin-8 (IL-8); γ-interferon-inducible protein-10 (IP-10); Platelet Factor 4 (PF4); the growth related oncogene (GRO) peptides GROα, GROβ and GROγ; monokine induced by gamma-interferon (MIG); epithelial neutrophil activating protein-78 (ENA-78); granulocyte chemotactic protein-2 (GCP-2); and the $NH_2$-terminal truncated forms of platelet basic protein (PBP), namely connective tissue activating protein-III (CTAP-III), β-thromboglobulin (βTG) and neutrophil activating peptide-2 (NAP-2).

IL-8 is a peptide of approximately 8 kD, and is about 72 amino acids in length, with this length varying according to the post-translational processing in different cell types (Yoshimura et al., 1989; Strieter et al., 1989b). The IL-8 gene was initially identified by analyzing the genes transcribed by human blood mononuclear cells stimulated with Staphylococcal enterotoxin A (Schmid and Weissman, 1987). IL-8 production is induced by tumor necrosis factor and by interleukin-1 (Strieter et al., 1989a; 1989b; 1990a).

The first biological roles of IL-8 to be defined were those connected with its ability to stimulate neutrophil chemotaxis and activation (Yoshimura et al., 1987a; Schroder et al., 1988; Peveri et al., 1988; Larsen et al., 1989). If neutrophils are 'primed', e.g., by E. coli endotoxin (also known as lipopolysaccharide or LPS), IL-8 also stimulates the neutrophil to release certain enzymes, such as elastase and myeloperoxidase.

Physiologically, high concentrations of IL-8 have been connected with inappropriate neutrophil activation and certain disease conditions, such as adult respiratory distress syndrome (ARDS) (Miller et al., 1992; Donnelly et al., 1993); rheumatoid arthritis (Brennan et al., 1990; Koch et. al., 1991a; Seitz et al., 1991); pseudogout (Miller and Brelsford, 1993); and cystic fibrosis (McElvaney et al., 1992; Nakamura et al., 1992; Bedard et al., 1993). It has also been reported that IL-8 participates in inflammatory processes in the eye that may contribute to tissue destruction (de Boer et al., 1993; Ferrick et al., 1991; Wakefield and Lloyd, 1992) and that IL-8 is involved in corneal neovascularization (Strieter et al., 1992a).

IP-10 is an interferon-inducible chemokine, the exact function(s) of which have yet to be elucidated (Luster et al., 1985). It is believed that IP-10 may have a role in cellular immune and inflammatory responses (Luster and Ravetch, 1987a). IP-10 has been reported to exert an anti-tumor effect in vivo, but not in vitro (Luster and Leder, 1993). The mechanism underlying the in vivo anti-tumor effects was suggested to involve T cell recruitment, and, more specifically, to likely be a result of secondary T cell products (Luster and Leder, 1993).

Information concerning the nucleic acids encoding IL-8 has been available for a number of years (e.g., Lindley et al., 1988; Schmid and Weissmann, 1987; Matsushima et al., 1988; Hébert et al., 1991). Truncated and genetically engineered variants of IL-8 have also been described (Moser et. al., 1993; Baggiolini et al., 1994). IP-10-encoding sequences are also available (Luster et al., 1985; Luster and Ravetch, 1987b). Furthermore, the genomic organization of IL-8 and IP-10 has now been analyzed (Mukaida et al., 1989; Modi et al., 1990; Luster et al., 1987; Luster and Ravetch, 1987a; Kawahara and Deuel, 1989).

PF4 was originally identified for its ability to bind to heparin, leading to inactivation of heparin's anticoagulation function (Deutsch and Kain, 1961). PF4 was later reported to be capable of attenuating the growth of murine melanoma and human colon cancer (Sharpe et al., 1990). The three dimensional structure of PF4 has been reported (St. Charles et al., 1989). MIG is a CXC chemokine that appears to be only expressed in the presence of γ-interferon (γ-IFN) (Farber, 1993).

ENA-78 and GCP-2 were initially identified on the basis of their ability to induce neutrophil activation and chemotaxis (Walz et al., 1991; Baggiolini et al., 1994). GCP-2 has been more recently studied by Proost et. al. (1993a; 1993b). NAP-2, CTAP-III (and βTG) are proteolytic cleavage products of PBP (Walz and Baggiolini, 1990). The βTG structure has been described by Begg et al. (1978).

GROα, GROβ, and GROγ, are closely related CXC chemokines, with GROα originally described for its melanoma growth stimulatory activity (Anisowicz et al., 1988). GROα is also termed MGSA; GROβ is also termed MIP-2α; and GROγ is also termed MIP-2β (Wolpe et al., 1988). GRO peptides have been proposed to contribute to would healing in vitreoretinopathy (Jaffe et al., 1993). GRO genes have been reported to be over-expressed at sites of injury and neovascularization, and are said to be important in would healing (Martins-Green et al., 1990, 1991; Iida and Grotendorst, 1990). However, a review of the scientific literature shows that the functions of the GRO genes have yet to be clearly defined, with roles in negative growth regulation, alteration of the extracellular matrix and in cell cycle control being proposed (Anisowicz et al., 1988; Martins-Green et al., 1990, 1991).

As mentioned above, one of the well documented actions of IL-8 at the cellular level is that it activates neutrophils, as assessed by the induction of neutrophil chemotaxis and enzyme release. However, certain other CXC chemokines, including PF4, are reported to be virtually inactive towards neutrophils (Walz et al., 1989). IL-8 is believed to bind to two different receptors on neutrophils, whereas other chemokines seem to bind to only one receptor (Holmes et al., 1991; Murphy and Tiffany, 1991; LaRosa et al., 1992, Cerretti et al., 1993). The IL-8 receptors are coupled to GTP-binding proteins (G proteins), allowing transmission of the IL-8 signal into the cell (Wu et al., 1993).

The three dimensional structure of IL-8 has been elucidated by NMR (Clore et al., 1990) and by X-ray crystallography (Clore and Gronenborn, 1992; Baldwin et al., 1991). A freely movable amino terminal end is followed by three beta pleated sheets and an alpha helix is located at the carboxyl-terminal end (Oppenheim et al., 1991). Despite the structural information available, there are several lines of conflicting evidence regarding which portions of the IL-8 polypeptide mediate receptor binding. From the literature, it seems that both the amino- (Clark-Lewis et al., 1991a; Moser et al., 1993) and carboxyl-terminal ends (Clore et al., 1990) may be involved in IL-8 binding to its receptors.

The issue of the precise function of IL-8 receptors on neutrophils appears to be further complicated by the fact that certain neutrophil receptors also bind to other CXC chemokines, particularly NAP-2 and GROα (Moser et al., 1991). However, in studying NAP-2 and IL-8, Petersen et. al. (1994) reported that although these cytokines bind to the same sites on neutrophils, they interact in different ways. Particular discrepancies in binding affinities, receptor densities and biological effects were reported, leading the authors to conclude that these CXC chemokines could mediate different biological functions by interacting with common receptors, but in an individual manner (Petersen et. al., 1994).

The amino acid sequence ELR (Glu Leu Arg) located within IL-8, and found within the N-terminus of certain other CXC chemokines, has been proposed to be involved in IL-8 receptor binding to neutrophils. The ELR motif of IL-8 has thus been proposed to be involved in mediating certain of the biological functions of IL-8, particularly neutrophil activation (Hébert et al., 1991; Clark-Lewis et al., 1991b; 1993; Moser et al., 1993). In this regard, Clark-Lewis et al. (1993) reported that adding the ELR motif to PF4 allowed the resultant modified PF4 to bind to IL-8 receptors and to activate neutrophils.

Following the Clark-Lewis et al. (1993) studies, it appears to be generally accepted that the N-terminal ELR motif is important for IL-8 binding to certain well-characterized receptors, and that ELR is required for certain of the IL-8 biological activities, namely neutrophil attraction, activation, chemotaxis and enzyme release. The ELR motif is absent in molecules such as PF4 and IP-10, which may explain why these molecules are devoid of neutrophil binding and attracting activities (Baggiolini et al., 1994).

However, as a caveat to the above ELR-PF4 data, even the same studies by the Clark-Lewis group resulted in the finding that adding the ELR motif to IP-10 and to the CC chemokine, monocyte chemoattractant protein-1 (MCP-1), did not impart neutrophil-activating properties to these chemokines. This led Clark-Lewis to the conclusion that the ELR motif was necessary, but not sufficient, for IL-8 receptor binding and neutrophil activation (Clark-Lewis et. al., 1993). These authors also implied that other regions of the IL-8 protein are important for neutrophil activation (Clark-Lewis et al., 1993); and later stated that additional structural requirements need to be identified for the design of inhibitors with potential therapeutic applications (Moser et. al., 1993).

Furthermore, other differences do exist between IL-8 and PF4 that may account for differential receptor binding and biological properties. For example, Clore et. al. (1990) proposed that the distribution of positively-charged residues in the 59–67 amino acid region may be an important determining factor in recognition and activity.

Naturally occurring chemokines that are inactive towards neutrophils have not been reported to possess antagonistic activity against chemokines that exhibit chemotactic and activating activity towards these cells. However, Moser et al. (1993) described certain synthetic IL-8 analogues that inhibited IL-8-mediated neutrophil responses and that qualify, in certain terms, as IL-8 antagonists. However, in these studies it was found that even a single IL-8 derivative would exert differential effects on various neutrophil responses, such as chemotaxis, exocytosis and respiratory burst (Moser et al., 1993).

Additional published papers have suggested that further diverse structural elements are required for CXC chemokine actions. For example, one group of workers reported that changing $Tyr_{28}$ and $Arg_{30}$ in MCP-1 results in an IL-8-like molecule, and hypothesized that one or both of these residues are important for cytokine-receptor binding (Beall et al., 1992). Brandt et. al. (1993) identified a novel molecular variant of NAP-2 that had enhanced biological activity. This variant was found to be truncated at the C-terminus, lacking from one to three amino acid residues, and these authors suggested that proteolytic modification at the C-terminus plays a role in the regulation of NAP-2-biological activity (Brandt et. al., 1993).

It has also been shown that structurally similar CXC chemokines, such as NAP-2 and CTAP-III (each derived from the same precursor), have markedly different activities towards neutrophils (Walz et al., 1989). Proost et. al. (1993a) also showed that although GCP-2 is structurally related to IL-8 and GROα, it has different biological actions. Therefore, there does not appear to be a consensus in the art as to the important functional regions present even within the IL-8 primary structure, let alone an agreement as to important functional regions in all CXC chemokines.

It has further been reported that certain CXC chemokines have angiogenic functions. An example of an angiogenic CXC chemokine is IL-8, which induces angiogenesis in ex vivo models and in vivo (Koch et al., 1992b; Strieter et al., 1992a; Hu et al., 1993). Antibodies against IL-8 and IL-8 antisense oligonucleotides block the angiogenic activity of IL-8 (Koch et al., 1992b; Smith et al., 1994). Anti-IL-8 strategies have thus been proposed as a potential means for treating cancer (Smith et al., 1993; Burdick et al., 1994; Smith et al., 1994). One CXC chemokine, PF4, has been described as having angiostatic properties (Maione et al., 1990) and, in another study, has also been reported to inhibit the growth of certain cancers (Sharpe et al., 1990).

In contrast to the information concerning the action of CXC chemokines on isolated neutrophils, their actions on other cell types and their actions in vivo have not been well defined in many cases. Although useful in that particular field of study, the data regarding neutrophil activation is not particularly relevant to the complex issues of angiogenesis. In fact, there is a significant lack of data concerning the angiogenic or angiostatic properties of the CXC chemokines. For example, there is little, if any, information on the types of receptors, or even on the types of cells, that may be responsible for mediating the ultimate effects of CXC chemokines on the vasculature. As to the regions of these molecules that are believed to exert such effects, the teaching in the art appears to be particularly confused.

For example, two groups of workers proposed the angiostatic site of PF4 to be the heparin-binding site of the molecule, i.e., to lie within the C-terminus (Maione et al., 1990; Sharpe et al., 1990; Han et al., 1992). However, one of these groups (Maione et al., 1991) later distinguished the angiostatic site from the heparin-binding site by using a non heparin-binding PF4 analogue. Maione et al. (1991) then proposed that the angiostatic site was located in another, distinct region of the C-terminal part of the molecule.

There are no reports in the literature indicating that angiostatic chemokines can inhibit the angiogenic activity of angiogenic chemokines or other angiogenic cytokines (e.g., bFGF). In addition, the literature does not contain any examples that describe the introduction of angiogenic activity to angiostatic chemokines or the introduction of angiostatic activity to angiogenic chemokines through the manipulation of the chemokines' structures. Thus, there is no definitive information in the prior art as to the important functional regions in the angiogenic and angiostatic chemokines. As the CXC chemokines are involved in important physiological processes, it is evident that a more precise understanding of the structural elements that control their biological activity is needed.

SUMMARY OF THE INVENTION

The present invention, in a general and overall sense, concerns the inventors' discovery that CXC chemokines having the ELR (Glu Leu Arg) motif are angiogenic and those lacking the ELR motif are angiostatic. Although now seen to be elegantly simple, this discovery represents a marked advance over the confused and conflicting teachings of the prior art and provides new uses of the CXC chemokines and other molecules.

A particular feature of this invention is the identification of two angiostatic agents, namely IP-10 and MIG, each of which lack the ELR motif. These known CXC chemokines have not been previously identified as having angiostatic activity. The characterization of CXC chemokines according to the absence of the newly-discovered angiogenic motif was followed by the generation of experimental data confirming the angiostatic activity of IP-10, MIG and CXC chemokines modified to remove the ELR motif. The angiogenic activity of previously poorly-characterized CXC chemokines, such as GCP-2, was then established, as was the angiogenic activity of MIG modified to include the ELR motif.

The discovery that IP-10 and MIG block ELR CXC chemokine-induced angiogenesis could not be expected from a study of the published scientific literature, particularly as IP-10 and MIG are known not to block CXC chemokine-induced neutrophil activation (DeWald et. al., 1992). The present invention allows, for the first time, angiogenic or angiostatic chemokines to be identified or designed without laborious experimentation and avoiding the expense of trial and error screening.

As used herein, the term CXC chemokine is used to refer to a cytokine that has the amino acid motif Cys Xaa Cys located in the N-terminal region, or a derivative or mutant thereof. Examples of CXC chemokines include IL-8; ENA-78; GCP-2; GROα (MGSA), GROβ (MIP-2β) and GROγ (MIP-2β); CTAP-III; NAP-2; βTG; IP-10; MIG and PF4. For simplicity, the terms "CXC chemokine" and "CXC chemokine composition" are used to describe both the native or wild type chemokines and those CXC chemokines with sequences altered by the hand of man (engineered chemokines).

A CXC chemokine that contains the amino acid motif ELR is referred to as an "ELR-CXC chemokine (ELR-CXC)", whereas a CXC chemokine that does not contain this motif is be termed an "XXX-CXC chemokine", or referred to as XXX-CXC. Examples of ELR-CXC chemokines include IL-8, ENA-78, GCP-2, GROα, GROβ, GROγ, CTAP-III, NAP-2 and βTG. Examples of XXX-CXC chemokines include IP-10, MIG and PF4.

The term "wild type" CXC chemokine refers to those ELR-CXC or XXX-CXC chemokines that have an amino acid sequence as found in the chemokine in the natural environment. This term therefore refers to the sequence characteristics, irrespective of whether the actual molecule is purified from natural sources, synthesized in vitro, or obtained following recombinant expression of a CXC chemokine-encoding DNA molecule in a host cell.

The terms "mutant, variant or engineered" CXC chemokine refer to those ELR-CXC or XXX-CXC chemokines the amino acid sequence of which have been altered with respect to the sequence of the chemokine found in nature. This term thus describes CXC chemokines that have been altered by the hand of man, irrespective of the manner of making the modification, e.g., whether recombinant DNA techniques or protein chemical modifications are employed.

"Native" CXC chemokines are those that have been purified from their natural sources, such as from tissues or from cultured, but otherwise unaltered, cells. Native CXC chemokines will also most generally have wild type sequences.

"Recombinant" CXC chemokines are those molecules produced following expression of a CXC chemokine recombinant DNA molecule, or gene, in a prokaryotic or eukaryotic host cell, or even following translation of an RNA molecule in an in vitro translation system. "Synthetic" CXC chemokines are those chemokines produced using synthetic chemistry, most usually in the form of automated peptide synthesis. Both recombinant and synthetic CXC chemokines may have either wild type or mutant sequences, as designed.

The preparation of wild type, mutant, native, recombinant and synthetic CXC chemokines will be straightforward to those of skill in the art in light of the present disclosure. Techniques for the operation of automated peptide synthesizers, and for the expression of recombinant proteins (see e.g., Sambrook et al., 1989) are standard practice in the art and are further described herein in detail. To prepare a recombinant CXC chemokine composition, all that is required is to express the CXC chemokine gene, including wild type and mutant genes, in a recombinant host cell and to collect the expressed CXC chemokine protein to obtain the composition.

In certain embodiments, the present invention concerns methods for inhibiting angiogenesis. These methods generally comprise administering to an animal a biologically effective amount of a CXC chemokine composition, preferably a pharmaceutically acceptable composition, that comprises, or results in the production of, an XXX-CXC chemokine other than PF4. XXX-CXC chemokines include IP-10, MIG and ELR-CXC chemokines that have been modified to remove the amino acid sequence ELR, and combinations of such agents. "Biologically effective amounts" are those amounts that function to inhibit or reduce angiogenesis in the animal or in a defined biological site within the animal.

An understanding of cytokine and CXC chemokine interactions and networks, as disclosed herein, allows for compositions other than the CXC chemokines themselves to be used in the present invention. This is the meaning of "a composition that comprises or results in the production of", as used herein. For example, IFNγ results in the production of IP-10 and MIG, and could thus be used in the context of an angiostatic CXC chemokine. IL-10 decreases IP-10 and MIG levels (via decreasing IFNγ), and can thus be used similarly to angiogenic CXC chemokines.

"CXC chemokine compositions" may comprise one or more CXC chemokine proteins, polypeptides or peptides. Equally, "CXC chemokine compositions" may comprise one or more genes, nucleic acid segments or cDNAs that encode one or more wild type or engineered CXC chemokine proteins, polypeptides or peptides. As described hereinbelow, the coding segments or genes may be in the form of naked DNA, or housed within any one of a variety of gene therapy vehicles, such as recombinant viruses or cells, including tumor cells and tumor infiltrating lymphocytes, modified to contain and express the encoded CXC chemokine protein, polypeptide or peptide. The use of antisense CXC chemokine oligonucleotides is also contemplated.

As used herein, the term "inhibiting angiogenesis" is used in the same manner as the terms "inducing or establishing angiostasis". This means that the process(es) of new or abnormal blood vessel growth (neovascularization) is reduced. "New blood vessel growth" refers to the inappropriate growth of blood vessels, as may occur in disease states. The term "new" describes blood vessels that are present in a number in excess of that observed in the normal state, this term does not represent the age of any particular vessel within a given individual.

Any consistently observed reduction of angiogenesis in response to the presence of a particular composition is evidence of the inhibition of angiogenic activity, and establishes the composition as a useful inhibitory or angiostatic composition. However, it will be understood that the most useful agents will result in a significant reduction in angiogenesis. "A significant reduction in angiogenesis or angiogenic activity" is defined herein as a consistently observed marked reduction or inhibition of angiogenesis, or the establishment of a significant angiostatic state.

Many systems are available for assessing angiogenesis. For example, as angiogenesis is required for solid tumor growth, the inhibition of tumor growth in an animal model may be used as an index of the inhibition of angiogenesis. Angiogenesis may also be assessed in terms of models of wound-healing, in cutaneous or organ wound repair; and in chronic inflammation, e.g., in diseases such as rheumatoid arthritis, atherosclerosis and idiopathic pulmonary fibrosis (IPF). It may also be assessed by counting vessels in tissue sections, e.g., following staining for marker molecules, e.g., CD3H, Factor VIII or PECAM-1.

Two systems are currently preferred by the present inventors for assessing angiogenesis. One is the endothelial cell chemotaxis assay. An angiogenic agent is identified in such an assay by acting to consistently promote endothelial cell chemotaxis above control values. In contrast to assays concerning neutrophil chemotaxis, inhibition of endothelial cell chemotaxis is evidence of anti-angiogenic activity. Anti-angiogenic agents can thus be identified by consistently reducing the endothelial cell chemotaxis back below the levels stimulated by an angiogenic agent. Such reductions are evidenced herein, e.g., in FIG. 11, FIG. 15, FIG. 22A, FIG. 22B, FIG. 22C, FIG. 30A, FIG. 30B, FIG. 31 FIG. 34A, FIG. 34B and FIG. 34C.

The system most preferred by the present inventors for assessing angiogenesis is the corneal micropocket assay of neovascularization, as may be practiced using rat corneas. This in vivo model is widely accepted as being generally predictive of clinical usefulness. For example, as described in many review articles and papers such as those by O'Reilly et. al. (1994), Li et. al. (1991) and Miller et. al. (1994).

In the corneal micropocket assay, an angiogenic agent is an agent that consistently acts to promote the ingrowth of one or more blood vessels within the cornea, preferably without evidence of the influx of leukocytes. Most preferably, an angiogenic agent will be one that promotes the growth of a significant number blood vessels within the cornea. "Significant" or "positive neovascularization" is herein defined as sustained directional ingrowth of capillary sprouts and/or hairpin loops towards a corneal implant that contains the test chemokine or substance. Many instances of angiogenesis in this model are shown herein, by way of example only, see FIG. 7A, FIG. 7B and FIG. 14B.

In the corneal micropocket neovascularization assay, a significant reduction in angiogenesis is evidenced by a consistently observed marked reduction in the number of blood vessels within the cornea. Such negative responses, which are evidence of angiostasis, are preferably defined as those corneas showing only an occasional sprout and/or hairpin loop that displayed no evidence of sustained growth when contacted with the test substance. For a "marked reduction" to occur, it is not necessary that the number of blood vessels be reduced to zero, but rather that the blood vessel growth in the presence of a candidate inhibitory or angiostatic composition be much reduced in comparison to blood vessel growth in the absence of the inhibitor.

Examples of such inhibition of angiogenesis are evident by comparing FIG. 16F to FIG. 16B; FIG. 18B to FIG. 18E; FIG. 24A & FIG. 24B to FIG. 24E & FIG. 24F; and by comparing FIG. 25A and FIG. 25B to FIG. 25E and FIG. 25F. Inhibition of angiogenesis by MIG is particularly evidenced by comparing FIG. 29F to FIG. 29D, by comparing FIG. 29J to FIG. 29H and by comparing FIG. 29L to FIG. 29K, which show MIG inhibition of bFGF-, IL-8- and ENA-78-induced angiogenesis, respectively.

It is important to note that, in the present context, the inhibition of angiogenesis does not simply mean inhibition, antagonism or competition of one particular CXC chemokine. This is particularly exemplified with reference to IL-8. For example, the engineered angiostatic variant of IL-8 that contains TVR in place of ELR is capable of inhibiting angiogenesis induced, not only by native IL-8, but also by ENA-78 (FIG. 25A and FIG. 25B vs. FIG. 25E and FIG. 25F) and even by the non-CXC chemokine bFGF (FIG. 24A and FIG. 24B vs. FIG. 24E and FIG. 24F).

Further evidence of the newly discovered angiostatic properties of the CXC chemokines that do not contain the ELR motif is presented herein. For example, FIG. 14A, FIG. 14B, FIG. 14C and FIG. 14D show that IP-10 inhibits IL-8-induced angiogenesis; FIG. 16A, FIG. 16B, FIG. 16C, FIG. 16D, FIG. 16E and FIG. 16F show that IP-10 inhibits bFGF-induced angiogenesis; FIG. 18A, FIG. 18B and FIG. 18C show that IP-10 inhibits ENA-78-, GROα, and GCP-2 induced angiogenesis, respectively. The ability of IP-10 to inhibit IL-8-induced angiogenesis is in contrast to its known failure to inhibit IL-8-induced neutrophil activation. Further studies of the inventors' show that MIG inhibits not only ENA-78- and IL-8-, but also bFGF-induced angiogenesis.

Therefore, although a precise understanding of the mechanisms of action of the CXC chemokines is not necessary to practice the invention, it should be noted that both the natural and synthetic (engineered) non-ELR chemokines have definite angiostatic properties and do not function solely by competition or antagonism of a predominant angiogenic CXC chemokine, such as IL-8.

Certain currently preferred compounds for use in inhibiting angiogenesis are IP-10, MIG and CXC chemokines that have been modified to remove or mutate the ELR motif sequence. IP-10 may be purchased from Pepro Tech Inc. (Rocky Hill, N.J.), or may be prepared as described in any one of many published scientific articles, for example, Luster et al. (1985, 1987), and Luster and Ravetch (1987a, 1987b), each incorporated herein by reference.

MIG will most likely be prepared by expressing a nucleic acid molecule including a sequence as described by Farber (1993), incorporated herein by reference. A currently preferred method for preparing MIG is described in Example XIII and utilizes fusion protein production and subsequent cleavage.

The CXC chemokines that may be modified to remove the ELR sequence include IL-8, ENA-78, GCP-2, GROα, GROβ, GROγ, CTAP-III, NAP-2 and βTG. IL-8 may be purchased from many suppliers, e.g., R & D Systems, Minneapolis, Minn., or Genzyme; or may be prepared as described in any one of many published scientific articles, e.g., Schmid and Weissman (1987), Lindley et al. (1988), and Matsushima et al. (1988), each incorporated herein by reference. A currently preferred method is to prepare IL-8 as a recombinant fusion protein, and to cleave the protein to yield the IL-8 product (as described in Example XII).

ENA-78 may be purchased from R & D Systems. It may also be prepared using published methodology, such as described by, for example, Walz et al. (1991), Power et. al. (1994), Corbett et al. (1994) and Chang et. al. (1994), each incorporated herein by reference.

GROα, GROβ and GROγ are available from R & D Systems, Minneapolis, Minn. and from Austral Biologicals, Calif. The GRO genes and peptides may also be prepared as described in papers by, e.g., Anisowicz et al. (1988), Haskill et al. (1990), and Iida and Grotendorst (1990), each incorporated herein by reference.

CTAP-III, NAP-2 and βTG may be prepared using the methodology of Walz et. al. (1989), which is incorporated herein by reference. The methods of Walz and Baggiolini (1990) and Begg et al. (1978), each incorporated herein by reference, may also be used to prepare CTAP-III, NAP-2 and βTG. GCP-2 preparation may be achieved by the methods of Proost et. al. (1993a; 1993b), each incorporated herein by reference.

In addition to the foregoing, representative amino acid sequences of the various CXC chemokines are disclosed herein, as follows:

IP-10 amino acid sequence, SEQ ID NO:1;
MIG amino acid sequence, SEQ ID NO:2;
IL-8 amino acid sequence, SEQ ID NO:3;
ENA-78 amino acid sequence, SEQ ID NO:4;
GROα amino acid sequence, SEQ ID NO:5;
GROβ amino acid sequence, SEQ ID NO:6;
GROγ amino acid sequence, SEQ ID NO:7;
PBP amino acid sequence, SEQ ID NO:8;
CTAP-III amino acid sequence, SEQ ID NO:9;
βTG amino acid sequence, SEQ ID NO:10;
NAP-2 amino acid sequence, SEQ ID NO:11; and
GCP-2 amino acid sequence, SEQ ID NO:12.

Several of the above sequences represent the CXC chemokine prior to processing. Using the following information, processed forms may be readily made. IP-10 is processed after Gly at position 21; MIG is processed after Gly at position 22. IL-8 is processed after Arg at position 27; ENA-78 is processed after Ser at position 36; GROα and GROβ are processed after Gly at position 34; and GROγ is processed after Gly at position 33. PBP is processed after Ala at position 34. Physiologically, further processing of PBP gives CTAP-III, βTG and NAP-2, as represented by the above sequences. GCP-2 of SEQ ID NO: 12 may also be processed to give peptides with two, five and eight amino acids removed from the N-terminus.

It is important to note that each of the CXC chemokines are relatively short polypeptides. Each chemokine could thus be made using the presently available automated peptide synthesis technology. Smaller peptides could also be generated and then joined, resulting in the desired product.

The ELR triplet may simply be removed from the ELR-CXC chemokine compounds to create an angiostatic agent. However, in that various techniques of mutation or modification are known and easily practiced, it is currently preferable that the ELR motif be exchanged for a different amino acid triplet, most preferably one that occurs naturally in an angiostatic CXC chemokine. "Modified to remove" in the present application therefore encompasses both deletion and exchange or substitution. By changing the ELR amino acids rather than removing them, it is contemplated that the overall structure of the CXC chemokine will be less disturbed. Also, it is possible that the resultant modified CXC chemokine may be less immunogenic when administered to a patient.

A preferred example of a CXC chemokine that may be modified to remove the ELR sequence is IL-8 (also previously known as neutrophil-activating factor, monocyte-derived neutrophil-activating peptide, monocyte-derived neutrophil-chemotactic factor and neutrophil-activating peptide-1). Particular examples of modified IL-8 polypeptides are those in which the amino acid sequence ELR has been replaced with the amino acid sequence DLQ or the amino acid sequence TVR, both of which inhibit angiogenesis (see, e.g., FIG. 22A, FIG. 22B, FIG. 22C; FIG. 23D and FIG. 23E).

It is contemplated that virtually any combination of amino acids may be used to replace the ELR of an angiogenic CXC chemokine. However, any such mutant CXC chemokine generated should be tested to ensure that the anti-angiogenic activity is high enough to warrant progression to clinical practice. In preferred embodiments, the ELR motif will be exchanged for a triplet sequence that occurs in the naturally occurring angiostatic CXC chemokines. This is the origin of the amino acid sequences DLQ and TVR employed in the IL-8 mutants; with DLQ naturally being present in PF4 and TVR being found in IP-10. DLQ, TVR and KGR (from MIG) are thus preferred for replacing the ELR motif.

It will be understood that for human administration, the use of CXC chemokines purified from human cells or tissues, or recombinant CXC chemokines that comprise a sequence substantially as found in the human proteins and polypeptides, will generally be preferred. However, the use of CXC chemokines from other mammalian sources is by no means excluded.

In using the native or modified CXC chemokines in the invention, or even a gene that expresses such a chemokine, it is currently preferred to use the full-length protein or a gene that expresses such a molecule. However, it is also contemplated that shorter polypeptides or peptides will be effective in modifying angiogenesis or angiostasis, so long as the polypeptide or peptide contains the CXC motif and either the ELR motif or a substitution thereof. Therefore, biologically active fragments are encompassed by the invention.

Exemplary peptides that may be tested for use in inhibiting angiogenesis include VPLSRTVRCTC (SEQ ID NO:13) derived from IP-10; TPVVRKGRCSC (SEQ ID NO:14) derived from MIG; and even EAEEDGDLQCLC (SEQ ID NO:15) derived from PF4. Exemplary peptides that are envisioned for use in promoting angiogenesis include VPLSRELRCTC (SEQ ID NO:16), derived from IP-10; TPVVRELRCSC (SEQ ID NO:17) derived from MIG; and EAEEDGELRCLC (SEQ ID NO:18), derived from PF4.

CXC chemokine peptides of any length between about 8 or 9 amino acids and the length of the complete protein, or even longer, may be employed if desired. This includes peptides and polypeptides of about 10, 20, 30, 40, 50, about 100, or even about 150 amino acids in length. Additional peptidyl regions, may be added to the CXC chemokines if desired, and CXC chemokine-fusion proteins may also be used.

The CXC chemokine compositions for use in the invention may include proteins or peptides that have been modified or "biologically protected". Biologically protected compositions, particularly peptides, have certain advantages over unprotected peptides when administered to human subjects and, as disclosed in U.S. Pat. No. 5,028,592 (incorporated herein by reference). Protected peptides therefore often exhibit increased pharmacological activity.

Compositions for use in the present invention may also comprise CXC chemokines that include all L-amino acids, all D-amino acids or a mixture thereof. The use of D-amino acids may be advantageous in certain embodiments, again particularly with peptides, as such peptides are known to be resistant to proteases naturally found within the human body, may be less immunogenic, and can therefore be expected to have longer biological half lives.

In certain embodiments, the angiostatic CXC chemokine will be administered to the animal or human subject by administering a composition that comprises a gene that expresses an XXX-ELR CXC chemokine other than PF4, as exemplified by IP-10, MIG and CXC chemokines that have been modified to remove the amino acid sequence ELR. As used herein, the term "gene that expresses" is used to refer to a gene, cDNA or other nucleic acid coding unit that encodes a particular CXC chemokine and that is capable of expressing the chemokine coding unit to produce the protein, polypeptide or peptide. cDNAs will generally be preferred over genomic sequences due to their ease of preparation and use.

The genes and cDNAs encoding the various CXC chemokines are well known to those of skill in the art. For example, IP-10 nucleic acid sequences are described in Luster et al. (1985) and Luster and Ravetch (1987b); and MIG nucleic acid sequences are described in Farber (1990), which concerns the mouse sequence, and Farber (1993), which concerns the preferred human sequence. Each of the foregoing being incorporated herein by reference.

IL-8 nucleic acid sequences are described in Lindley et al. (1988), Schmid and Weissmann (1987) and Matsushima et al. (1988); ENA-78 nucleic acid sequences are described in Walz et al. (1991), Power et. al. (1994), Corbett et al. (1994) and Chang et. al. (1994); and GROα, GROβ and GROγ nucleic acid sequences are described in Anisowicz et al. (1988), Martins-Green et al. (1990, 1991), Iida and Grotendorst (1990), Richmond et al. (1988) and Haskill et al. (1990), each incorporated herein by reference.

CTAP-III, NAP-2 and βTG protein and nucleic acid sequences are highly related. An exemplary nucleic acid sequence is described in Wenger et. al. (1989); incorporated herein by reference. The GCP-2 amino acid sequence of Proost et. al. (1993b) and SEQ ID NO:12 may also be used to obtain GCP-2 cDNAs and genes, as described herein.

In addition, representative nucleic acid sequences of various CXC chemokines are disclosed herein. These include the IP-10 nucleic acid sequence of SEQ ID NO:89; the MIG nucleic acid sequence of SEQ ID NO:72; the IL-8 nucleic acid sequence of SEQ ID NO:77; and the ENA-78 nucleic acid sequence of SEQ ID NO:88. Further exemplary sequences included are the GROα nucleic acid sequence of SEQ ID NO:90; the GROβ nucleic acid sequence of SEQ ID NO:91; the GROγ nucleic acid sequence of SEQ ID NO:92; and the PBP nucleic acid sequence of SEQ ID NO:93 that results in CTAP-III, βTG and NAP-2 sequences.

In using a nucleic acid segment that expresses a CXC chemokine, or that expresses an antisense CXC chemokine, the nucleic acid segment itself may be administered to the animal. This is based upon the knowledge that cells can take up naked DNA and express the encoded proteins or peptides, or the antisense mRNA. The utilization of this technology, and variations thereof, such as those described by Ulmer et al. (1993); Tang et al. (1992), Cox et al. (1993), Fynan et al. (1993), Wang et al. (1993), Gal et. al. (1993) and Whitton et al. (1993), each incorporated herein by reference, is therefore contemplated. The CXC chemokine DNA segments may be used in virtually any form, including naked DNA and plasmid DNA, and may be administered to the animal in a variety of ways, including parenteral, mucosal and gene-gun inoculations, as described, for example, by Fynan et al. (1993).

The use of recombinant viruses engineered to express CXC chemokines (or antisense versions thereof) is contemplated for use in the gene therapy embodiments. A variety of viral vectors, is such as retroviral vectors, herpes simplex virus (U.S. Pat. No. 5,288,641, incorporated herein by reference), cytomegalovirus, and the like may be employed, as described by Miller (1992, incorporated herein by reference). Recombinant adeno-associated virus (AAV) and AAV vectors may also be employed, such as those described by Kotin (1994) and in U.S. Pat. No. 5,139,941, incorporated herein by reference. Recombinant adenoviral vectors are often used in the art and are particularly contemplated for use with the CXC chemokines. Techniques for preparing replication-defective infective viruses are well known, as exemplified by Ghosh-Choudhury and Graham (1987); McGrory et al. (1988); and Gluzman et al. (1982), each incorporated herein by reference. Liposome formulations are currently particularly preferred.

The compositions for use in the inhibitory methods described herein may contain only a single angiostatic CXC chemokine or CXC chemokine gene, or they may contain more than one such agent. The chemokine compositions may themselves be combined with other distinct angiostatic agents, or with other molecular entities such as antibodies, immunotoxins, chemotherapeutic agents, and the like, as may be desired for use in the treatment of a particular disease or patient. Similarly, the treatment methods may be used alone or in conjunction with other modes of therapy.

In other embodiments, the invention provides further methods for the inhibition of angiogenesis, which methods generally comprise administering to an animal a biologically effective amount of a pharmaceutically acceptable composition that comprises one or more biological agents that inhibit an ELR-CXC chemokine other than IL-8, as exemplified by inhibiting one or more of ENA-78, GCP-2, CTAP-III, NAP-2 or βTG. Such biological "inhibitory agents" include antisense oligonucleotide constructs, polyclonal and monoclonal antibodies and, also, other molecular entities that function to inhibit ELR-CXC chemokines other than IL-8, and preferably, that inhibit one or more of ENA-78, GCP-2, CTAP-III, NAP-2 or βTG genes, mRNAs or proteins.

CXC chemokine antisense oligonucleotide constructs will generally be designed to inhibit the transcription, translation or both, of a given CXC chemokine gene so that the level of the resultant protein product is reduced or diminished. Antisense oligos complementary to nucleic acid sequences of one or more of ENA-78, GCP-2, CTAP-III, NAP-2 and βTG may be used to inhibit ELR-CXC chemokine gene expression in a given animal or human subject, thereby effecting the inhibition of angiogenesis. The antisense constructs may include antisense versions of CXC chemokine promoter, control region, exon, intron and/or exon:intron boundary sequences. The preparation of antisense oligos will be straightforward to those of skill in the art, given the details of the coding sequences in the present disclosure and in the published scientific literature.

In certain embodiments, one may wish to employ CXC chemokine antisense constructs that include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Further biological inhibitory agents suitable for use in inhibiting ELR CXC chemokines, and angiogenesis, are polyclonal or monoclonal antibodies that bind to (have binding affinity for) and inhibit an ELR-CXC chemokine other than IL-8, as exemplified by ENA-78, GCP-2, CTAP-III, NAP-2 or βTG. Polyclonal and monoclonal antibodies (MAbs) against CXC chemokines are available commercially, e.g., from R & D Systems. MAbs may also be generated using the well-established monoclonal antibody technology, which is known to those of skill in the art and is further described in the present disclosure. The more useful antibodies are contemplated to be those that neutralize at least between about 20 and about 30 ng of a particular CXC chemokine at a dilution of about 1:1000. In any embodiment involving antibodies, monoclonal antibodies, including humanized constructs, will be preferred.

The methods for inhibiting angiogenesis provided by the invention may be used in many contexts. For example, as angiogenesis is generally required for significant tumor growth, the anti-angiogenic strategies of the invention may be aimed specifically at attenuating tumor growth and/or metastasis. Typical vascularized tumors that may be treated using this invention include, but are not limited to, carcinomas and even sarcomas of the lung, breast, ovary, stomach, pancreas, larynx, esophagus, testes, liver, parotid, biliary tract, colon, rectum, cervix, uterus, endometrium, kidney, bladder, prostate and thyroid; melanomas; gliomas; neuroblastomas; and the like. Non-small cell lung carcinomas (NSCLC), squamous cell carcinomas and adenocarcinomas are particularly suitable for treatment.

The anti-angiogenic methods may also be used to treat other diseases, including benign tumors, that rely on blood vessel growth. Such diseases particularly include hemangiomas, rheumatoid arthritis, atherosclerosis and idiopathic pulmonary fibrosis (IPF); but also include BPH, vascular restenosis, arteriovenous malformations (AVM), meningioma, neovascular glaucoma, psoriasis, angiofibroma, hemophilic joints, hypertrophic scars, osler-weber syndrome, pyogenic granuloma retrolental fibroplasia, scleroderma, trachoma, vascular adhesions, synovitis, dermatitis and even endometriosis. The levels of IL-8 and ENA-78 are herein shown to be elevated in hemangiomas.

Diseases and disorders associated with inappropriate blood vessel growth in the eye are particularly contemplated for treatment in accordance with the invention. These include pterygium, diabetic retinopathy and neovascularization associated with corneal injury or grafts.

IL-8 has been identified as at least one causal agent of injury in the adult respiratory distress syndrome (ARDS) (Miller et al., 1992); chronic bronchitis; rheumatoid arthritis (Brennan et al., 1990; Seitz et al., 1991; Koch et. al., 1991a); pseudogout (Miller and Brelsford, 1993); and cystic fibrosis (McElvaney et al., 1992; Nakamura et al., 1992; Bedard et al., 1993). It is therefore contemplated that the present invention may prove useful in treating one or all of the above diseases.

The potential use of IL-8 mutants and other non-ELR CXC chemokines to inhibit the inappropriate actions of IL-8 in other disease states, such as those above, is based upon the inventors' assessment that these chronic diseases may have an angiogenic component. The invention is believed to modulate angiogenic-angiostatic responses, at least in part, through effects on endothelial cells. The invention is not particularly contemplated for use in modulating chemokine actions on neutrophils or in treating diseases that result solely from inappropriate neutrophil actions.

To treat any one of the above conditions, or any other disorder associated with increased angiogenesis, one would identify a patient having or suspected of having such a disease or disorder and administer to the patient an inhibitory composition comprising one or more XXX-ELR chemokine proteins or genes, other than PF4, including one or more ELR-CXC chemokine proteins or genes that has been modified to remove the amino acid sequence ELR. Equally, one may administer to the patient an inhibitory composition comprising one or more antibodies or antisense oligos directed against an ELR-CXC chemokine other than IL-8, such as being directed against ENA-78, GCP-2, CTAP-III, NAP-2 or βTG. The inhibitory composition is administered in an amount effective to inhibit angiogenesis.

To reduce or control angiogenesis in this manner, one would generally administer a biologically effective amount of a pharmacologically acceptable inhibitory composition to an animal or human patient, in a manner effective to contact the area where inappropriate angiogenesis is occurring. Biological contact may be achieved simply by administering the composition to the animal or patient using virtually any pharmaceutical formulation and delivery method.

The formulation and delivery methods will generally be adapted according to the site of angiogenesis and the disease to be treated. Exemplary formulations include, but are not limited to, those suitable for parenteral administration, e.g., intravenous, intramuscular or subcutaneous administration, including formulations encapsulated in micelles, liposomes or drug-release capsules (active agents incorporated within a biocompatible coating designed for slow-release); ingestible formulations, e.g., for the treatment of gastric and duodenal ulcers; formulations for topical use, such as creams, ointments and gels; ophthalmic preparations; and other formulations such as inhalants, aerosols and sprays.

In certain embodiments, it will be preferred to inject the non-ELR angiostatic chemokine(s) directly into a localized site, such as a tumor site (intralesional injection) or joint. The procedures described in Sharpe et al. (1990) and Maione et al. (1991), each incorporated herein by reference, may be advantageously followed.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as *Remington's Pharmaceutical Sciences,* 18th ed., 1980, Mack Publishing Co., incorporated herein by reference.

The biologically effective amounts of the angiostatic CXC chemokines are considered to fall within a fairly broad range, in that low levels may be used to achieve at least some useful anti-angiogenic activity and higher levels used to achieve more significant biological effects. As disclosed herein, a variety of different chemokine concentrations proved effective in the corneal neovascularization assay, with a concentration of about 10 nM (between about 50 ng and about 80 ng) being particularly effective. Clinical doses that result in a local concentration of chemokine of about 10 nM are therefore contemplated to be particularly useful.

Naturally, in a clinical context, the amount of the CXC chemokine composition administered will depend on the host animal or patient, the condition to be treated and the route of administration. The precise amounts of active agent required to be administered will depend on the judgment of the practitioner and may be optimized to each individual by monitoring the biological effects and adjusting the dose accordingly.

Notwithstanding the fact that some dosage modification may be necessary, as is standard practice in the art, the determination of a suitable dosage range for use in humans will be straightforward in light of the data presented herein. For example, to inhibit angiogenesis doses of IP-10, MIG or an engineered XXX-CXC chemokine in the order of between about 0.1 mg/kg body weight (mg/kg) and about 10 mg/kg (including all integers between these values); per individual are contemplated.

In terms of antibodies that bind to, e.g., ENA-78, GCP-2, CTAP-III, NAP-2 or βTG, effective amounts will be clinically equivalent amounts to the amount of IL-8 antibodies herein shown to reduce human tumor size and metastasis in a mouse model (FIG. 46; Table 6).

In further embodiments, the invention provides methods for stimulating angiogenesis. These methods generally comprise preparing CXC chemokine composition, preferably a pharmaceutically acceptable composition, that comprises, or results in the production of, an ELR-CXC chemokine other than IL-8, and administering the composition to an animal or human subject in an amount effective to stimulate angiogenesis. Natural chemokines, e.g., ENA-78, GCP-2, CTAP-III, NAP-2 and βTG, and engineered CXC chemokines modified to contain the amino acid sequence ELR in the N-terminal region may be employed.

ENA-78, GCP-2, CTAP-III, NAP-2 AND βTG, each of which contain the ELR motif, newly-identified as the angiogenic motif, will therefore be useful as angiogenic agents. These particular CXC chemokines have not been previously identified as having such angiogenic activities. CXC chemokines modified to contain the amino acid sequence ELR will generally be non-ELR chemokines into which the ELR sequence has been introduced. "Contain" in this sense of containing the ELR sequence therefore encompasses CXC chemokines into which the ELR sequence has been added, and also those CXC chemokines that have been mutated or otherwise engineered to replace a distinct amino acid triplet with the ELR motif.

Particular examples of non-ELR CXC chemokines that may be modified to include the ELR motif are IP-10 and MIG. As shown in FIG. 45A and FIG. 45B, the inventors have modified MIG by the introduction of the ELR motif and shown that the resultant engineered chemokine has angiogenic activity (contrast with FIG. 45C and FIG. 45D).

Still further embodiments of the invention concern the stimulation of angiogenesis and wound healing by administering to an animal or patient a pharmaceutically acceptable composition that comprises an antibody that binds to and inhibits an XXX-CXC chemokine other than PF4; or an antisense oligonucleotide that binds to and inhibits an XXX-CXC chemokine other than PF4. It is currently preferred to inhibit IP-10 or MIG or an IP-10 or MIG gene or RNA. Such compositions will inhibit the angiostatic properties of these CXC chemokines, as newly-discovered, and will result in increased angiogenesis.

Following the inventors' discovery of the function of the ELR motif in angiogenesis, it will be apparent that the teachings regarding the inhibition of angiogenesis described above can be readily applied to the stimulation of angiogenesis. Therefore human or other sources of CXC chemokines may be used; wild type, mutant, native, recombinant and synthetic ELR-CXC chemokines may be used, either alone or in combination; and the CXC chemokines may take the form of either proteins, polypeptides, peptides; or genes, nucleic acid segments, cDNAs, recombinant viruses or recombinant host cells that express ELR-CXC chemokine proteins, polypeptides or peptides.

Full-length or truncated ELR-CXC chemokines or their genes may be employed in these aspects of the invention, as may significantly shorter peptides. By way of example only, smaller peptides that are envisioned for use in stimulating angiogenesis include SAKELRCQC (SEQ ID NO:19) derived from IL-8; AGPAAAVLRELRCVC (SEQ ID NO:20) derived from ENA-78; DSDLYAELRCMC (SEQ ID NO:21) derived from CTAP-III; AELRCMCIKTTS (SEQ ID NO:22) derived from NAP-2; ESLDSDLYAEL-RCMC (SEQ ID NO:23) derived from βTG; ASVATEL-RCQC (SEQ ID NO:24) derived from GROα; APLATEL-RCQC (SEQ ID NO:25) derived from GROβ; ASVVTELRCQC (SEQ ID NO:26) derived from GROγ; and GPVSAVLTELRCTCLVRTLR (SEQ ID NO:27) derived from GCP-2. The ELR-CXC chemokine peptides may be biologically protected, and may include L-amino acids, D-amino acids or a mixture thereof.

The terms "stimulating or eliciting angiogenesis" mean that the process(es) of new blood vessel growth is enhanced. Any consistently observed increase in angiogenesis in response to the presence of a particular composition is evidence of angiogenic activity, and establishes the composition as a useful substance. CXC chemokines with significant angiogenic activity will often be preferred. "Significant angiogenic activity" is defined herein as the establishment of angiogenesis in a previously silent system or model, or a consistently observed marked increase in angiogenesis. The corneal micropocket assay of neovascularization will again be a preferred model for assessing angiogenesis.

The stimulation of angiogenesis will generally be useful in the context of wound and sore healing. Other uses contemplated include, for example, in the treatment of vascular grafts and transplants and, particularly, in the treatment of skin, gastric and duodenal ulcers.

In still further embodiments, the invention provides methods for promoting wound-healing, which methods generally comprise contacting a wound or ulcer site of an animal with a biologically effective amount of a CXC chemokine composition comprising one or more ELR-CXC chemokines other than a GRO protein. IL-8, ENA-78, GCP-2, CTAP-III, NAP-2, βTG and XXX-CXC chemokine polypeptides or peptides modified to contain the ELR motif may be used, as may genes that encode any of the foregoing. It is also contemplated that antibodies and antisense oligos that bind to the IP-10 and/or MIG (XXX-CXC chemokine) proteins and nucleic acids, respectively, may be employed in chronic wound healing.

The present invention particularly contemplates the use of the ELR CXC chemokines in the treatment of chronic wounds and ulcers. Although XXX-CXC chemokines are required in the overall wound-healing process, the inventors have discovered that the continued presence of non-ELR CXC chemokines correlates with chronic, non-healing wounds. Such wounds would thus benefit from the application of ELR CXC chemokines to redress the balance. ELR chemokines are herein shown to peak during natural wound healing FIG. 9A, FIG. 9B, FIG. 9C, FIG. 9D, FIG. 9E and FIG. 9F. It is contemplated that treatment with ELR CXC chemokines would be conducted for several days, with the dosage being reduced over time.

Although systemic administration is possible, local or directed administration of ELR-CXC chemokines is preferred for use in wound-healing. The chemokines may be added to the wound site, e.g., in the form of a cream, ointment, gel or lyophilized powder; formulated in an ingestible composition to reach an ulcer in the stomach or duodenum; or may be incorporated into a wound dressing that is applied to the wound site.

Biologically effective amounts will be those amounts that promote at least some wound-healing, with amounts that result in significant improvement of the healing process being preferred. The amount of the CXC chemokine compositions used in any given context will depend on the particular animal or patient and the site, type and degree of the wound or injury to be treated or healed. Notwithstanding the fact that some dosage modification may be necessary, as is standard practice in the art, doses of ELR chemokines of between about 0.1 mg/kg and about 10 mg/kg are again contemplated.

The invention also provides wound dressings, bandages and kits thereof that comprise one or more ELR-CXC chemokines, other than GRO proteins. IL-8, ENA-78, GCP-2, CTAP-III, NAP-2, $\beta$TG and XXX-CXC chemokine polypeptides and peptides modified to contain the ELR motif are contemplated. ELR chemokines formulated into hydrocolloid dressings are particularly contemplated.

The invention also has important non-clinical uses, such as, for example, in bioassays of angiostasis and angiogenesis. By providing both positive and negative controls in assays of angiogenesis, the invention may be used to standardize such assays and provide control values against which the effectiveness of other candidate substances may be measured. By stimulating angiogenesis, the invention may also be used to promote tumor growth in experimental animals. Tumor-bearing animals are important tools in the development of anti-cancer drugs and strategies, therefore methods to increase the rate of tumor growth will be useful in providing target animals within a reduced time from inoculation with tumor cells.

In addition to providing many therapeutic and assay methods, the present invention also provides for certain diagnostic and prognostic methods. For example, the presence of an increased amount of one or more angiogenic CXC chemokines within a biological sample suspected of being from a benign or malignant tumor, as compared to the amount of the CXC chemokine from a sample of the corresponding normal tissue, will often be indicative of the presence of such a tumor. The present examples demonstrate the novel finding that the levels of ENA-78 and GRO$\alpha$ are elevated in benign and malignant tumors and that the level of the cytokine IL-10 (an indirect angiogenic agent) is increased in squamous cell carcinomas.

It is further contemplated that increased levels of the angiogenic ELR-containing CXC chemokines within or associated with a tumor will likely correlate with a more rapidly growing tumor and/or a tumor that is more likely to produce metastatic satellite tumors (see evidence in Table 6).

Likewise, increased levels of the angiostatic non-ELR CXC chemokines will correlate with a less rapidly growing tumor and/or a tumor that is less likely to metastasize. Naturally, decreased ELR-CXC chemokine levels will be associated with less aggressive tumors and decreased XXX-CXC chemokine levels with more aggressive tumors. This also applies to the levels of other chemokines and cytokines, such as IL-10 and the interferons (IFNs) that act to modulate and regulate the levels of the CXC chemokines.

The invention thus further provides methods for characterizing a tumor, a preferred example of which comprises obtaining a sample from the tumor and testing the sample for the presence of one or more of GRO$\alpha$, GRO$\beta$, GRO$\gamma$, ENA-78, GCP-2, CTAP-III, NAP-2, $\beta$TG or IL-10, wherein an increased amount one or more of the foregoing molecules is indicative of a tumor with increased angiogenic activity. IL-10 is indicative of angiogenesis by virtue of the fact that IL-10 decreases IFN$\gamma$, which in turn decreases IP-10 and MIG, and thus reduces the levels of the angiostatic CXC chemokines.

The use of diagnostic/prognostic tests using a panel, or plurality, of ELR CXC chemokines is contemplated to be particularly useful. Thus the sample will preferably be tested for the presence or increased levels of more than one of the ELR CXC chemokines or IL-10. For example, testing with one of GRO$\alpha$, GRO$\beta$ or GRO$\gamma$; in combination with one of CTAP-III, NAP-2 or $\beta$TG; testing with IL-10 in combination with one of IL-8 or ENA-78; or testing with the entire panel of IL-8, GRO$\alpha$, GRO$\beta$, GRO$\gamma$, ENA-78, GCP-2, CTAP-III, NAP-2, $\beta$TG and IL-10 may be conducted. Defining the angiogenic activity within a given tumor in these ways is particularly useful as it will better allow appropriate treatment strategies to be defined and implemented.

The testing of the sample may take the form of testing for the presence of the particular protein, e.g., using antibody detection, or a biological assay of a fluid or tissue sample, e.g., using the endothelial cell chemotaxis or corneal micropocket assay of neovascularization. Testing may also take the form of testing for the presence of a nucleic acid sequence that encodes the CXC chemokine protein, e.g., using RT-PCR or nucleic acid hybridization technology.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B are sections (100×) of normal lung stained with control and anti-IL-8 antibodies, respectively; FIG. 1C (100×), FIG. 1E (200×), and FIG. 1G (400×) are sections if IPF lung immunostained with control antibodies, demonstrating the lack of nonspecific staining in the IPF lung specimen; FIG. 1D (100×), FIG. 1F (200×), and FIG. 1H (400×) are sections of IPF lung immunostained with specific IL-8 antibodies, demonstrating that islands of fibroblasts, relatively devoid of leukocytes, are significant cellular sources of IL-8 protein in these IPF lung specimens.

FIG. 2A and FIG. 2B are stained with H & E to demonstrate the histopathology of the hemangiomas (400×); FIG. 2C (200×) and FIG. 2E (400×) are sections of hemangiomas immunostained with control antibodies, demonstrating the lack of nonspecific staining; FIG. 2D (200×) and FIG. 2F (400×) are sections of hemangiomas immunostained with specific IL-8 antibodies, demonstrating that keratinocytes, endothelial cells, and tissue macrophages are significant cellular sources of IL-8 in these benign tumors. In addition, IL-8 appears to be immunostaining the extracellular matrix components of the tumor.

FIG. 3A and FIG. 3B are stained with H & E to demonstrate the histopathology of the hemangiomas (400×); FIG. 3C (200×), FIG. 3E (200×), and FIG. 3G (400×) are sections of hemangiomas immunostained with control antibodies, demonstrating the lack of nonspecific staining; FIG. 3D (200×), FIG. 3F (200×), and FIG. 3H (400×) are sections of hemangiomas immunostained with specific ENA-78 antibodies, demonstrating that keratinocytes, endothelial cells, and tissue macrophages are significant cellular sources of ENA-78 in these benign tumors. In addition, ENA-78 appears to be immunostaining the extracellular matrix components of the tumor.

FIG. 7A and FIG. 7B are A549 (bronchoalveolar cell carcinoma cell line) and squamous cell carcinoma tissue aqueous extracts in the presence of control antibodies, respectively; both FIG. 7A and FIG. 7B demonstrate a significant angiogenic response; FIG. 7C and FIG. 7D are A549 and squamous cell carcinoma tissue aqueous extracts in the presence of neutralizing IL-8 antibodies, respectively; both FIG. 7C and FIG. 7D demonstrate significant attenuation of angiogenic activity in the presence of neutralizing IL-8 antibodies.

FIG. 14A is control pellet alone; FIG. 14B is pellet containing IL-8 (80 ng); FIG. 14C is pellet containing IP-10 (80 ng); and FIG. 14D is pellet containing combined IL-8 (80 ng) and IP-10 (80 ng). All photomicrographs are at 50× magnification.

FIG. 16A, FIG. 16B, FIG. 16C, FIG. 16D, FIG. 16E and FIG. 16F. One example of a rat corneal micropocket assay of neovascularization in the presence or absence of bFGF, with or without IP-10. FIG. 16A and FIG. 16B are the same pellet containing bFGF (80 ng) at 25× and 50× magnification, respectively. FIG. 16C and FIG. 16D are the same pellet containing IP-10 (80 ng) at 25× and 50× magnification, respectively. FIG. 16E and FIG. 16F are the same pellet containing combined bFGF (80 ng) and IP-10 (80 ng) at 25× and 50× magnification, respectively.

FIG. 17A and FIG. 17B are the same pellet containing bFGF (80 ng) at 25× and 50× magnification, respectively. FIG. 17C and FIG. 17D are the same pellet containing IP-10 (80 ng) at 25× and 50× magnification, respectively. FIG. 17E and FIG. 17F are the same pellet containing combined bFGF (80 ng) and IP-10 (80 ng) at 25× and 50× magnification, respectively.

FIG. 18A is ENA-78 (50 ng); FIG. 18B is GROα (50 ng); FIG. 18C is GCP-2 (50 ng); FIG. 18D is ENA-78 (50 ng) and IP-10 (50 ng); FIG. 18E is GROα (50 ng) and IP-10 (50 ng); and FIG. 18F is GCP-2 (50 ng) and IP-10 (50 ng).

FIG. 21A is SCCA+ control antibodies (25× magnification); FIG. 21B is SCCA+ control antibodies (50× magnification); FIG. 21C is SCCA+ anti-IP-10 anti-bodies (25× magnification); and FIG. 21D is SCCA+anti-IP-10 antibodies (50× magnification).

FIG. 22A, using IL-8 in combination with each of TRV/IL-B and DLQ/IL-8, amounts are indicated; FIG. 22B, using increasing amounts (as indicated) of TRV/IL-8 in combination with IL-8; FIG. 22C, using increasing amounts (as indicated) of DLQ/IL-8 in combination with IL-8. These data show that both TRV/IL-8 and DLQ/IL-8 inhibit IL-8 in this angiogenesis-related assay.

FIG. 23A is control; FIG. 23B is IL-8 (50 ng); FIG. 23C is TVR/IL-8 (50 ng); FIG. 23D is DLQ/IL-8 (50 ng); and FIG. 23E is IL-8+TVR/IL-8.

FIG. 24A and FIG. 24B are bFGF (50 ng) alone at a magnification of 25× and 50×, respectively. FIG. 24C and FIG. 24D are TVR-IL-8 (50 ng) alone at a magnification of 25× and 50×, respectively. FIG. 24E and FIG. 24F are combined bFGF (50 ng) and TVR-IL-8 (50 ng) at a magnification of 25× and 50×, respectively.

FIG. 25A and FIG. 25B are ENA-78 (50 ng) alone at a magnification of 25× and 50×, respectively. FIG. 25C and FIG. 25D are TVR-IL-8 (50 ng) alone at a magnification of 25× and 50×, respectively. FIG. 25E and FIG. 25F are combined ENA-78 (50 ng) and TVR-IL-8 (50 ng) at a magnification of 25× and 50×, respectively.

FIG. 29A and FIG. 29B are both MIG alone at two magnifications. FIG. 29C and FIG. 29D are two magnifications of bFGF alone, and FIG. 29E and FIG. 29F are two magnifications of bFGF in combination with MIG. FIG. 29G and FIG. 29H are two magnifications of IL-8 alone, and FIG. 29I and FIG. 29J are two magnifications of IL-8 in combination with MIG. These panels show MIG inhibition of bFGF- and IL-8-induced angiogenesis. FIG. 29K is a single magnification of ENA-78 alone, and FIG. 29L is a single magnification of ENA-78 in combination with MIG, confirming inhibition of ENA-78-induced angiogenesis.

FIG. 30A, IL-8 (80 ng/ml) was used to induce endothelial cell chemotaxis, the ability of MIG to inhibit IL-8-induced endothelial cell chemotaxis is shown; FIG. 30B, ENA-78 (80 ng/ml) was used to induce endothelial cell chemotaxis, the ability of MIG to inhibit ENA-78-induced endothelial cell chemotaxis is shown.

FIG. 33A, inhibition of IL-8 (80 ng/ml)-induced endothelial cell chemotaxis in response to PF4; FIG. 33B, inhibition of ENA-78 (80 ng/ml)-induced endothelial cell chemotaxis in response to PF4; and FIG. 33C, inhibition of bFGF (50 ng/ml)-induced endothelial cell chemotaxis in response to PF4.

FIG. 34A, inhibition of IL-8 (80 ng/ml)-induced endothelial cell chemotaxis in response to IP-10; FIG. 34B, inhibition of ENA-78 (80 ng/ml)-induced endothelial cell chemotaxis in response to IP-10; and FIG. 34C, inhibition of bFGF (50 ng/ml)-induced endothelial cell chemotaxis in response to IP-10.

FIG. 35A is Control antibodies; FIG. 35B is IL-8 (400×); and FIG. 35C is ENA-78 (400×).

FIG. 37A, FIG. 37B, FIG. 37C, FIG. 37D, FIG. 37E and FIG. 37F are gross pathological specimens of A549 tumors at 2, 3, 4, 5, 6, and 7 weeks, respectively. FIG. 37G is the tumor at 8 weeks in the flank of a SCID mouse host.

FIG. 38A and FIG. 38D are H & E of tumor at 200× and 400×, respectively; FIG. 38B and FIG. 38E are control sera at 200× and 400×, respectively; and FIG. 38C and FIG. 38F are immunolocalization of IL-8 at 200× and 400×, respectively.

FIG. 39A is lung metastasis (100×); FIG. 39B is control sera (400×); and FIG. 39C is immunolocalization of IL-8 (400×).

FIG. 41A (200×) and FIG. 41C (400×) are H & E of A549 tumors exposed to control antibodies; FIG. 41B (200×) and FIG. 41D (400×) are H & E of A549 tumors exposed to neutralizing IL-8 antibodies.

FIG. 45A and FIG. 45B are ELR-MIG alone, demonstrating the angiogenic effects of the genetically engineered ELR-MIG. FIG. 45C and FIG. 45D are the same concentration of wild-type MIG alone, showing no angiogenic effects. FIG. 45E and FIG. 45F are combined MIG and ELR-MIG, showing inhibition of ELR-MIG by wild type MIG.

FIG. 47A and FIG. 47B are A549/SCID mouse tumor homogenates and control antibodies (50× magnification and 25× magnification, respectively); and FIG. 47C and FIG. 47D are A549/SCID mouse tumor homogenates and anti-IL-8 antibodies (50× magnification and 25× magnification, respectively).

DETAILED DESCRIPTION OF THE PREFERRED EMBODIMENTS

Figures 1A, 1B, 1C, 1D, 1E, 1F, 1G, 1H:
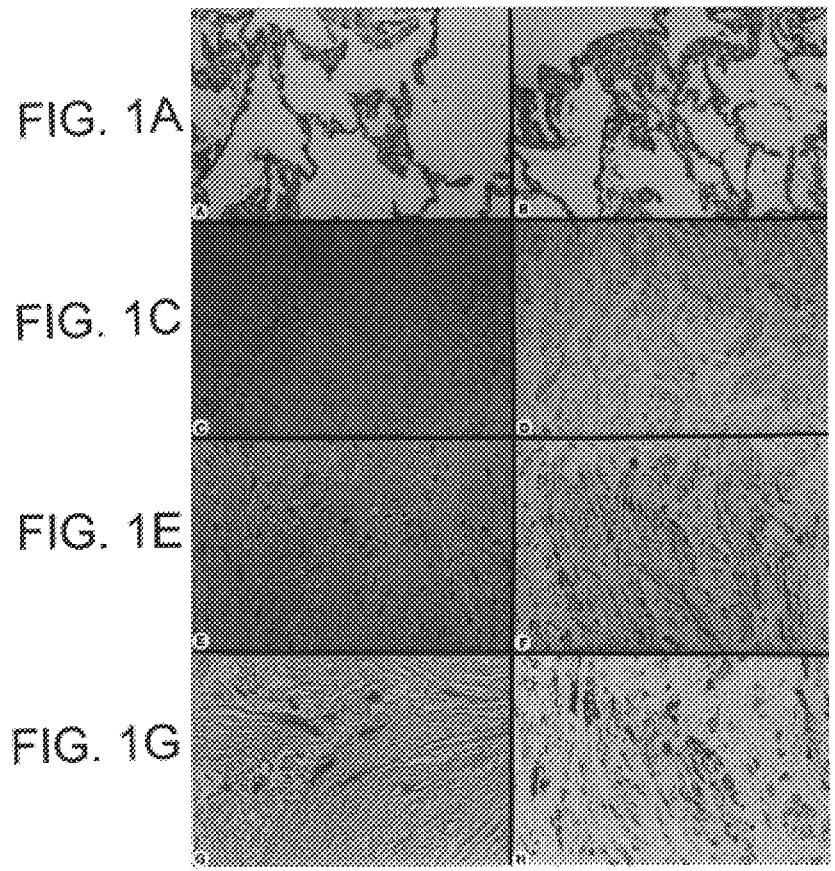
FIG. 1A, FIG. 1B, FIG. 1C, FIG. 1D, FIG. 1E, FIG. 1F, FIG. 1G, FIG. 1H. Photomicrographs of the immunolocalization of interleukin-8 (IL-8) in normal lung and the lung of a patient with idiopathic pulmonary fibrosis (IPF).
Figures 2A, 2B, 2C, 2D, 2E, 2F:
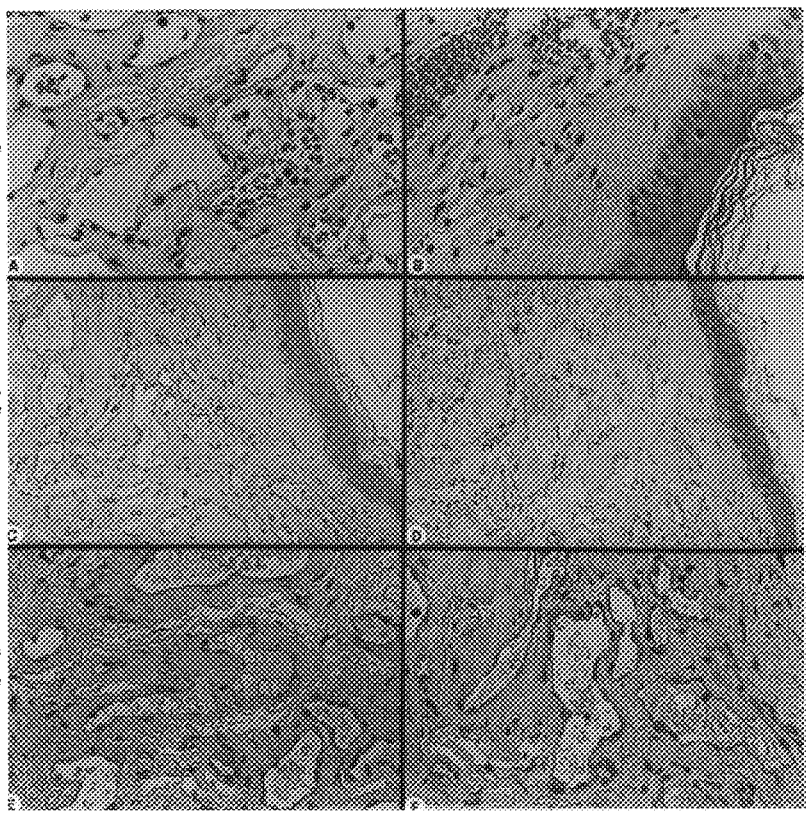
FIG. 2A, FIG. 2B, FIG. 2C, FIG. 2D, FIG. 2E and FIG. 2F. Photomicrograph of the immunolocalization of interleukin-8 (IL-8) in hemangiomas.
Figures 3A, 3B, 3C, 3D, 3E, 3F, 3G, 3H:
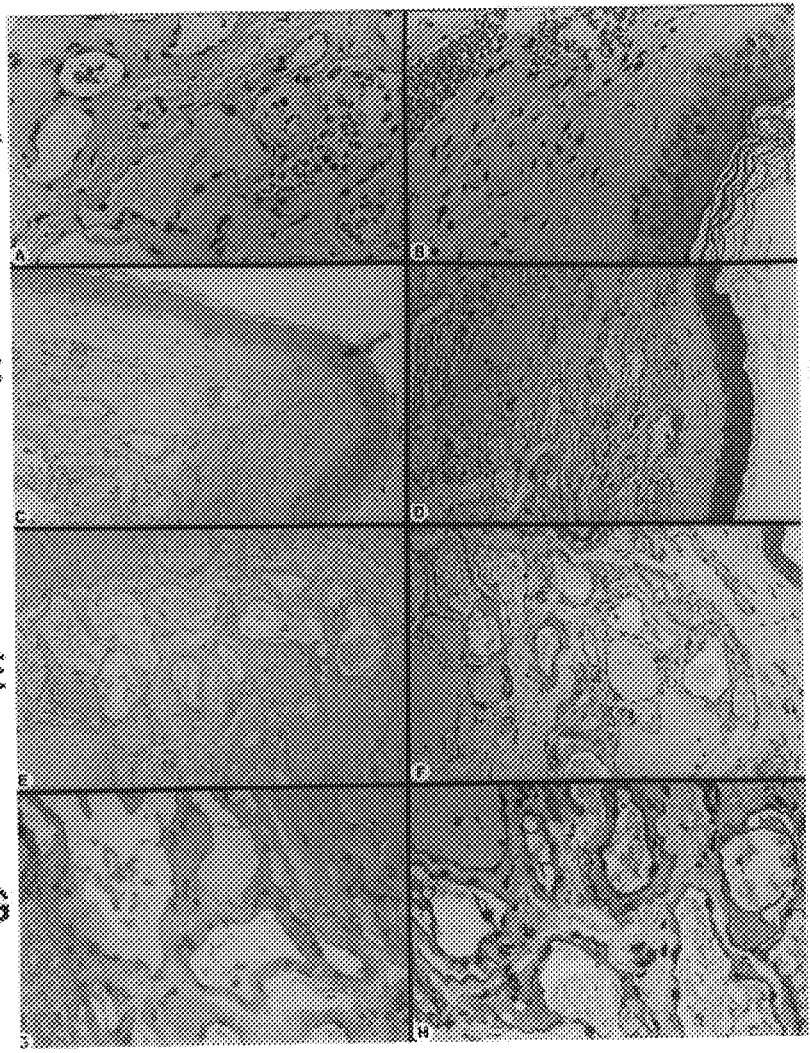
FIG. 3A, FIG. 3B, FIG. 3C, FIG. 3D, FIG. 3E, FIG. 3F, FIG. 3G, FIG. 3H. Photomicrograph of the immunolocalization of epithelial neutrophil activating protein (ENA-78) in hemangiomas.

Lung cancer is the leading cause of malignancy-related mortality in the United States (Garfinkel, 1991). While the incidence of several other malignancies has declined or remained stable, the occurrence of bronchogenic carcinoma has escalated to near-epidemic proportions. Over 150,000 new cases are diagnosed and an equal number of deaths annually are attributable to bronchogenic carcinoma in the U.S. (Garfinkel, 1991).

Despite attempts to advance early diagnosis and employ combination therapies, the clinical response of this tumor yields an overall five-year survival rate for lung cancer patients of less than 15% (Faber, 1991). A projection of lung cancer mortality through the end of the 20th century predicts that even with a reduction in smoking incidence, lung cancer in this decade will continue to increase at a rate of 53.2 deaths per year per 100,000 population (Faber, 1991). Clearly, new strategies for therapy are necessary.

The process of tumor growth and metastasis is complex and requires the highly orchestrated interactions of transformed neoplastic cells, tissue resident cells (i.e., fibroblasts, macrophages, and endothelial cells) and recruited cells (i.e., platelets, neutrophils, monocytes, and lymphocytes) from the circulation. One of the potential mechanisms which allow for the maintenance of tumor growth is a dysregulation of the balance of growth stimulatory and inhibitory factors. This dysregulation allows for the perpetuation of tumor growth and eventual metastasis.

While carcinogenesis is a complex process that involves multiple stages of initiation, promotion, and neoplastic transformation, the actual growth of the tumor beyond the size of 1 to 2 mm in diameter and dissemination is dependent upon angiogenesis. Based on a growing body of evidence, it is clear that a multitude of cytokines regulate angiogenesis and tumor growth. However, these cytokines may not express this full potential as individual polypeptides, but collectively in a "cytokine network".

Recently, interleukin-8 (IL-8), a member of the CXC chemokine family, has been found to be mediate angiogenesis. In contrast, platelet factor 4 (PF4), another member of the CXC chemokine family, has been shown to have angiostatic properties. In analyzing IL-8 and PF4, the inventors' reasoned that it is the presence of the N-terminal ELR (Glu-Leu-Arg) motif, which precedes the first cysteine amino acid residue of IL-8, that renders the chemokine angiogenic. Although the ELR motif has been described as important in neutrophil receptor binding, it has not been previously suggested to be linked to angiogenesis.

The inventors propose that angiogenesis associated with wound healing and tumor growth is dependent upon members of the CXC chemokine family acting as either angiogenic or angiostatic factors. This paradigm predicts that the biological balance in the expression of these CXC chemokines dictates whether the neoplasm grows and develops metastatic potential or remains dormant and regresses. The inventors' novel discoveries are outlined in the following sections.

Tumorigenesis is an Example of Exaggerated Wound Repair

In order for tumor growth, such as non-small cell lung cancer (NSCLC), to succeed within the host, a complex interplay must occur between transformed neoplastic cells and non-transformed resident and recruited immune and non-immune cells (i.e., fibroblasts, endothelial cells, and subpopulations of leukocytes) (Whalen, 1990). While carcinogenesis or neoplastic transformation is dependent upon multiple genetic and epigenetic events (Shields and Harris, 1993), the salient feature of all solid tumor growth is the presence of neovascularization (Folkman and Cotran, 1976; Folkman, 1985). In the absence of local capillary proliferation and delivery of oxygen and nutrients, neoplasms cannot grow beyond the size of 1–2 mm in diameter (Folkman and Cotran, 1976; Folkman, 1985; Bouck, 1990).

Folkman first proposed in 1972 that tumors are angiogenesis-dependent, with tumor growth correlating with a concomitant increase in vascular supply. In support of this contention is the finding that tumor cells contiguous with neovascularization have the highest [$^3$H]thymidine-labeling index, whereas, tumor cells further removed from capillaries have the lowest [$^3$H]thymidine-labeling index (Folkman, 1985). Certain tumors have been found to produce factors which are directly angiogenic, while others may depend upon neovascularization induced by products of resident cells or elicited leukocytes (Folkman, 1985; Atherton, 1977; Zetter, 1980).

These events are analogous to the formation of granulation tissue during the evolution of wound repair. Interestingly, tumor growth and metastasis may be perceived as a form of exaggerated wound repair, requiring the continued matrix support of granulation tissue (Whalen, 1990). In order to appreciate the complexity of this event, one must appreciate the sequence of events that are involved in normal wound repair.

Normal wound repair is responsible for the rapid restoration of tissue integrity and function following a variety of insults, including trauma, burns, and infection. While healing is a complex interplay between humoral, cellular, and extracellular matrix networks, this process occurs in a sequential, yet overlapping manner. Following injury, the reparative process immediately begins with hemorrhage and extravasation of plasma into the wound. This results in activation of the intrinsic and extrinsic coagulation pathways, leading to fibrin deposition, and establishment of a provisional matrix (Clark et al., 1982).

Platelet activation and degranulation also occur during coagulation, leading to the deposition of a number of cytokines into the provisional matrix. These cytokines include: TGFα, TGFβ, PDGF, PF4, platelet-derived endothelial cell growth factor, and NAP-2, a proteolytic cleavage product of platelet basic protein (Davidson, 1992; Walz and Baggiolini, 1993). These cytokines are either important growth factors or chemotaxis for the elicitation of leukocytes, endothelial cells, fibroblasts, and keratinocytes (Davidson, 1992). Thus, coagulation and platelet activation provide the initial foundation for subsequent cellular recruitment.

The elicitation of leukocytes into a wound is dependent upon a dynamic and complex series of events. The steps which lead to leukocyte recruitment include: endothelial cell activation and expression of endothelial cell-derived adhesion molecules, leukocyte activation and expression of leukocyte-derived adhesion molecules, leukocyte-endothelial cell adhesion, leukocyte diapedesis, and leukocyte migration beyond the vascular barrier via established chemotactic gradients (Strieter et al., 1993). While adhesion interactions between leukocytes (L-selectin, $\beta_1$, and $\beta_2$ integrin adhesion molecules) and endothelial cells (P-selectin, E-selectin, ICAM-1, and VCAM-1 adhesion molecules) are a prerequisite event for successful leukocyte extravasation at sites of inflammation, the subsequent steps leading to diapedesis and migration beyond the vascular compartment are dependent upon both the continued expression of $b_1$ and $b_2$ integrins and the movement along a leukocyte-specific chemokine gradient (Strieter et al., 1993).

Neutrophils are usually the first leukocytes to arrive at the wound, with their primary function being to phagocytize debris. However, these leukocytes have the capacity to produce a number of cytokines that are instrumental in orchestrating the progression of wound repair. These cytokines include, but are not limited to: IFN-α, M-CSF, G-CSF, TNF, IL-1, IL-1α, IL-6, IL-8, MIP-1α, and TGF-β (Wertheim et al., 1993; Grotendorst et al., 1989; Kasama et al., 1993). While neutrophils are important in initial host defense in the wound, the second wave of leukocytes consists of mononuclear cells, with the mononuclear phagocyte representing a pivotal leukocyte in the progression of wound repair. The mononuclear phagocyte has the ability to generate a number of inflammatory mediators that are important in transforming the provisional matrix to more mature granulation tissue (Davidson, 1992; Grotendorst et al., 1989; Sibille and Reynolds, 1990).

The transition of wound repair from acute inflammation to granulation tissue is an essential event, as the granulation tissue consists of appropriate extracellular matrix constituents, fibroblasts, endothelial cells, leukocytes, and mediators that form either the connective tissue foundation or stimulus for neovascularization. The process of angiogenesis is paramount, as this process sustains a continual supply of oxygen and nutrients to the cellular constituents of the wound, and provides a substructure for the eventual re-epithelialization of the wound surface. During the early phases of granulation tissue formation, the immature connective tissue resembles undifferentiated mesenchyme with the presence of persistent fibrin, an embryonic form of fibronectin, a predominance of collagen type III, as compared to collagen type I, and a highly vascularized capillary bed (French-Constant et al., 1989; Kurkinen et al., 1980; Epstein, 1974).

This phase is followed by transformation to mature granulation tissue that is associated with increased deposition of collagen type I, fibronectin, and protease-dependent remodeling of the extracellular matrix (Donoff et al., 1971). This granulation tissue provides the foundation for the initiation of re-epithelialization of the wound surface. As basal keratinocytes migrate from the wound edge over the surface of the mature granulation tissue, keratinocytes at the wound margin begin to proliferate. This response is followed by epidermal regeneration and production of basement membrane extracellular constituents (fibronectin, type IV and VII collagen, heparin sulfate proteoglycans, and laminin) that provides the integrity of the epidermal to dermal structures (Davidson, 1992).

While the sequential, yet overlapping interplay of coagulation, inflammation, formation of granulation tissue, and re-epithelialization is necessary for restoration of tissue function under normal conditions of wound repair, certain of these events appear to be exaggerated and essential to the survival of transformed neoplastic cells.

Angiogenesis is Vital in Wound-Healing and Tumorigenesis

Angiogenesis, the growth of new capillary blood vessels, is one of the most pervasive and essential biological events encountered in the mammalian organism (Folkman and Cotran, 1976; Auerbach, 1981; Polverini, 1989; Folkman and Klagsbrun, 1987). A number of physiological and pathological processes, such as embryonic development, the formation of inflammatory granulation tissue during wound healing, and the growth of malignant solid tumors, are strictly dependent upon the recruitment of new capillaries.

Normally in the adult mammalian organism, physiological angiogenesis occurs infrequently, yet can be rapidly induced in response to a number of diverse physiologic stimuli. Among the most extensively studied of these angiogenesis-dependent physiological processes is normal wound repair (Leibovich and Weisman, 1988). An important feature of wound-associated angiogenesis is that it is locally transient and tightly controlled. The rate of capillary endothelial cell turn over in adult organisms is typically measured in months or years (Engerman et al., 1967; Tannock and Hayashi, 1972). However, when normally quiescent endothelial cells lining venules are stimulated, they will degrade their basement membrane and proximal extracellular matrix, migrate directionally, divide, and organize into new functioning capillaries invested by a new basal lamina all within a matter of days. This dramatic amplification of the microvasculature is nevertheless temporary, for as rapidly as they are formed they virtually disappear with similar swiftness, returning the tissue vasculature to homeostasis.

This demonstrates two key aspects of the angiogenic response: first, the formation of new capillary blood vessels is rapid and controlled; and second, it is transient, and characterized by regression to a physiologic steady-state level. The abrupt termination of angiogenesis that accompanies the resolution of the wound response suggests two possible mechanisms of control, neither of which are mutually exclusive. First, under circumstances not well understood, there is probably a marked reduction in the synthesis and/or elaboration of angiogenic mediators. Second, a simultaneous increase occurs in the level of substances which inhibit new vessel growth (Bouck, 1990).

While angiogenesis under conditions of normal wound repair appears to be under strict control and is self-limited, during neoplastic transformation, neovascularization is exaggerated. It appears that tumors are continually renewing and altering their vascular supply (Folkman, 1985). Interestingly, normal vascular mass is approximately 20% of the total tissue mass, whereas, during tumorigenesis, tumor vascular mass may be as great as 50% of the total tumor (Folkman, 1985). These findings are consistent with the observations that neovascularization is both a marker of preneoplastic lesions as well as an event that perpetuates tumor growth (Folkman, 1985; Folkman et al., 1989; Maiorana and Gullino, 1978).

This is further exemplified by the fact that the magnitude of tumor-derived angiogenesis has been shown to correlate with metastasis of melanoma, prostate cancer, breast cancer, and NSCLC (Herlyn et al., 1987; Weidner et al., 1991; Weidner et al., 1993; Macchiarini et al., 1992). In addition, these studies would support the notion that tumor-associated angiogenesis is dysregulated, with a biological imbalance that favors either the over-exuberant production of local angiogenic factors or the suppression of endogenous angiostatic factors (Folkman, 1985; Folkman et al., 1989; Eisenstein et al., 1975).

Although most investigations studying angiogenesis have focused on the identification and mechanism of action of angiogenic factors, recent evidence suggests that angiostatic factors may play an equally important role in the control of neovascularization (Bouck, 1990; Eisenstein et al., 1975; Sorgente et al., 1975; Brem and Folkman, 1975; Lee and Langer, 1983; Langer et al., 1980; Brem et al. 1977; Lutty et al., 1983; Madri et al., 1988; Ingber et al., 1986).

Angiogenesis is Regulated by Angiogenic and Angiostatic Factors

A role for inhibitors in the control of angiogenesis was first suggested by the work of Eisenstein and colleagues (Eisenstein et al., 1975), and Sorgenti and associates (Sorgente et al., 1975), where they observed that hyaline cartilage was particularly resistant to vascular invasion. They reported that a heat labile guanidium chloride extract prepared from cartilage contained an inhibitor of neovascularization. Later Brem and Folkman (1975) and their co-workers Lee and Langer (1983) showed that a similar or identical extract from rodent neonatal and shark cartilage was able to effectively block neovascularization and growth of tumors in vivo.

Similar inhibitors of angiogenesis have been reported from other cell and tissue extracts (Brem and Folkman, 1975; Lee and Langer, 1983; Langer et al., 1980; Brem et al., 1977; Lutty et al., 1983), and for a variety of natural and artificial agents including: inhibitors of basement membrane biosynthesis (Madri et al., 1988; Ingber et al., 1986; Ingber and Folkman, 1988; Maragoudakis et al., 1988); placental RNase inhibitor (Shapiro and Vallee, 1987); lymphotoxin (Sato et al., 1987); interferons (Sidky and Borden, 1987); prostaglandin synthetase inhibitors (Peterson, 1986); heparin-binding fragments of fibronectin (Homandberg et al., 1986); protamine (Taylor and Folkman, 1982); angiostatic steroids (Crum et al., 1985); several anti-neoplastic and anti-inflammatory agents (Polverini and Novak, 1986; Lee et al., 1987); PF4 (Maione et al., 1990); thrombospondin-1 (Good et. al., 1990); angiostatin (O'Reilly et. al., 1994); and antagonists to $\alpha_v\beta_3$ integrins (Brooks et. al., 1994).

Many of these compounds have several biological activities. For example, PF4 blocks immunosuppression and inhibits bone resorption. Although most inhibitors can act directly on the endothelial cell to block migration and/or mitogenesis in vitro, their effects in vivo may be considerably more complex, involving additional cells and their products.

Angiogenic and Angiostatic Factors in Chronic Inflammatory Disease and Aberrant Wound Healing Several lines of evidence suggest that a biological imbalance in the production of angiogenic and angiostatic factors contributes to the pathogenesis of several angiogenesis-dependent disorders. For example, in rheumatoid arthritis the unrestrained proliferation of fibroblasts and neovascularization leads to the formation of prolonged and persistent granulation tissue whose degradative enzymes contribute to profound destruction of joint spaces (Harris, 1976).

Koch et al. (1986; 1992a) have shown that a subpopulation of macrophages isolated from rheumatoid synovium produce factors that are potentially angiogenic in vivo and chemotactic for capillary endothelial cells in vitro. The inability of macrophages to express appropriate angiogenic activity may also contribute to the pathogenesis of other diseases that are associated with defective angiogenesis. Blood monocyte-derived macrophages from patients with scleroderma fail to stimulate the expected angiogenic activity when exposed to the agonist, lipopolysaccharide (LPS) (Koch et al., 1992b), suggesting that a defect in macrophage responsiveness to activating signals may contribute to the attenuated neovascularization that is encountered in scleroderma.

Psoriasis, a common genetic skin disease, is a well known angiogenesis-dependent disorder that is characterized by marked dermal neovascularization. The inventors have recently reported that keratinocytes derived from psoriatic plaques are potentially angiogenic compared to normal keratinocytes. Interestingly, this aberrant phenotype is due, in part, to a combined defect in the overproduction of the angiogenic cytokine, IL-8, and a deficiency in the production of the angiogenesis inhibitor thrombospondin-1. The net result is a proangiogenic environment (Rastinejad et al., 1989; Good et al., 1990; Tolsma et al., 1993; DiPeitro and Polverini, 1993).

It is now well established that angiogenesis is a tightly regulated process that is under complex positive and negative control. It is also apparent that a feature common to most chronic inflammatory disorders and tumorigenesis is the presence of over-exuberant angiogenesis. In rheumatoid arthritis, psoriasis, or tumorigenesis, neovascularization may be aberrantly up-regulated. Although the complement of angiogenic and angiostatic regulators of neovascularization may vary among different physiologic and pathologic settings, the recognition of this dual mechanism of biological control is necessary to gain a more thorough understanding of this complex process and its significance in promoting tumor growth.

Re-Epithelialization in Normal Wound Healing

The process of re-epithelialization following a wound is necessary to re-establish the integrity of the integument as a protective barrier to the environment. During wound repair, one of the most critical components of re-epithelialization is keratinocyte migration and proliferation (Woodley et al., 1986).

Basal keratinocytes first migrate from the margin toward the center of the wound, followed by hyperplasia of the keratinocytes in the epidermis juxtaposition to the wound. While the re-epithelialization process is complex as a result of a coordinated interaction of several factors required to stimulate both chemotaxis and proliferation, the termination of re-epithelialization may be equally regulated and dependent upon inhibitory signals that prevent persistent keratinocyte migration and proliferation. The keratinocyte is now recognized as an important participant in mediating wound repair with the capability to respond to and release a number of cytokines that are involved in both growth and inflammatory/immunologically mediated events (McKay and Leigh, 1991; Nickoloff, 1991; Nickoloff and Turka, 1993; Ansel et al., 1993).

Historically, three of the most important growth factors that stimulate keratinocyte migration and proliferation in vitro are EGF, IGF-1, and TGFα (Barrondon and Gree, 1987; Greaves, 1980; Brown et al., 1986; Nickoloff et al., 1988). Interestingly, the ability of these growth factors to promote keratinocyte growth is correlated to their capacity to stimulate extracellular matrix production (Nickoloff et al., 1988). These results suggest that the biological activities of various cytokines may be mediated, in part, through their ability to modulate the endogenous production of extracellular matrix molecules by keratinocytes.

In contrast to growth promoting activities, a number of cytokines display inhibitory activity for keratinocyte motility and proliferation. These include TGFβ, IFNγ, IFNα, IFNβ, and TNFα and β (McKay and Leigh, 1991; Symington, 1989; Yaar et al., 1985; Nickoloff et al., 1991; Shipley et al., 1986; Nickoloff and Mitra, 1989). Their effects on keratinocyte biology are both direct and indirect, including influences on extracellular matrix production and cell surface receptors for growth promoting cytokines, such as EGF (McKay and Leigh, 1991; Symington, 1989; Yaar et al., 1985; Nickoloff et al., 1991; Shipley et al., 1986; Nickoloff and Mitra, 1989). Thus, in the context of wound repair, re-epithelialization and the return of integument integrity is dependent upon an orchestrated network of promoters and inhibitors of keratinocyte biology.

CXC Chemokines Mediate Inflammation and Reparative Processes

As described above, the fidelity of wound repair is dependent upon the ability of cells to communicate with one another. While cellular communication is often accomplished through direct cell-to-cell contact via specific cellular adhesion molecules, cells may signal one another through soluble mediators, such as cytokines. These polypeptide molecules often have pleiotropic effects on a number of biological functions including proliferation, differentiation, recognition, and cellular recruitment. Their actions are mediated through paracrine and autocrine signaling. However, under certain conditions, these molecules may behave as hormones.

Recently, a new family of cytokines have been identified that appear to have proinflammatory and reparative activities (Baggiolini et al., 1989; 1992; Matsushima and Oppenheim, 1989; Oppenheim et al., 1991; Miller and Krangel, 1992). These cytokines in their monomeric forms are all less than 10 kD and are characteristically basic heparin-binding proteins. This family displays four highly conserved cysteine amino acid residues, with the first two cysteines separated by one non-conserved amino acid residue. In general, these cytokines appear to have specific chemotactic activity for neutrophils. Because of their chemotactic properties and the presence of the CXC cysteine motif, these cytokines have been designated the CXC chemokine family.

Interestingly, these chemokines are all clustered on human chromosome 4, and exhibit between 20% to 50% homology on the amino acid level (Baggiolini et al., 1989; 1992; Matsushima and Oppenheim, 1989; Oppenheim et al., 1991; Miller and Krangel, 1992). Over the last decade, 12 different CXC chemokines have been identified and include platelet factor-4 (PF4), $NH_2$-terminal truncated forms of platelet basic protein [PBP; connective tissue activating protein-III (CTAP-III), beta-thromboglobulin (βTG), and neutrophil activating protein-2 (NAP-2)], interleukin-8 (IL-8), growth-related oncogene (GROα, GROβ, GROγ), γ-interferon-inducible protein (IP-10), monokine induced by gamma-interferon (MIG), epithelial neutrophil activating protein-78 (ENA-78), and granulocyte chemotactic protein-2 (GCP-2) (Baggiolini et al., 1989; 1992; Matsushima and Oppenheim, 1989; Oppenheim et al., 1991; Miller and Krangel, 1992; Farber, 1993; Proost et al., 1993a; 1993b; Walz et al., 1991).

PF4, the first member of the CXC chemokine family to be described, was originally identified for its ability to bind to heparin, leading to inactivation of heparin's anticoagulation function (Deutsch and Kain, 1961). Both IP-10 and MIG are interferon-inducible CXC chemokines (Farber, 1993; Kaplan et al., 1987). Although IP-10 appears to be induced by all three interferons (IFNα, IFNβ, and IFNγ), MIG is unique in that it appears to be only expressed in the presence of IFNγ (Farber, 1993). While IFNγ induces the production of IP-10 and MIG, this cytokine has been found to attenuate the expression of both IL-8 and ENA-78 (Gusella et al., 1993 and observations). These findings would suggest that members of the CXC chemokine family demonstrate disparate regulation in the presence of IFNγ.

GROα, GROβ and GROγ are closely related CXC chemokines, with GROα originally described for its melanoma growth stimulatory activity (Anisowicz et al., 1988; Anisowicz et al., 1987; Richmond and Thomas, 1988). IL-8, ENA-78, and GCP-2 were all initially identified on the basis of their ability to induce neutrophil activation and chemotaxis (Baggiolini et al., 1989; 1992; Matsushima and Oppenheim, 1989; Oppenheim et al., 1991; Miller and Krangel, 1992; Farber, 1993; Proost et al., 1993a; Walz et al., 1991).

IL-8 has been the most studied CXC chemokine family member and has been found to be produced by an array of cells including monocytes, alveolar macrophages, neutrophils, keratinocytes, mesangial cells, epithelial cells, hepatocytes, fibroblasts, and endothelial cells (Baggiolini et al., 1989; 1992; Matsushima and Oppenheim, 1989; Oppenheim et al., 1991; Miller and Krangel, 1992; Yoshimura et al., 1987b; Matsushima et al., 1988; Strieter et al., 1988; 1989a; 1989b; Thornton et al., 1990; Elner et al., 1990; Strieter et al., 1990a; Standiford et al., 1990; Strieter et al., 1990b; Brown et al., 1991; Rolfe et al., 1991; Nickoloff et al., 1991; Strieter et al., 1992c). Interestingly, IL-8 is expressed in neoplasms and produced by a number of transformed neoplastic cells (Thornton et al., 1990; Standiford et al., 1990; Hotta et al., 1990; VanMeir et al., 1992; Abruzzo et al., 1992). While numerous investigations have shown both in vivo and in vitro the importance of IL-8 in acute inflammation, as a chemotactic/activating factor for neutrophils, only recently has it become apparent that this CXC chemokine may be important in wound repair and tumorigenesis.

The Role of CXC Chemokines in Angiogenesis

The inventors and others have found that IL-8 is a potent angiogenic factor (Koch et al., 1992a; Strieter et al., 1992a; Hu et al., 1993). Recombinant IL-8 mediates both endothelial cell chemotactic and proliferative activity in vitro and angiogenic activity in vivo (corneal micropocket model in both rats and rabbits). The inventors found that endothelial cell chemotaxis in response to recombinant IL-8 at a concentration of 1.25 nM was comparable to chemotaxis toward recombinant bFGF at a concentration of 6 nM (Koch et al., 1992a). Similar concentrations were found to induce angiogenesis in the corneal micropocket model.

Since monocytes/macrophages may represent a major source of angiogenic activity in wounds, chronic diseases, and solid tumors (Polverini, 1989), the inventors extended their studies to determine whether IL-8 was a predominant angiogenic factor liberated by normal human monocytes activated in vitro or by synovial macrophages isolated from rheumatoid arthritis synovial tissues (Koch et al., 1992a). Conditioned media from both populations of mononuclear phagocytes induced significant chemotactic activity for endothelial cells. Furthermore, when these supernatants were exposed to neutralizing antibodies to IL-8, endothelial cell chemotaxis was markedly reduced (Koch et al., 1992a). Similar neutralization was seen utilizing the same conditioned media, in the corneal micropocket model of angiogenesis.

To further demonstrate that the angiogenic effect was attributable to IL-8, the inventors used an IL-8 anti-sense oligonucleotide strategy to inhibit the production of IL-8 at the pretranslational level (Koch et al., 1992a). Monocytes were stimulated with endotoxin in the presence of either an IL-8 anti-sense or sense oligonucleotides in concentrations greater than 5 μM. The conditioned media from monocytes treated in the presence of IL-8 anti-sense inhibited endothelial chemotactic activity by 84%, as compared to the IL-8 sense oligonucleotide treated monocytes.

Similar results were found in the in vivo corneal micropocket model of angiogenesis. These findings indicated that IL-8, at concentrations of approximately 10 ng can function as a mediator of angiogenesis. The amount of IL-8 compares with amounts reported for the induction of corneal angiogenic activity by TNFα, aFGF, bFGF, angiogenin, angiotropin, and endothelial cell growth factor (Koch et al., 1992a).

Interestingly, another member of the CXC chemokine family, PF4, has been shown to have angiostatic properties (Maione et al., 1990). In addition, PF4 in vivo, via its angiostatic properties, could be found to attenuate the growth of murine melanoma and human colon cancer (Sharpe et al., 1990). These investigators had initially hypothesized that the angiostatic activity of PF4 was secondary to its heparin binding domain (within the COOH-terminus of the molecule) (Maione et al., 1990; Sharpe et al., 1990), however, they recently produced a PF4 analogue that lacked the heparin-binding domain and functional heparin binding, and found that the PF4 analogue was equipotent in vivo to native PF4 for the attenuation of tumor growth (Maione et al., 1991).

The above findings would suggest that members of the CXC chemokine family could be unique in their ability to function as either angiogenic or angiostatic factors in neovascularization, and the biological balance in the magnitude of expression of these angiogenic and angiostatic CXC chemokines within a tumor may dictate the overall tumor angiogenic activity.

Although it remains unclear that the COOH-terminus of these molecules dictates their biological role in angiogenesis, the differences in CXC chemokine function could be explained by another structural domain. Recently, both Hébert and associates (1991) as well as Clark-Lewis and colleagues (1993) have demonstrated a salient amino acid sequence in the primary structure of the CXC chemokine family that appears, in part, to account for the ability of these chemokines to function in neutrophil chemotaxis and activation.

It was demonstrated that the three amino acid residues that immediately preceded the first cysteine amino acid are important in binding and activation of neutrophils. These amino acids are Glu-Leu-Arg, the ELR motif. The ELR motif is absent in certain members of the CXC chemokine family (PF4, IP-10, and MIG) that display reduced potency in mediating neutrophil chemotaxis. Interestingly, when the ELR motif was introduced into PF4, this chemokine gained 1000-fold potency in mediating neutrophil chemotaxis (Clark-Lewis et al., 1993).

The present inventors reasoned that the structural differences in the ELR motifs may explain the disparity of angiogenic activity of the CXC chemokine family. This would support the hypothesis that a biological imbalance in the expression of angiogenic and angiostatic CXC chemokines is important to the perpetuation of neovascularization during tumor growth and metastasis.

The Role of CXC Chemokines in Re-epithelialization

While IL-8 has been demonstrated to have significant angiogenic activity, other investigators have demonstrated that IL-8 is an important cytokine in influencing keratinocyte biology. Psoriasis is a chronic disorder of the skin with evidence of accentuated angiogenic activity and hyperplasia of keratinocytes (Nickoloff, 1991). This skin disease is associated with primarily a mononuclear cellular infiltration, and has been demonstrated to contain significant levels of IL-8 expressed within basal keratinocytes (Nickoloff et al., 1991; Sticherling et al., 1991; Anttila et al., 1992). In addition, these studies have demonstrated immunoreactivity of IL-8 in normal skin that is predominantly located in the suprabasal keratinocytes (Sticherling et al., 1991; Anttila et al., 1992). The absence of immunolocalization of IL-8 within Langerhans cells, endothelial cells, or mast cells of psoriatic lesions was especially intriguing (Nickoloff et al., 1991).

Recently, several studies have provided additional insight into the potential function of IL-8 in the epidermis, other than its ability to induce neutrophil chemotaxis and angiogenesis. Michel and associates (Michel et al., 1992), demonstrated that IL-8 was extremely potent, in a dose-dependent fashion, for the induction of keratinocyte chemotaxis and proliferation. This effect was directly attributable to the presence of specific IL-8 receptors on keratinocytes.

The keratinocyte binding studies showed that IL-8 ligand/receptor interaction was specific for the dimeric form of IL-8, and in concentrations compatible with optimal neutrophil chemotactic and angiogenic activity (Koch et al., 1992b; Baggiolini et al., 1989; 1992; Matsushima and Oppenheim, 1989; Oppenheim et al., 1991; Miller and Krangel, 1992; Strieter et al., 1992a; Hu et al., 1992). In addition, this group has recently demonstrated elevated expression of IL-8 receptors in psoriatic lesions, as compared to normal skin (Schulz et al., 1993).

Although IL-8 may have a direct effect on inducing keratinocyte chemotaxis and proliferation, recent work by Valyi-Nagy and colleagues (Valyi-Nagy et al., 1992) demonstrated that IL-8 stimulation could induce keratinocyte production of TGFα without changing the expression of TGFα receptors. These findings suggest that IL-8 directly and indirectly, via the production of TGFα, may influence keratinocyte biology. The above findings support the inventors' concept that IL-8 and other members of the CXC chemokine family are important promoters or inhibitors of angiogenesis and re-epithelialization during wound repair.

Chronic Venous Stasis Leg Ulcers

Chronic venous stasis leg ulcers represent a non-healing wound secondary to failure of adequate angiogenesis and re-epithelialization. Such ulcers are a significant chronic disabling medical condition. The prevalence of this disorder is approximately 0.5% to 1% of the general population (Goldman et al., 1992; Baker et al., 1991; Coon et al., 1973; Callam et al., 1985; Burnand, 1990).

Although chronic venous stasis ulcers can occur in young adults, the peak occurrence of this disorder is in the sixth to seventh decade of life (Goldman et al., 1992; Baker et al., 1991; Coon et al., 1973; Callam et al., 1985; Burnand, 1990). In individuals less than the age of 40, equivalent sexual predisposition is seen in this disorder. However, over the age of 40 the ratio of chronic venous stasis ulcers increases to 3:1 for females to males (Goldman et al., 1992; Baker et al., 1991; Coon et al., 1973; Callam et al., 1985; Burnand, 1990). The vast majority of these patients have documented venous disease usually as a result of previous deep venous thrombosis leading to chronic ambulatory venous insufficiency and hypertension (Goldman et al., 1992; Baker et al., 1991; Coon et al., 1973; Callam et al., 1985; Burnand, 1990).

The elevated venous pressure contributes to the formation of brawny edema of the lower extremities and eventually ulceration. These leg ulcerations are characterized by the persistent loss of overlying integument and subcutaneous tissue due to alterations in the local microcirculation that are characterized by ischemia and chronic inflammation. These changes include: a reduction in neovascularization, thickened basement membrane, disruption of normal pericyte-capillary relationship, increased vascular permeability with lymphatic microangiopathy, deposition of pericapillary fibrin, increased leukocyte adhesion to endothelium and activation. These findings contribute to persistent microvascular injury and tissue ischemia (Goldman et al., 1992; Baker et al., 1991; Coon et al., 1973; Callam et al., 1985; Burnand, 1990; Wenner et al., 1980; Mourad et al., 1989; Vanscheidt et al., 1991; Browse and Burnand, 1982; Vanscheidt et al., 1990).

Recently, Herrick and associates (Herrick et al., 1992) performed sequential biopsies from the margins of venous leg ulcers during healing. These investigators demonstrated that initial biopsies at baseline showed prominent pericapillary "fibrin cuffs", variable inflammation, hemosiderin deposition, and local hemorrhage. Interestingly, the fibrin cuffs were composed of several components of basement membrane (laminin, fibronectin, tenascin, and collagen), trapped leukocytes, and fibrin.

After 2 weeks of occlusive pressure dressings, an increase in the presence of acute inflammation and granulation tissue with augmented deposition of fibronectin was noted (Herrick et al., 1992). By the fourth week of occlusive pressure dressings, the majority of wounds demonstrated complete re-epithelialization with a reduction of fibrin cuffs (Herrick et al., 1992). Thus the pathophysiologic alterations of the local venous stasis ulcer microcirculation and persistence of several components of the coagulation phase of wound repair appear to contribute to the perpetuation of the chronic ulcer state. This results in the failure to heal the surrounding tissue. These findings would support the notion that the mechanisms involved in normal wound repair (angiogenesis and re-epithelialization) are either absent or inhibited in the context of persistent chronic venous leg ulcers.

The Role of CXC Chemokines in Wound Repair

The inventors have developed a new model to explain the role of CXC chemokines during primary intention, secondary intention, and chronic wound repair. The inventors propose that the sequential morphological phases of wound repair are mediated by the balance in expression of promoter (chemokines containing the ELR motif) and inhibitor (chemokines that lack the ELR motif) CXC chemokines of angiogenesis and re-epithelialization.

The acute wound is associated with a rapid coagulation event with the generation of a predominant fibrin provisional matrix and the release of platelet-derived cytokines. Initially, the balance of the magnitude of CXC chemokines will favor inhibitors of angiogenesis (PF4), as the platelet is the first "cellular" response in the wound. However, as the transition of the wound evolves toward the cellular phase of inflammation, the balance shifts in favor of CXC chemokines that are involved in neutrophil elicitation (ENA-78 and IL-8). This stage of wound repair is essential since it provides a mechanism for wound debridement via leukocyte activation and phagocytosis.

The hallmark of the transition to the formation of granulation tissue is the exuberant angiogenic activity found within the provisional matrix. This phase of wound repair will demonstrate the continued presence of CXC chemokines that promote angiogenesis and re-epithelialization (ENA-78 and IL-8), whereas inhibitors (IP-10 and PF4) of angiogenesis and re-epithelialization will be present in order to regulate and control this event. As granulation tissue matures and re-epithelialization is well underway, CXC chemokine (ENA-78 and IL-8) promoters of re-epithelialization will continue to be significantly present during this phase of wound repair. However, in order to avoid hyperplastic re-epithelialization, as seen in psoriasis, the CXC chemokine inhibitor (IP-10) of keratinocyte migration and proliferation will balance the effects of IL-8 and ENA-78, and allow the epidermis to return to state of homeostasis.

In contrast to the normal evolution of wound repair, chronic venous stasis ulcer wounds appear to have been "locked" in the early coagulation phase of wound repair, with histopathologic evidence suggesting the persistence of fibrin and other components of coagulation, such as platelet degranulation products (PF4). In the chronic venous stasis ulcer, CXC chemokines that inhibit angiogenesis and re-epithelialization (PF4 and IP-10) will prevail over the expression of the promoters (IL-8 and ENA-78).

The Role of CXC Chemokines in Tumorigenesis

The inventors' new model is also directly applicable to tumorigenesis. The model is again based on the proposal that angiogenesis associated with tumor growth is dependent upon members of the CXC chemokine family acting as either angiogenic or angiostatic factors. This paradigm predicts that the balance in the expression of these CXC chemokines dictates whether the neoplasm grows, eventually developing metastatic potential, or regresses. The net angiogenic activity during the progression of tumorigenesis is mediated by the biological imbalance that favors the expression of angiogenic CXC chemokines (ELR-CXC), as compared to the angiostatic CXC chemokines (which may be termed XXX-CXC).

Both neoplastic cells, and non-transformed immune and non-immune cells, will be found to be significant cellular sources of both angiogenic and angiostatic CXC chemokines. However, the magnitude of expression and the biological imbalance will favor the production of angiogenic CXC chemokines (ELR-CXC). This effect results in tumor growth, invasion, and metastasis beyond the confines of its origin. The production of IL-10 by both neoplastic cells and surrounding non-transformed immune and non-immune cells will have a significant, yet indirect, impact on the generation of angiostatic (XXX-CXC) chemokines (IP-10 and MIG). These CXC chemokines are primarily induced by IFN-γ, which is known to be significantly attenuated in the presence of IL-10. Under these circumstances, IL-10 expression in the context of tumorigenesis can be viewed as an indirect promoter of angiogenesis.

The present discoveries may be utilized in conjunction with certain techniques that are well-known in the biological arts and that are further described in the following sections.

Production of CXC Chemokines

Synthetic CXC chemokines and chemokine analogues may be produced by using an automated solid-phase tert-butyloxycarbonyl and benzyl protection strategy (Clark-Lewis et al., 1993; Clark-Lewis et al., 1991). The purity of these chemokines should be assessed by reverse-phase HPLC and isoelectric focusing. The primary structures of the chemokines may be verified by Edman sequencing methods (Clark-Lewis et al., 1991). The correct covalent structure is assessable by ion-spray spectrometry (Clark-Lewis et al., 1993; Clark-Lewis et al., 1991).

The use of recombinant expression systems in the preparation of CXC chemokines is particularly contemplated. To express a recombinant CXC chemokine, whether mutant or wild-type, in accordance with the present invention one would prepare an expression vector that comprises a CXC chemokine-encoding nucleic acid under the control of one or more promoters. The "upstream" promoters stimulate transcription of the DNA and promote expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as $E.\ coli$ and $B.\ subtilis$ transformed with recombinant bacteriophage DNA, plasmid DNA or cosmid DNA expression vectors.

Certain examples of prokaryotic hosts are $E.\ coli$ strain RR1, $E.\ coli$ LE392, $E.\ coli$ B, $E.\ coli$ X 1776 (ATCC No. 31537) as well as $E.\ coli$ W3110 (F-, lambda-, prototrophic, ATCC No. 273325); bacilli such as $Bacillus\ subtilis$; and other enterobacteriaceae such as $Salmonella\ typhimurium$, $Serratia\ marcescens$, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, $E.\ coli$ is often transformed using pBR322, a plasmid derived from an $E.\ coli$ species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as $E.\ coli$ LE392. Further useful vectors include pIN vectors (Inouye et al., 1985); and pGEX vectors, for use in generating glutathione S-transferase (GST) soluble fusion proteins for later purification and separation or cleavage.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase, or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more CXC chemokine coding sequences.

In a useful insect system, *Autograph californica* nuclear polyhidrosis virus (AcNPV) is used as a vector to express foreign genes. The virus grows in *Spodoptera frugiperda* cells. The CXC chemokine coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein, particularly as differential cleavage and processing of various CXC chemokines is known to occur naturally.

Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for glycosylation and phosphorylation may be used if desired, with a cell that conducts proper CXC chemokine processing being preferred.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired CXC chemokine gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg1 I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CXC chemokines in infected hosts, as is described in more detail below.

Specific initiation signals may also be required for efficient translation of CXC chemokine coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., 1987).

For long-term, high-yield production of recombinant CXC chemokine proteins, stable expression is preferred. For example, cell lines that stably express constructs encoding CXC chemokines may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt- cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

Currently preferred methods for producing CXC chemokines by recombinant expression are described herein. For example, mutant IL-8 production (TVR-IL-8 and DLQ-IL-8) is described in Example XII and MIG production is described in Example XVI.

To produce recombinant CXC chemokines from additional or alternative sources may require the cloning of a given CXC chemokine, for example, GCP-2. This involves techniques routinely employed by those of skill in the art in which a DNA molecule encoding the CXC chemokine protein is obtained from a DNA library in a form separate from other portions of DNA in the library. Both cDNA and genomic DNA clones may be obtained.

The first step in such cloning procedures is the screening of an appropriate DNA library. The screening procedure may be an expression screening protocol employing antibodies directed against the CXC chemokine protein, or even based upon an activity assay. Alternatively, screening may be based on the hybridization of oligonucleotide probes, designed from a consideration of portions of the amino acid sequence of the protein, or from the DNA sequences of genes encoding related proteins.

As the amino acid sequences for several CXC chemokines are included herein, along with certain known DNA sequences, the operation of such screening protocols in order to clone other CXC chemokines will be straightforward to those of skill in the art, as described in Sambrook et al. (1989). Antibodies against the CXC chemokines are also available and can be further generated, as described herein.

Site-Specific Mutagenesis

Site-specific mutagenesis is a technique useful in the preparation of individual peptides, or biologically functional equivalent proteins or peptides, through specific mutagenesis of the underlying DNA. This technique is particularly useful in combination with the recombinant expression protocols, as described above, in the context of creating mutant CXC chemokines for use in the present invention. In site-specific mutagenesis, one or more nucleotide sequence changes are introduced into the DNA through the use of specific oligonucleotide sequences.

In the context of the present invention, mutations concerning the ELR motif are particularly relevant. The nucleotide codons that encode the amino acids Glu, Leu and Arg (E, L and R) are GAA and GAG; UUA, UUG, CUA, CUC, CUG and CUU; and AGA, AGG, CGA, CGC, CGG and CGU, respectively. A table of amino acids and their codons is presented herein (Table 1) for use in the design of CXC chemokine probes and primers. TVR, DLQ, KGR and any other mutant CXC chemokine may be easily prepared by those of skill in the art using the following information.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The nucleotide sequence changes are introduced into the DNA through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, the primers have about 5 to 10 residues on both sides of the junction of the sequence being altered to ensure correct hybridization.

In general, the technique of site-specific mutagenesis is well known in the art, as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

Site-directed mutagenesis is generally performed by first obtaining a single-stranded vector or melting apart the two strands of a double stranded vector which includes within its sequence a DNA sequence that encodes a CXC chemokine component. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected CXC chemokine cDNAs or genes using site-directed mutagenesis is provided as a means of producing potentially useful species and is not meant to be limiting as there are other ways in which sequence variants may be obtained. For example, recombinant vectors encoding a mutant CXC chemokine cDNA or gene may be prepared by cassetting;

and chemokine genes may even be treated with mutagenic agents to obtain sequence variants, as used in the mutagenesis of plasmid DNA using hydroxylamine.

Currently preferred methods for producing mutant CXC chemokines are described herein, for example, mutant IL-8 production (TVR-IL-8 and DLQ-IL-8) is described in Example XII and engineered ELR-MIG production is described in Example XVI.

Monoclonal Antibody Generation

Monoclonal antibodies that bind to a particular wild-type or mutant CXC chemokine, including recombinant chemokines, may be readily prepared. Means for generating and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition of a CXC chemokine and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a CXC chemokine peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the CXC chemokine immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected CXC chemokine immunogen composition, e.g., including purified or partially purified CXC chemokine proteins, polypeptides and peptides. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

A molecular cloning approach may also be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Human Skin/SCID Mouse Chimeric Model of Skin Transplantation

This model allows the wound-healing therapeutic strategies of the invention to be optimized prior to clinical use. The use of SCID mice as an immunologic sanctuary for full thickness human skin xenografts provides an excellent environment for the analysis of human skin biology. SCID mice maintain the presence of circulating platelets, neutrophils, monocytes, and natural killer cells. The use of primary and secondary intention wounds in SCID mice allows for both a rapid and prolonged analysis of the wound repair process.

To create human skin/SCID mice, the procedure of Yan et al. (1993) is used with human full-thickness skin (1.5 cm in diameter). Weights and ages of the animals range from 18 to 25 g and 4 to 6 weeks, respectively. Animals are studied after a period of 4 to 6 wks post-xenograft transplantation, as this period of time assures adequate engraftment.

The following protocol has been developed to assess the rapidly developing alterations which are likely to occur in wound repair. Primary intention wounds are created by a Surgicutt bleeding time device (International Technidyne Corp., Edison, N.J.). Secondary intention wounds are created by a 2 mm skin biopsy device (Baker's Biopsy Punch, Cummins Derm. Inc., Miami, Fla.). Animals are sacrificed in the following time-dependent manner: 1, 2, 3, 4, 6, 8, 10, 12, 16, 20, 24, 28, and 32 days post-wound. The wounds are considered healed with evidence by light microscopy of complete re-epithelialization. Six mice are used in each group and for each manipulation. This number is the minimum number of mice that has historically been found to result in statistical significance (Lukacs et al., 1993).

6 mm skin biopsies are taken (Baker's Biopsy Punch, Cummins Derm. Inc., Miami, Fla.) of the primary or secondary intention wounds, to control and standardize for the tissue volume. The skin biopsy is processed for CXC chemokine content and hydroxyproline content, reflecting total collagen formation.

Human NSCLC/SCID Mouse Chimeric Model of Tumorigenesis

This model allows the various therapeutic strategies of the invention to be optimized prior to clinical use. The model provides for an assessment of tumorigenesis, spontaneous metastasis and experimental lung colonization. The rationale for the use of NSCLC cell lines [Calu-6 (anaplastic), A549 (adenocarcinoma), Calu-1 (squamous cell carcinoma), and Calu-3 (adenocarcinoma)] is based on both their previous use in immunodeficient mice and their heterogeneous characteristics that include: tumorigenicity (Calu-6>A549>Calu-3>Calu-1); spontaneous lung metastasis (from a subcutaneous location; Calu-6>A549>Calu-1>Calu-3); experimental lung colonization (experimental metastasis; Calu-6>A549>Calu-1>Calu-3); secretion of matrix metalloproteinases and tissue inhibitors of metalloproteinases (Calu-6>A549>Calu-1>Calu-3); expression of integrin cell adhesion receptors; and expression of the suppressor gene, p53.

Either intact NSCLC tumors or cell lines may be used. Tumor growth is assessed by tumor size and mass, while spontaneous metastasis and lung colonization (experimental metastasis) is determined by histopathologic analysis of the lungs.

The human NSCLC/SCID mouse model particularly involves the use of SCID mice of between the ages of 4 to 6 weeks. SCID mice should only be used if their serum Ig is <1 µg/ml. Human NSCLC/SCID mice chimera receive 20 µl of anti-asialo GM1 (aASGM1; Wako Chemicals, Dallas Tex.) by tail vein 24 hrs prior to tumor implantation. This therapy removes host-derived NK cells.

Using intact human NSCLC, 1 mm$^3$ specimens (grossly devoid of necrosis and weighed) are placed subcutaneously into the bilateral flank regions of a cohort group of SCID mice. Using the NSCLC cell lines (Calu-6, A549, Calu-1, and Calu-3), semiconfluent grown tumor cells are harvested and a cohort group of SCID are given $10^6$ cells and $5 \times 10^5$ cells in 100 μl of PBS injected into bilateral flank regions and tail vein, respectively.

At least one group of SCID mice form the treatment group and are administered angiostatic CXC chemokines or antibodies against angiogenic CXC chemokines. All mice are monitored daily for both evidence of illness and measurement of tumor size by digital engineers calipers.

Animals are sacrificed on a weekly basis for 16 weeks or sooner if the tumor size reaches 3 cm or the animals appear ill. Animals that appear ill are sacrificed, necropsy performed, and excluded from the study if their illness is for reasons other than tumor burden. At time of sacrifice, tumors in the subcutaneous location are measured and weighed. The experimental lung tumor colonization or spontaneous lung metastasis is then determined.

The administration of angiostatic CXC chemokines or neutralizing antibodies to each of the angiogenic CXC chemokines will have a significant attenuating effect on tumor growth within SCID mice. However, if significant attenuation is not found with single angiostatic CXC chemokines or neutralizing antibodies against a single angiogenic CXC chemokine, then combinations of CXC chemokines or neutralizing antibodies will be employed.

Pharmaceutical Compositions and Kits

Pharmaceutical compositions of the present invention will generally comprise an effective amount of the CXC chemokine protein, gene or antibody composition dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral Formulations

The CXC chemokine protein, gene or antibody compositions for use in the invention will often be formulated for parenteral administration, e.g., formulated for injection via the intravenous, intramuscular, sub-cutaneous or other such routes, particularly including direct instillation into a tumor or disease site. The preparation of an aqueous composition that contains a CXC chemokine agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The CXC chemokines or antibodies can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the other required ingredients. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of the CXC chemokine composition admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 18th Ed. Mack Publishing Company, 1980, incorporated herein by reference. Moreover, for human administration, preparations should meet sterility, pyrogenicity, general safety and purity standards as required by FDA Office of Biological Standards.

The therapeutically effective doses are readily determinable using an animal model, as detailed herein. Experimental animals bearing solid tumors are frequently used to optimize appropriate therapeutic doses prior to translating to a clinical environment. Such models are known to be very reliable in predicting effective anti-cancer strategies. Mice bearing solid tumors are particularly widely used in pre-clinical testing. Some variation in dosage will necessarily occur depending on the condition of the subject being treated. The person responsible for administration will, in any event, determine the appropriate dose for the individual subject. Such optimization and adjustment is routinely carried out in the art and by no means reflects an undue amount of experimentation.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. For example, topical formulations that are appropriate for treating pathological conditions such as dermatitis and psoriasis, and particularly, ophthalmic formulations for the treatment of, e.g., diabetic retinopathy and various corneal diseases, disorders and injury.

Ingestible Formulations

Although not generally preferred for most embodiments, active CXC compounds may be administered orally for use in the treatment of peptic ulcers, i.e., gastric and duodenal ulcers. Oral delivery may also be used in other cases with agents that are generally resistant, or have been rendered resistant, to proteolysis by digestive enzymes. Such compounds are contemplated to include chemically designed or modified agents; dextrorotatory peptidyl agents; liposomal formulations; and formulations in time release capsules to avoid peptidase and lipase degradation.

For oral administration as may be used in ulcer treatment, the active CXC chemokine protein, genes or antibody compounds may be administered with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. The amount of active compounds in such therapeutically useful compositions is such that a suitable dosage unit will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparaben as preservatives, a dye and flavoring, such as cherry or orange flavor. Of course, any material used in preparing any dosage unit form should be pharmaceutically pure and substantially non-toxic in the amounts employed.

In addition, the active compounds may be incorporated into sustained-release preparation and formulations. The teachings of Remington's Pharmaceutical Sciences, 18th Ed. Mack Publishing Company, 1980, at pages 1633–1665, 1676–1693 and, particularly beginning at page 1682, are incorporated herein by reference for the purpose of even further describing appropriate available oral and sustained-release preparations.

Liposomal Formulations

CXC chemokine protein, genes or antibody compositions may also be formulated in liposomal preparations if desired. The preparation and use of liposomes is based on the fact that phospholipids form liposomes when dispersed in water, depending on the molar ratio of lipid to water. Several U.S. patents concern the preparation and use of liposomes that encapsulate biologically active materials, e.g., U.S. Pat. Nos. 4,485,054; 4,089,801; 4,234,871; and 4,016,100; each incorporated herein by reference.

The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for use with the present invention will contain cholesterol, or even PEG.

The ability to trap solutes varies between different types of liposomes. For example, multilamellar vesicles (MLVs) are moderately efficient at trapping solutes, but small unilamellar vesicles (SUVs) are inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior dictates that liposomes concentrate only in those organs and tissues accessible to their larger size.

As the liposomes are carried in the blood and the present invention is particularly concerned with angiogenic behavior, individual liposome sizes are not considered to be a problem. Mostly, it is contemplated that intravenous injection of liposomal preparations would be used, but other routes of administration are also conceivable. In certain embodiments, targeting components may even be admixed with a liposome surface to direct the contents to a specific receptor(s) located on a target cell surface, such as a neutrophil.

Liposomal-drug preparations are available that have enhanced retention on mucosal tissues and are suitable for ophthalmic use. For example, U.S. Pat. Nos. 4,818,537; 4,804,539; and 5,064,655 are incorporated herein by reference for the purpose of describing liposome-gel compositions suitable for use in the eye.

Topical Formulations

The formulation of CXC chemokine agents for topical use, such as in creams, ointments and gels is also contemplated. The preparation of oleaginous or water-soluble ointment bases is also well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate.

Various water-soluble ointment bases may also be used, including glycol ethers and derivatives, polyethylene glycols, polyoxyl 40 stearate and polysorbates. Even delivery through the skin may be employed if desired, e.g., by using transdermal patches, iontophoresis or electrotransport.

Ophthalmic Formulations

The anti-angiogenic CXC chemokines may also be formulated into pharmaceutical compositions suitable for use as ophthalmic solutions in the treatment of inappropriate angiogenesis in the eye. Ophthalmic preparations are prepared in accordance with conventional pharmaceutical practice, see for example "Remington's Pharmaceutical Sciences" 18th Edition, pages 1581–1595 (Mack Publishing Co., Easton, Pa.).

The ophthalmic preparation will contain a CXC chemokine protein or gene composition in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The use of ophthalmic-liposome preparations, as described above and in U.S. Pat. Nos. 4,818,537, 4,804,539, and 5,064,655, is also contemplated.

Wound Dressings

Figure 8A:
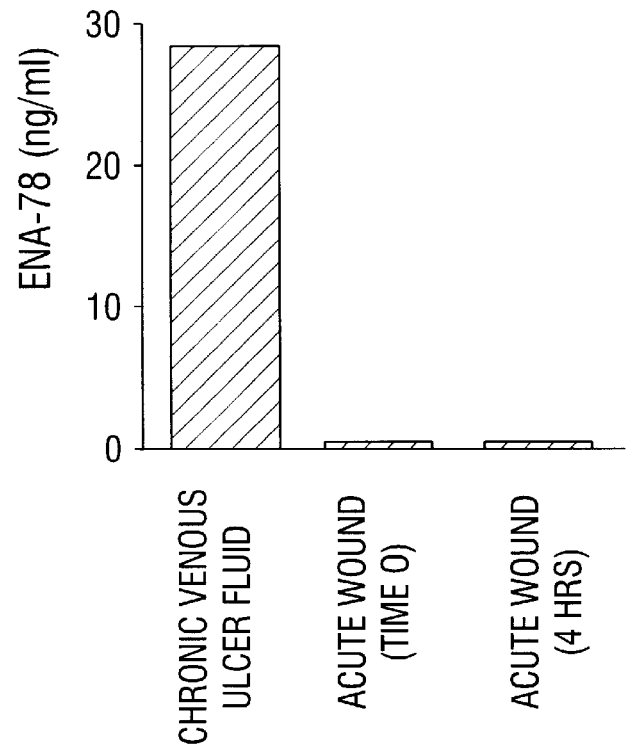
FIG. 8A, FIG. 8B and FIG. 8C. The presence of PF4 (FIG. 8C), IL-8 (FIG. 8B), and ENA-78 (FIG. 8A) in both acute and chronic would fluid.
Figure 8B:
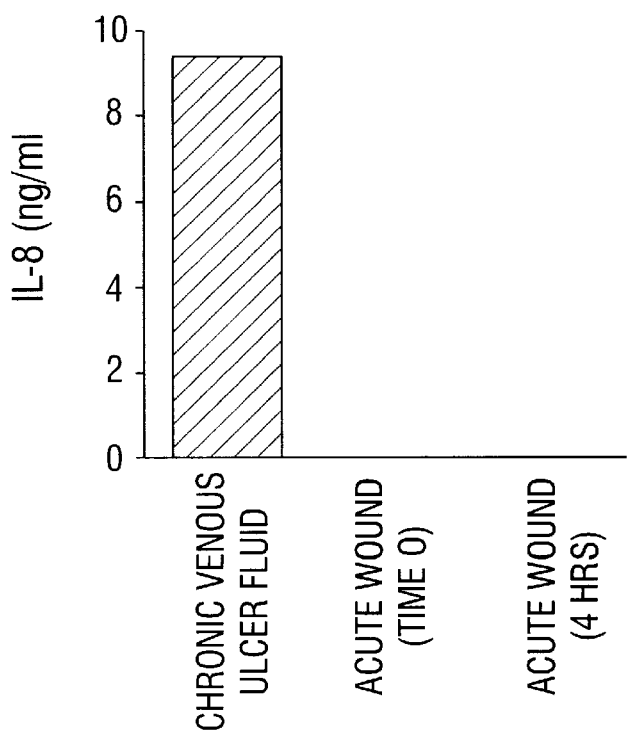
Figure 8C:
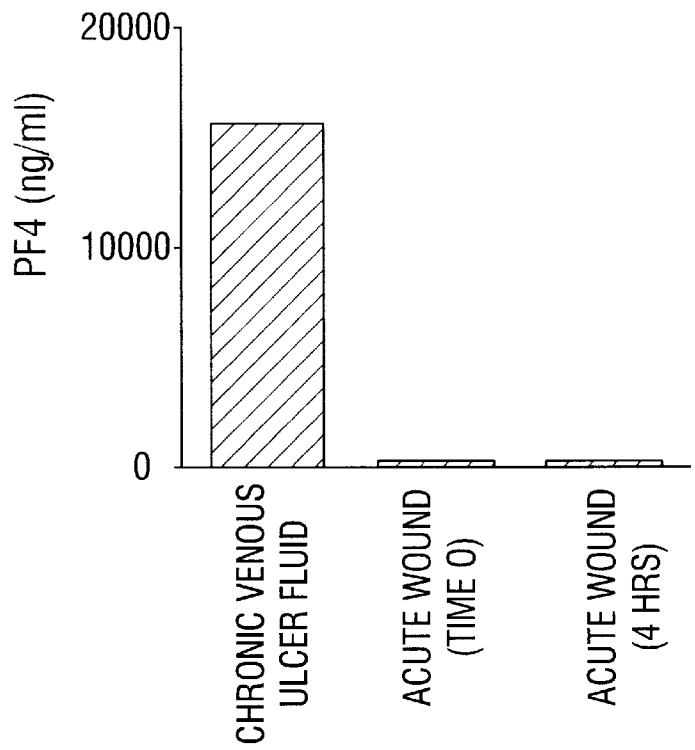

Given the data in FIG. 9A, FIG. 9B, FIG. 9C, FIG. 9D, FIG. 9E and FIG. 9F, showing that ELR CXC chemokines peak during normal wound-healing, and the data in FIG. 8A, FIG. 8B and FIG. 8C, showing that the non-ELR CXC chemokine, PF4, persists in chronic wounds, it is evident that the ELR CXC chemokines can be used in wound-healing. The invention thus further includes wound-dressings and bandages that comprise biological effective amounts of one or more ELR CXC chemokine. Hydrocolloid dressings, such as those described in Example VI, are preferred for use with the chemokines.

The wound-dressings and bandages may be packaged in kits and in suitable container means. The dressing or bandage may be prepared to include the CXC chemokine composition, or may be provided free from the CXC chemokine but with a second container that comprises the chemokine. When the CXC chemokine components are provided in one or more liquid solutions, the liquid solution is an aqueous solution, with a sterile aqueous solution being particularly preferred. CXC chemokine components may also be provided as dried powder(s) which can then be reconstituted by the addition of a suitable solvent. It is envisioned that the solvent may also be provided in another container means.

The container means of the kit will generally include at least one sealed package, vial, test tube, flask, bottle, syringe or other container means, into which the wound-dressing or bandage and, optionally, a CXC chemokine composition, may be placed. Separate CXC chemokine compositions may be suitably aliquoted. A second and/or third container means for containing a sterile, pharmaceutically acceptable buffer or other diluent may also be included.

The kits may also contain a means by which to place or secure the wound-dressing or bandage in position in animal, including adhesive strips. The kits will also typically include a means for containing the individual sealed packages and other containers in close confinement for commercial sale, such as, e.g., injection or blow-molded plastic containers into which the components are placed and retained.

Gene Therapy

Adenoviral vectors are one form of gene therapy vehicle particularly contemplated for use in this invention. Rosenfeld et. al. (1991; 1992) and Stratford-Perricaudet et. al. (1990; 1992) describe uses of adenovirus. Stratford-Perricaudet et. al. (1990) have shown that adenovirus-mediated gene transfer can be used to treat a rare recessive genetic disorder, ornithine transcarbamylase (OTC) deficiency, in newborn mice. Rosenfeld et. al. (1992) used adenovirus to transfer the gene for cystic fibrosis transmembrane conductance regulator (CFTR) into the pulmonary epithelium of rats, and observed expression of the CFTR protein in lung airway cells.

Recombinant adenovirus containing a vector that expresses one or more CXC chemokines may be used to supply the chemokines in vivo. Such recombinant adenovirus will be replication defective. For example, as achieved through the deletion of the viral early region 1 (E1A) region such that the virus is competent to replicate only in cells, such as human 293 cells, which express adenovirus early region 1 genes from their cellular genome. This is important because the virus will therefore not kill normal cells that do not express early gene products. Techniques for preparing replication defective adenoviruses are well known in the art as exemplified by Ghosh-Choudhury et. al., (1987); McGrory et. al., 1988; and Gluzman et. al. (1982).

The particular cell line used to propagate the recombinant adenoviruses of the present invention is not critical to the present invention. The recombinant adenovirus vectors can be propagated on, e.g., human 293 cells, or in other cell lines that are permissive for conditional replication-defective adenovirus infection, e.g., those which express adenovirus E1A gene products "in trans" so as to complement the defect in a conditional replication-defective vector. Further, the cells can be propagated either on plastic dishes or in suspension culture, in order to obtain virus stocks thereof.

Other than the requirement that the adenovirus vector be replication defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

The promoter used to express the CXC chemokine is not critical to the present invention. As described above, many promoters may be used, such as the human cytomegalovirus (CMV) immediate early gene promoter (Thomsen et. al., 1984), which results in the constitutive, high-level expression foreign genes. The selection of a promoter that is regulated in response to specific physiologic signals can permit inducible expression of the CXC chemokine, if desired. For example, if the CXC chemokine gene were to be expressed from the human PAI-1 promoter, the expression would be inducible by tumor necrosis factor.

In that vectors for use in adenoviral-based gene therapy are replication defective, they will typically not have an adenovirus E1 region. Thus, it will be most convenient to introduce one or more CXC chemokine coding regions at the position from which the E1 coding sequences have been removed. However, the position of insertion of the coding region within the adenovirus sequences is not critical to the present invention. The CXC chemokine transcription unit may also be inserted in lieu of the deleted E3 region in E3 replacement vectors as described previously by Karlsson et. al. (1986).

Moreover, where a cDNA insert is employed one will typically desire to include a polyadenylation signal to effect proper polyadenylation of the CXC chemokine message. The nature of the polyadenylation signal is again not believed to be crucial to the successful practice of the invention, and any such sequence may be employed. SV40 and protamine gene polyadenylation signals are convenient and known to function well.

Pharmaceutical compositions comprising viral CXC chemokine gene vectors are dispersed in pharmacologically acceptable solutions or buffers. Preferred solutions include neutral saline solutions buffered with phosphate, lactate, Tris, and the like. Of course, one will desire to purify the vector sufficiently to render it essentially free of undesirable contaminant, such as defective interfering viral particles or endotoxins and other pyrogens such that it will not cause any untoward reactions in the individual receiving the vector construct. A preferred means of purifying an adenovirus, for example, involves the use of buoyant density gradients, such as cesium chloride gradient centrifugation.

Recombinant adenovirus are often administered in amounts of between about $5 \times 10^9$ and $5 \times 10^{12}$ virus particles, which may be given either as a single bolus injection, as an intravenous infusion over several hours, or may be injected into a tumor site. It should also be pointed out that because the adenovirus vector employed in replication defective, it will not be capable of replicating in the cells that are ultimately infected. Moreover, it has been found that the genomic integration frequency of adenovirus is usually fairly low, typically on the order of about 1%. Thus, where continued treatment in certain individuals is required it may be necessary to reintroduce the virus every 6 months to a year.

Detection of CXC Chemokines in Biological Samples

The expression of angiogenic CXC chemokines is contemplated to correlate with the vascularization of tumors and thus with their progressive nature. The magnitude of the expression of angiogenic CXC chemokines is also contemplated to correlate with patient mortality. The use of specific immunohistochemistry, ELISAs, Northern blotting, PCR analyses and in situ hybridization are proposed for use in determining the levels of CXC chemokines within biological samples of normal and diseased tissues.

Biopsies from normal tissues and tumors, standardized to control tissue volume, may be processed by, e.g., freezing in liquid nitrogen, placing in OCT embedding medium and freezing in liquid nitrogen, fixing in 4% paraformaldehyde followed by paraffin embedding, or dispersing to a single cell suspension in a protease mixture.

The tissue samples may then be homogenized, sonicated and subjected to aqueous extraction. This allows for use in protein detection by ELISAs, where the results should be normalized to either the volume of tissue or total protein (TP); and for use in mRNA detection by Northern blotting or RT-PCR analyses, where the results should be normalized to beta-actin mRNA.

Tissue for ELISAs will be processed in PBS alone (when used in bioassays) or PBS containing an anti-protease cocktail. Direct ELISAs for each of the CXC chemokines may be performed as previously described (Evanoff et al., 1992; Strieter et al., 1992b; Burdick et al., 1993).

For Northern blot analyses, total tissue RNA is isolated using polyA mRNA further enriched by batch oligo-dT cellulose (type 77F, Pharmacia, Piscataqay, N.J.). Formaldehyde/1% agarose gels are used to separate mRNA, which is transblotted to nitrocellulose, baked, prehybridized, and hybridized with $^{32}$P-5'-end-labeled anti-sense oligonucleotide probes.

Exemplary probes include the following (SEQ ID NO:28 through SEQ ID NO:41):

IL-8, 5'-AGC-CCT-CTT-CAA-AAA-CTT-CTC-3';
ENA-78, 5'-CTT-TGT-TGC-CGC-CGT-CGA-GG-3';
IP-10, 5'-TTC-AGT-AAA-TTC-TTG-ATG-GCC-3';
PF4, 5'-CAG-CGG-GGC-TTG-CAG-GTC-CAA-3';
GROα, 5'-AAG-AGC-TGG-CGA-GGA-GGT-GCC-3';
GROβ, 5'-GTG-GCT-CTC-CGA-GAA-CGG-CGA-3';
GROγ, 5'-TTA-TGC-ATG-GTT-GAG-AC T-GGA-3';
mMIG, 5'-CTA-GGC-AGG-TTT-GAT-CTC-CGT-3';
hMIG, 5'-CAG-ATA-CTC-TCT-GGA-GGC-TGC-3';
mMIP-2, 5'-AGC-GAG-GCA-CAT-CAG-GTA-CG-3';
hIL-10, 5'-AGA-TCC-GAT-TTT-GGA-GAC-CTC-3';
mIL-10, 5'-GCC-TGG-GGC-ATC-ACT-TCT-AC-3';
hIFNg, 5'-TTA-CTG-GGA-TGC-TCT-TTC-GAC-3';
βactin, 5'-GCT-CGG-CCG-TGG-TGG-TGA-AGC-3'.

Blots are washed, autoradiographed, and quantitated using a computer video imaging system. NIH Image 1.49 software may be used to detect and quantify mRNA from the autoradiographs. Equivalent amounts of mRNA/gel are monitored by assessing beta-actin.

For RT-PCR amplification, one μg of poly-A mRNA from specific samples is reversed transcribed into cDNA utilizing a BRL reverse transcription kit and oligo (dT) 12–18 primers. Primers taken from the sequences disclosed herein may be generated, e.g., using a computer assisted system AMPLIFY which allows one to predict primer interactions that will give a single amplified product.

The exemplary primers for use include the following pairs (SEQ ID NO:42 through SEQ ID NO:71), with the amplification fragment sizes also shown:

| | |
|---|---|
| IL-B1 | 350 bp; Matsushima et al., 1988; 5'-AAG—CTG—GGG—GTG—GCT—CTG—TTG-3', sense; 5'-AGC—CCT—CTT—CAA—AAA—CTT—CTC-3', anti-sense; |
| ENA-78, | 204 bp; Walz et al., 1991; 5'-GAA—CTG—CGG—TGC—GTG—TGT—TT-3', sense; 5'-CTT—TGT—TGC—CGC—CGT—CGA—GG-3', anti-sense; |
| IP-10 | 240 bp, Luster and Ravetch, 1987b; 5'-GAT—TTG—CTG—CCT—TAT—CTT—TCT-3', sense; 5'-TTC—AGT—AAA—TTC—TTG—ATG—GCC-3', anti-sense; |
| PF4, | 231 bp; Poncz et al., 1987; 5'-CTG—GGG—TTG—CTG—CTC—CTG—CCA-3', sense; 5'-CAG—CGG—GGC—TTG—CAG—GTC—CAA-3', anti-sense; |
| βActin | 550 bp; Tokunaga et al., 1986; 5'-GTG—GGG—CGC—CCC—AGG—CAC—CA-3', sense; 5'-GCT—CGG—CCG—TGG—TGG—TGA—AGC-3' anti-sense; |
| GROα, | 337 bp, Anisowicz et al., 1988; 5'-CAG—GTG—GTA—TCT—TCA—GCG—CAG-3', sense; 5'-AAG—AGC—TGG—CGA—GGA—GGT—GCC-3', anti-sense, |
| GROβ, | 284 bp, Haskill et al., 1990; 5'-AGG—CGG—TTA—TCT—CGG—TAT—CTC-3', sense; 5'-GTG—GCT—CTC—CGA—GAA—CGG—CGA-3', anti-sense; |
| GROγ | 259 bp, Haskill et al., 1990; 5'-AGG—CTG—TAT—CTT—CAG—CGA—GGT-3', sense; 5'-TTA—TGC—ATG—GTT—GAG—ACT—GGA-3', anti-sense; |
| mMIG | 277 bp, Farber, 1990; 5'-ACA—TTC—TCG—GAC—TTC—ACT—CCA-3' sense; 5'-CTA—GGC—AGG—TTT—GAT—CTC—CGT-3', anti-sense; |
| hMIG | 628 bp, Farber, 1993; 5'-TCC—ACC—TAC—AAT—CCT—TGA—AAG-3', sense; 5'-CAG—ATA—CTC—TCT—GGA—GGC—TGC-3' anti-sense; |
| mIP-10 | 379 bp, Vanguri and Farber, 1990; 5'-AAG—CGC—TTC—ATC—CAC—CG-3', sense; 5'-GCG—TGG—CTT—CTC—TCC—AG-3' anti-sense; |

| | |
|---|---|
| mMIP-2 | 359 bp, Wolpe et al., 1989; 5'-GCT—GGC—CAC—CAA—CCA—CCA—GG-3', sense; 5'-AGC—GAG—GCA—CAT—CAG—GTA—CG-3', anti-sense; |
| hIL-10 | 530 bp; Vieira et al., 1991; 5'-CAG—TCT—GAG—AAC—AGC—TGC—ACC-3', sense; 5'-AGA—TCC—GAT—TTT—GGA—GAC—CTC-3' anti-sense; |
| mIL-10 | 278 bp; Vieira et al., 1991; 5'-GCT—ATG—TTG—CCT—GCT—CTT—AC-3', sense; 5'-GCC—TGG—GGC—ATC—ACT—TCT—AC-3' anti-sense; |
| hIFNg | 501 bp; Brenner et al., 1989; 5'-ATG—AAA—TAT—ACA—AGT—TAT—ATC-3', sense; 5'-TTA—CTG—GGA—TGC—TCT—TTC—GAC-3' anti-sense. |

The amplification buffer contains 50 mM KCl, 10 mM Tris-HCl pH 8.3, and 3.5 mM MgCl. Specific oligonucleotide primers are added (200 ng/sample) to the buffer, along with 1 μl of the reverse transcribed cDNA sample. The cDNA is preferably amplified using the following cycling parameters: The mixture is first incubated for 5 min at 94° C. and then cycled 30 times at 95° C. for 30 sec, 55° C. for 45 sec, and elongated at 72° C. for 75 sec. This format allows optimal amplification with a minimum of nonspecific amplification of any contaminating cDNA (Lukacs et al., 1993). After amplification the sample (20 μl) is separated on a 2% agarose gel containing 0.3 ug/ml of ethidium bromide and the bands visualized and photographed using a translucent UV source.

For in situ hybridizational analyses, specific mRNA is localized in tissue using a nonradioactive technique. Briefly, three micron thick paraffin embedded sections (10 total) on poly-L-lysine slides are dewaxed in xylene and rehydrated in varying concentrations of ETOH. The slides are rinsed in DEPC $H_2O$, immersed in 0.2N HCl for 20 min, washed in 2×SSC preheated to 70° C. for 10 min, post-fixed in 0.4% paraformaldehyde at 4° C. for 20 min, and rinsed in DEPC $H_2O$. The slides are prehybridized and hybridized in the presence of digoxigenin (11-dUTP) labeled anti-sense or sense oligonucleotide probes (see above).

Specificity of the hybridization is determined by: a) pretreating some of the slides with RNase A (40 ug/ml in 2XSSC) prior to the hybridization with specific cytokine anti-sense probe; b) pretreating with excess cold anti-sense probe; and/or c) using a labeled sense probe. A computer enhanced video imaging system is used to detect the cellular source and quantify immunostaining of the in situ mRNA.

Tissue biopsies may also be processed in the presence or absence of neutralizing anti-CXC chemokine antibodies and used in bioassays of angiogenesis, such as the rat corneal micropocket assay described herein. The differential results in the presence and the absence of such antibodies provides another measure of the CXC chemokine levels.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

IL-8 and ENA-78 are Present in Nonmalignant Disorders Associated with Prominent Angiogenesis Several diseases are associated with an over expression of angiogenic activity, which appears to be associated with the maintenance and progression of the chronic disease state. Disorders associated with the presence of chronic inflammation, such as rheumatoid arthritis, atherosclerosis, and idiopathic pulmonary fibrosis (IPF) are examples of nonmalignant diseases with chronic angiogenic activity (Zetter, 1988). Persistent neovascularization in these disorders is a prerequisite for perpetuation of fibroproliferation (Zetter, 1988; Clark, 1993). The inventors postulated that the fibroproliferative nature of IPF makes this a representative disease to assess the presence of an angiogenic factor, such as IL-8.

The inventors obtained open lung biopsies from patients undergoing thoracic surgery for reasons other than interstitial lung disease (normal lung) and from patients with IPF, and performed immunolocalization -or IL-8. Immunohistochemical localization of IL-8 was achieved by using fresh tissue specimens obtained at time of thoracotomy and fixing in 4% paraformaldehyde for 24 hours prior to transferring to 70% ethanol. Paraffin-embedded tissue sections were dewaxed with xylene and rehydrated through graded concentrations of ethanol. Samples were then stained for IL-8 using a modification of the inventors' previously described technique (Standiford et al., 1990).

Briefly, nonspecific binding sites were blocked with normal goat serum (BioGenex, San Ramon, Calif.) before washing and applying a 1:1000 concentration of either control (rabbit) or rabbit anti-human IL-8 serum. Slides were then rinsed and overlaid with secondary biotinylated goat-anti rabbit IgG (1:35) and then incubated. After washing twice with Tris-buffered saline, slides were overlaid with a 1:35 dilution of alkaline phosphatase conjugated to streptavidin (BioGenex), and incubated. Fast Red (BioGenex) reagent was used for chromogenic localization of IL-8 antigen. After optimal color development, sections were immersed in sterile water, counterstained with Mayer's hematoxylin, and coverslipped using an aqueous mounting solution.

Significant immunolocalization of IL-8 was found within islands of proliferating fibroblasts and extra-cellular matrix from the IPF specimen as compared to normal lung (compare FIG. 1A, FIG. 1B, FIG. 1C, FIG. 1D, FIG. 1E, FIG. 1F, FIG. 1G and FIG. 1H). The areas associated with IL-8 immunolocalization were essentially devoid of infiltrating leukocytes. This finding was in agreement with previous studies which had demonstrated significant levels of IL-8 present in other chronic inflammatory disorders that display markedly elevated angiogenic activity (Nickoloff, 1991; Koch et al., 1991a; 1993).

To ascertain whether the presence of IL-8 or other ELR motif-containing CXC chemokines were associated with benign tumors known to have a dependency on angiogenesis, the inventors obtained specimens of hemangiomas and performed immunohistochemistry for the presence of IL-8 and ENA-78 protein. Hemangiomas are benign tumors of capillary origin where tumor growth is absolutely dependent upon neovascularization (Zetter, 1988; Mulliken and Glowacki, 1982). Immunolocalization of both IL-8 and ENA-78 was found to be significantly present in hemangioma specimens (compare FIG. 2A, FIG. 2B, FIG. 2C, FIG. 2D, FIG. 2E and FIG. 2F; compare FIG. 3A, FIG. 3B, FIG. 3C, FIG. 3D, FIG. 3E, FIG. 3F, FIG. 3G and FIG. 3H). Control antibodies failed to demonstrate nonspecific staining (FIG. 2C, FIG. 2E, FIG. 3C, FIG. 3E, FIG. 3G). Keratinocytes, endothelial cells and mononuclear cells in the hemangiomas were found to significantly express both IL-8 and ENA-78. Interestingly, the extracellular matrix, especially the basement membrane of the vessels, was significantly immunopositive for these chemokines. This finding is consistent with the ability of chemokines to bind to glycosaminoglycans (Baggiolini et al., 1989; 1992; Matsushima and Oppenheim, 1989; Oppenheim et al., 1991; Miller and Krangel, 1992).

EXAMPLE II

IL-8 is Significantly Elevated in NSCLC

Since the growth of solid tumors shares many features with wound repair (Whalen, 1990; McKay and Leigh, 1991), and tumorigenesis and metastasis are dependent upon angiogenesis (Folkman, 1985; Bouck, 1990; Folkman and Klagsbrun, 1987; Folkman et al., 1989; Maiorana and Gullino, 1978; Herlyn et al., 1987; Weidner et al., 1991; Weidner et al., 1993; Macchiarini et al., 1992), the inventors characterized the angiogenic biology of CXC chemokines in the context of NSCLC.

The antigenic determination of the CXC chemokine content of normal lung and bronchogenic tumor tissue specimens was determined using samples obtained from consented individuals undergoing thoracotomy for suspected primary bronchogenic carcinoma in accordance with the University of Michigan I.R.B. approval. Samples of tumor, and normal lung distal to tumor, were homogenized in PBS upon recovery from the operating room. Specimens were then filtered through 0.45 micron Sterile Acrodiscs (Gelman Sciences) and frozen at $-70°$ C. until thawed and assayed.

A specific ELISA for IL-8 and other CXC chemokines was employed to determine their level in the tissue samples (Bacon et al., 1989). Samples were run in parallel for total protein (TP) content (Pierce, Rockford, Ill.). Determinations were expressed as ng of CXC chemokine per mg total protein (TP). Results were tabulated based on final histological diagnosis as determined by University Hospital pathologists.

Figure 4A:
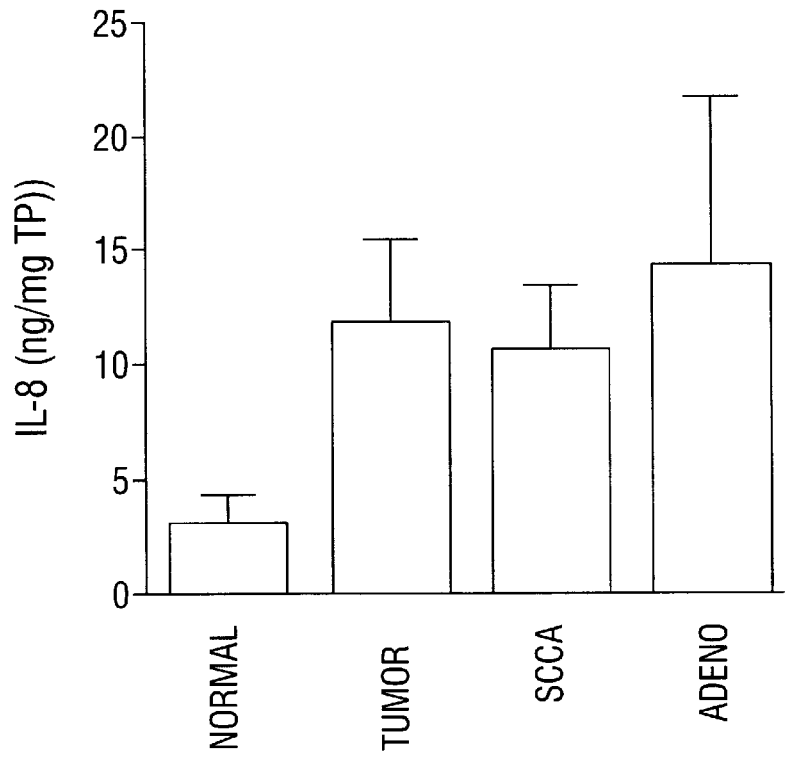
FIG. 4A, FIG. 4B and FIG. 4C. The presence of IL-8 (FIG. 4A), GROα (FIG. 4B), and PF4 (FIG. 4C) in bronchogenic carcinoma as compared to normal lung. "Tumor" represents combined chemokine levels from both adenocarcinomas and squamous cell carcinomas (SCCA). Chemokines were measured by specific ELISAs from tissue aqueous extracts and normalized to total protein (TP) content.
Figure 4B:
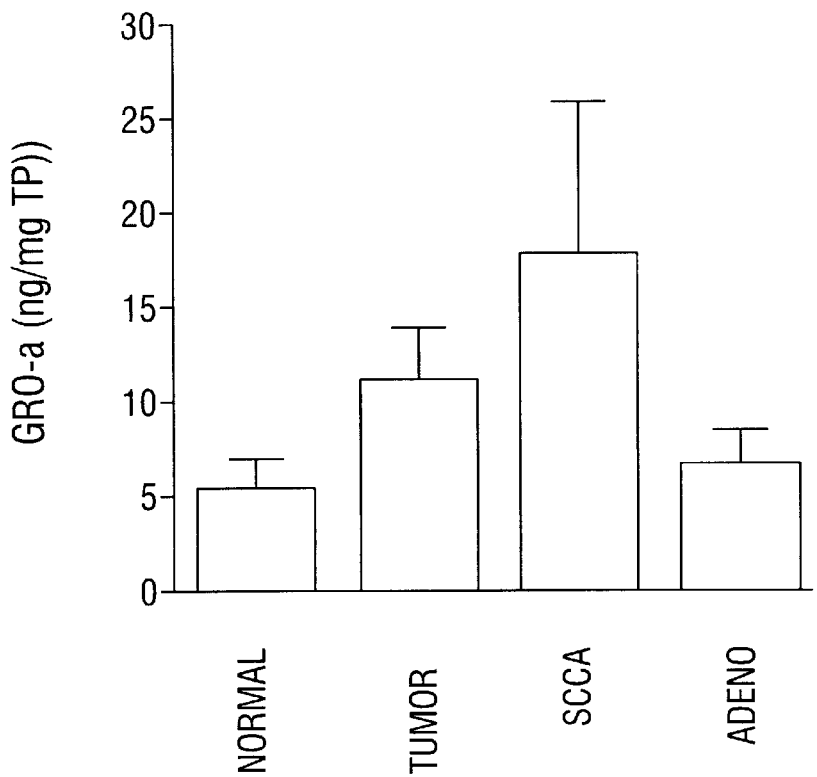
Figure 4C:
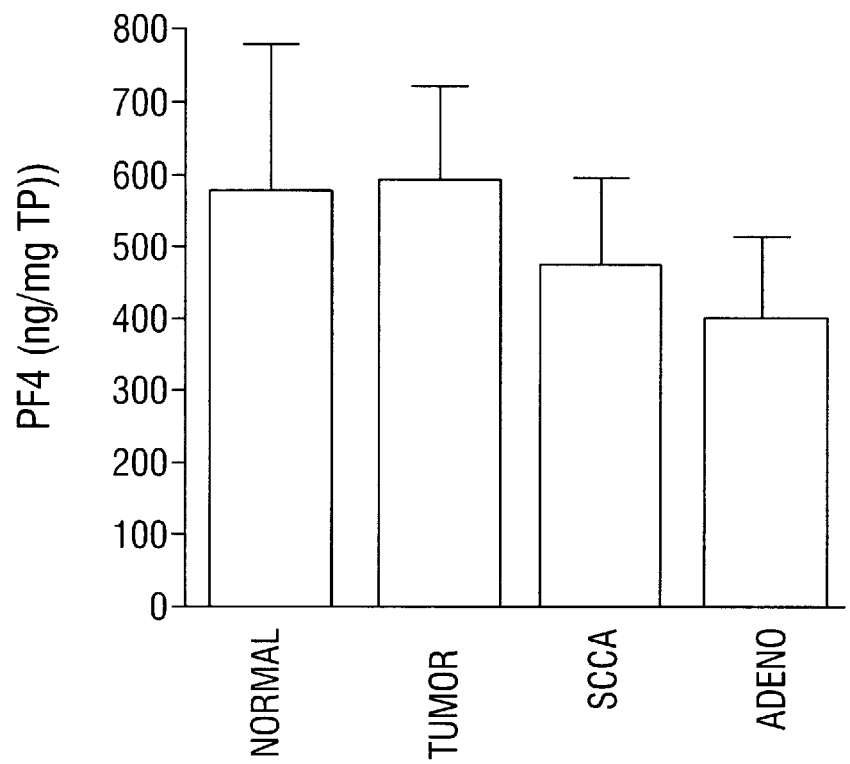

Using the specific ELISA to detect IL-8 in human tissue homogenates of both normal lung and NSCLC, IL-8 was found in a 4-fold excess in tumor tissue as compared to normal lung tissue, normalized to total protein (FIG. 4A). Normal lung tissue contained 2.6±0.7 ng/mg TP of IL-8, as compared with 11.9±3.8 ng/mg TP for tumor specimens. There were similar elevations of IL-8 from tumors of adenocarcinoma and squamous cell histology, 14±7 ng/mg TP and 10.8±3 ng/mg TP, respectively. In addition, GROα was found to be elevated in tumors (11±3 ng/mg TP), especially of squamous cell (17.6±7.8 ng/mg TP) histology (FIG. 4B). In contrast, PF4, a known inhibitor of angiogenesis (Maione et al., 1990; Sharpe et al., 1990; Maione et al., 1991), was found in the tumor tissue homogenates to be equivalent to normal lung tissue, 592.4±127.8 ng/mg TP and 579.1±195.3 ng/mg TP for tumors and normal lung tissue, respectively (FIG. 4C).

The inventors next utilized immunohistochemical localization of IL-8 to determine the cellular origins of antigenic IL-8 in tumor tissue. Previous studies have demonstrated that human tumors and neoplastic cell lines may directly elaborate IL-8 (Thornton et al., 1990; Standiford et al., 1990; Hotta et al., 1990; VanMeir et al., 1992; Abruzzo et al., 1992; Kasahara et al., 1991; Kaashoek et al., 1991). Results from immunostaining of tumor sections confirmed heterogeneous tumor cell production of IL-8 in both adenocarcinomas and squamous cell carcinomas of the lung.

The heterogeneity of the tumor cell expression was of interest, especially since the inventors had shown by immunohistochemistry that only 36% to 38% of A549 cells (bronchoalveolar carcinoma cell line) expressed IL-8 (Standiford et al., 1990). The findings of heterogeneous expression of IL-8 by tumor cells suggests the feasibility that a specific subclone of neoplastic cells may exist that function as the primary cellular source of tumor-derived IL-8. These results also revealed that non-transformed stromal cells within the local desmoplastic response may serve as significant cellular sources for IL-8, especially the squamous cell carcinoma phenotype. Importantly, these specific findings may be reflected in the different clinical behaviors of squamous cell and adenocarcinomas. The more aggressive course of adenocarcinomas could be related to its capacity to generate a sufficient angiogenic signal (IL-8), independent from the surrounding host responding immune and non-immune cells.

EXAMPLE III

Tumor-Derived IL-8 Stimulates Angiogenesis-Associated Responses

To determine the relative contribution of IL-8 to the total angiogenic activity of NSCLC the inventors employed the following strategies. First, concentrated tissue homogenates from normal lung, adenocarcinoma, and squamous cell carcinomas, as well as tissue extracts from suspensions of a bronchoalveolar carcinoma cell line (A549), were normalized to TP and evaluated for endothelial cell chemotactic activity (Koch et al., 1992a). Results for tissue samples were expressed as percentage of chemotactic activity induced by a standard of 50 ng/ml recombinant human IL-8.

The endothelial cell cherotaxis assays were performed in 48-well, blind well chemotaxis chambers (Nucleopore Corp., Maryland) as previously described (Koch et al., 1986). Nucleopore chemotaxis membranes (5 micron pore size) were prepared by soaking them sequentially in 3% acetic acid overnight and for 2 hr. in 0.1 mg/ml gelatin. Membranes were rinsed in sterile water, dried under sterile air, and stored at room temperature for up to 1 month.

Bovine adrenal gland capillary endothelial cells (BCE), maintained in gelatin-coated flasks in DME with 10% FBS were used as the target cells. Twenty four hours before use BCE were starved in DME with 0.1% BSA. Twenty five microliters of cells, suspended at a concentration of $1 \times 10^6$ per ml in DME with 0.1% BSA were dispensed into each of the bottom wells. A chemotaxis membrane was positioned atop the bottom wells, chambers were sealed, inverted, and incubated for 2 hours to allow cells to adhere to the membrane. Chambers were then reinverted, 50 ml test media was dispensed into the top wells and reincubated for an additional 2 hours. Membranes were then fixed and stained with Diff-Quick staining kit American Scientific Products) to enumerate membrane-bound cells, and cells that had migrated through the membrane to the opposite surface were counted. Four replicates, 10 fields per replicate, were tested for each sample, and studies were repeated at least three times. Results were expressed as the total number of endothelial cells that migrated across the filter in 10 high power (400×) fields.

IL-8 neutralization studies utilized a polyclonal rabbit anti-human-IL-8 antibody (Koch et al., 1992b; Standiford et al., 1990). Additional neutralization studies employed the commercially available neutralizing goat anti-human-TGFa antibody and rabbit anti-bFGF (R & D Systems, Minneapolis, Minn.).

Figure 5:
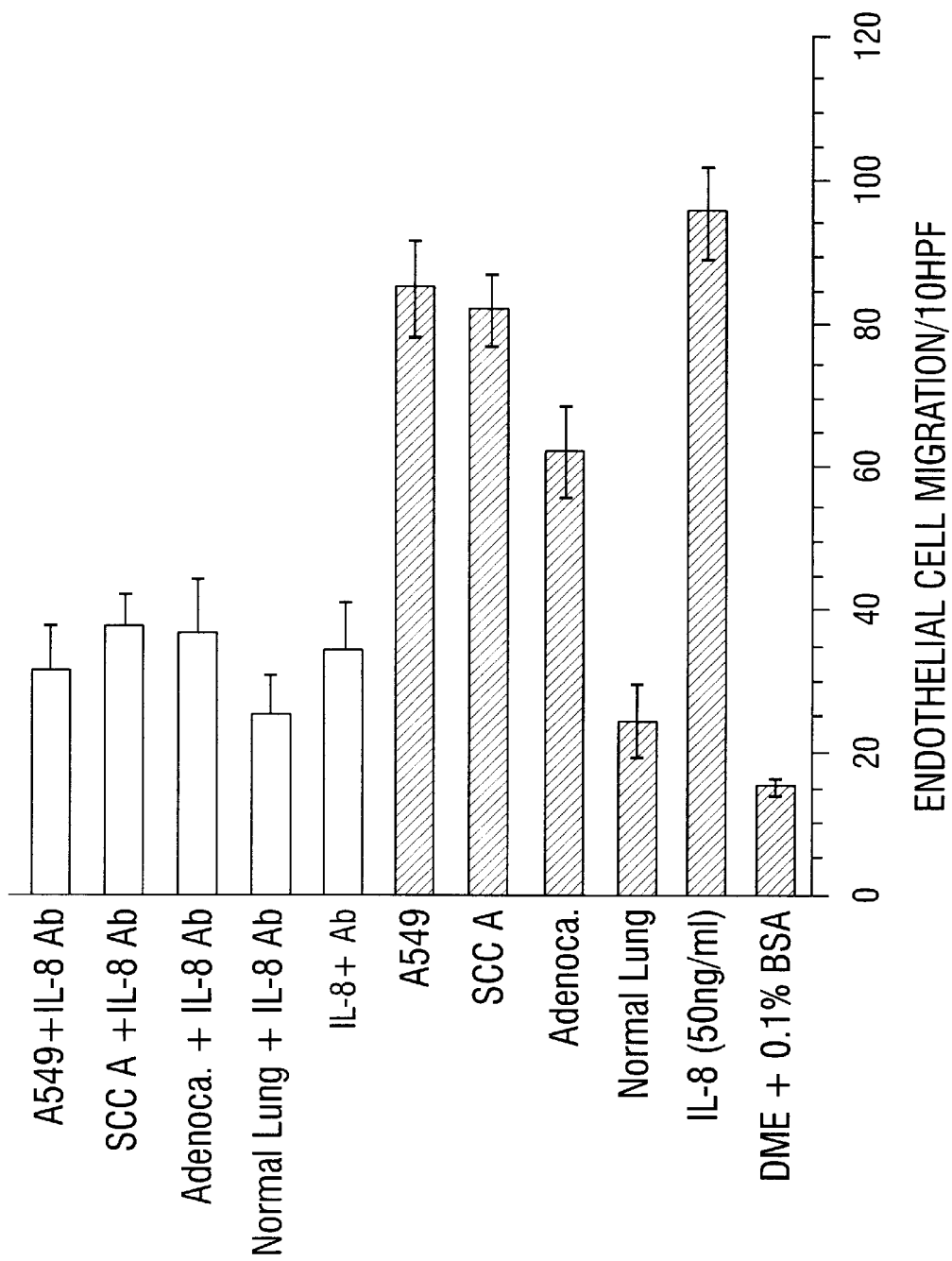
FIG. 5. Neutralizing interleukin-8 (IL-8) antibodies significantly attenuate endothelial cell chemotaxis. Tissue aqueous extracts from normal lungs, A549 (adenocarcinoma cell line), squamous cell carcinomas, and adenocarcinomas were assessed for endothelial cell chemotactic activity in the presence of control or neutralizing IL-8 antibodies, as compared to control media (DME+0.1%) or IL-8 standard (50 ng/ml).

As illustrated in FIG. 5, samples from adenocarcinoma, squamous cell carcinoma, and A549 cells demonstrated 62%, 84%, and 86%, respectively, of the maximal endothelial cell chemotaxis induced by the IL-8 standard. Endothelial cell chemotaxis in response to media alone was 16% of the IL-8 standard. The addition of neutralizing IL-8 antibodies to each of the tumor specimens attenuated the endothelial cell chemotactic activity by approximately 42% to 63% for each of the tumor specimens. This was equivalent to the background level of the IL-8 standard in the presence of neutralizing -L-8 antibodies. The above data suggested that a significant portion of tumor-derived endothelial cell chemotaxis was mediated directly by IL-8.

Figure 6:
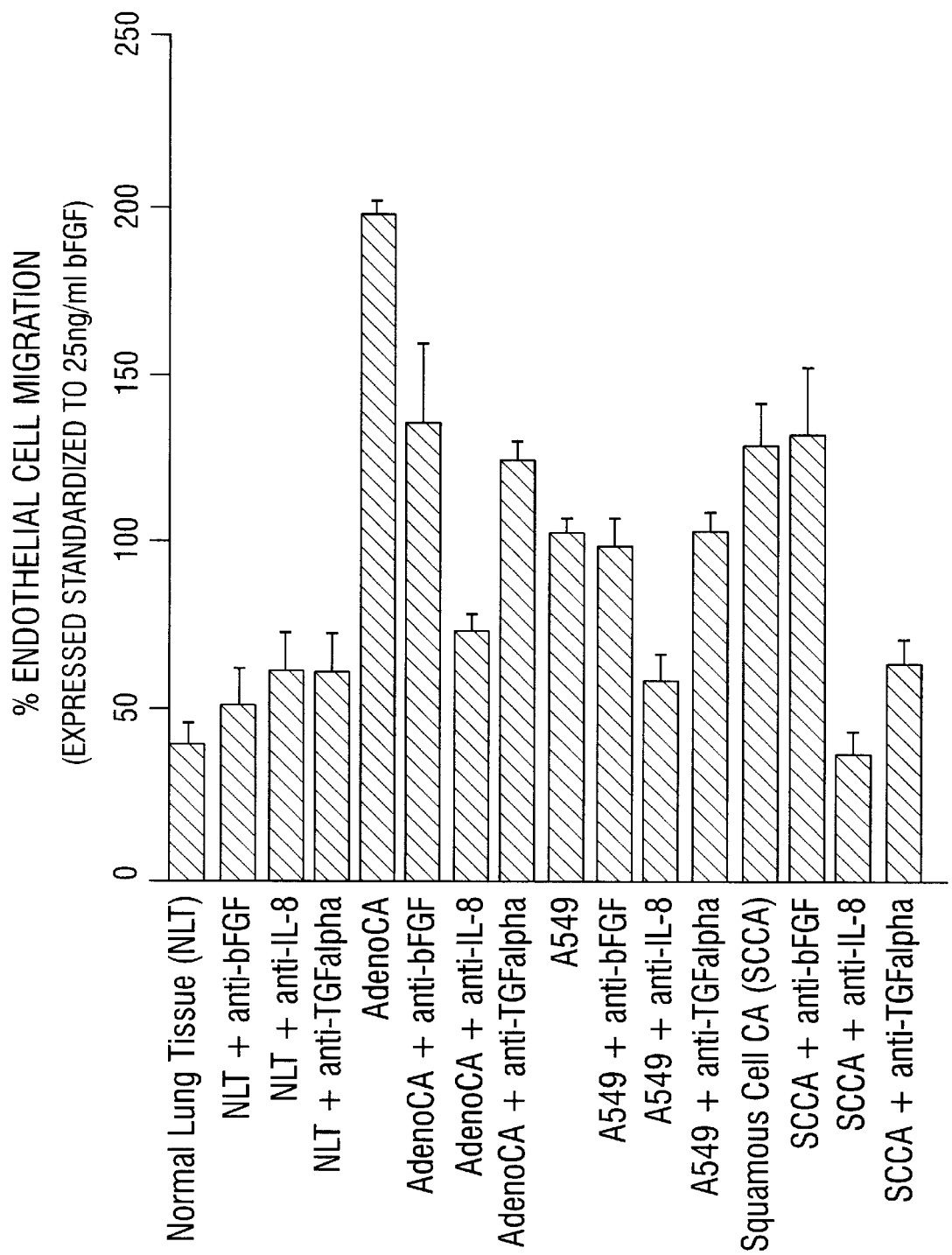
FIG. 6. Neutralizing IL-8 more than bFGF and TGFα antibodies significantly attenuate endothelial cell chemotaxis. Tissue aqueous extracts from normal lungs, A549 (adenocarcinoma cell line), squamous cell carcinomas (SCCA), and adenocarcinomas (adeno) were assessed for endothelial cell chemotactic activity in the presence of control or neutralizing IL-8, bFGF, and TGFα, antibodies. Chemotaxis expressed as % of 25 ng/ml bFGF.
Figure 7A:
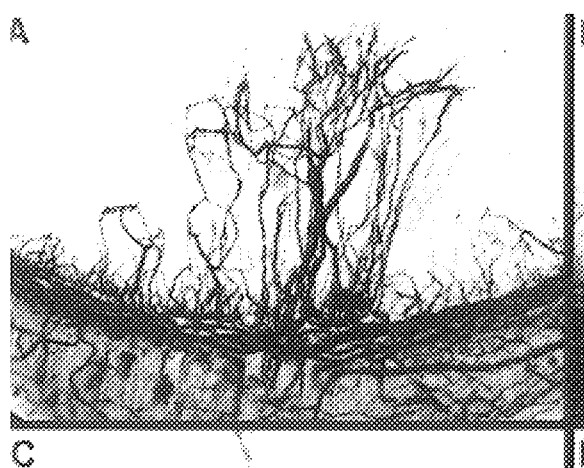
FIG. 7A, FIG. 7B, FIG. 7C and FIG. 7D. Representative photographs of cornea neovascularization. Neutralizing interleukin-8 (IL-8) antibodies significantly attenuated neovascularization in the corneal micropocket (rat cornea).
Figure 7B:
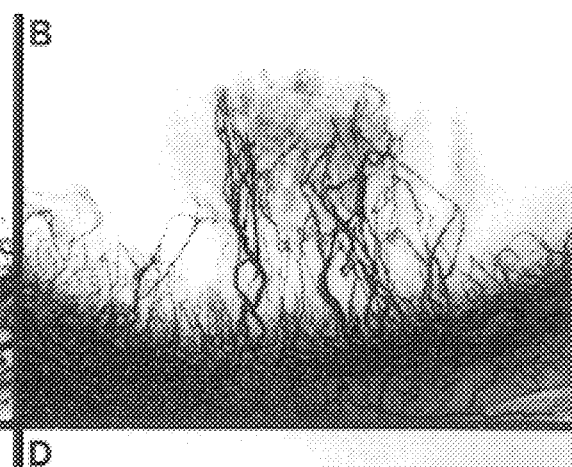
Figure 7C:
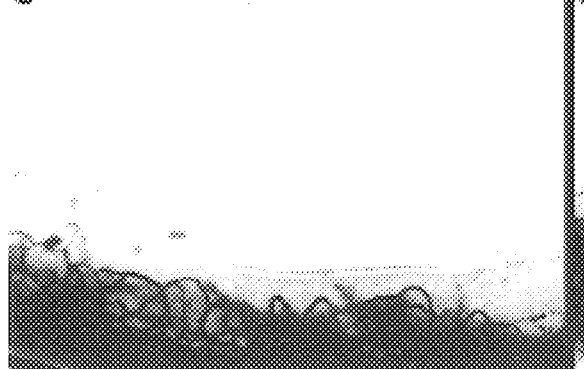
Figure 7D:
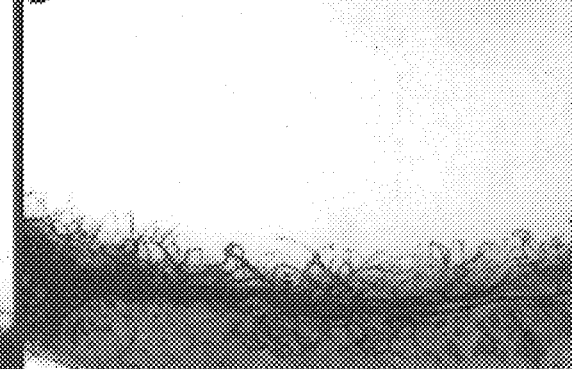

To further examine the angiogenic signal from tumor specimens in an attempt to characterize the relative contributions of other known angiogenic factors such as bFGF and TGFα, a second series of endothelial cell chemotactic studies were performed in the presence of specific neutralizing IL-8, bFGF, or TGFa antibodies (FIG. 6). Results were standardized to the response generated from a standard of 25 ng/ml bFGF.

Normal lung tissue generated only 40% of standard endothelial cell chemotactic activity, and was not significantly affected by the addition of any of the neutralizing antibodies. Tumor samples alone generated a brisk chemotactic response, with 198%, 130%, and 104% of the standard (bFGF) bioactivity, respectively, for samples of adenocarcinoma, squamous cell carcinoma, and A549 cell line tissue. Neutralizing antibodies to IL-8 resulted in a significant reduction of endothelial cell chemotactic response to tumor tissue, with a decline to 75%, 39%, and 61% of the standard bioactivity, respectively, for adenocarcinoma, squamous cell carcinoma, and A549 samples. Anti-bFGF antibodies had no significant effect on the chemotactic response from samples of A549 cells/tissue or squamous cell carcinoma tissue, however, these antibodies reduced the endothelial cell chemotactic activity from adenocarcinoma tissue from 198% to 137% of the standard bioactivity. Interestingly, the neutralization of TGFα had no significant effect on the chemotactic response to adenocarcinoma or to the A549 cell/tissue, however, these antibodies demonstrated a significant reduction in the chemotactic response to squamous cell carcinoma tissue, from 130% to 71% of the standard bioactivity.

Although bFGF and TGFα have been previously described as potential angiogenic factors involved in tumor angiogenesis (Whalen, 1990; Folkman, 1985; Zetter, 1988; Schwigerer, 1988; McKay and Leigh, 1991), these studies suggest that a primary angiogenic signal for NSCLC neovascularization is directly mediated by tumor-associated IL-8.

EXAMPLE IV

Inhibition of IL-8 Attenuates Angiogenesis In Vivo

The inventors next evaluated the angiogenic signal mediated by tumor-derived IL-8 in an in vivo model of angiogenesis. The previously well-characterized corneal micropocket model in the rat was employed (Koch et al., 1991b; 1992a; Polverini et al., 1977). Briefly, 5 mg total protein of each specimen was combined with a equal volume of sterile Hydron casting solution, and 5 ml aliquots were pipetted onto the surface of 1 mm Teflon rods glued to the surface of a glass petri dish. Pellets were air-dried in a laminar flow hood (1 hour) and refrigerated overnight. Prior to implantation pellets were rehydrated with a drop of lactated ringers solution.

Animals were anesthetized with metofane and injected with sodium pentobarbital intraperitoneally. A retrobulbar injection of 0.1 ml of 2% lidocaine was made before intracorneal implantation of the Hydron pellet into a surgically created intracorneal pocket approximately 1.5 mm from the limbus. The animals were examined daily with a stereomicroscope. Seven days after implantation, animals were re-anesthetized and perfused sequentially with lactated Ringers solution followed by colloidal carbon. Corneas were harvested, flattened and photographed.

Positive neovascularization responses were recorded only if sustained directional ingrowth of capillary sprouts and hairpin loops towards the implant were observed. Negative responses were recorded when either no growth was observed or when only an occasional sprout or hairpin loop displaying no evidence of sustained growth was detected. Animals were handled in accordance with the University of Michigan U.L.A.M. protocols.

It was found that control samples of either 50 ng recombinant IL-8 or 25 ng recombinant bFGF induced positive corneal angiogenic responses in 80% and 100% of the corneas, respectively (Table 2). Samples from normal lung, adenocarcinoma, squamous cell carcinoma and A549 cells produced positive angiogenic responses in the cornea of 17% (1/6), 75% (3/4), 66% (2/3) and 100% (4/4), respectively. Neutralizing IL-8 antibodies completely abrogated the angiogenic response to IL-8 controls (0/4), but had no effect upon angiogenesis induced by bFGF (3/3).

TABLE 2

Angiogenic activity of IL-8, bFGF, and pulmonary tumor samples in the corneal micropocket (rat cornea) in the presence or absence of neutralizing IL-8 antibodies.

| | Proportion of positive responses | |
|---|---|---|
| Test sample | (−) anti-Il-8 Ab | (+) anti-IL-8 Ab |
| Controls | | |
| HBSS | 0/3 (0) | 0/4 (0) |
| IL-8 (50 ng) | 4/5 (80) | 0/4 (0) |
| bFGF (25 ng) | 3/3 (100) | 3/3 (100) |
| Lung Tissue | | |
| Normal lung | 1/6 (17) | 0/4 (0) |
| Squamous cell CA | 2/3 (66) | 1/5 (20) |
| Adenocarcinoma | 3/4 (75) | 1/5 (20) |
| A549 cell line | 4/4 (100) | 0/5 (0) |

The addition of neutralizing IL-8 antibodies to tumor tissue samples resulted in a significant reduction in the cornea angiogenic response. A549 cell homogenates, which had yielded a 100% neovascularization rate, demonstrated no angiogenic activity in the presence of neutralizing antibodies to IL-8 (0/5). Neutralizing antibodies to IL-8 caused a reduction in tumor sample angiogenesis of both adenocarcinoma and squamous cell carcinoma with 80% (four of five) and 80% (four of five) inhibition of angiogenesis, respectively. The addition of neutralizing IL-8 antibodies to normal lung samples did not induce a positive angiogenic response (0/4), while normal lung samples with control antibodies had a 17% positive angiogenic response (1/6). Importantly, there was no infiltration of the corneal tissue by inflammatory cells in any of the test samples or controls, suggesting that the angiogenic responses were mediated entirely by factors present in tumor tissue, rather than by any additional contributions from infiltrating inflammatory cell products.

A representative photomicrograph of corneal neovascularization in response to the above tissue specimens is demonstrated in FIG. 7A, FIG. 7B, FIG. 7C and FIG. 7D. These studies demonstrate a significant portion of angiogenic activity from NSCLC is directly mediated by tumor-associated IL-8.

EXAMPLE V

CXC Chemokines in Acute and Chronic Wounds

As described earlier, the inventors reasoned that the sequential morphological phases of wound repair are mediated by the balance in expression of promoter CXC chemokines (containing the ELR motif) and inhibitor CXC chemokines (lacking the ELR motif). Initially, inhibitory CXC chemokines, such as PF4, will be present as the platelet is the first "cellular" response in the wound. As the transition of the wound evolves toward the cellular phase of inflammation, the balance will shift to the CXC chemokines, such as ENA-78 and IL-8, that elicit neutrophils and stimulate angiogenic activity. However, inhibitors such as IP-10 and PF4 will still be present in order to regulate and control this event. In contrast to the normal evolution of wound repair, it is a proposal of the inventors' that chronic non-healing wounds will be locked in the early coagulation phase of wound repair and will have persistent PF4.

To test this proposal, the inventors initially examined both human acute (leg incision) and chronic (venous leg ulcer) wound fluid for the presence of IL-3, ENA-78, and PF4. Normal saline (3 ml) was placed into the wound and allowed to equilibrate for 10 min. The fluid was centrifuged to remove cellular debris and analyzed in ELISAs.

PF4, ENA-78 and IL-8 levels were 15667 ng/ml (FIG. 8C), 27 ng/ml (FIG. 8A) and 9 ng/ml (FIG. 8B) from the chronic wound, respectively. In contrast, PF4, ENA-78, and IL-8 levels were 153 ng/ml (FIG. 8C), 0.7 ng/ml (FIG. 8A), and 0 ng/ml (FIG. 8B), respectively, from the acute wound, immediately at the time of incision, and 231.6 ng/ml (FIG. 8C), 0.5 ng/ml (FIG. 8A), and 0 ng/ml (FIG. 8B), respectively, from the incisional wound at 4 hrs.

These initial data (i.e., high PF4 and low to undetectable ENA-78 and IL-8) suggest that both the acute wound, during the coagulation phase of wound repair, and the chronic wound display a CXC chemokine profile that favors the CXC chemokines that lack the ELR motif. In normal wound-healing, the PF4 levels would be expected to fall. The continued high expression of PF4 in the chronic wound thus supports the inventors' new model, and indicates that ELR CXC chemokines would likely be of use in treating chronic non-healing wounds.

Subsequent data have shown that a peak of ENA-78, GROα and IL-8 occurs during normal wound-healing, and that the levels of PF4 fall (FIG. 9A, FIG. 9B, FIG. 9C, FIG. 9D, FIG. 9E, FIG. 9F; Example VII, below).

EXAMPLE VI

Chronic Wound Dressings are Reservoirs of CXC Chemokines

Although occlusive pressure and various wound dressings appear to have a role in healing of chronic venous ulcers by providing a barrier to isolate the wound from bacterial or other environmental contamination, the specific mechanism (s) for their effect remains to be fully elucidated. Recently, investigations have demonstrated that Duoderm CGF® in combination with compression facilitated greater and more rapid chronic venous stasis ulcer healing, as compared to compression alone (Cordts et al., 1992).

Duoderm® is a hydrocolloid dressing with an outer waterproof polyurethane foam bonded to a matrix of hydrocolloid particles and a hydrophobic polymer. The hydrocolloid particles absorb exudate, swell, and eventually form a soft, moist gel in the wound. A skin seal forms around the margin of the wound from an interaction between skin moisture and the Duoderm wafer. The portion of the dressing in contact with the open wound is non-adherent and is designed to facilitate the formation of granulation tissue without removal of this delicate tissue with dressing changes. The Duoderm CGF® (control gel formula) allows for greater exudate absorption by the Duoderm wafer. This dressing may be left in place for up to 7 days. Transorbent™ (Brady Medical Products Co., Milwukee, Wis.) is a similar product to Duoderm but with an improved ability to absorb exudate. Since the CXC chemokines are soluble polypeptides in an aqueous environment, the inventors postulated that these cytokines may be absorbed by this dressing (hydrocolloid particles) and held as a reservoir in juxtaposition to the floor of the chronic venous ulcer.

To test this hypothesis, the inventors obtained three pieces (1.0 $cm^2$/piece) of one week old hydrocolloid dressings from the margins of three ulcers, each from a patient undergoing occlusive pressure polyurethane hydrofoam dressing therapy for their chronic venous leg ulcers. The individual samples were snap frozen in liquid nitrogen and stored at −80° C. until further processed.

The dressings were initially homogenized using a tissue tearer followed by sonica-ion in a solution containing PBS and a cocktail of antiproteases consisting of 2 mM phenyl methyl sulfonyl fluoride (PMSF), 1 ug/ml each of antipan, aprotinin, leupeptin, and pepstatin A. The samples were centrifuged at 30,000× g and filtered through 1.2 micron filters prior to analyzing in the CXC chemokine ELISAs. In addition, a new dressing alone or new dressing spiked with recombinant CXC chemokine (10 ng) were processed in the same manner.

Figure 8D:
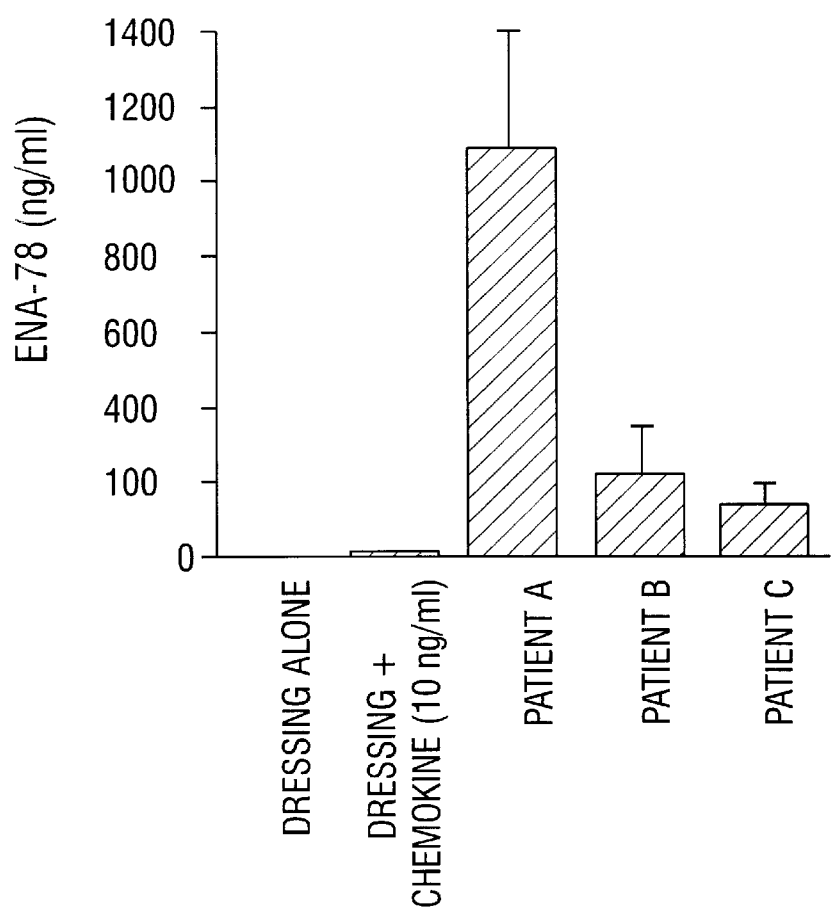
FIG. 8D, FIG. 8E and FIG. 8F. The presence of PF4 (FIG. 8F), IL-8 (FIG. 8E), and ENA-78 (FIG. 8D) in one week old biologic dressings (polyurethane hydrofoam, a hydrocolloid dressing) from three patients with chronic venous stasis ulcers, as compared to dressings alone or spiked with 10 ng/ml of each respective CXC chemokine.
Figure 8E:
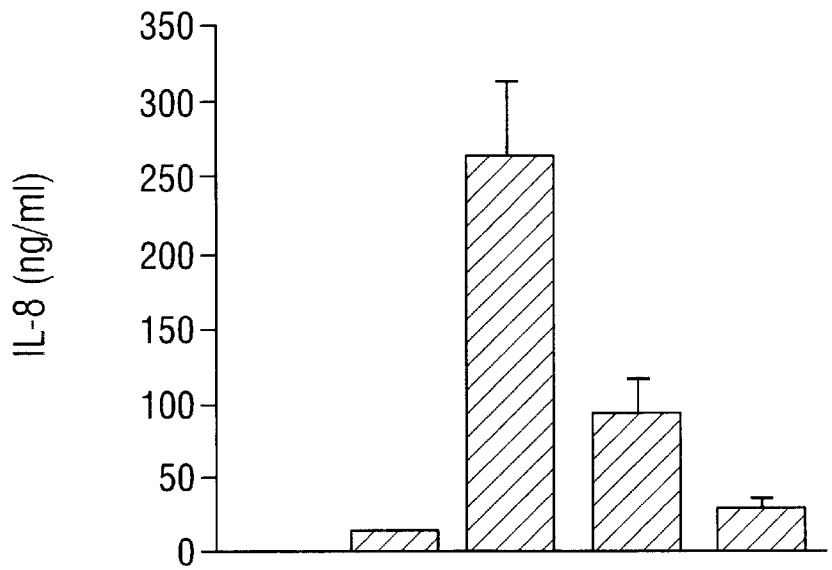
Figure 8F:
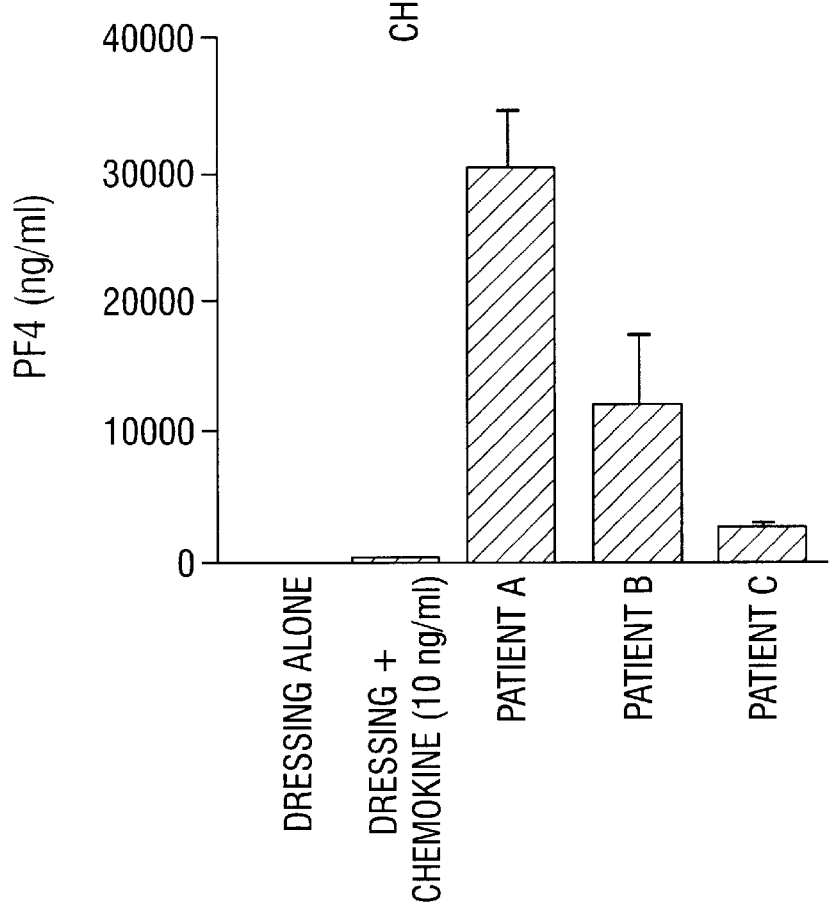
Figure 9A:
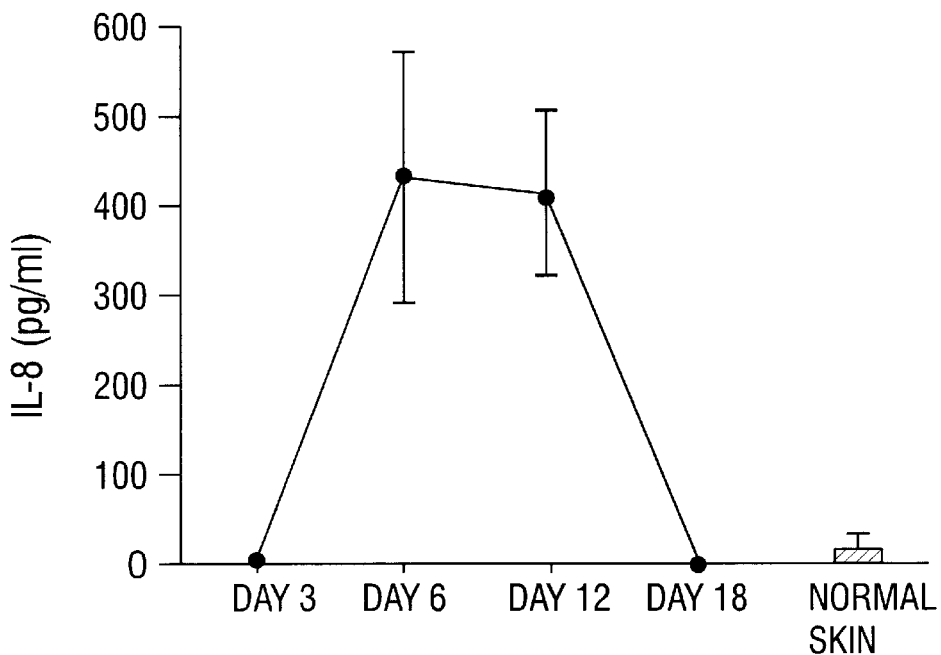
FIG. 9A, FIG. 9B, FIG. 9C, FIG. 9D, FIG. 9E and FIG. 9F. Time course of CXC chemokine production from the human skin/SCID mouse chimera wound model, as compared to normal skin, correlated to re-epithelialization of the wound. IL-8 is shown in FIG. 9A; GROα is shown in FIG. 9B; ENA-78 in FIG. 9C; IP-10 in FIG. 9D; and PF4 in FIG. 9E. Re-epithelialization of the wound is shown in FIG. 9F.
Figure 9B:
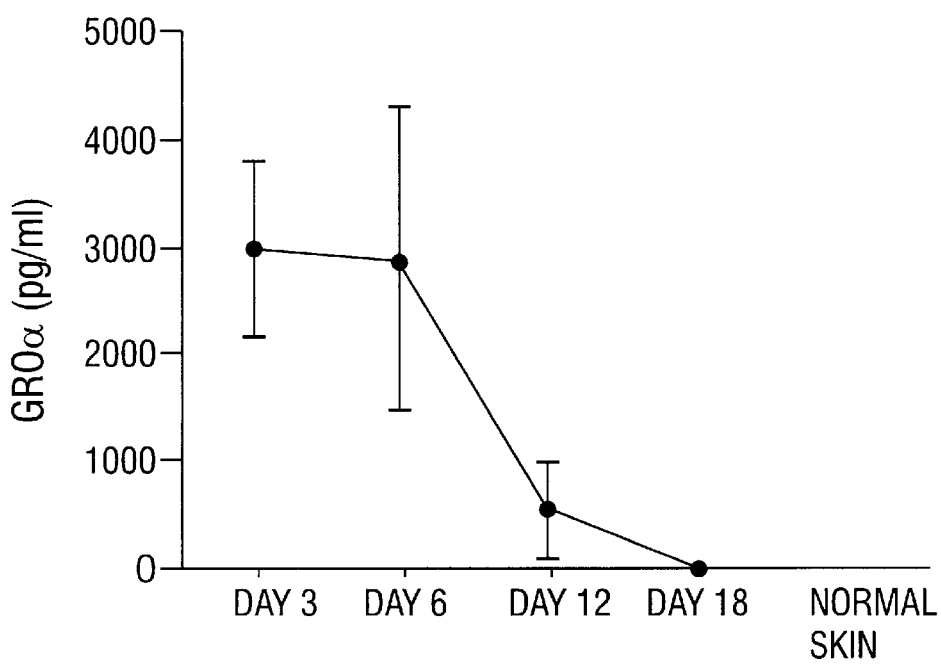
Figure 9C:
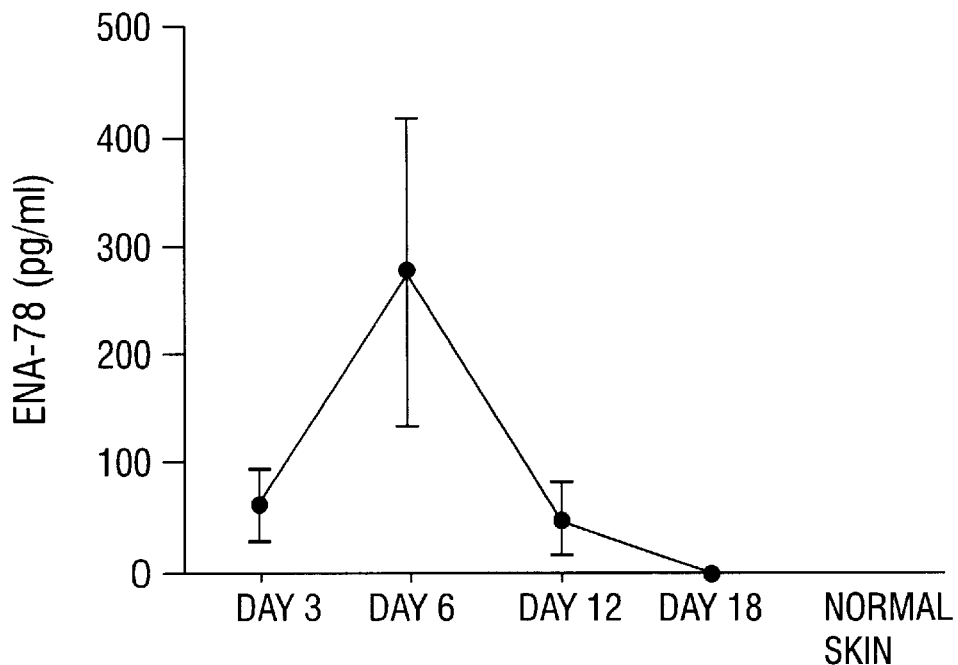
Figure 9D:
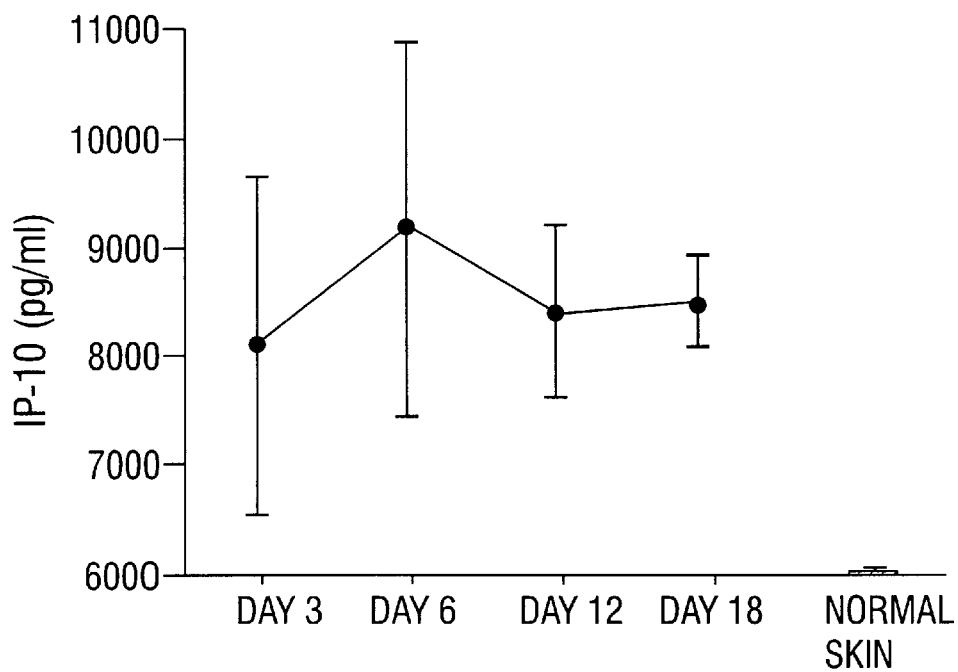
Figure 9E:
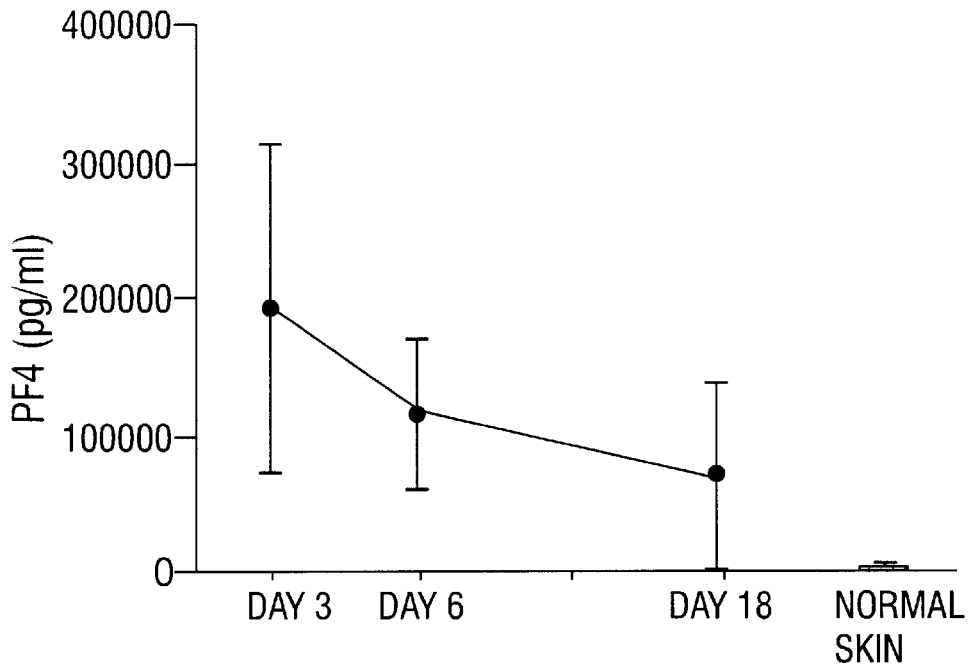
Figure 9F:
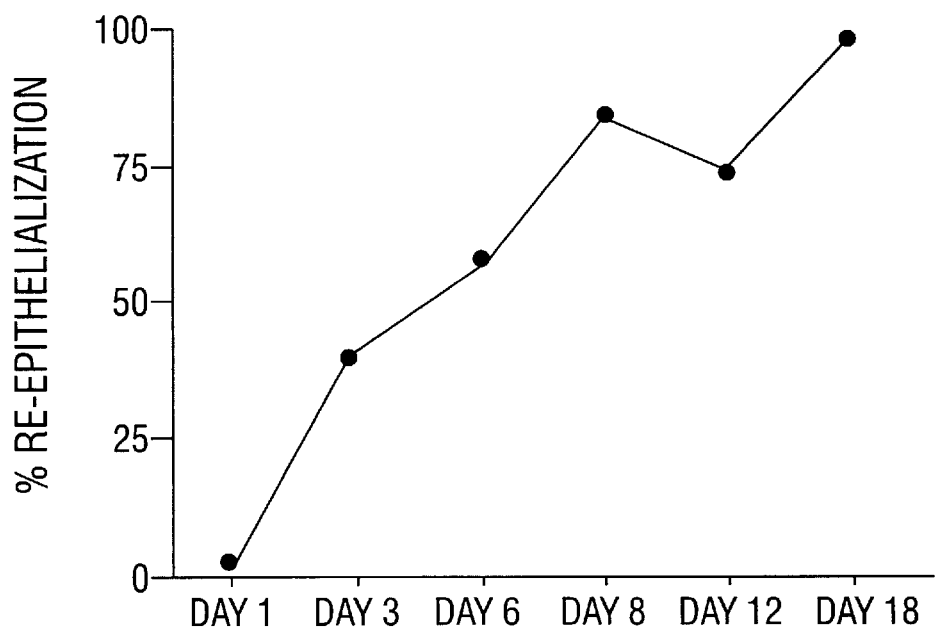

PF4, IL-8, and ENA-78 were significantly elevated from the dressings isolated from patients undergoing occlusive pressure polyurethane hydrofoam dressings, as compared to either the dressing alone or dressing spiked with recombinant CXC chemokine (FIG. 8D, FIG. 8E, FIG. 8F, respectively).

Furthermore, the inventors studied levels of CXC chemokines in a temporal manner from patients undergoing therapy for chronic venous stasis leg ulcers with occlusive hydrocolloid dressings. All patients had evidence of clinical healing of their wounds by week 8. Wound fluid was extracted from their dressings weekly, and CXC chemokines were assessed by specific ELISA. The dressing wound fluid during healing demonstrated that PF4 and IP-10 were elevated from 2 to 4 weeks, which was followed by an increase in IL-8, ENA-78, and GROα from 4 to 8 weeks. Interestingly, 2 mm punch biopsies from the margin and centers of the healing ulcers obtained at 0, 1, and 4 weeks demonstrated increasing concentrations of IP-10, whereas, the wound center demonstrated a pattern of CXC expression similar to that of the dressings.

These findings suggest that these biological dressings may function as a reservoir for the maintenance of CXC chemokine in juxtaposition with the chronic wound and influence the progress of wound healing.

EXAMPLE VII

The Human Skin/SCID Mouse Chimera Skin Transplantation Model

A number of studies in vivo have studied the process of wound repair in various animal models (Davidson, 1992; Clark, 1993; Stout et al., 1993). However, since differences exist between animal and human skin, the ideal in vivo model is to study wound repair in human skin. While studies have been performed in vivo in human skin to characterize the expression of adhesion molecules and cytokines (Griffiths et al., 1991; Leung et al., 1991), these studies are limited and have not provided information regarding the potential role or contribution these molecules play in mediating skin lesions.

In order to characterize the qualitative and quantitative presence of the CXC cytokines and determine their net contribution to human wound repair in vivo, the inventors have modified a recently described model (Yan et al., 1993), and transplanted full thickness human skin onto severe combined immunodeficient (SCID) mice to create a human skin/SCID mouse chimera.

One of the major strengths of this model system is that human skin is utilized for all of the studies. From a morphological perspective, the architecture of the epidermis and dermis in human skin is very distinctive, if not unique. In no other species are the dermal papillae as well developed as they are in human skin, and human epidermis displays a characteristic basket-weave configuration in the stratum corneum (Bosma et al., 1983). Thus, both epidermal and dermal components are anatomically distinctive and obviously critical functional interactions are dependent on important spatial considerations. These structure/function determinants are preserved by using full-thickness skin samples that not only include intact viable epidermis that produces a normal stratum corneum, but also papillary and reticular dermis to ensure the important crosstalk communication between epidermis and dermis is maintained.

For these morphological reasons, this model system is clearly superior to previous wound healing models using rodents or pig skin as substitutes for human skin. The model retains normal human skin histology 4 weeks post-xenograft transplantation without evidence of inflammation and with a normal distribution of human dermal dendritic cells (DDC) by immunohistochemical localization XIIIa. Furthermore, in the context of the evolution of wound repair in this model, the generation of granulation tissue retains its human origin (Juhasz et al., 1993).

Interestingly, even in the absence of T and B cells in the SCID mouse, using the human skin/SCID mouse chimera model the inventors created a secondary intention wound with a 2 mm punch biopsy and demonstrated that the skin wound at day 3 showed all of the salient features of the complex, yet overlapping processes of coagulation, inflammation, formation of granulation tissue, and the initiation of re-epithelialization of the wound. These features are analogous to the events in human acute wounds.

In subsequent studies, human skin was engrafted for 4 weeks on a cohort group of SCID mice, followed by the induction of a secondary intention (2 mm) wound on the human skin xenograft. The mice were sacrificed in a temporal manner over the next 18 days post-wound. Punch biopsies (4 mm) skin specimens were obtained from the wounds and analyzed by either light microscopy for evidence of re-epithelialization or measurement of CXC chemokines by specific ELISA.

The CXC chemokines were significantly elevated from the acute wounds, as compared to a 4 mm punch biopsy of normal human skin on SCID mice (FIG. 9A, FIG. 9B, FIG. 9C, FIG. 9D, FIG. 9E and FIG. 9F). The CXC chemokines that are promoters of angiogenesis and re-epithelialization were found to have distinct patterns of expression with peak levels of IL-8, ENA-78, and GRO$\alpha$ achieved by 3 to 6 days post-wound. All of these CXC chemokines declined to baseline levels by day 18, that were equivalent to normal skin.

In contrast, IP-10 a CXC chemokine with angiostatic activity and inhibitory effects for keratinocyte proliferation and chemotaxis remained elevated, even at day 18 post-wound. Although PF4 was significantly elevated by day 3 post-wound, PF4 levels were seen to decline toward baseline over the next 12 days. Significant human neovascularization was seen at day 6 post-wound by immunolocalization of anti-human CD34. 100% re-epithelialization of the wound occurred by day 18 post-wound.

These findings suggest that a potential dynamic/temporal imbalance exists in the expression of CXC chemokines during acute wound repair. This imbalance favors an early predominance of CXC chemokines that are promoters of angiogenesis and re-epithelialization. This is consistent with their importance in mediating neovascularization and initiation of re-epithelialization post-wound. However, by day 12 to 18, the balance shifts in favor of the CXC chemokines with angiostatic and inhibitory activity for keratinocyte proliferation and chemotaxis. This finding is consistent with the skin returning to homeostasis with a profile of more mature granulation tissue and control of keratinocyte hyperplasia.

EXAMPLE VIII

The ELR Motif Controls the Endothelial Cell Chemotactic and Keratinocyte Proliferative Activities of the CXC Chemokines To support their discovery that the ELR motif controls the angiogenic activity of the CXC chemokines, the inventors also noted that the interferons (IFN$\alpha$, IFN$\beta$, and IFN$\gamma$) all inhibit wound repair, especially angiogenesis and re-epithelialization (Sidky and Borden, 1987; Zetter, 1988; McKay and Leigh, 1991; Symington, 1989; Yaar et al., 1985; Nickoloff et al., 1991; Shipley et al., 1986; Nickoloff and Mitra, 1989; Klagsbrun and D'Amore, 1991; Pober and Cotran, 1990; Stout et al., 1993; Demaeyer and Demaeyer-Guignard, 1988). These cytokines up-regulate IP-10 and MIG from a number of cells, including keratinocytes, fibroblasts, endothelial cells, and mononuclear phagocytes (Farber, 1993; Kaplan et al., 1987).

This suggested to the inventors that the interferons exert their negative influence in the context of wound repair by up-regulating the production of IP-10 and MIG, that act in an autocrine and paracrine manner to suppress angiogenesis. As IFN$\alpha$, IFN$\beta$, and IFN$\gamma$ are potent inhibitors of both monocyte-derived IL-8 and ENA-78 (Gusella et al., 1993), this supports the concept that IFN$\alpha$, IFN$\beta$ and IFN$\gamma$ shift the biological balance of CXC chemokines toward those chemokines that lack the ELR motif and are angiostatic.

Figure 10:
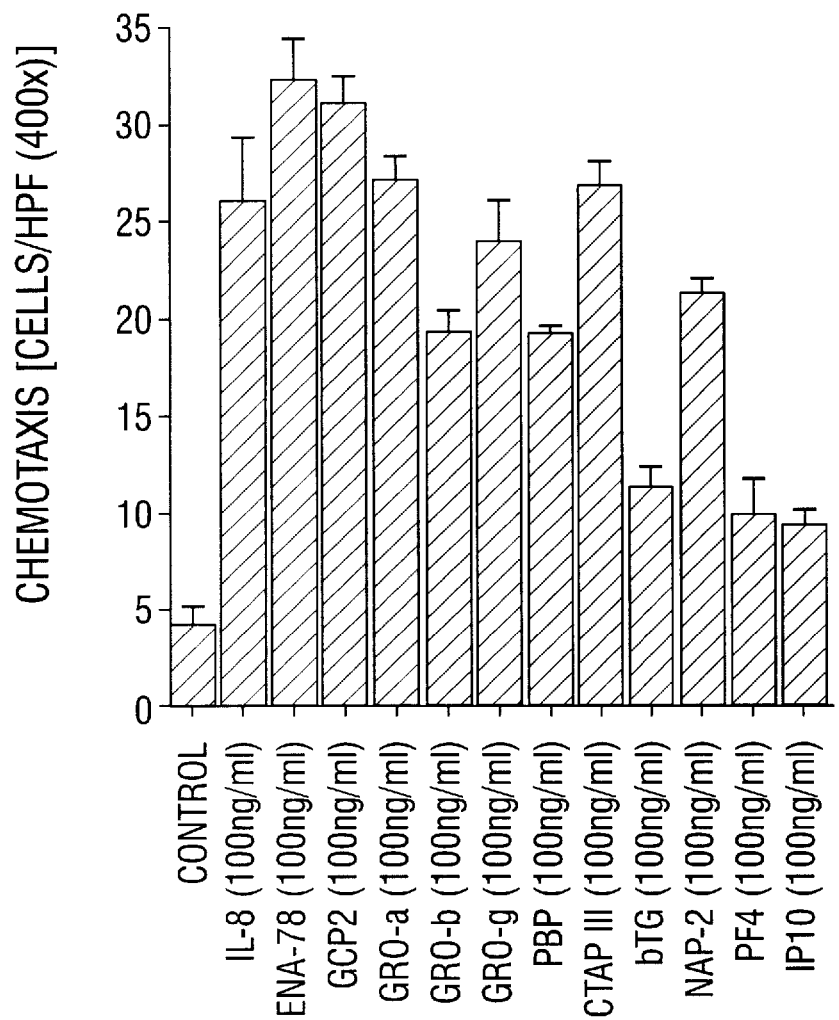
FIG. 10. Endothelial cell chemotaxis in response to CXC chemokines. Control=control media (DME+0.1%).

To confirm this hypothesis, the inventors performed endothelial cell chemotaxis in the presence or absence of CXC chemokines that contain the ELR motif (IL-8, ENA- 78, GCP-2, GROα, GROβ, GROγ, PBP, CTAP-III, and NAP-2) and CXC chemokines that lack the ELR motif (IP-10 and PF4) (FIG. 10). In a similar fashion to IL-8, all of the CXC chemokines that contained the ELR motif demonstrated significant endothelial cell chemotactic activity, whereas the endothelial cell chemotactic activity induced by either IP-10 or PF were similar to control (background). This is clearly shown in Table 3.

TABLE 3

Endothelial Cell Chemotaxis [Cells/HPF (400X)]

| Condition (10 nM) | Fold increase over control |
|---|---|
| IL-8 | 6.05 ± 0.744 |
| ENA-78 | 7.51 ± 0.465 |
| GCP2 | 7.21 ± 0.349 |
| GRO$_\alpha$ | 6.28 ± 0.279 |
| GRO$_\beta$ | 4.49 ± 0.205 |
| GRO$_\gamma$ | 5.51 ± 0.511 |
| PBP | 4.42 ± 0.134 |
| CTAIII | 6.21 ± 0.279 |
| bTG | 2.63 ± 0.205 |
| NAP2 | 4.88 ± 0.134 |
| MIG | 0.856 ± 0.081 |

Figure 11:
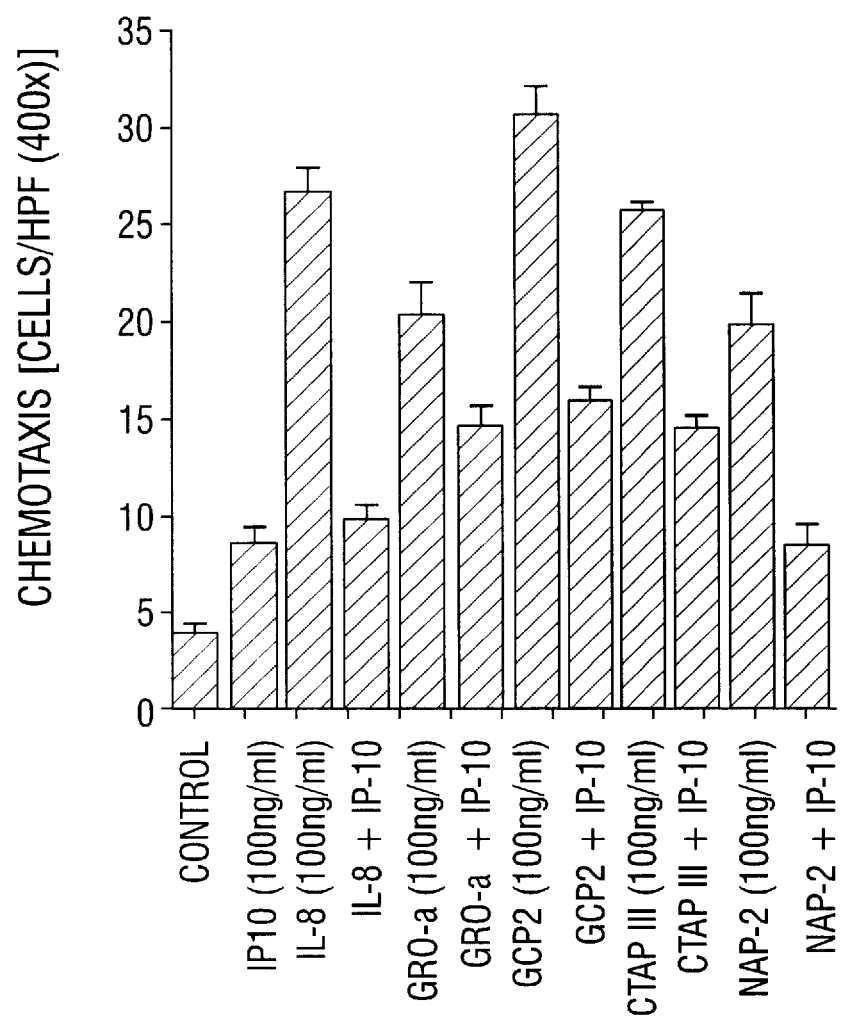
FIG. 11. Endothelial cell chemotaxis in response to CXC chemokines. IP-10 attenuates endothelial cell chemotactic activity induced by ELR motif containing CXC chemokines. Control=media alone (DME+0.1%).

To delineate whether IP-10 (lacking the ELR motif) could modulate the (ELR motif) CXC chemokine-induced endothelial cell chemotactic activity, IL-8, GROα, CTAP-III, and NAP-2 were assessed for endothelial cell chemotaxis in the presence of IP-10 (FIG. 11). The presence of IP-10 significantly attenuated endothelial cell chemotactic activity in response to CXC chemokines containing the ELR motif. Moreover, PF4 in a similar fashion to IP-10, also attenuated CXC chemokine-induced endothelial cell chemotactic activity.

Figure 12:
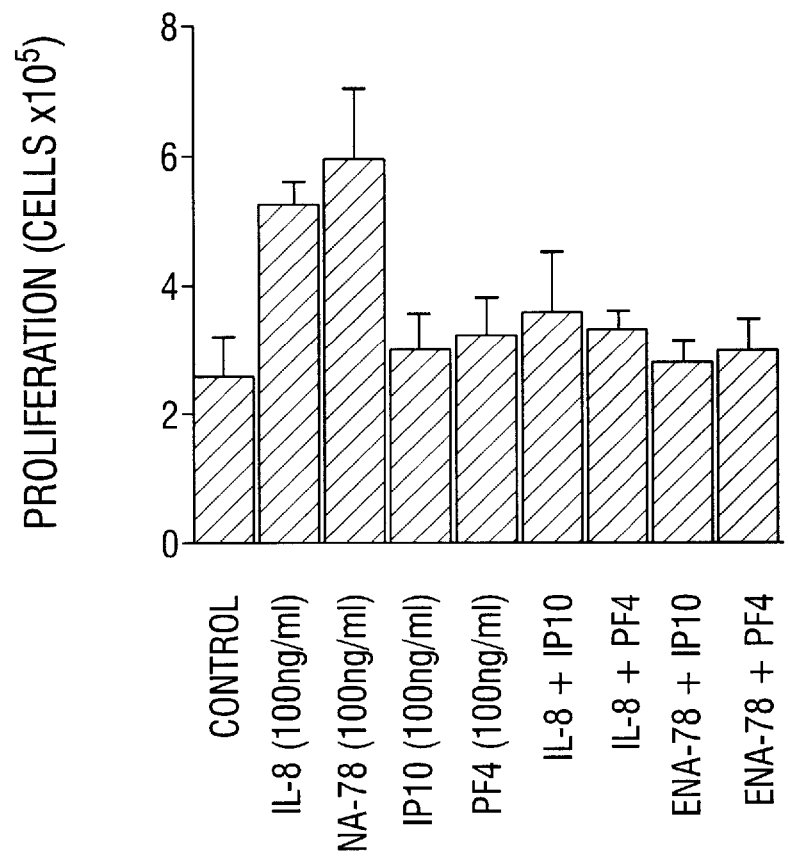
FIG. 12. Keratinocyte proliferation in response to CXC chemokines. Keratinocytes in defined media containing EGF were exposed to interleukin-8 (IL-8), epithelial neutrophil activating protein (ENA-78), gamma interferon inducible protein (IP-10), platelet factor 4 (PF4), a combination of IL-8 (100 ng/ml) and IP-10 (100 ng/ml), a combination of IL-8 (100 ng/ml) and PF4 (100 ng/ml), a combination of ENA-78 (100 ng/ml) and PF4 (100 ng/ml) for 48 hrs. $2 \times 10^5$ keratinocytes were initially plated in 35 mm culture plates in the presence of CXC chemokines and cultured for 48 hrs, followed by trypsinization and cell count.

The inventors further performed keratinocyte proliferation assays in the presence or absence of varying concentrations of IL-8, ENA-78, IP-10, and PF4 either alone or in combination. ENA-78, in a similar fashion to IL-8, was again found to significantly augment keratinocyte proliferation (FIG. 12). Both PF4 and IP-10 again failed to induce keratinocyte proliferation over unstimulated controls (FIG. 12). When keratinocytes were exposed to either IL-8 or ENA-78 in combination with either IP-10 or PF4 in equal concentrations, keratinocyte proliferation was significantly attenuated (FIG. 12).

EXAMPLE IX

IP-10 is an Inhibitor of IL-8 and bFGF-Induced Angiogenesis

In this example, the inventors provide further evidence that interferon γ-inducible protein 10 (IP-10) (lacking the ELR motif) is a potent inhibitor of angiogenesis. IP-10 is shown to inhibit both IL-8 and basic fibroblast growth factor (bFGF)-induced endothelial chemotaxis in vitro and corneal neovascularization in vivo in a dose-dependent manner.

Human recombinant IL-8 and IP-10 were purchased from Pepro Tech Inc. (Rocky Hill, N.J.). bFGF was purchased from R & D Systems Inc. (Minneapolis, Minn.). In statistical analyses, data are expressed as means±SEM. Data that appeared to be statistically significant were compared by Student's t-test and considered significant if p<0.05.

Endothelial cell chemotaxis was performed in 48-well chemotaxis chambers (Nucleopore Corp.) as described in Example III and by Koch et al. (1986; 1992b) and Smith et al. (1994). The results here were expressed as the number of endothelial cells that migrated per HPF. Each sample was assessed in triplicate. Studies were repeated at least three times.

In vivo angiogenic activity was assayed in the avascular cornea of Long Evans rat eyes, as previously described in Example IV and by Koch et al. (1991b; 1992b); Strieter et al. (1992a); and Smith et al. (1994). Six days after implantation, animals were pretreated i.p. with 1000 Units of heparin, anesthetized with ketamine (150 mg/Kg), and perfused with 10 mls of colloidal carbon via the left ventricle. Corneas were harvested and photographed. Positive neovascularization responses were recorded only if sustained directional in growth of capillary sprouts and hairpin loops towards the implant were observed. Negative responses were recorded when either no growth was observed or when only an occasional sprout or hairpin loop displaying no evidence of sustained growth was detected.

Figure 13:
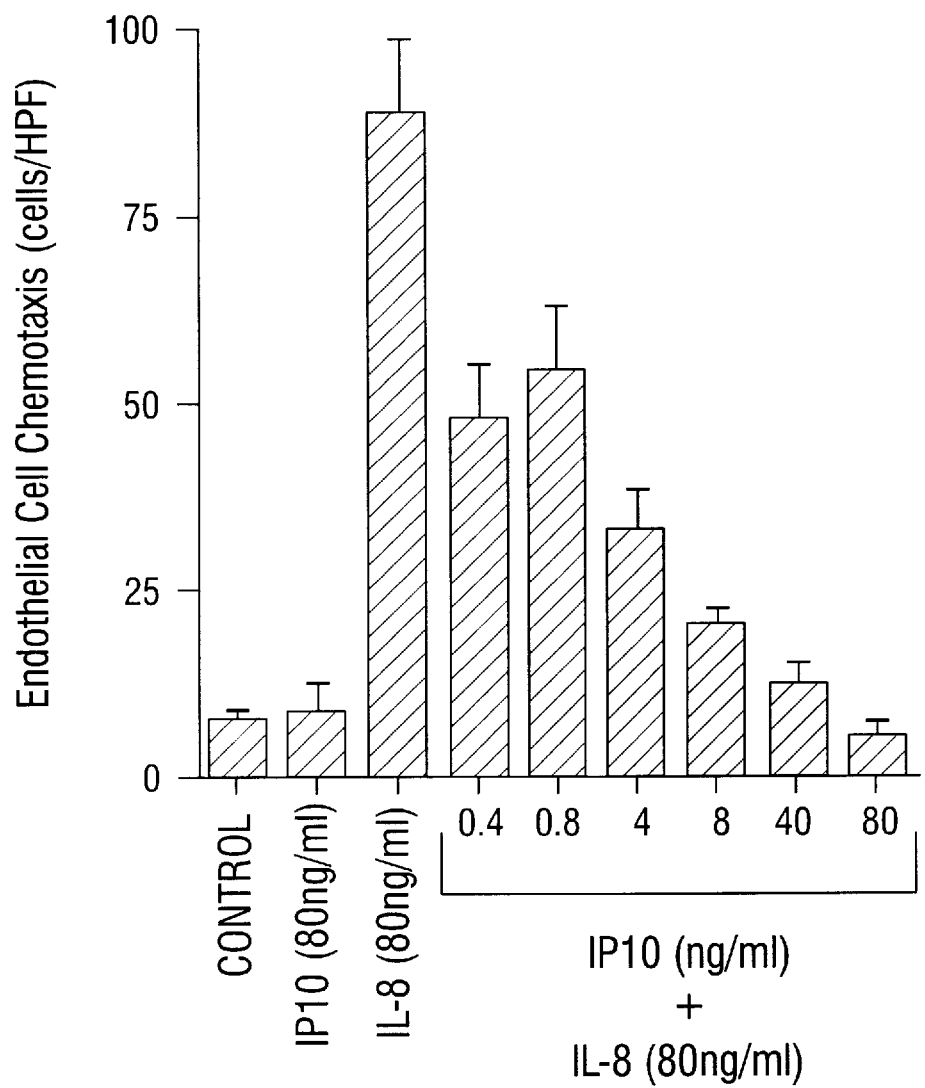
FIG. 13. Endothelial cell chemotaxis in the presence or absence of IL-8, with or without IP-10. Control is media alone.
Figures 14A, 14B, 14C, 14D:
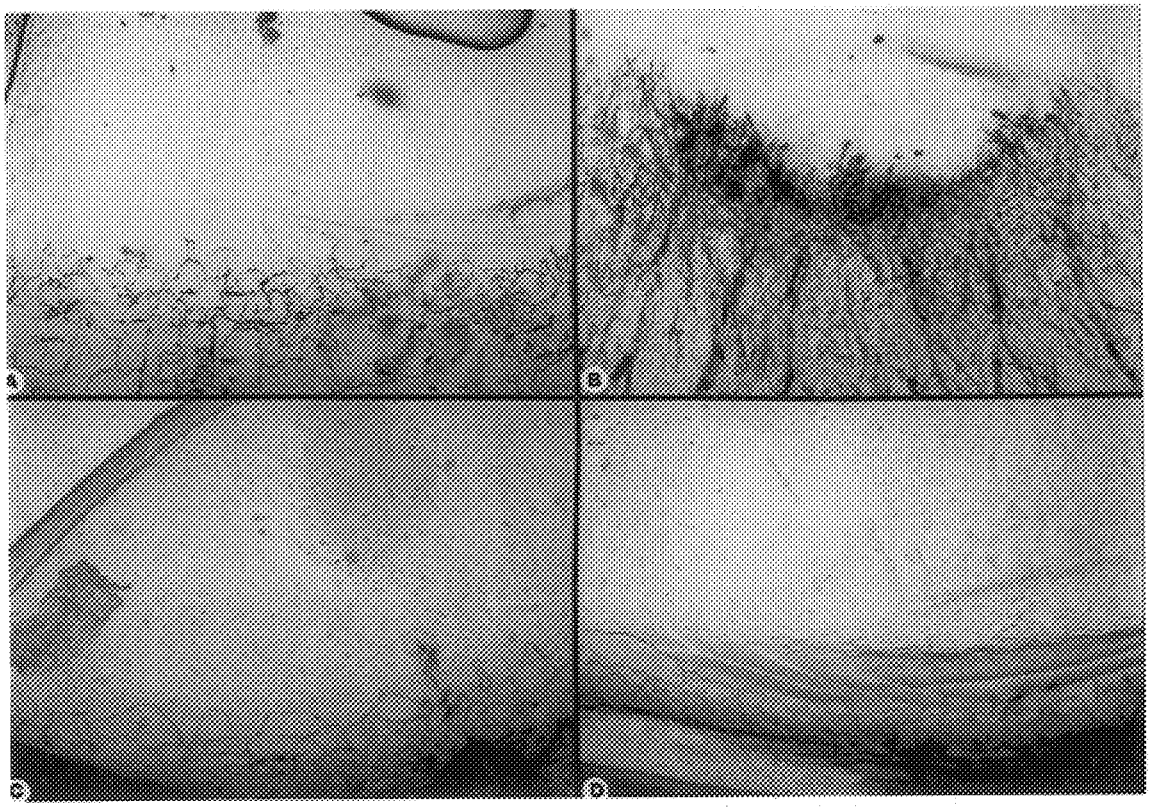
FIG. 14A, FIG. 14B, FIG. 14C and FIG. 14D. Rat corneal micropocket assay of neovascularization in the presence or absence of IL-8, with or without IP-10.

To assess the affect of IP-10 on angiogenic activity, the inventors began their evaluation by utilizing endothelial cell chemotaxis in the presence or absence of IL-8 (80 ng/ml) and varying concentrations of IP-10 (0.4 ng/ml to 80 ng/ml) (FIG. 13). IL-8 alone (89±10 cells per HPF) resulted in maximal endothelial chemotaxis, as compared to either media (control; 7.5±1.5 cells per HPF) or IP-10 (8±4 cells per HPF) alone.

When IL-8 (80 ng/ml) was combined in the presence of varying concentrations of IP-10 (0.4 ng/ml to 80 ng/ml), IP-10 was found to significantly attenuate IL-8 induced chemotactic activity by 46% to 93%, respectively. The inhibitory potency of IP-10 for IL-8-induced endothelial chemotaxis was similar to that of PF4.

To determine the affect of IP-10 on neovascularization in vivo, the inventors next evaluated the effect of this chemokine on IL-8-induced angiogenesis utilizing the rat corneal micropocket model (Koch et al., 1992b; Strieter et al., 1992a; Smith et al., 1994). As shown in FIG. 14A, FIG. 14B, FIG. 14C and FIG. 14D, Hydron pellets alone or incorporated with either IP-10 (80 ng), IL-8 (80 ng), or IL-8 (80 ng) combined with IP-10 (80 ng) were embedded into the normally avascular rat cornea. IL-8 induced positive correal angiogenic responses in >90% of the corneas (n=6) without evidence for neutrophilic infiltration.

In contrast, Hydron pellets alone (n=6) or incorporated with IP-10 (n=6) resulted in a positive neovascular response in <17% of the corneas. Moreover, when IP-10 was added to Hydron pellets incorporated with IL-8, IP-10 significantly abrogated IL-8 induced angiogenic activity in >83% of the corneas (n=6).

Figure 15:
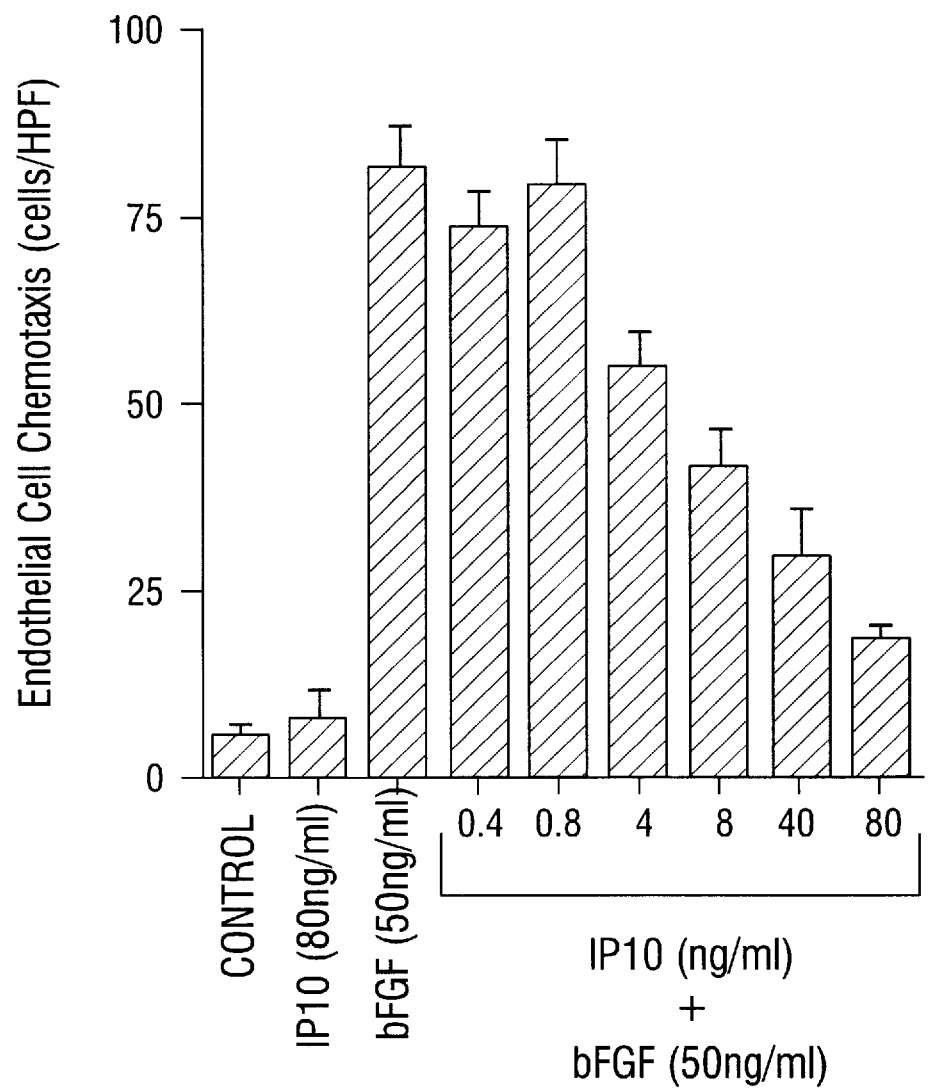
FIG. 15. Endothelial cell chemotaxis in the presence or absence of bFGF, with or without IP-10. Control is media alone.
Figures 16A, 16B:
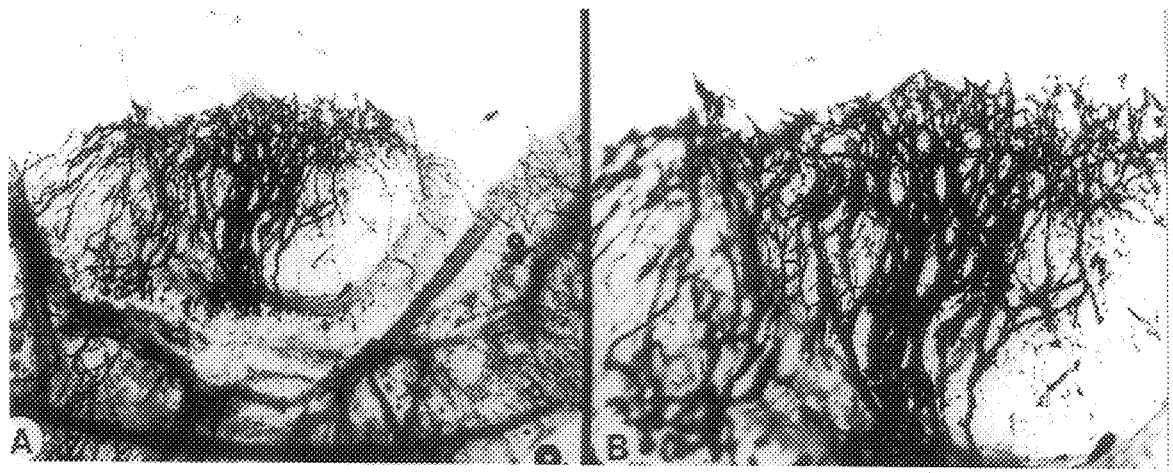
Figures 17A, 17B:
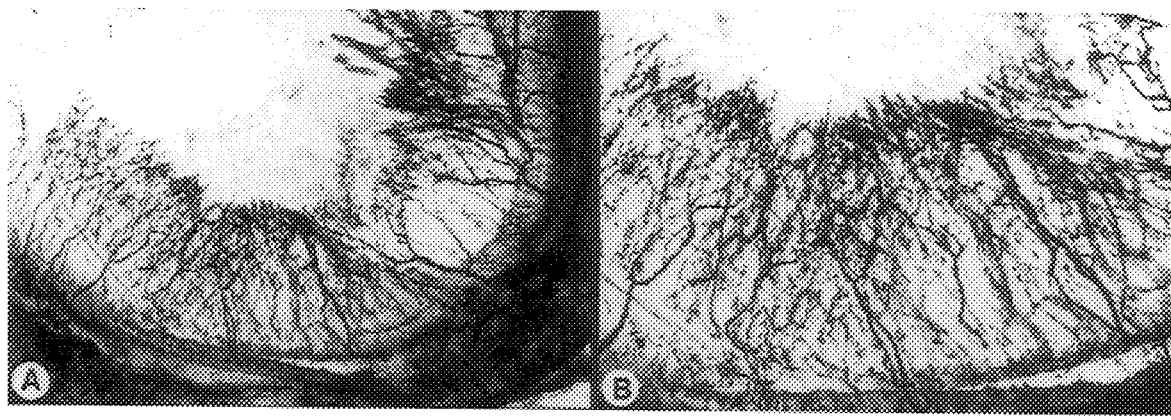
FIG. 17A, FIG. 17B, FIG. 17C, FIG. 17D, FIG. 17E and FIG. 17F. A second example of a rat corneal micropocket assay of neovascularization in the presence or absence of bFGF, with or without IP-10.
Figure 17C:
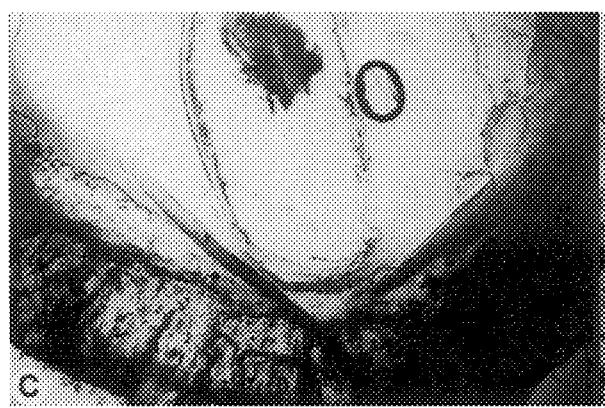
Figure 17D:
Figures 17E, 17F:
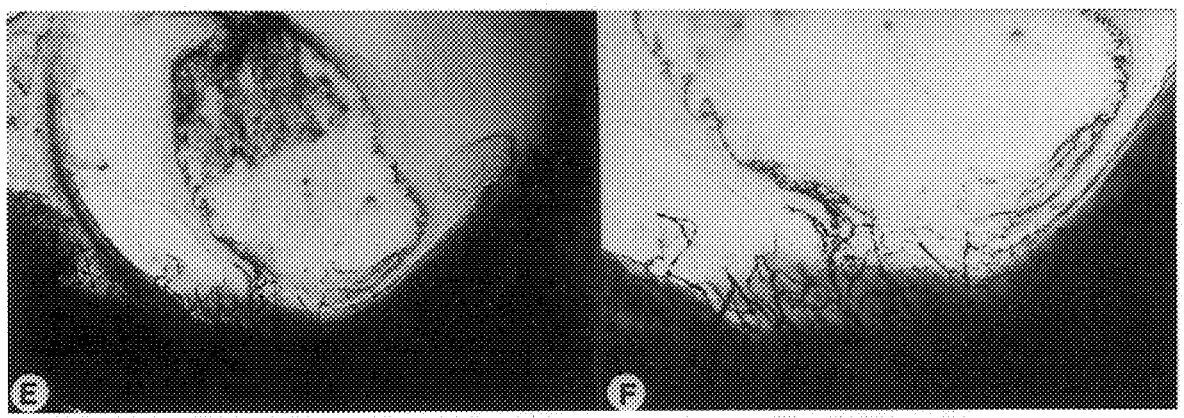
Figure 18A:
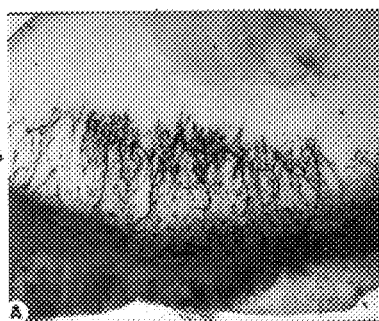
FIG. 18A, FIG. 18B, FIG. 18C, FIG. 18D, FIG. 18E and FIG. 18F. Representative photograph of corneal neovascularization.
Figure 18B:
Figure 18C:
Figure 18D:
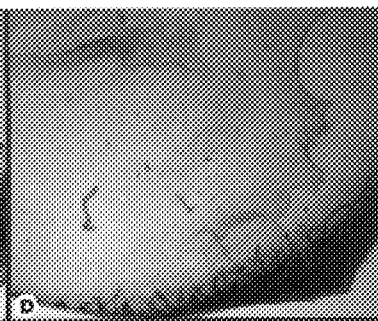
Figure 18E:
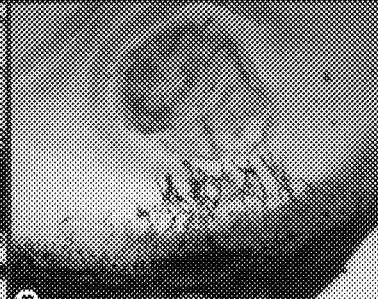
Figure 18F:
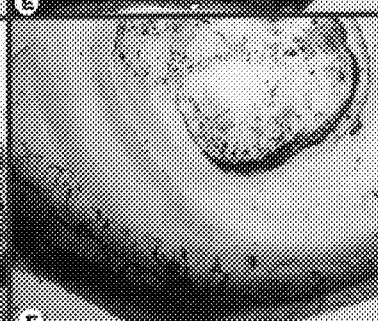

The inventors next determined whether IP-10 could attenuate the angiogenic activity of bFGF, a well studied angiogenic factor and a non-chemokine (Folknian and Cotran, 1976; Folkman and Klagsbrun, 1987; Leibovich and Weisman, 1988; Bouck, 1990), using endothelial cell chemotaxis in the presence or absence of bFGF (50 ng/ml) and varying concentrations of IP-10 (0.4 ng/ml to 80 ng/ml) (FIG. 15). bFGF alone induced maximal endothelial chemotaxis (85±5 cells per HPF), as compared to either media (control; 6±2 cells per HPF) or IP-10 (8±4 cells per HPF) alone. IP-10 in a dose-dependent manner (4 ng/ml to 80 ng/ml) was found to significantly inhibit bFGF-induced endothelial chemotaxis by 33% to 76%, respectively. These findings were similar to the affect of IP-10 on IL-8 angiogenic activity.

The inventors extended their studies to assess the affect of IP-10 on bFGF-induced neovascularization in vivo. Hydron pellets incorporated with bFGF, IP-10 (80 ng) or a combination thereof were embedded into rat corneas (FIG. 16A, FIG. 16B, FIG. 16C, FIG. 16D, FIG. 16E, FIG. 16F; and FIG. 17A, FIG. 17B, FIG. 17C, FIG. 17D, FIG. 17E, FIG. 17F). bFGF induced positive corneal angiogenic responses in 100% of the corneas (n=6). In contrast, the addition of IP-10 into Hydron pellets incorporated with bFGF (n=6) resulted in a significant reduction of bFGF-induced neovascularization within the corneas, <20% of the corneas were positive.

EXAMPLE X

IP-10 Inhibits ENA-78-, GRO- and GCP-2-Induced Angiogenesis

This example shows both that ENA-78, GCP-2, GROα, GROβ, GROγ and NAP-2, in a similar concentration to IL-8, all cause significant cornea neovascularization, and that IP-10 inhibits such angiogenesis.

The endothelial cell chemotaxis and in vivo angiogenic activity assays were performed as described in Example IX. In addition to IL-8, each of ENA-78, GCP-2, GROα, GROβ, GROγ and NAP-2 were found to induce cornea neovascularization without any evidence for inflammatory cellular infiltration.

The fact that IP-10, in equivalent molar concentrations, attenuates ENA-78-, GCP-2- and GROα-induced angiogenesis in vivo is particularly shown in FIG. 18A, FIG. 18B, FIG. 18C, FIG. 18D, FIG. 18E and FIG. 18F.

EXAMPLE XI

Figure 19A:
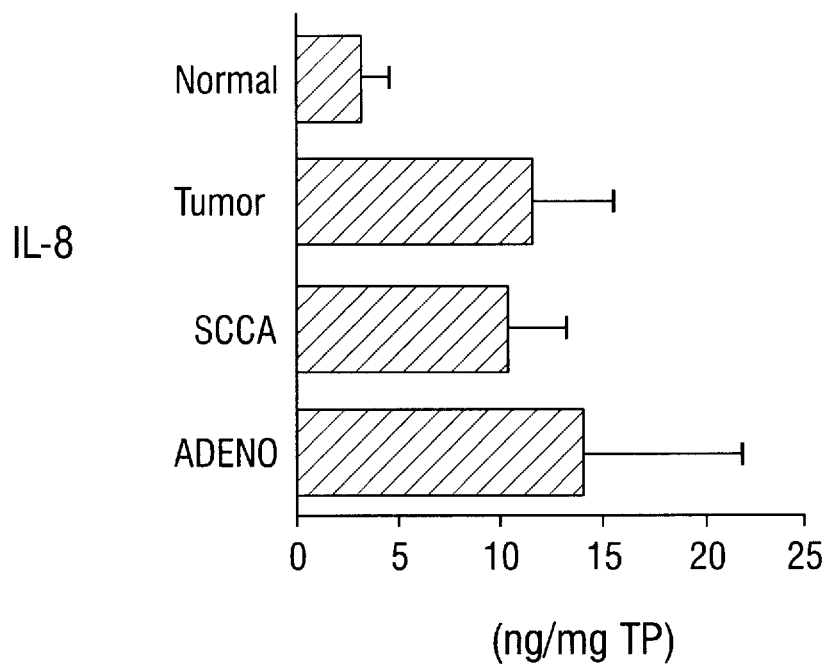
FIG. 19A, FIG. 19B, FIG. 19C, FIG. 19D and FIG. 19E. The presence of IL-8 (FIG. 19A), ENA-78 (FIG. 19B), GROα (FIG. 19C), PF4 (FIG. 19D), and IP-10 (FIG. 19E) in bronchogenic carcinoma as compared to normal lung. "Tumor" represents chemokine levels from both adenocarcinomas and squamous cell carcinomas (SCCA). Chemokines were measured by specific ELISAs from tissue aqueous extracts and normalized to total protein (TP) content.

IP-10 is Reduced in Adenocarcinomas and Inhibits Squamous Cell Carcinoma Angiogenesis In addition, to the studies of IL-8, GROα and PF4 (Example II; FIG. 19A, FIG. 19C and FIG. 19D), the inventors examined the immunohistochemical localization of ENA-78 and IP-10 in normal lung and NSCLC.

Figure 19B:
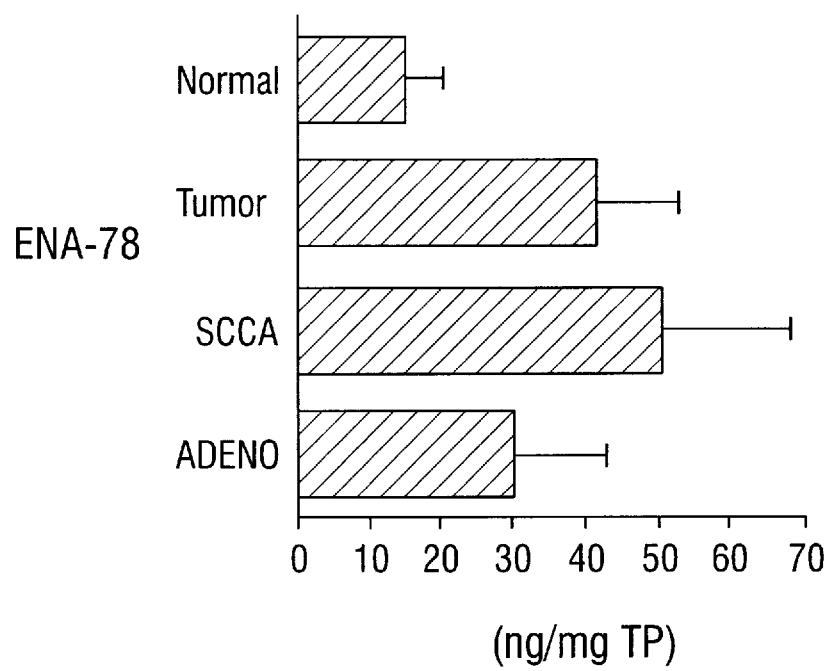
Figure 19C:
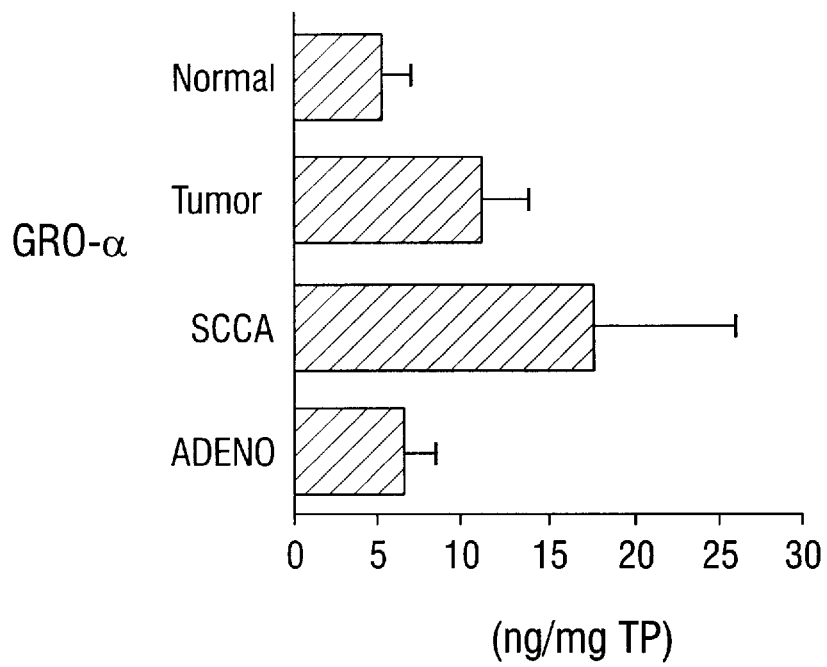
Figure 19D:
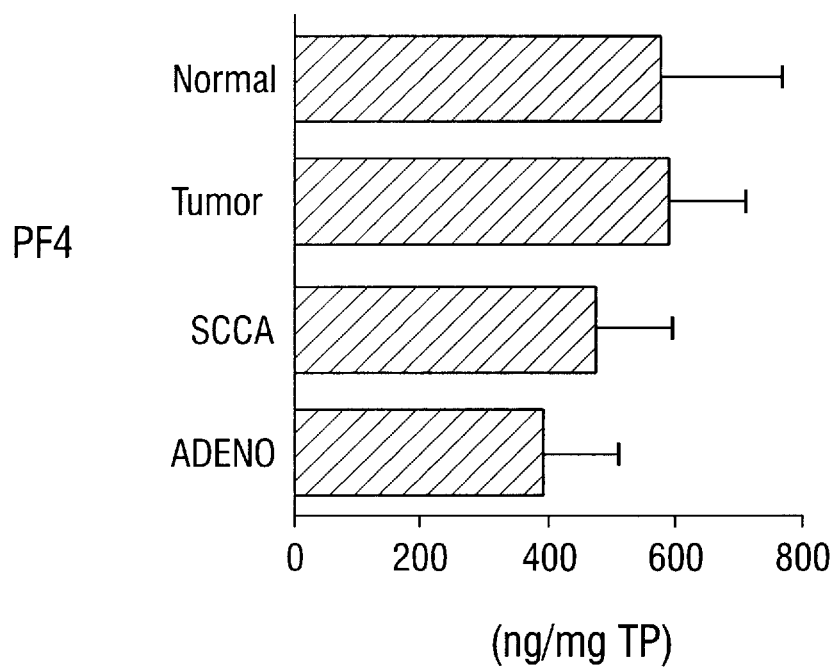

Using an ELISA, ENA-78 was found in a 3-fold excess in tumor tissue as compared to normal lung tissue, normalized to total protein (FIG. 19B). Normal lung tissue contained 15±6 ng/mg TP of ENA-78, as compared with 43.6±10 ng/mg TP for tumor specimens. There were similar elevations of ENA-78 from adenocarcinomas and squamous cell carcinomas.

Figure 19E:
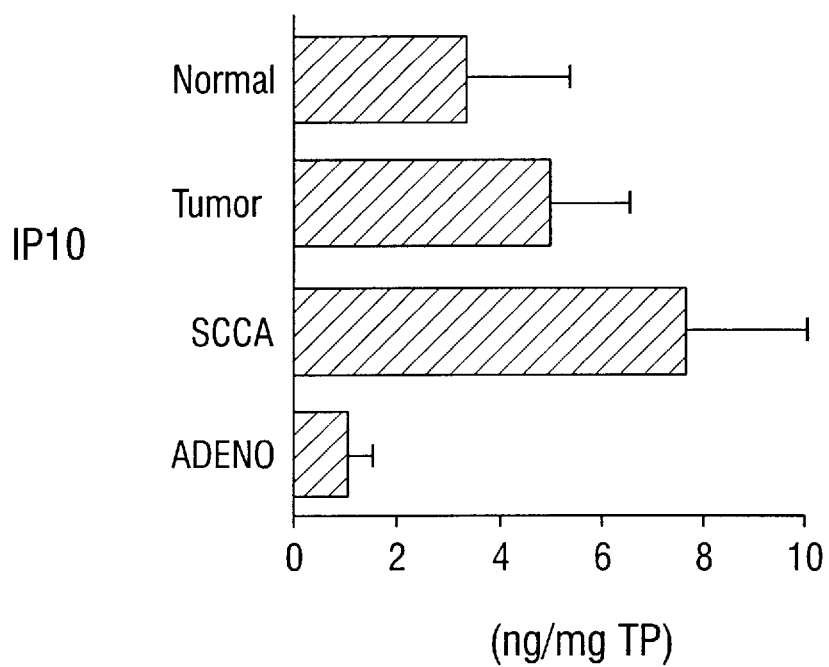

Although IP-10 levels trended toward being greater in tumors than in normal lung tissue homogenates (FIG. 19E), IP-10 was significantly lower in adenocarcinomas (0.9±0.5 ng/mg TP) than in normal lung tissue (3.6±2 ng/mg TP).

Figure 20:
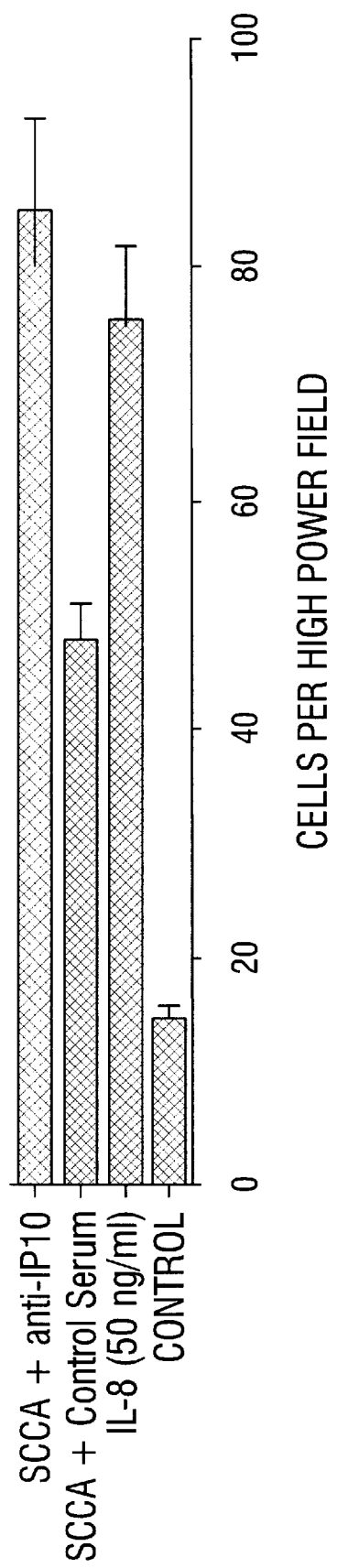
FIG. 20. The effect of Neutralizing IP-10 antibodies in squamous cell carcinoma (SCCA). Tissue aqueous extracts from SCCA were assessed for endothelial cell chemotactic activity in the presence of control or neutralizing IP-10 antibodies, as compared to control media or IL-8 standard (50 ng/ml).
Figures 21A, 21B, 21C, 21D:
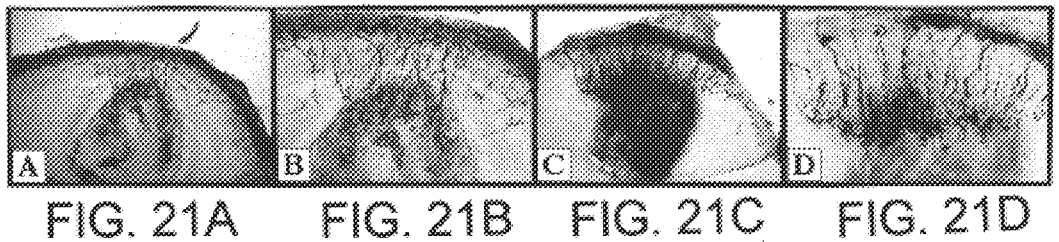
FIG. 21A, FIG. 21B, FIG. 21C and FIG. 21D. The effect of Neutralizing IP-10 antibodies in squamous cell carcinoma (SCCA). Corneal neovascularization.

To further substantiate that IP-10 acts as an endogenous angiostatic CXC chemokine to balance the effect of angiogenic factors in the context of NSCLC, the inventors assessed squamous cell carcinoma tissue homogenates for angiogenesis in the presence of neutralizing IP-10 or control antibodies. Using either endothelial cell chemotaxis (FIG. 20) or corneal micropocket model of neovascularization (FIG. 21A, FIG. 21B, FIG. 21C and FIG. 21D), it was found that neutralizing IP-10 antibodies (without evidence of LPS contamination) significantly augmented tumor-derived angiogenic activity by 2-fold. As anti-IP-10 increases angiogenesis, this is further evidence that IP-10 normally acts to decrease angiogenesis—i.e. is an angiostatic factor.

These findings further support the presence of an imbalance in ELR-CXC, as compared to non-ELR CXC chemokines, with the balance favoring a greater presence of angiogenic CXC chemokines in NSCLC tumors.

EXAMPLE XII

Engineered Variants of IL-8 with Altered ELR Motifs

In order to confirm that the ELR motif of the CXC chemokines is an important structural domain for their ability to induce angiogenesis, the inventors obtained mutants of IL-8, produced using either a strategy of synthetic production or site directed mutagenesis and expression. Wild-type/native IL-8 was mutated to either TVR-CXC/IL-8 (IP-10=TVR-CXC motif) or DLQ-CXC/IL-8 (PF4=DLQ-CXC).

In these studies, the *E. coli* K12 strain DH5αF' (Gibco/BRL) was used as host for the propagation and maintenance of M13 DNA and for expression of IL-8 proteins. Strain CJ236 (Kunkel et al., 1987) was used to prepare uracil-DNA for use in site-directed mutagenesis. pMAL-c2 (New England BioLabs) was used as the expression vector for all IL-8 cDNAs.

Site-directed mutagenesis followed the protocol described by Kunkel et al. (1987). Individual clones were sequenced using the dideoxynucleotide method (Sanger et al., 1977) with modifications described in the Sequenase® (United States Biochemical) protocol. A 197 bp Sac I (New England Biolabs) fragment from pMAL.hIL-8 (maltose binding protein-IleGluGlyArg-human IL-8 fusion protein expression vector) containing the coding sequence for the N-terminal 49 amino acids of the 72 amino acid form of human IL-8 sequence was subcloned to pUC118 (ATCC) digested with Sac I for site-directed mutagenesis. Clones containing confirmed IL-8 mutations were cleaved with Sac I and subcloned into pMAL.hIL-8 digested with Sac I.

The 72 amino acid mature form of IL-8 was amplified using polymerase chain reaction from an IL-8 cDNA in pET3a (obtained from I.U. Schraufstatter, Scripps Clinic). The 5' primer used, 5'-AGTGCTAAAGAACTTAGATG-3' (SEQ ID NO:86), encodes the beginning reading frame of IL-8, and the 3' primer, 5'-GGGATCCTCATGAATTCTC-3' (SEQ ID NO:87), contains a Bam HI restriction site immediately after the stop codon. The 220 bp PCR product was purified by gel electrophoresis, digested with Bam HI (New England Biolabs), subcloned into pMal-c2 previously digested with Xmn I and Bam HI (New England Biolabs) to generate pMal.hIL-8. Clones containing inserts were confirmed by sequencing. The wild-type IL-8 DNA sequence is represented by SEQ ID NO:77. The maltose binding protein-Factor—Xa—wild-type IL-8 sequence is represented by SEQ ID NO:78 (DNA) and SEQ ID NO:79 (amino acid).

Site-directed mutageriesis was used to modify amino acids Glu-4, Leu-5, Arg-6 to Thr Val Arg (TVR) or Asp Leu Gln (DLQ), generating TVR-IL-8 or DLQ-IL-8, respectively. Correct clones were identified by sequencing, and subcloned as SacI fragments from pUC118 into pMal.hIL-8 digested with SacI. The maltose binding protein—Factor Xet—TVR-IL-8 sequence is represented by SEQ ID NO:80 (DNA) and SEQ ID NO:81 (amino acid), and the maltose binding protein—Factor Xa—DLQ-IL-8 sequence is represented by SEQ ID NO:82 (DNA) and SEQ ID NO:83 (amino acid).

Cultures of *E. coli* strain DH5αF' harboring pMal.hIL-8, pMal.TVR-IL-8, or pMal.DLQ-IL-8 were grown in 1 liter LB media containing 50 μg/ml ampicilin to $OD_{600}$ ~0.5 at 37° C. with aeration and protein expression was induced by the addition of 0.3 mM final IPTG and continued incubation at 37° C. for 2 hours. Cells were harvested by centrifuging at 5800× g for 10 minutes, the pellet washed once in ice cold PBS, and resuspended in 10 ml ice cold lysis buffer. The resulting suspension was quick-frozen in liquid nitrogen.

After thawing, the suspension was sonicated using a Branson Sonifier 250 equipped with a microtip for 2 minutes at output setting 5 with a 40% duty cycle. The suspension was clarified by centrifugation at 9000× g, the supernatant was diluted five-fold in 10 mM NaPO$_4$, 500 mM NaCl, 1 mM EGTA, 0.25% Tween 20, pH 7.0 (column buffer), and loaded onto a 10 ml amylose resin (New England Biolabs) affinity column. After extensive washing with column buffer, the MBP-fusion protein was eluted with column buffer containing 10 mM maltose.

Mutein or wild-type IL-8 proteins were released by incubation with 1 μg Factor Xa (New England Biolabs)/OD$_{280}$ MBP fusion protein at room temperature overnight, and were then passed over a Mono S column (Pharmacia) equilibrated in 10 mM NaPO$_4$, pH 6.2, and eluted in a 0–1M NaCl gradient. 1 ml of amylose resin was added to fractions containing mutant or wild-type IL-8 protein to remove residual free MBP by incubation for 30 minutes at room temperature with gentle shaking. The resin was removed by centrifugation, and the supernatant was dialyzed against 0.5 mM NaPO$_4$, 20 mM NaCl, pH 7.5. Yields were ranged from 0.2 to 3.5 mgs for wild-type or mutant IL-8 proteins, and were ≧95% pure as assessed by SDS-PAGE and endotoxin-free (<1.0 EU/ml). Proteins were quantitated by AAA, and had accuracies of 93.1% for IL-8, 90.7% for TVR-IL-8, and 88% for DLQ-IL-8.

Figure 22A:
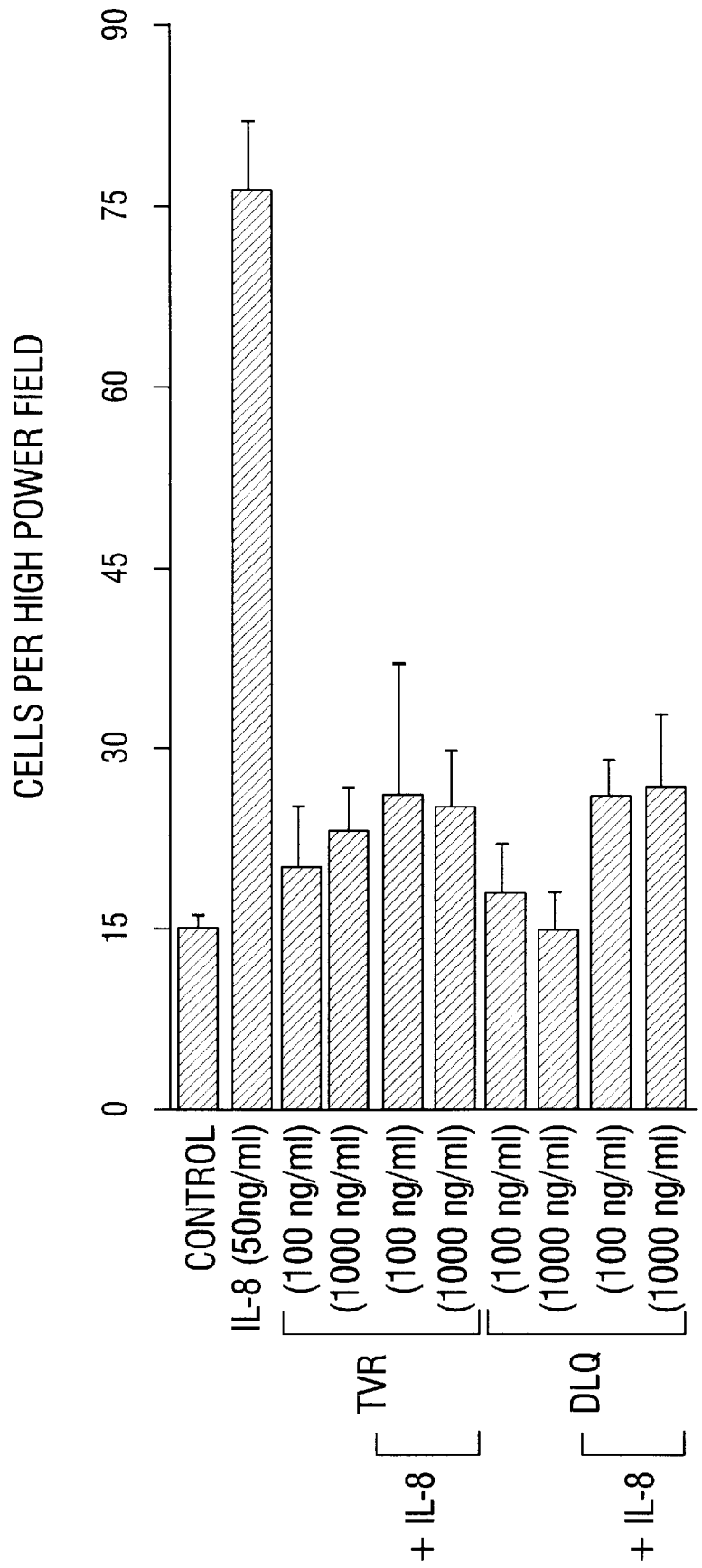
FIG. 22A, FIG. 22B and FIG. 22C. Endothelial cell chemotaxis in response to control media, IL-8 (50 ng/ml), IL-8 mutants (TRV/IL-8 and DLQ/IL-8), and IL-8 in combination with IL-8 mutants.
Figure 22B:
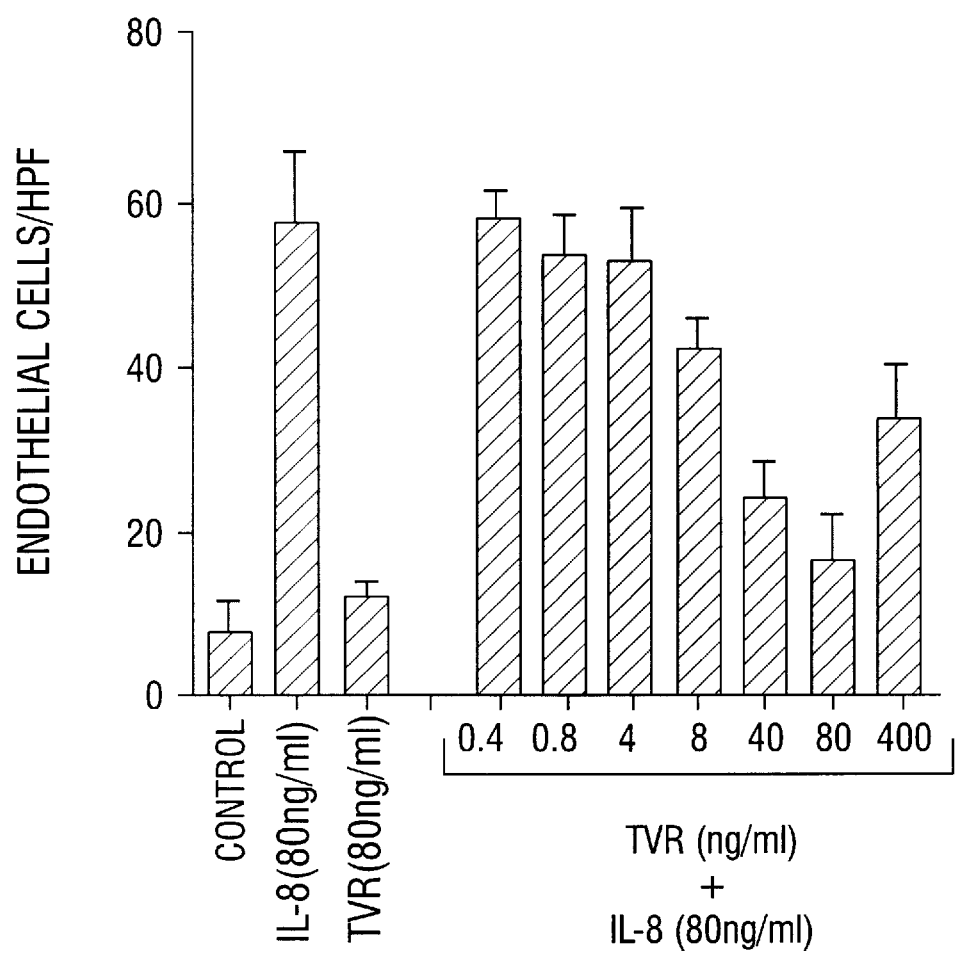
Figure 22C:
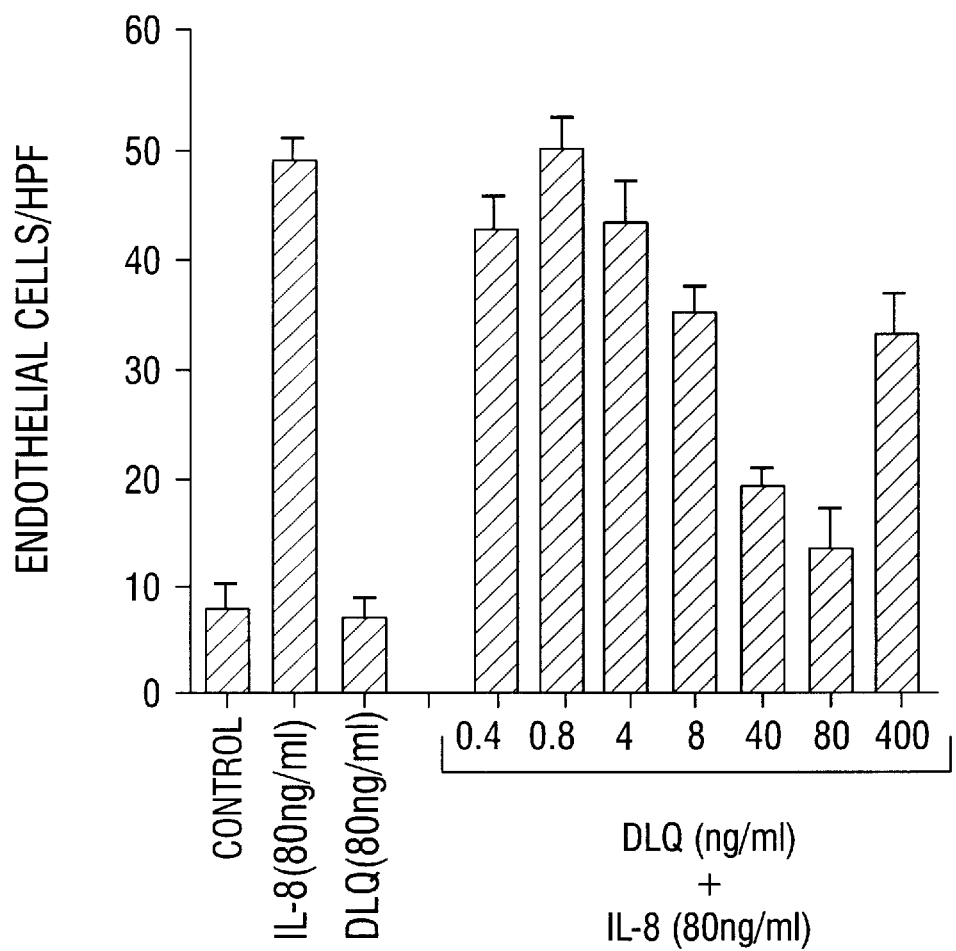
Figures 23A, 23B, 23C, 23D, 23E:
FIG. 23A, FIG. 23B, FIG. 23C, FIG. 23D and FIG. 23E. Corneal neovascularization.

The proteins so produced were used in angiogenesis studies. As shown in FIG. 22A, FIG. 22B and FIG. 22C, wild-type/native IL-8 induced significant angiogenic activity using the endothelial cell chemotaxis assay (and also using the corneal micropocket models of angiogenesis). In contrast, both the mutants of IL-8 failed to induce significant angiogenic activity above unstimulated controls.

Upon mixing IL-8 with each of the non-ELR mutants, it was found that both TRV/IL-8 and DLQ/IL-8 inhibited the actions of IL-8 in the endothelial cell chemotaxis assay. As this assay, in contrast to neutrophil assays, is an indicator of angiogenic activity, the ability of the mutants to inhibit IL-8-induced endothelial cell chemotax is is important evidence of their angiostatic properties. In fact, neither of the mutants induced neutrophil chemotaxis or inhibited the actions of IL-8 in the neutrophil cell chemotaxis assay.

In subsequent studies, both the TVR and DLQ mutants in similar concentrations to wild-type/native IL-8, using both endothelial cell chemotaxis or corneal micropocket model of neovascularization, were found to repeatedly attenuate IL-8 induced angiogenesis. The corneal micropocket studies are shown in FIG. 23A, FIG. 23B, FIG. 23C, FIG. 23D and FIG. 23E. These studies are important as they further supported the inventors' discovery that the ELR motif is a critical structural and/or functional domain that dictates whether CXC chemokines behave as either angiogenic or angiostatic factors.

Figures 24A, 24B:
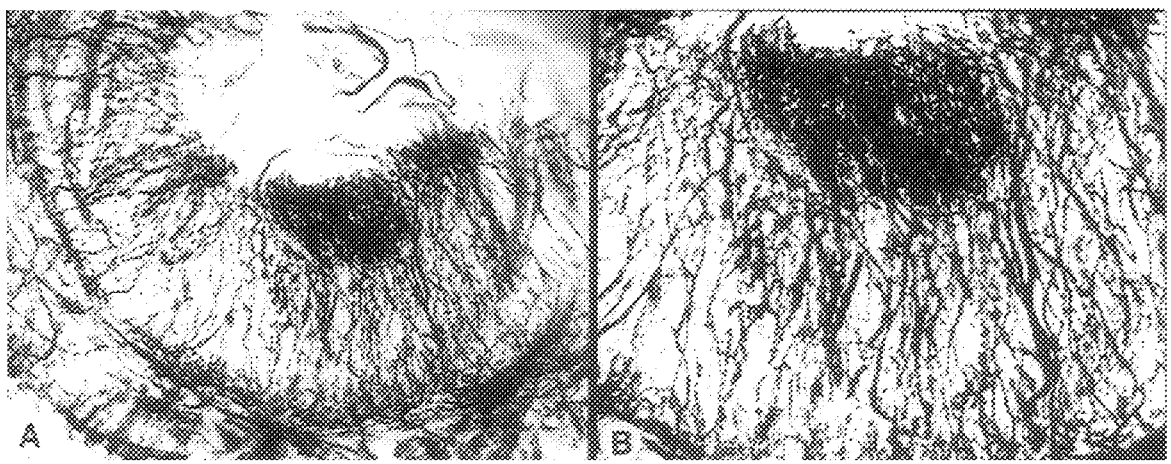
FIG. 24A, FIG. 24B, FIG. 24C, FIG. 24D, FIG. 24E and FIG. 24F. Photomicrograph of the effect of mutant TVR-IL-8 on bFGF-induced cornea neovascularization.
Figures 24C, 24D:
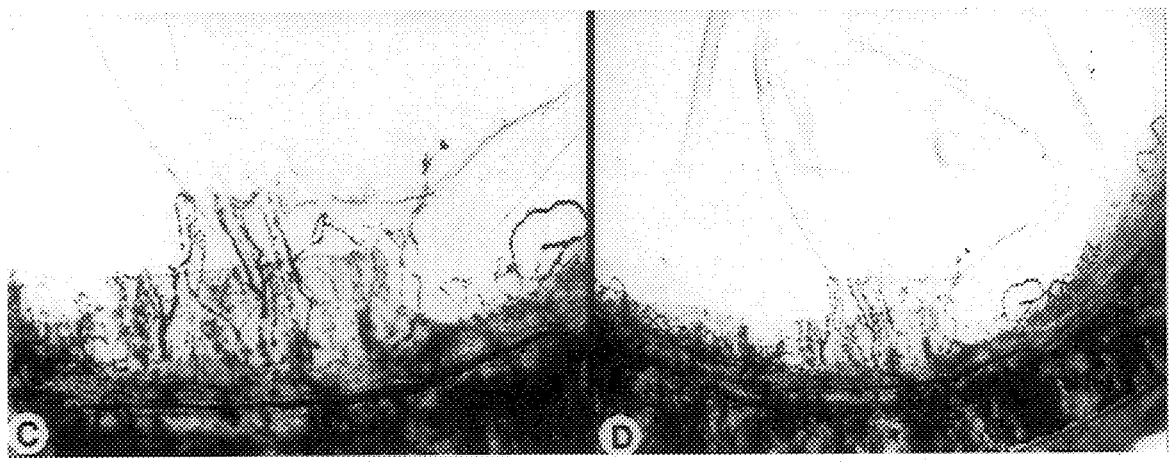
Figure 24E:
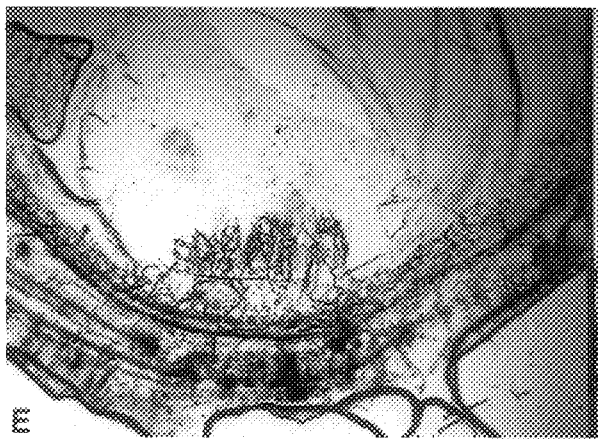
Figure 24F:
Figures 25A, 25B:
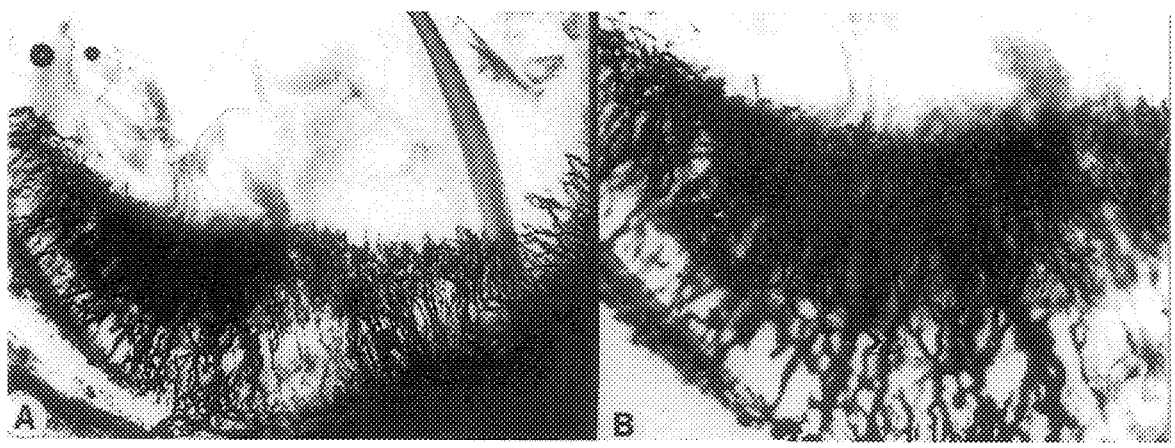
FIG. 25A, FIG. 25B, FIG. 25C, FIG. 25D, FIG. 25E and FIG. 25F. Photomicrograph of the effect of mutant TVR-IL-8 on ENA-78-induced cornea neovascularization.
Figures 25C, 25D:
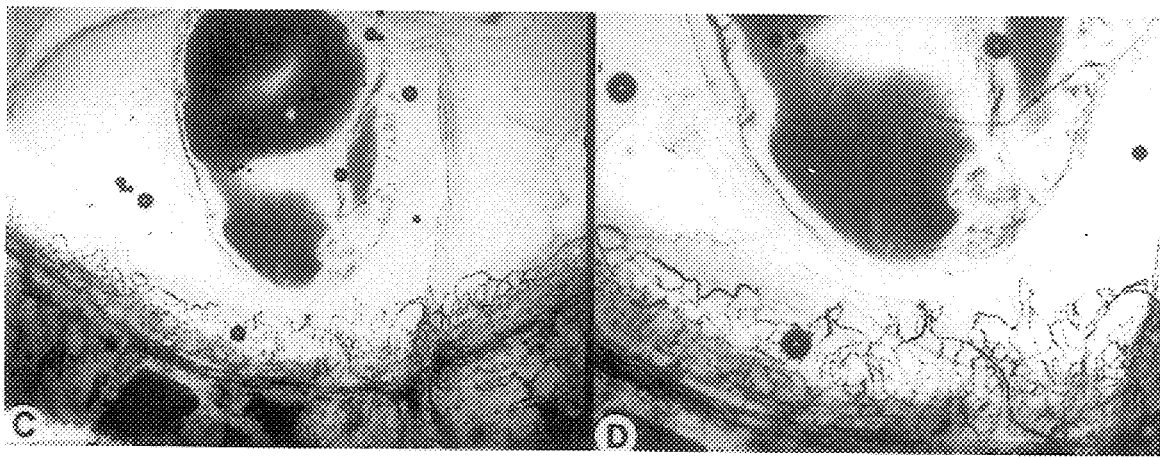
Figures 25E, 25F:
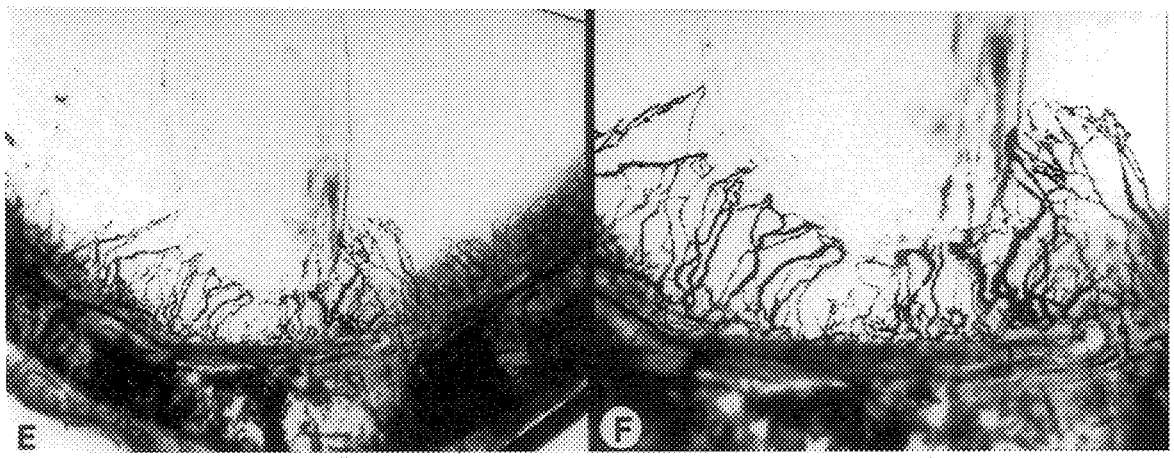

The effect of the mutant, TVR-IL-8, on cornea neovascularization induced by agents other than IL-8 was next determined. bFGF-induced cornea neovascularization is shown in FIG. 24A and FIG. 24B. The failure of TVR-IL-8 alone to induce cornea neovascularization is shown in FIG. 24C and FIG. 24D. The ability of TVR-IL-8 to inhibit bFGF-induced cornea neovascularization is shown in FIG. 24E and FIG. 24F. Similar results are shown in FIG. 25A, FIG. 25B, FIG. 25C, FIG. 25D, FIG. 25E and FIG. 25F for ENA-78-induced cornea neovascularization. TVR-IL-8 again inhibits ENA-78 effectively. These are very striking results, showing that the mutant is not simply acting as a competitive inhibitor of wild type IL-8.

Figure 26:
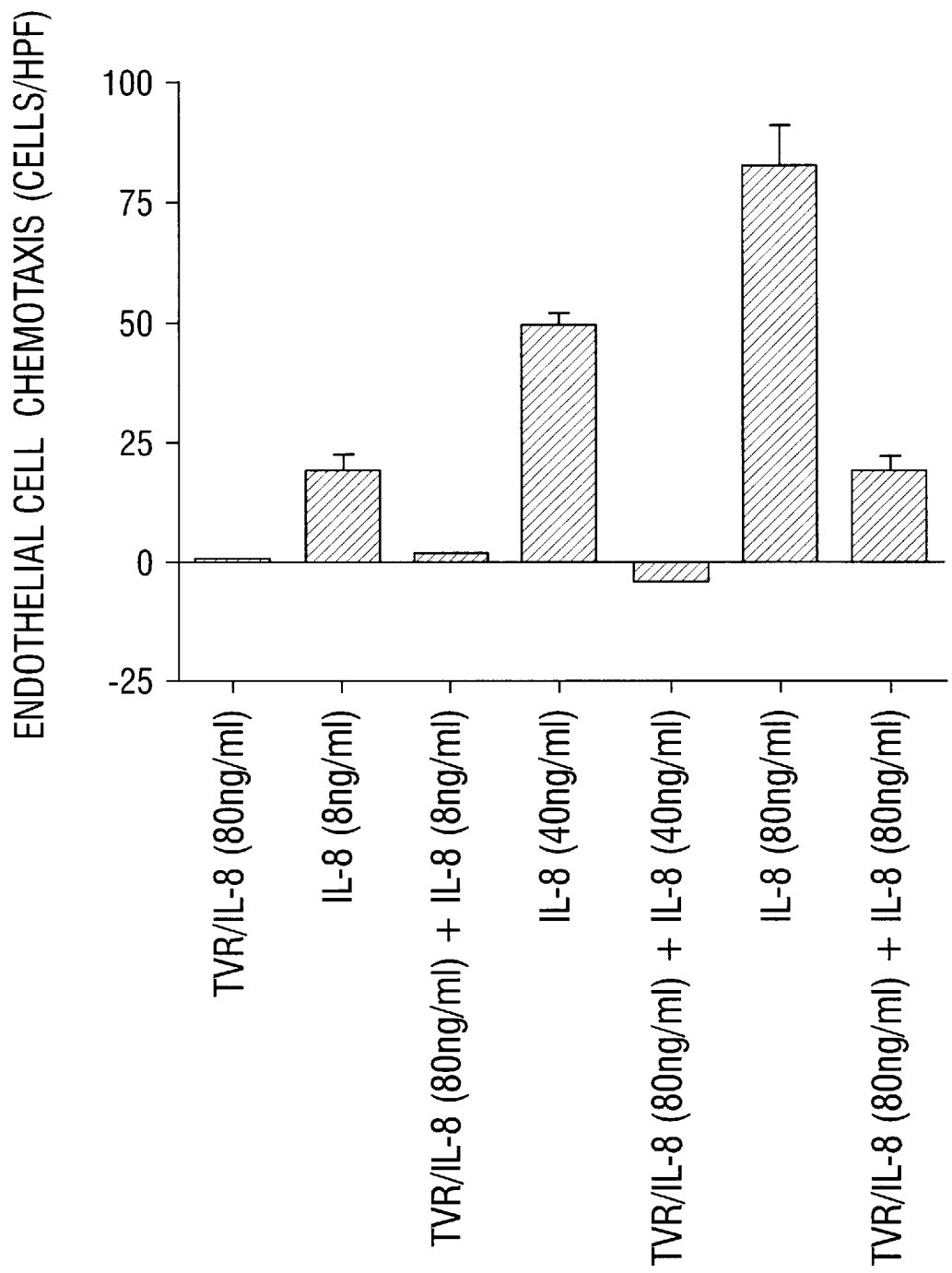
FIG. 26. Inhibition of IL-8-induced endothelial cell chemotaxis by TVR/IL-8. Endothelial cell chemotaxis is shown in response to varying concentrations (8, 40 and 80 ng/ml) of IL-8 alone and in response to varying concentrations (8, 40 and 80 ng/ml) of IL-8, each in combination with TVR/IL-8 at 80 ng/ml.
Figure 27:
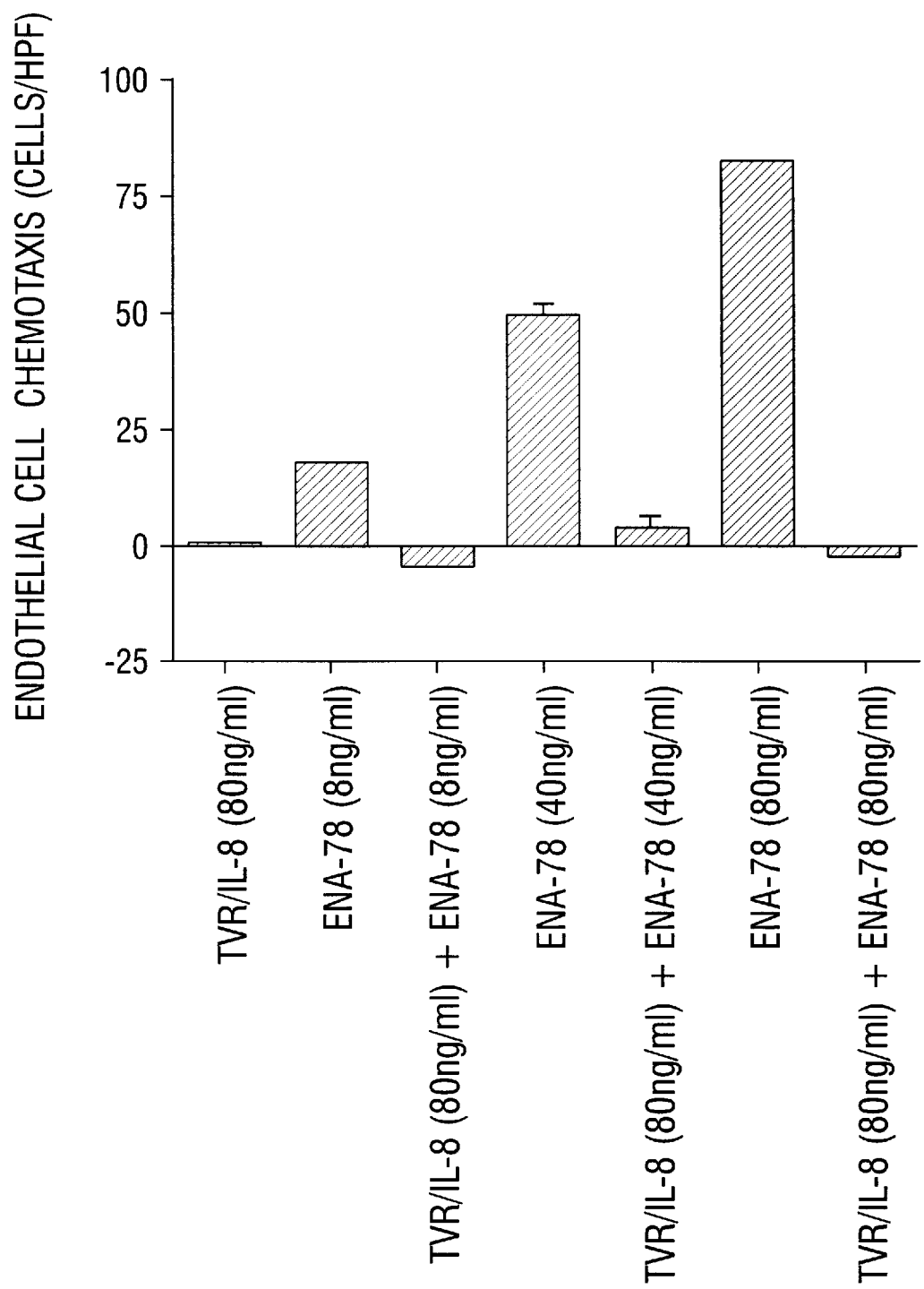
FIG. 27. Inhibition of ENA-78-induced endothelial cell chemotaxis by TVR/IL-8. Endothelial cell chemotaxis is shown in response to varying concentrations (8, 40 and 80 ng/ml) of ENA-78 alone and in response to varying concentrations (8, 40 and 80 ng/ml) of ENA-78, each in combination with TVR/IL-8 at 80 ng/ml.
Figure 28:
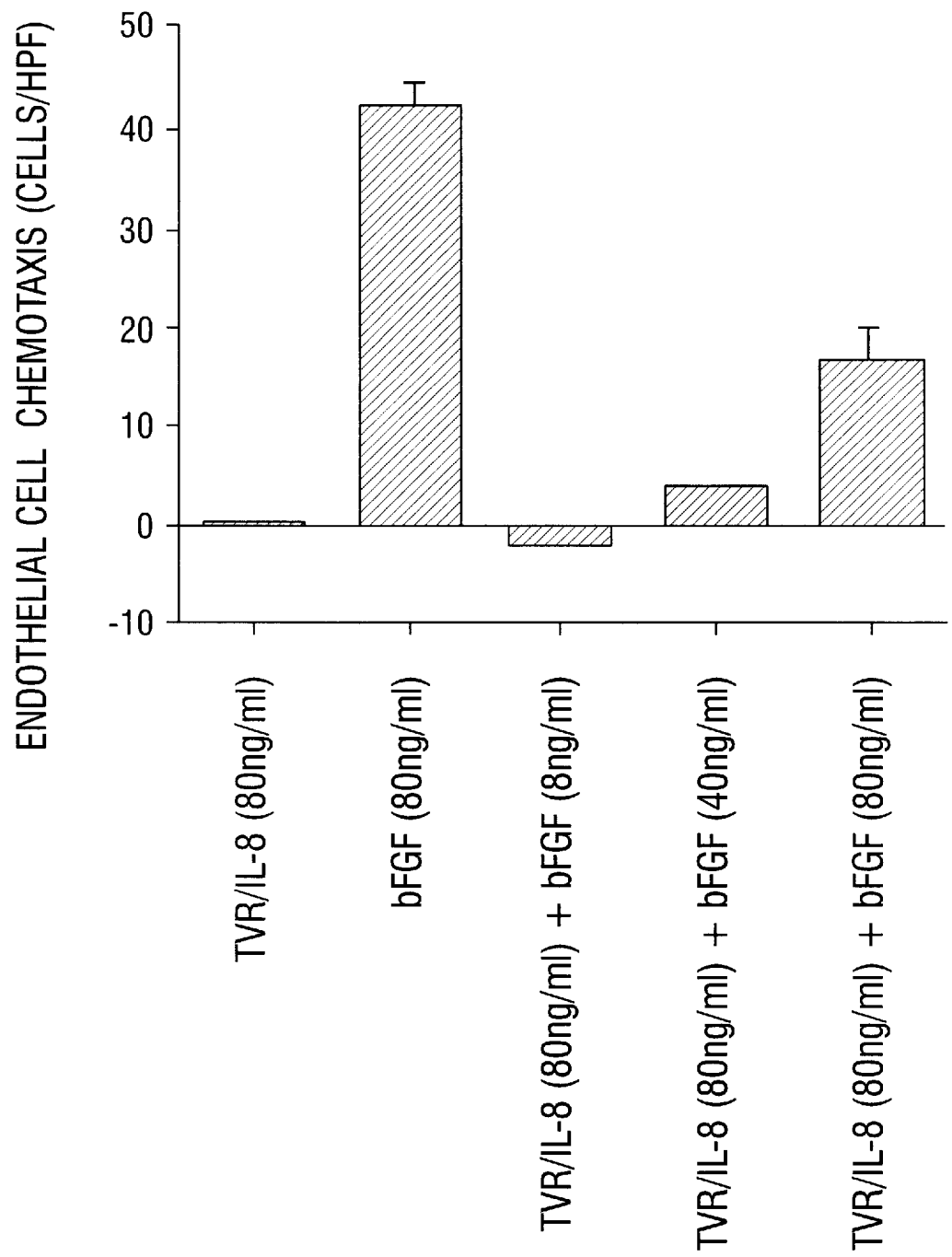
FIG. 28. Inhibition of bFGF-78-induced endothelial cell chemotaxis by TVR/IL-8. Endothelial cell chemotaxis is shown in response to varying concentrations (8, 40 and 80 ng/ml) of bFGF alone and in response to varying concentrations (8, 40 and 80 ng/ml) of bFGF, each in combination with TVR/IL-8 at 80 ng/ml.

TVR/IL-8 was also shown to have a significant ability to inhibit IL-8-induced endothelial cell chemotaxis (FIG. 26); ENA-78-induced endothelial cell chemotaxis (FIG. 27); and bFGF-induced endothelial cell chemotaxis (FIG. 28) at varying levels. It can be seen that the results in FIG. 26, FIG. 27 and FIG. 28 are particularly striking.

EXAMPLE XIII

MIG Inhibits Angiogenesis and Endothelial Cell Chemotaxis

This example shows that MIG is also effective in inhibiting angiogenesis.

MIG was prepared by in a similar manner to IL-8, as described above in Example XII, with pGEX 4T-1 (Pharmacia) being used as the expression vector for all MIG cDNAs. The open reading frame (ORF) of human MIG (Farber, 1993) was amplified from cDNA generated from interferon gamma-stimulated (1000 U/ml for 16 hours) THP-1 cells by polymerase chain reaction.

The 5' primer used, 5'-CAAGGTGGATCCATGAAGAAAAGTGGTGTTC-3' (SEQ ID NO:84), encodes a BamHI restriction site immediately upstream of the ATG start site. The 3' primer, 5'-GCAAGCTCTAGATTATGTAGTCITCTTTTGACGAGAACG-3' (SEQ ID NO:85), encodes a XbaI restricitic,n site immediately downstream of the TAA stop codon. The 402 bp fragment was subcloned to M13 mp19 and was confirmed as the human MIG ORF by sequencing. The wild-type MIG DNA sequence is represented by SEQ ID NO:72.

The glutathoine-S-transferase protein—Thrombin cleavage site—"wild-type" MIG sequence is represented by SEQ ID NO:73 (DNA) and SEQ ID NO:74 (amino acid). This is referred to as "wild-type" as Thr1 has been altered to Ser (in the cleaved product). Digestion of GST-MIG fusion protein with thrombin is predicted to release MIG protein having an N-terminal sequence GlySerPro, versus the predicted non-modified N-terminal sequence ThrPro.

Cultures of E. coli strain DH5αF' harboring GST-MIG (or GST-ELR-MIG) plasmid were grown in 1 liter LB media containing 50 μg/ml ampicilin to OD$_{600}$~0.5 at 22° C. with aeration and protein expression was induced by the addition of 0.1 mM final isopropyl b-D-thiogalactoside (IPTG) and continued incubation at 22° C. for 5–6 hours. After induction, the cells were harvested by centrifuging at 6,000× g for 10 minutes, the pellet washed once in ice cold PBS, and resuspended in 10 ml ice cold 10 mM HEPES, 30 mM NaCl, 10 mM EDTA, 10 mM EGTA, 0.25% Tween-20, 1 mM phenylmethylsulfonyl fluoride (PMSF; added fresh), pH 7.5 (lysis buffer).

The resulting suspension was quick-frozen in liquid nitrogen. After thawing, PMSF was again added to yield a final concentration of 2 mM. The suspension was sonicated using a Branson Sonifier 250 equipped with a microtip for 2 minutes at output setting 5 with a 40% duty cycle. Triton-X 100 was added to a final concentration of 1% and the lysate was nutated for 30 minutes at room temperature to aid in the solubilization of the fusion protein. The lsate was then centrifuged at 34,500× g for 10 minutes and the supernatant transferred to a fresh tube.

The GST-MIG protein was purified using the Pharmacia GST Purification Module (Pharmacia) essentially as described in the manufacturer's protocol. GST-fusion protein sonicate was passed over a 2 ml Glutathione Sepharose 4B column equilibrated in PBS. After washing with PBS, the GST-fusion protein was eluted with 3 column volumes of 10 mM reduced glutathione, 50 mM Tris-HCL, pH 8.0. 10 units of thrombin/$OD_{280}$ unit of fusion protein was added to the eluted GST-MIG or GST-ELR-MIG fusion protein and incubated at room temperature with occasional gentle mixing for 2–3 hours. MIG or ELR-MIG protein was $\geq 95\%$ cleaved from the GST protein under these conditions as monitored by SDS-PAGE (Laemmli, 1970).

The pH of the MIG-containing solution was adjusted to 4.0 using 0.5M sodium acetate, pH 4.0, filtered through a cellulose acetate 0.45 μm filter (Costar), and passed over a Mono S column (Pharmacia) equilibrated with 20 mM sodium acetate pH 4.0. MIG protein was eluted as a single peak using a 0–2M NaCl gradient, and dialyzed against 0.5 mM $NaPO_4$, 20 mM NaCl, pH 7.0. Purified MIG and ELR-MIG was obtained endotoxin-free (<1.0 EU/ml; QCL-1000 test, BioWhittaker), and yields ranged from 100–200 μg/L (quantitated by amino acid analysis (AAA)) with a purity of >95% (determined by SDS-PAGE, with apparent MW 16 kD; AAA accuracy >90%). Mass spectrometry of the purified MIG and ELR-MIG proteins confirmed their predicted mass.

Figures 29A, 29B:
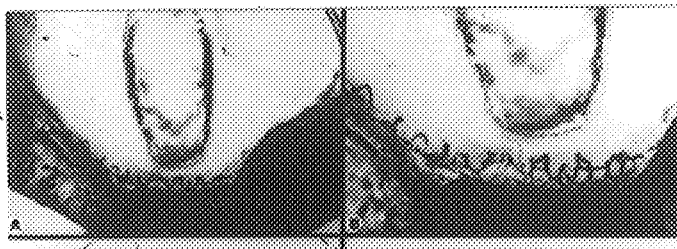
FIG. 29A, FIG. 29B, FIG. 29C, FIG. 29D, FIG. 29E, FIG. 29F, FIG. 29G, FIG. 29H, FIG. 29I, FIG. 29J, FIG. 29K and FIG. 29L. Photomicrograph of the effects of MIG on cornea neovascularization.
Figures 29C, 29D:
Figures 29E, 29F:
Figures 29G, 29H:
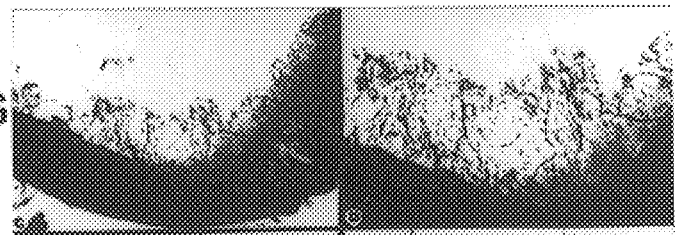
Figures 29I, 29J:
Figures 29K, 29L:
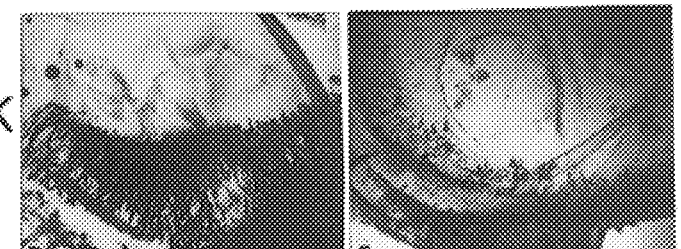

The MIG protein so produced was used in angiogenesis studies alone and in combination with IL-8-, ENA-78- and bFGF. MIG itself does not induce cornea neovascularization, as confirmed in FIG. 29A and FIG. 29B. MIG was found to effectively inhibit cornea neovascularization induced by IL-8 (compare both FIG. 29G and FIG. 29H to FIG. 29I and FIG. 29J) and by ENA-78 (compare FIG. 29K to FIG. 29L). MIG was further found to be equally capable of inhibiting cornea neovascularization induced by bFGF, an angiogenic factor that does not contain the ELR motif, as shown by comparing both FIG. 29C and FIG. 29D to FIG. 29E and FIG. 29F.

Figure 30A:
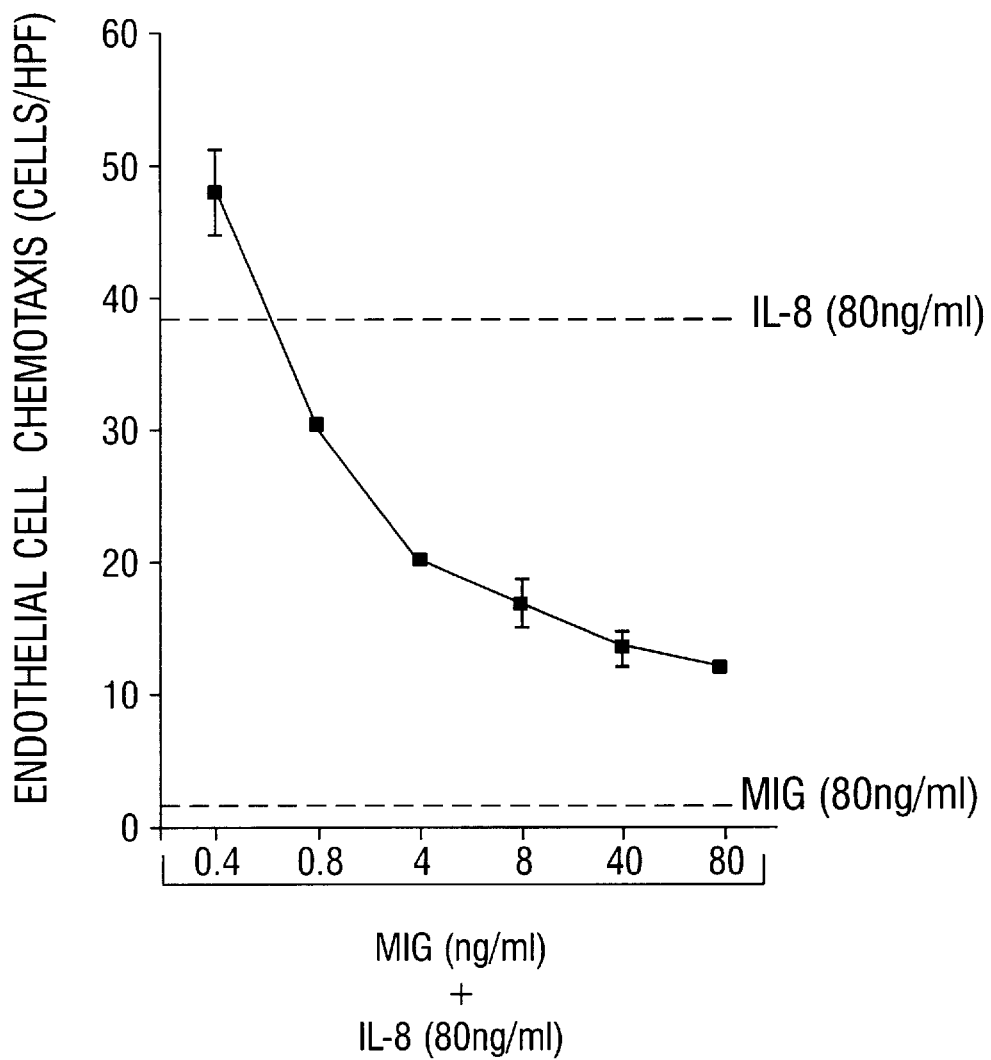
FIG. 30A and FIG. 30B. Inhibition of IL-8-induced and ENA-78-induced endothelial cell chemotaxis in response to varying concentrations of MIG.
Figure 30B:
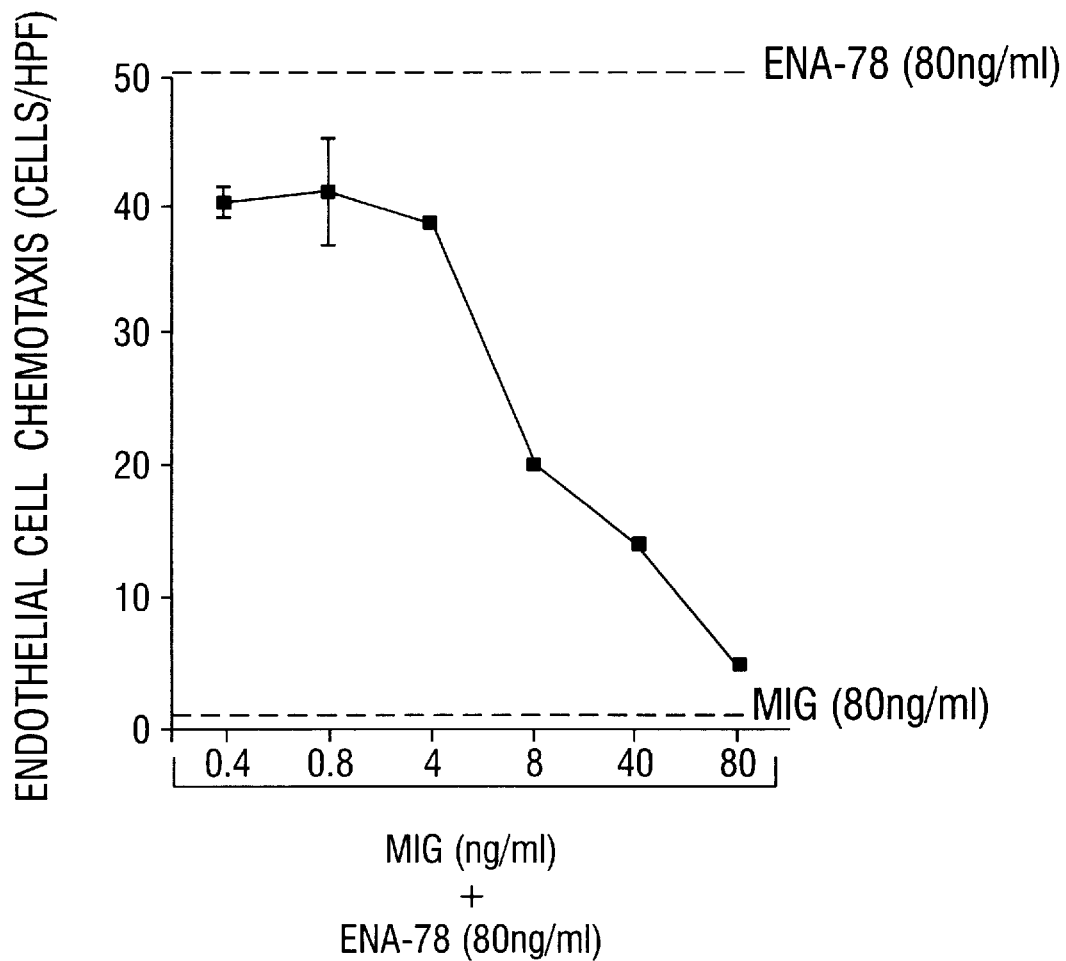
Figure 31:
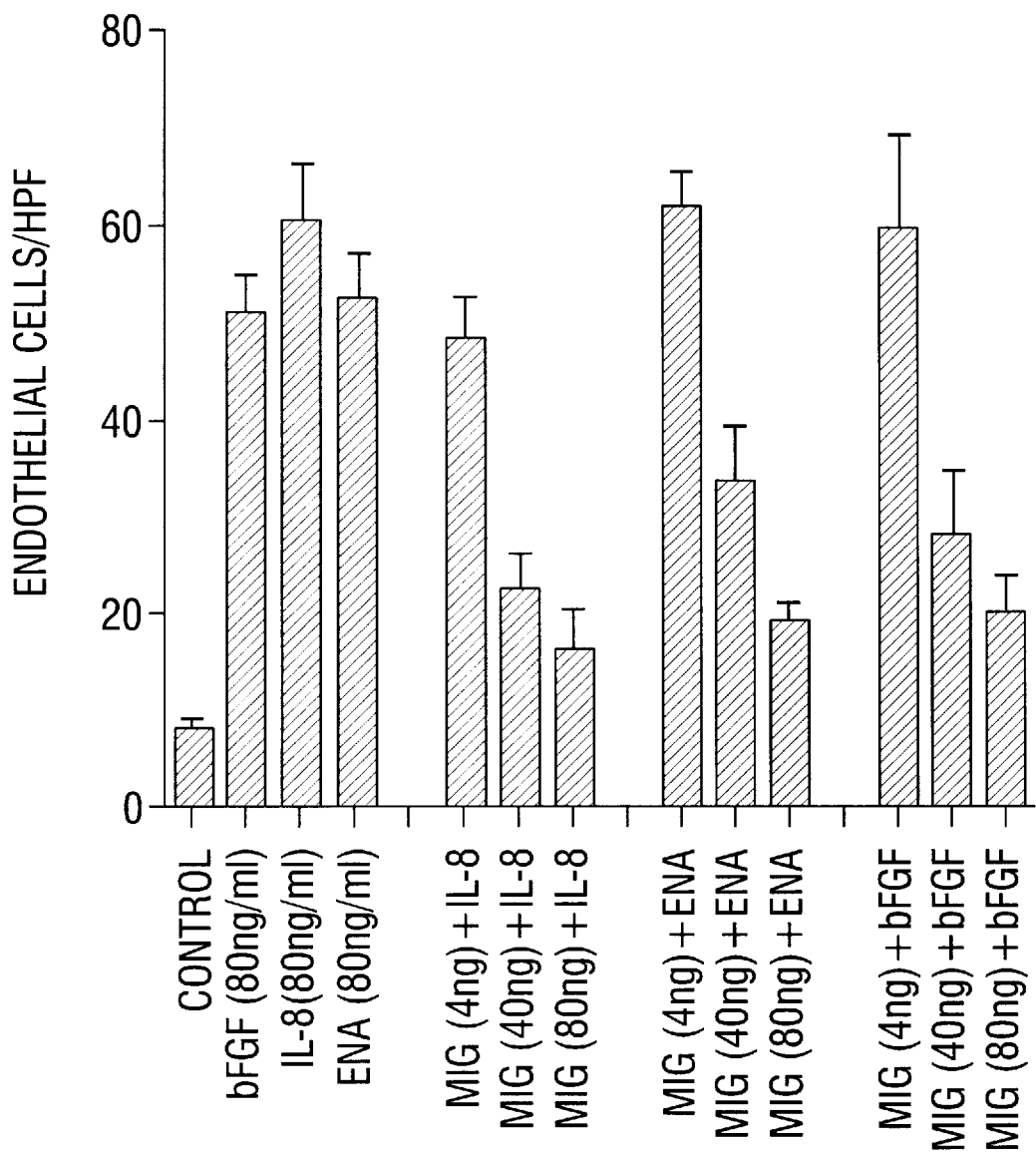
FIG. 31. Inhibition of IL-8-, ENA-78- (ENA) and bFGF-induced endothelial cell chemotaxis in response to the indicated concentrations of MIG.

MIG also inhibits IL-8-induced endothelial cell chemotaxis (FIG. 30A) and ENA-78-induced endothelial cell chemotaxis (FIG. 30B). Importantly, MIG was again found to inhibit endothelial cell chemotaxis induced by bFGF, the non-CXC molecule (FIG. 31).

EXAMPLE XIV

IP-10 and MIG Do Not Inhibit IL-8 Induced Neutrophil Chemotaxis

The results in Example IX, Example X and Example XIII demonstrate that IP-10 and MIG both inhibit endothelial cell chemotaxis, angiogenesis and neovascularization induced by CXC chemokines and non-chemokine angiogenic factors.

The effects of IP-10 and MIG on neutrophil chemotaxis were investigated as follows:

Heparinized venous blood was collected from healthy volunteers, mixed 1:1 with 0.9% saline and mononuclear cells were separated by Ficoll-Hypaque density gradient centrifugation. Human neutrophils were then isolated by sedimentation in 5% dextran/0.9% saline (Sigma Chemical Co.) and separated from erythrocytes by hypotonic lysis. After washing twice, neutrophils were suspended in Hank's balanced salt solution with calcium/magnesium (Gibco, Grand Island, N.Y.) at a concentration of $2\times10^6$ cells/ml. Neutrophils were >95% viable as determined by trypan blue exclusion.

Neutrophil chemotaxis was performed as previously described (Strieter et al., 1989a; 1989b). One hundred fifty microliters of specimen, $10^{-7}$M formylmethionylleucylphenylalanine (fMLP, Sigma Chemical Co.), or Hank's balanced salt solution (HBSS, Gibco, Grand Island, N.Y.) alone were placed in duplicate bottom wells of a blind-well chemotaxis chamber. A 3-micron pore size polycarbonate filter (polyvinylpyrrolidone-free, Nucleopore Corp.) was placed in the assembly and 250 ul of human neutrophil suspension placed in each of the top wells. Chemotaxis chamber assemblies were incubated at 37° C. in humidified 95% air/5% $CO_2$ 60 min. The filters were removed, fixed in absolute methanol, and stained with 2% toluidine blue (Sigma Chemical Co.). Neutrophils that had migrated through to the bottom of the filter were counted in 10 high power fields using a Javelin chromachip camera (Javelin Electronics, Japan) attached to a Olympus BH-2 microscope interfaced with a MacIntosh II computer containing an Image Capture 1000 frame grabber (Scion Corp., Walkersville, Md.) and image 1.40 software (NIH Public Software, Bethesda, Md.).

The ability of IP-10 and MIG to markedly inhibit angiogenesis, as exemplified by the inhibition of IL-8-induced angiogenesis, is in contrast to the failure of IP-10 and MIG to significantly inhibit IL-8-induced neutrophil activation. This is shown in Table 4.

TABLE 4

| Neutrophil Chemotaxis | |
|---|---|
| Condition (10 nM) | Cells/HPF |
| Control | 18.4 ± 1.8 |
| IP10 | 20.7 ± 4.15 |
| MIG | 8.6 ± 1.45 |
| IL-8 | 96.4 ± 6.5 |
| IL-8 + IP10 | 94.1 ± 9.28 |
| IL-8 + MIG | 78.6 ± 10.5 |

EXAMPLE XV

Interaction of CXC Chemokines in Endothelial Cell Chemotaxis

Figure 32:
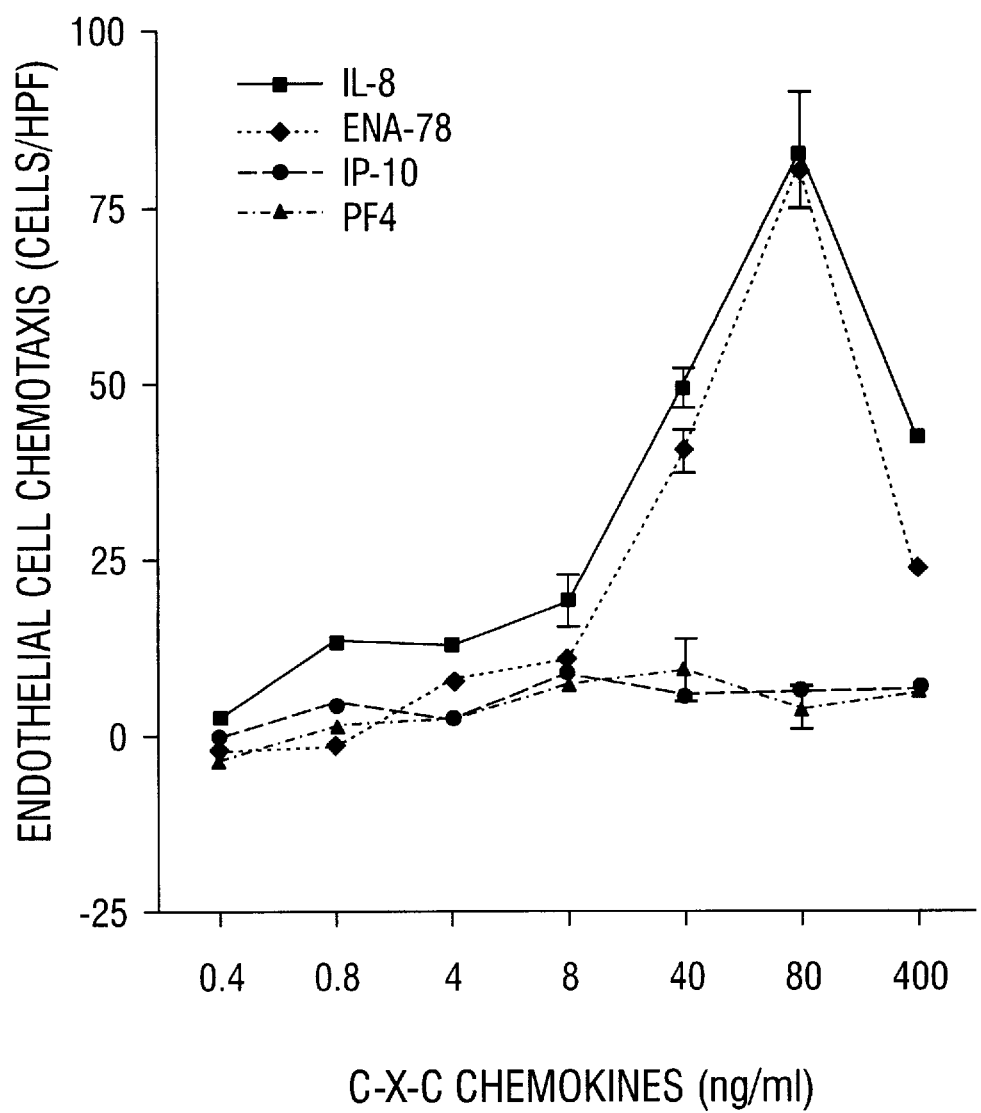
FIG. 32. Endothelial cell chemotaxis in response to varying concentrations of IL-8, ENA-7, IP-10 and PF4.

Endothelial cell cheinotaxis is induced in response to increasing concentrations of IL-8 and ENA-78, up to a certain level (FIG. 32). However, IP-10 and PF4, even at very high levels, fail to induce endothelial cell chemotaxis (FIG. 32).

Figure 33A:
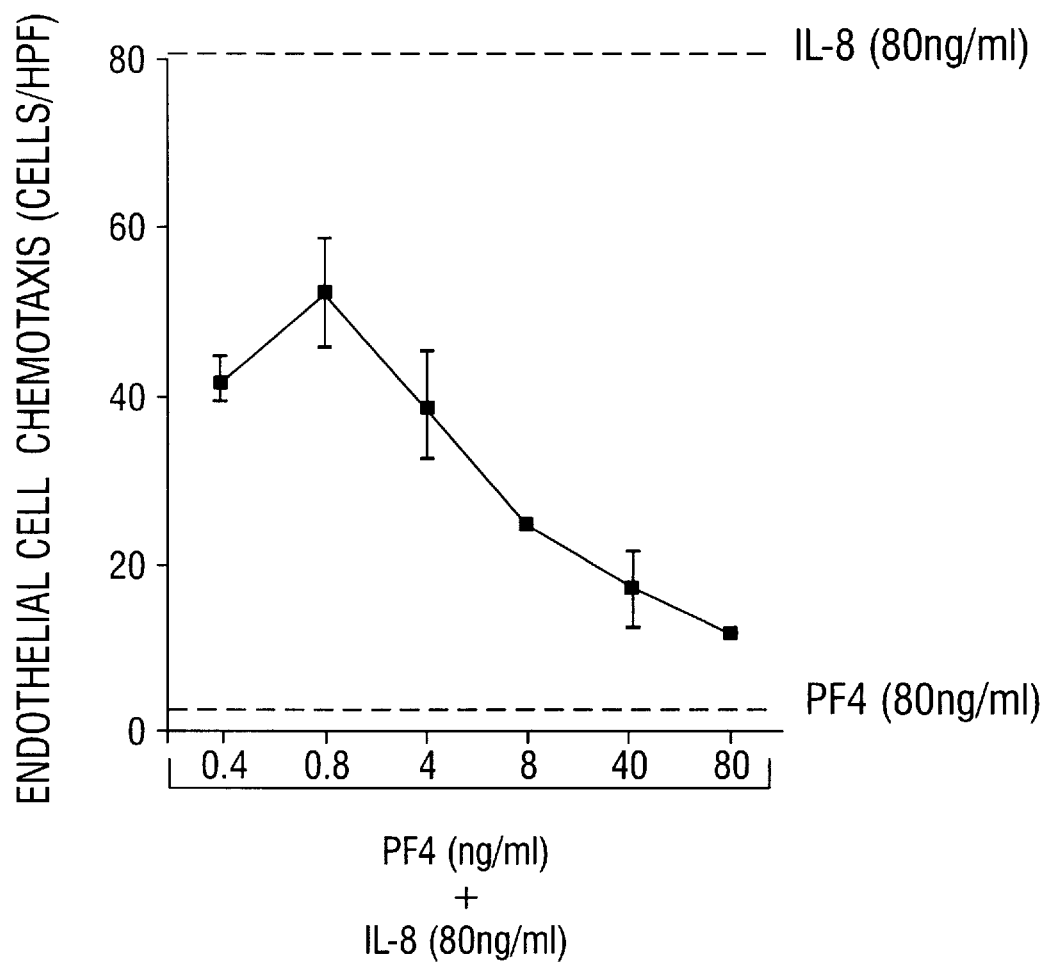
FIG. 33A, FIG. 33B and FIG. 33C. Inhibition of IL-8-, ENA-78- and bFGF-induced endothelial cell chemotaxis in response to varying concentrations of PF4.
Figure 33B:
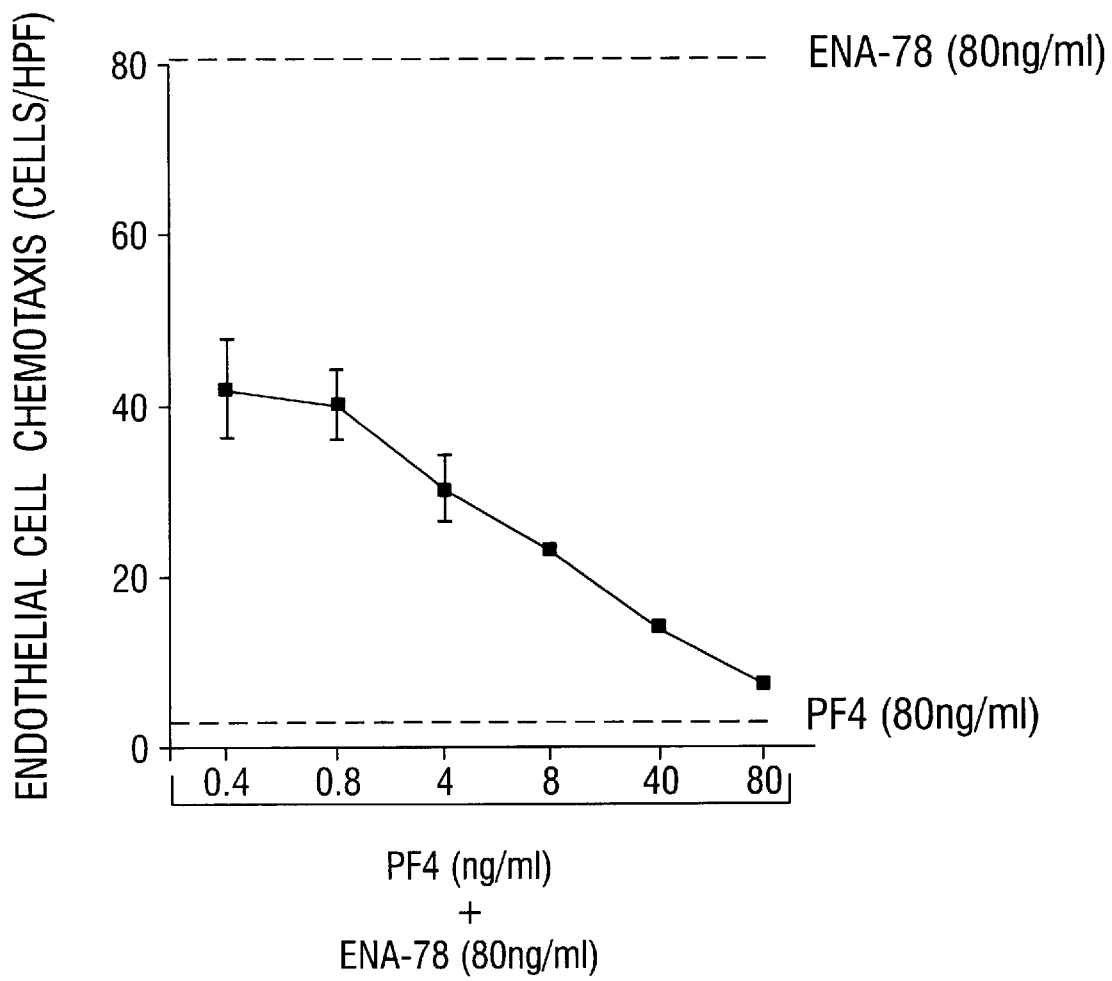
Figure 33C:
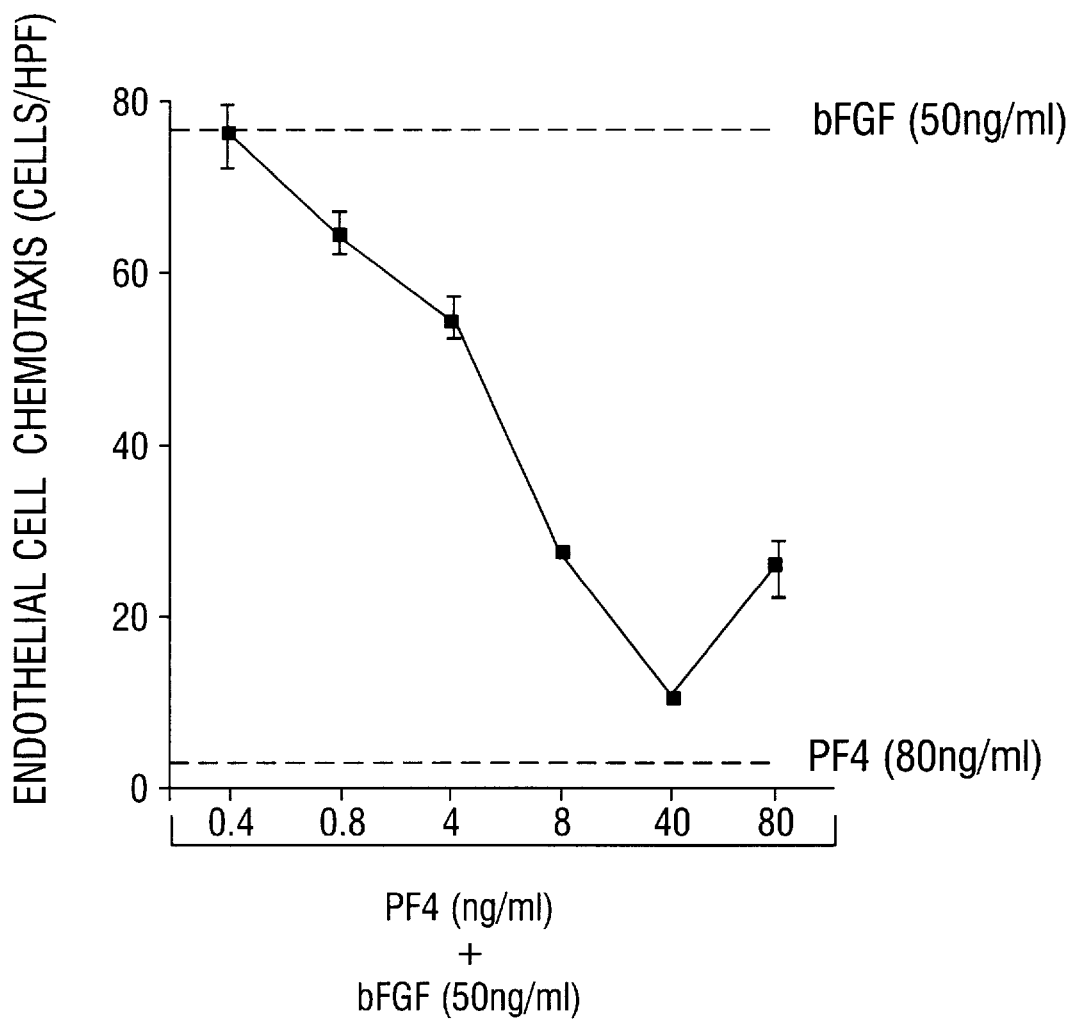
Figure 34A:
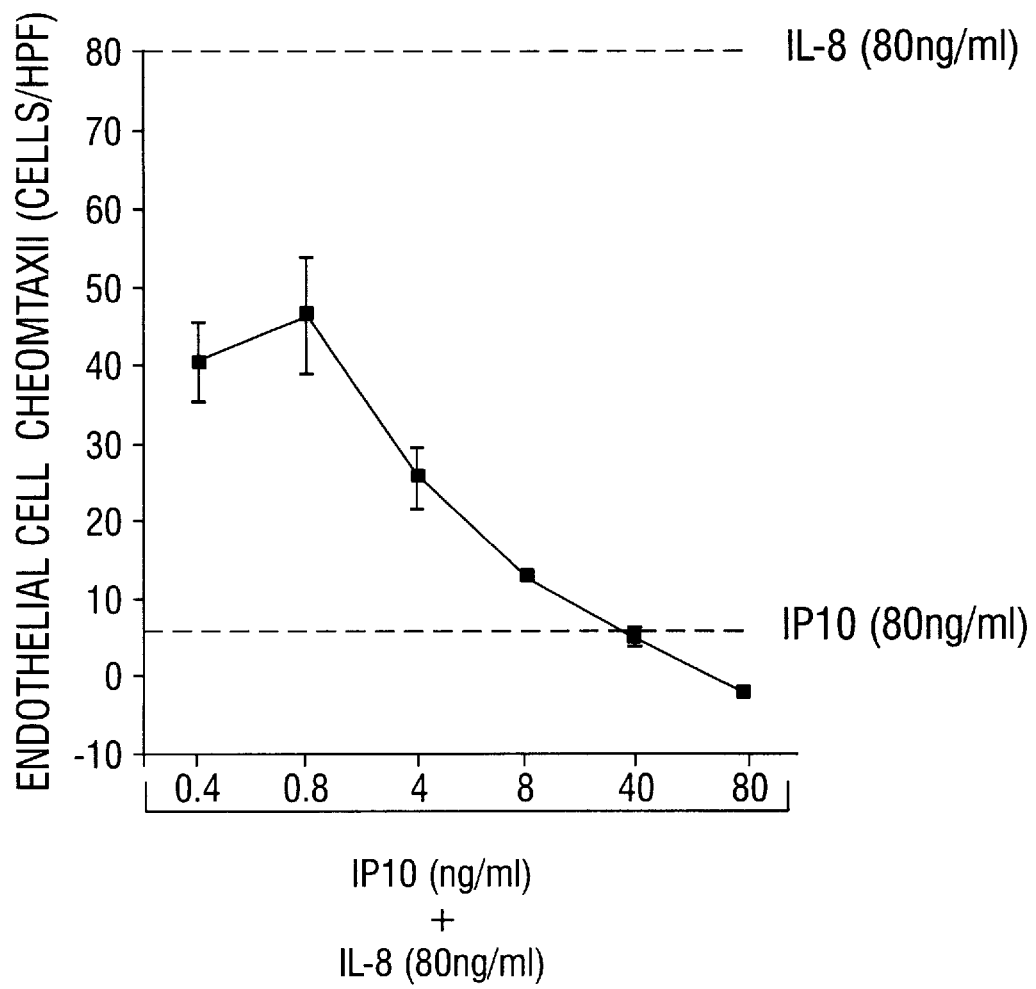
FIG. 34A, FIG. 34B and FIG. 34C. Inhibition of IL-8-, ENA-78- and bFGF-induced endothelial cell chemotaxis in response to varying concentrations of IP-10.
Figure 34B:
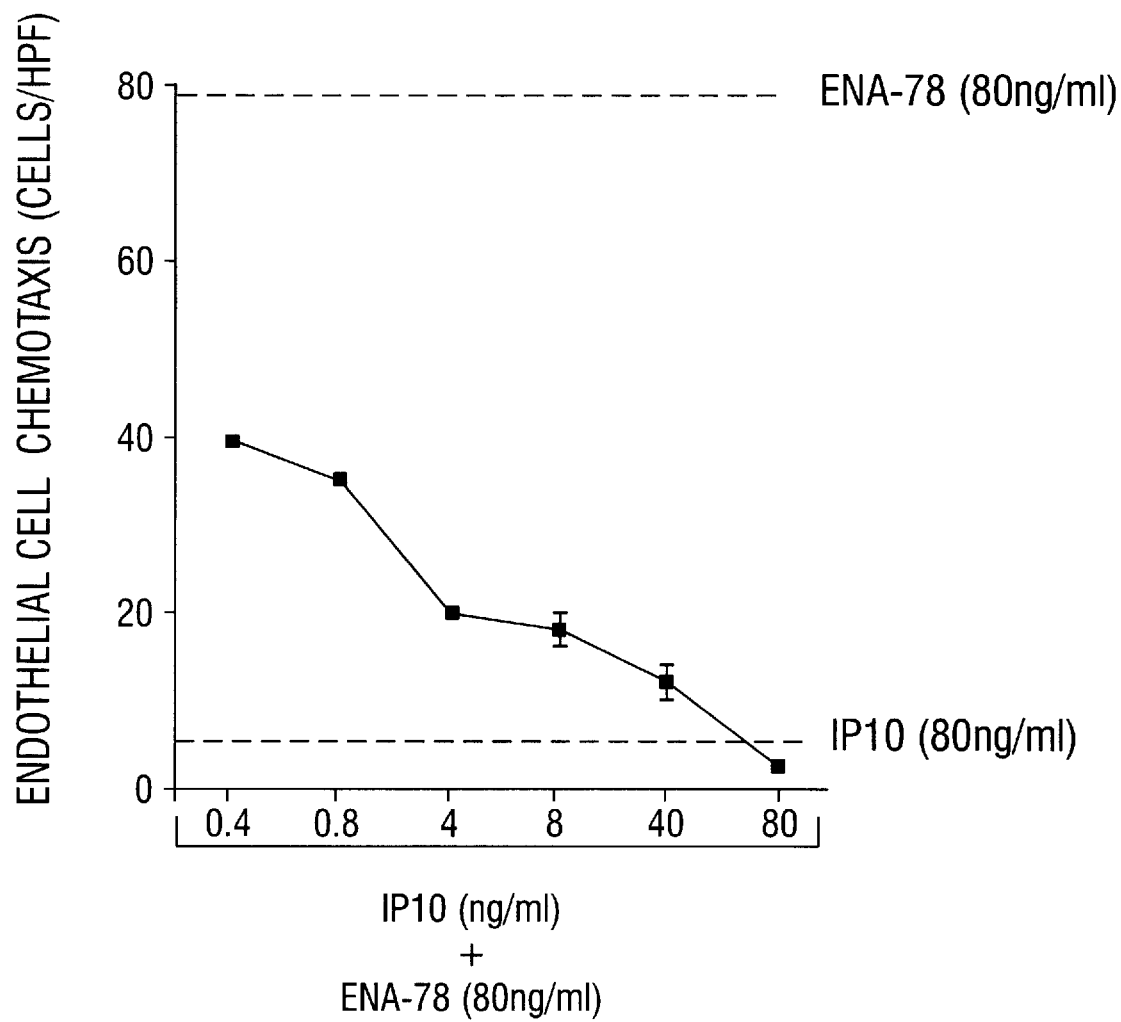
Figure 34C:
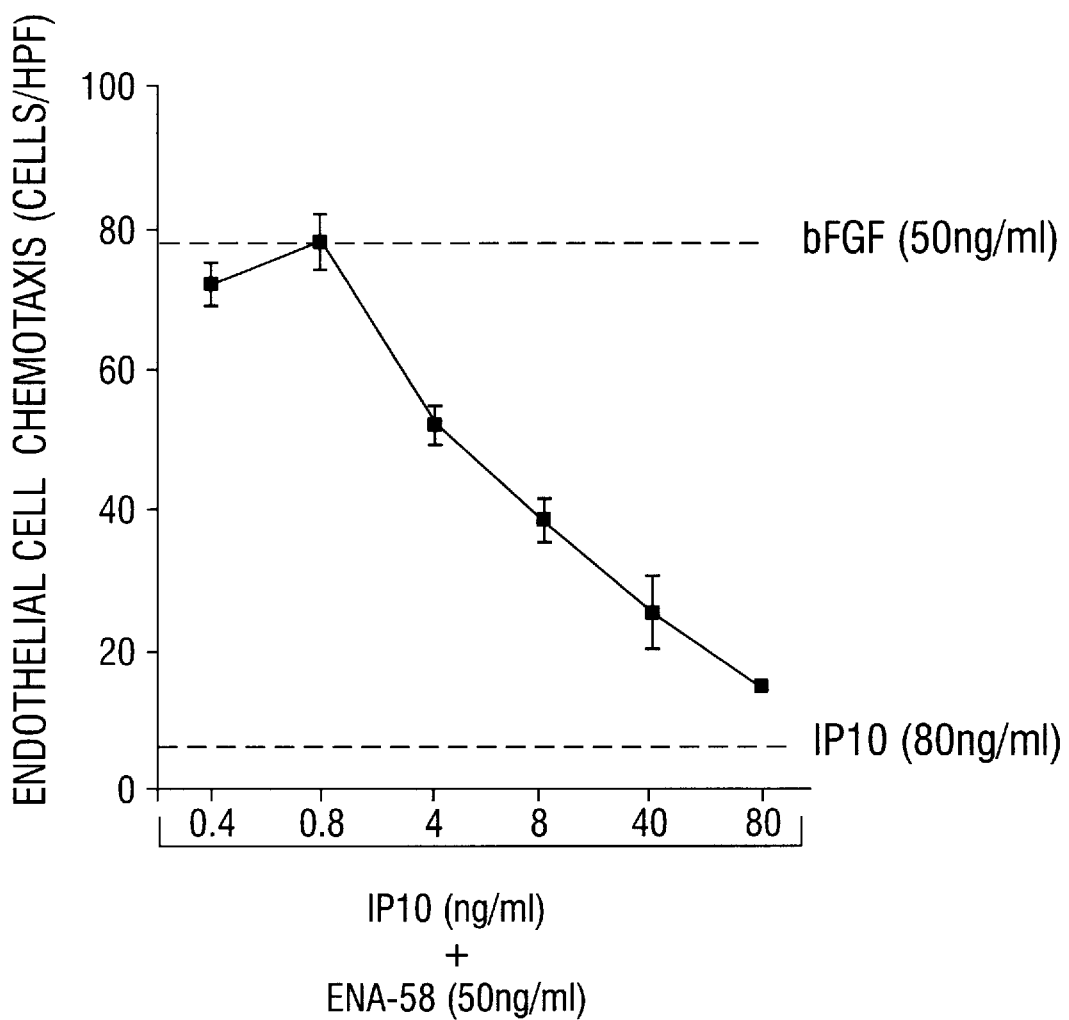

FIG. 33A, FIG. 33B and FIG. 33C show that increasing concentrations of PF4 are effective in inhibiting IL-8-, ENA-78-, and bFGF-induced endothelial cell chemotaxis, respectively. Similar effects were observed with increasing concentrations of IP-10, which are also capable of inhibiting IL-8-, ENA-78- and bFGF-induced endothelial cell chemotaxis (FIG. 34A, FIG. 34B, FIG. 34C).

EXAMPLE XVI

MIG Engineered to Contain the ELR Motif is Angiogenic

This example shows that engineering MIG to contain the amino acids ELR converts this angiostatic CXC chemokine into an angiogenic CXC chemokine.

ELR-MIG was prepared by in a similar manner to wild type MIG, as described above in Example XIII, using pGEX 4T-1 (Pharmacia) as the expression vector to generate glutathoine-S-transferase protein—Thrombin cleavage site—ELR MIG.

Thr-23 of the ORF sequence is the predicted N-terminal amino acid of the mature, secreted MIG protein (Farber, 1993), and will be hereto referred to as amino acid position 1. Amino acids Lys-6 and Gly-7 were modified to Glu and Leu, respectively, by site-directed mutagenesis, generating the MIG mutein ELR-MIG. A Bam HI restriction site was introduced overlapping Gly-(-1) and Thr-1 by site-directed mutagenesis (Kunkel et al., 1987), resulting in mutein MIG or ELR-MIG cDNAs encoding a Thr-1 to Ser substitution. 324 bp fragments obtained from correct M13 RF clones digested with BamHI/XbaI were subcloned to PGEX 4T-1 to generate glutathione-S-transferase-MIG fusion DNAs (GST-MIG or GST-ELR-MIG).

The sequence encoded by these DNAs contain the thrombin recognition sequence LVPRGS between the GST and MIG sequences. The glutathione-S-transferase protein—Thrombin cleavage site—ELR-MIG sequence is represented by SEQ ID NO:75 (DNA) and SEQ ID NO:76 (amino acid). Digestion of GST-MIG fusion protein with thrombin is predicted to release MIG protein having an N-terminal sequence GlySerPro, versus the predicted non-modified N-terminal sequence ThrPro. ELR-MIG protein was prepared as described above in Example XIII.

Figure 45:
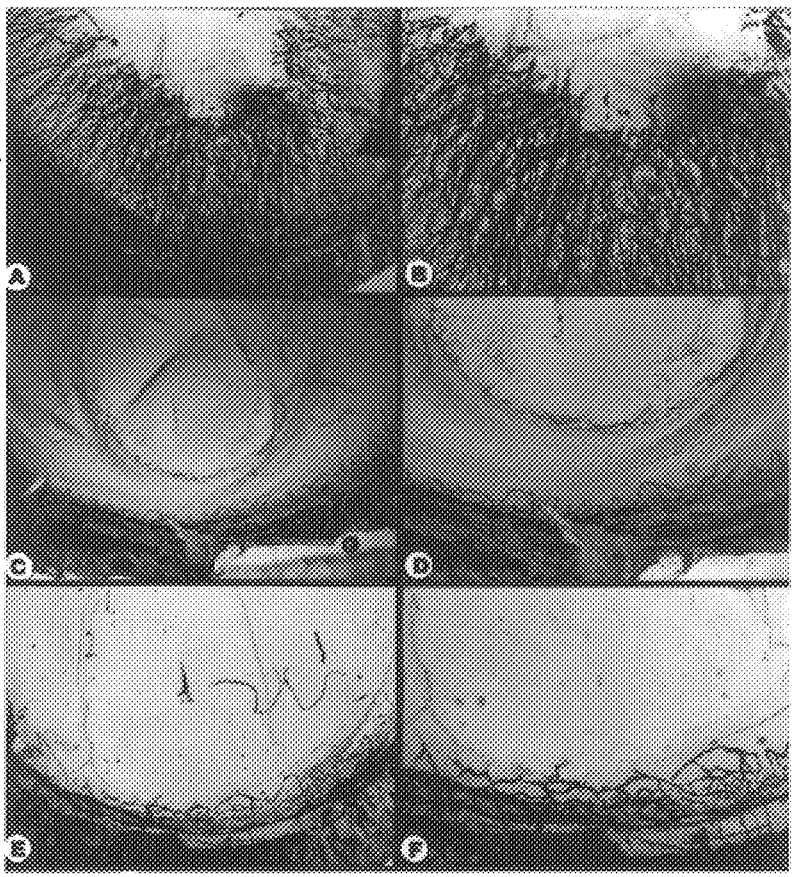
FIG. 45A, FIG. 45B, FIG. 45C, FIG. 45D, FIG. 45E and FIG. 45F. Photomicrograph of the effect of ELR-MIG on corneal neovascularization.

ELR-MIG at a concentration of 10 nM induced angiogenic responses in 8 out of 10 corneas, as compared to wild type MIG, which induced an angiogenic response in only 1 out of 7 corneas. Representative evidence of the angiogenic effects of ELR-MIG is shown in FIG. 45A and FIG. 45B. The angiogenic effects of the genetically engineered ELR-MIG seen in FIG. 45A and FIG. 45B are clearly contrasted with FIG. 45C and FIG. 45D, which are the same concentration of wild-type MIG. Inhibition of ELR-MIG angiogenic activity by wild type MIG is further shown in FIG. 45E and FIG. 45F, which represent the combination of MIG and ELR-MIG.

ELR-MIG, at concentrations of from 10 pM to 100 nM, failed to induce neutrophil chemotaxis. This is clearly defining evidence of the newly-discovered role of the ELR motif in angiogenesis.

Thus, the ELR motif is likely essential for dictating the angiogenic activity of the CXC chemokines that may bind to the recently described type I (A) IL-8 receptor on endothelial cells (Schonbeck et al., 1995). This endothelial cell receptor binds both IL-8 and NAP-2 with low-affinity (Schonbeck et al., 1995). In contrast, this receptor on neutrophils binds IL-8 and NAP-2 with high and low affinity, respectively (Holmes et al., 1991; Murphy and Tiffany, 1991; Lee et al., 1992; Murphy, 1994; Horuk, 1994). This finding is compatible with the ability of ELR containing CXC chemokines to bind to both endothelial cells and neutrophils. However, the mutants of wild-type IL-8, as well as IP-10 and MIG, inhibited CXC (ELR) chemokine-induced angiogenesis, but not neutrophil chemotaxis. Moreover, the mutants of wild-type IL-8, as well as IP-10 and MIG, also inhibited the angiogenic activity of the non-chemokine, bFGF, suggesting that a receptor system(s) other than the IL-8 receptor may be operative on endothelial cells that allows the angiostatic CXC chemokines to regulate both CXC (ELR) and bFGF-induce angiogenic activity.

EXAMPLE XVII

The Human NSCLC/SCID Mouse Chimera Tumor Model

While neoplastic transformation is dependent upon multiple genetic and epigenetic events (Shields and Harris, 1993), the success of tumorigenesis is dependent upon the complex biological interplay between the necplastic cells and the resident and recruited host responding cells. For example, in the absence of local neovascularization with delivery of oxygen and nutrients to the neoplastic cells, these neoplasms would not grow beyond the size of 1 to 2 mm in diameter (Folkman and Cotran, 1976; Folkman, 1985; Bouck, 1990).

In order to effectively study the complex biology of human solid tumors, human tumor xenografts in immuno-deficient mice have been developed. This has provided improved insight into the biology of tumor growth and metastasis (Mette et al., 1993; Mueller and Reisfeld, 1991; Wang et al., 1992; McLemore et al., 1988; Bankert et al., 1989; Phillips et al., 1989; Hendrickson, 1993; Rendt et al., 1993; Caamano et al., 1991; Zucker et al., 1992).

In order to refine the quantitative data on the presence of angiogenic and angiostatic CXC chemokines, and to allow the subsequent optimization of therapeutic strategies, the inventors have transplanted both intact human NSCLC and a NSCLC cell line (A549; adenocarcinoma and Calu 1; squamous cell carcinoma) into severe combined immuno-deficient (SCID) mice to create a human NSCLC/SCID mouse chimera.

Figures 35A, 35B, 35C:
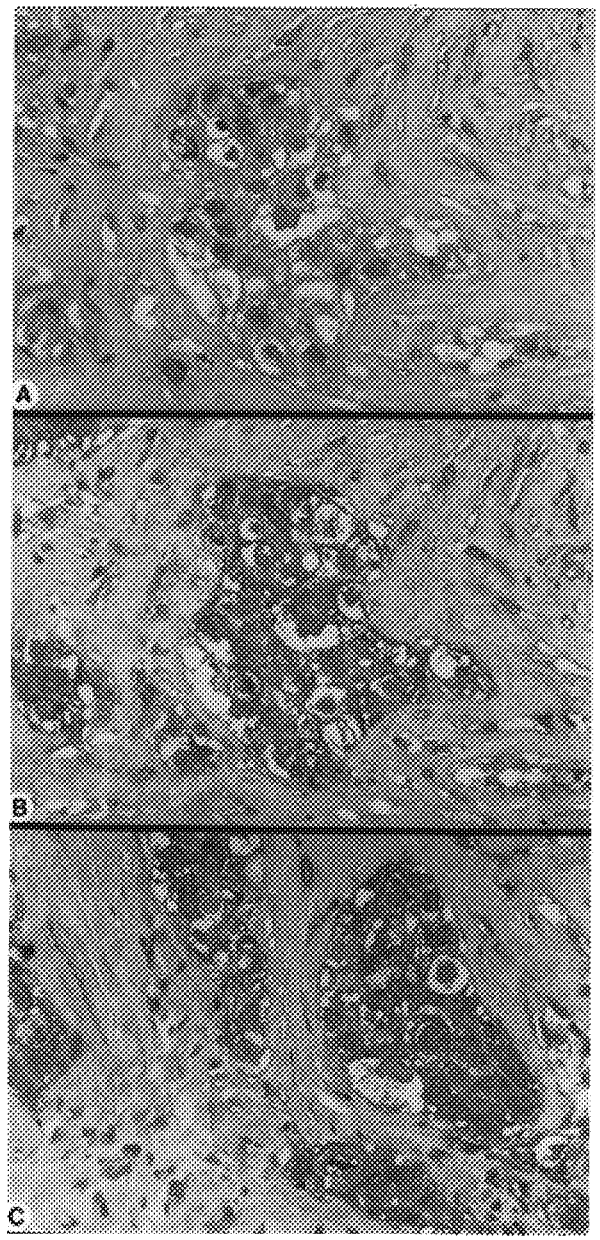
FIG. 35A, FIG. 35B and FIG. 35C. Photomicrographs of the immunolocalization of IL-8 and ENA-78 in adenocarcinoma within the human NSCLC/SCID mouse host.

The mice were evaluated prior to xenograft to have a murine serum Ig concentration of <1 $\mu$g/ml by ELISA. Freshly isolated intact NSCLC (adenocarcinoma) were cut into 1 mm$^3$ and placed subcutaneously into the bilateral flanks of SCID mice and allowed to grow for 4 weeks. At this time point the tumors measured 18–81 mm and the mice were sacrificed. The photomicrograph composite of human NSCLC within the human tumor/SCID stromal matrix is shown in FIG. 35A, FIG. 35.B and FIG. 35C. Immunohistochemistry for IL-8 (FIG. 35B) and ENA-78 (FIG. 35C) demonstrates the immunolocalization of these CXC chemokines within the viable NSCLC cells, stromal cells, and mononuclear cells, while the control antibodies failed to show nonspecific staining (FIG. 35A) while the control antibodies failed to show nonspecific staining. These findings suggested that natural human NSCLC remained viable in SCID mice and that they continue to express both IL-8 and ENA-78 that may have allowed them to generate angiogenic activity and survive in the SCID mouse host.

Figure 36A:
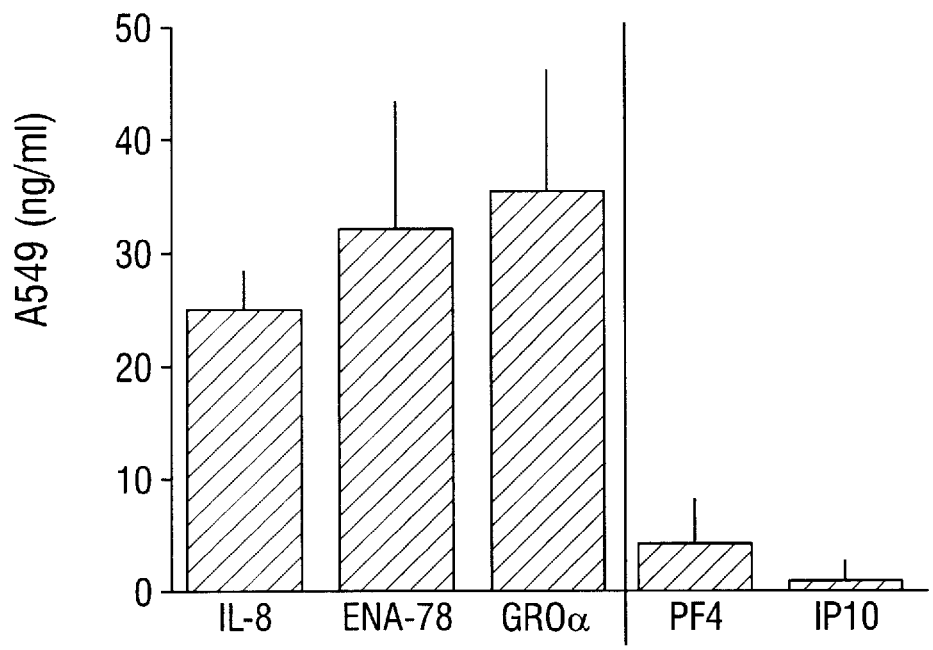
FIG. 36A and FIG. 36B. Levels of CXC chemokines in A549 (adenocarcinoma) and Calu-1 (squamous cell carcinoma) human NSCLC cell lines.
Figure 36B:
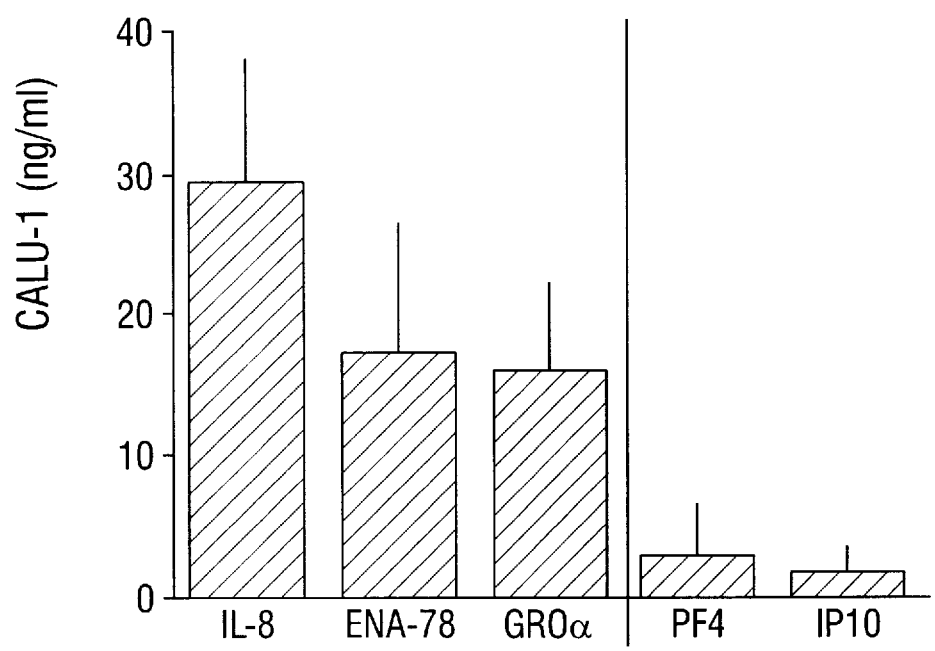

Since an important aspect of this invention is the proposal that overall tumor-derived angiogenesis is dependent upon an imbalance in the production of members of the CXC chemokine family that act as angiogenic rather than angiostatic factors, the inventors next assessed in vitro whether human NSCLC cell lines (A549 and Calu-1) produced disparate levels of angiogenic (IL-8, ENA-78, and GRO$\alpha$) and angiostatic (PF4 and IP-10) CXC chemokines (FIG. 36A, FIG. 36B). Both A549 and Calu-1 human NSCLC cell lines were found to constitutively produce high levels of angiogenic, as compared to angiostatic, CXC chemokines.

Interestingly, the A549 cells were found to constitutively produce greater levels of angiogenic CXC chemokines, and when grown in SCID for 4 weeks were found to induce tumors 2-fold greater in size than the Calu-1 NSCLC cell line. These findings corroborate the previous findings that A549 cells display greater tumorigenicity and spontaneous metastasis than Calu 1 cells in vivo.

While these in vitro studies were important in order to establish whether an imbalance in the production of angiogenic, as compared to angiostatic, CXC chemokines existed in NSCLC cell lines, the inventors next assessed whether an imbalance in their production occurred in vivo during tumorigenesis of A549 NSCLC cells in a SCID mouse host.

SCID mice received 10⁶ A549 cells suspended in 100 ul of PBS to each flank. The mice were sacrificed in a time-dependent manner at 2, 3, 4, 5, 6, and 7 weeks post-xenograft, tumors were analyzed for tumor growth and tumor-derived and plasma levels of CXC chemokines standardized to either TP or volume (biopsy).

Figures 37A, 37B, 37C, 37D, 37E, 37F, 37G:
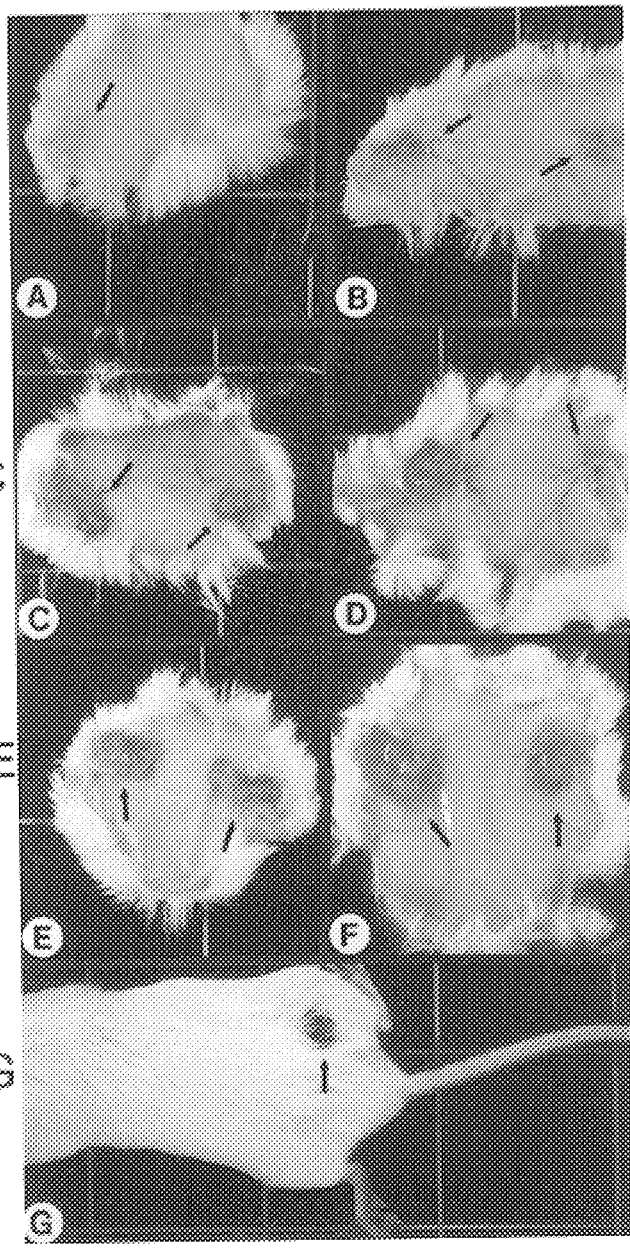
FIG. 37A, FIG. 37B, FIG. 37C, FIG. 37D, FIG. 37E, FIG. 37F and FIG. 37G. Gross pathology of A549 human NSCLC cell line (adenocarcinoma) growth in SCID mice.
Figures 38A, 38B, 38C, 38D, 38E, 38F:
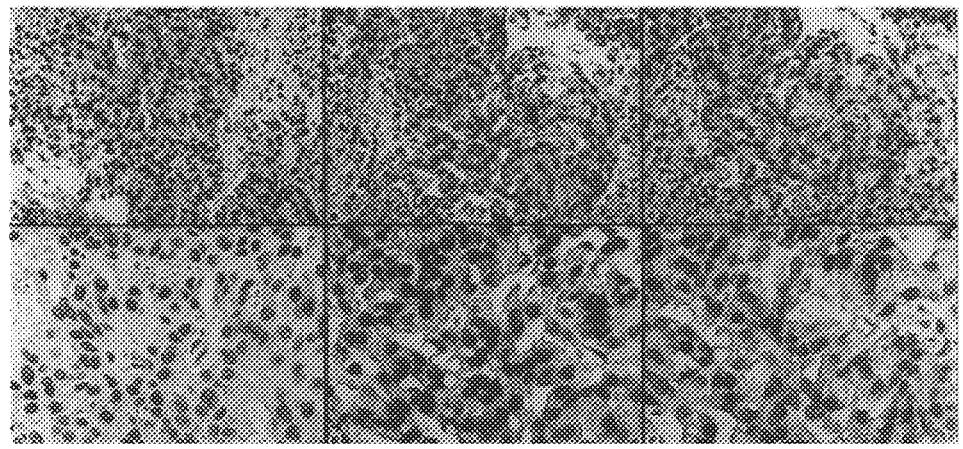
FIG. 38A, FIG. 38B, FIG. 38C, FIG. 38D, FIG. 38E and FIG. 38F. Immunolocalization of IL-8 from subcutaneous A549 human NSCLC tumors at 7 weeks in a SCID mouse host.
Figures 39A, 39B, 39C:
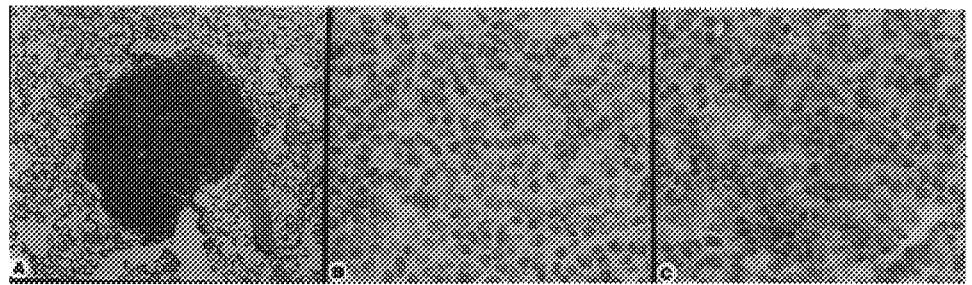
FIG. 39A, FIG. 39B and FIG. 39C. Immunolocalization of IL-8 from spontaneous lung metastasis of A549 human NSCLC tumors at 7 weeks in a SCID mouse host.

Shown in FIG. 37A, FIG. 37B, FIG. 37C, FIG. 37D, FIG. 37E, and FIG. 37F are the gross pathological specimens of A549 tumors at weeks 2, 3, 4, 5, 6, and 7, respectively, where FIG. 37G represents the tumor on the flank of a SCID mouse at week 8. Immunolocalization of IL-8 from A549 tumors at week 7, demonstrated a heterogeneous expression pattern, with 35±6% of the cells expressing IL-8 protein by image and analysis (FIG. 38A, FIG. 38B, FIG. 38C, FIG. 38D, FIG. 38E, FIG. 38F), whereas, IL-8 expression from spontaneous A549 tumor metastasis to the lungs of SCID mice at 7 to 8 weeks demonstrated a more homogenous pattern of immunolocalization of IL-8, with more than 80% of the cells expressing IL-8 protein by image analysis (FIG. 39A, FIG. 39B and FIG. 39C).

Figures 1, 40A:
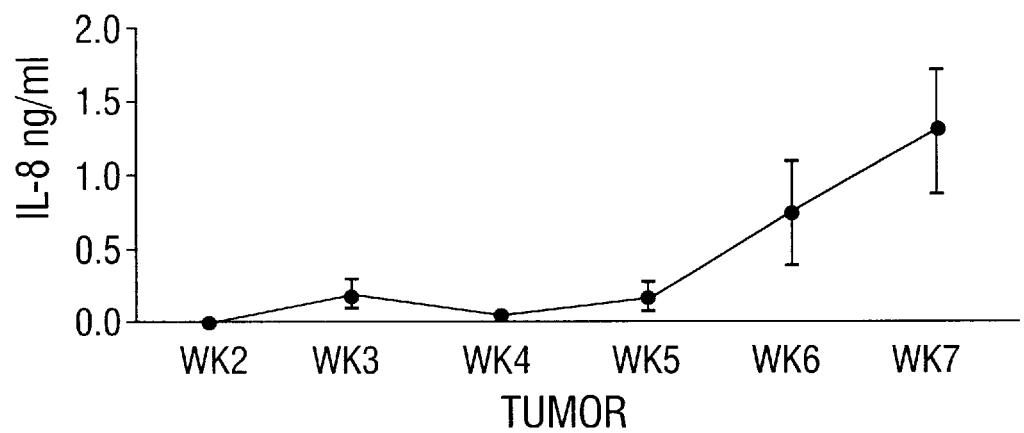
FIG. 40A-1, FIG. 40A-2, FIG. 40B-1, FIG. 40B-2, FIG. 40C-1, FIG. 40C-2, FIG. 40D, FIG. 40E-1, FIG. 40E-2, FIG. 40F-1 and FIG. 40F-2. Temporal expression of angiogenic (IL-8, FIGS. 40A-1–40A-2; ENA-78, FIGS. 40B-1–40B-2; GROα, FIGS. 40C-1–40C-2) and angiostatic (PF4, FIGS. 40E-1–40E-2 and IP-10, FIGS. 40F-1–40F-2) CXC chemokines, compared to tumor growth (FIG. 40D) of A549 human NSCLC cells in SCID mice.
Figures 2, 40A:
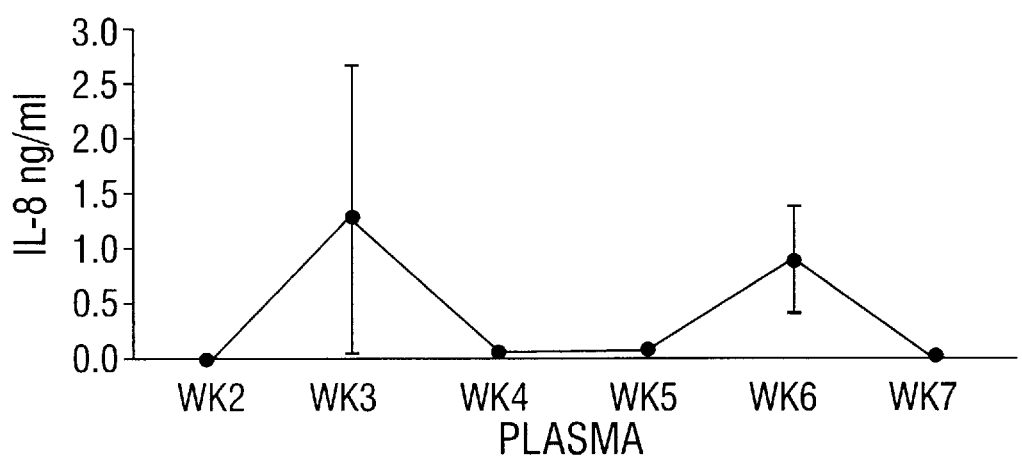
Figures 1, 40B:
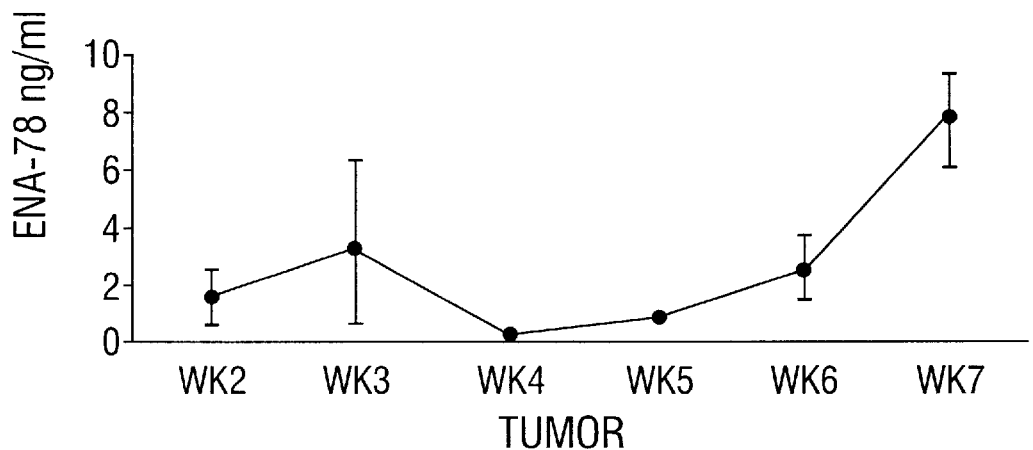
Figures 2, 40B:
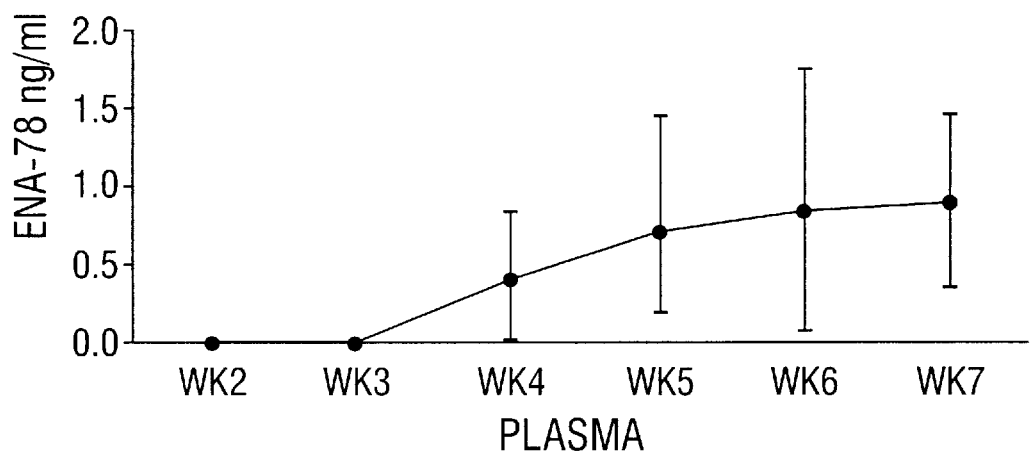
Figures 1, 40C:
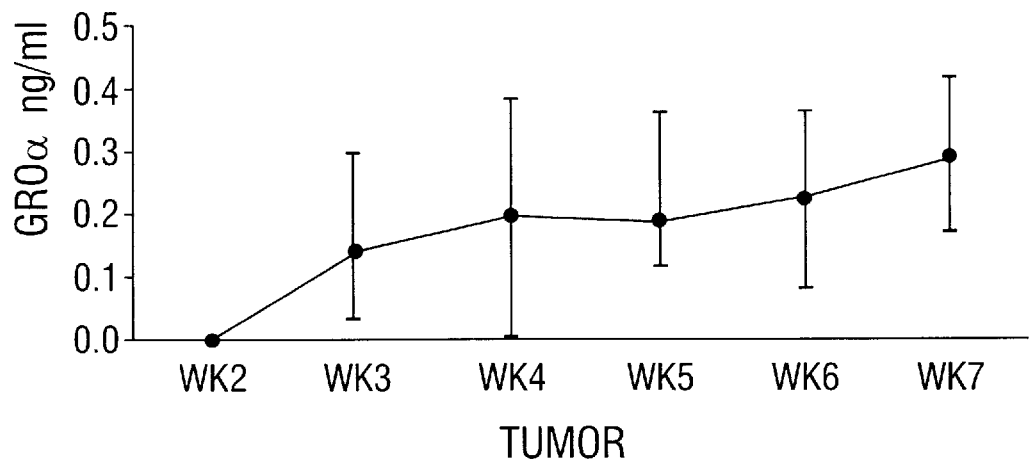
Figures 2, 40C:
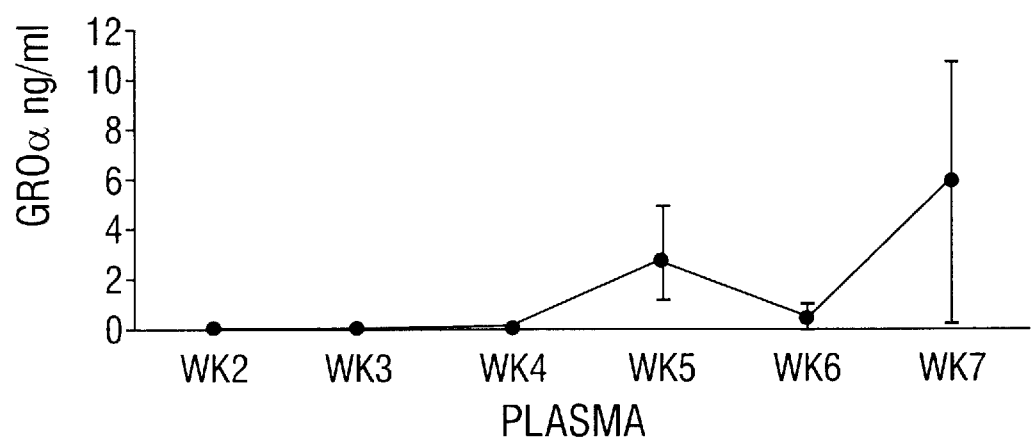
Figure 40D:
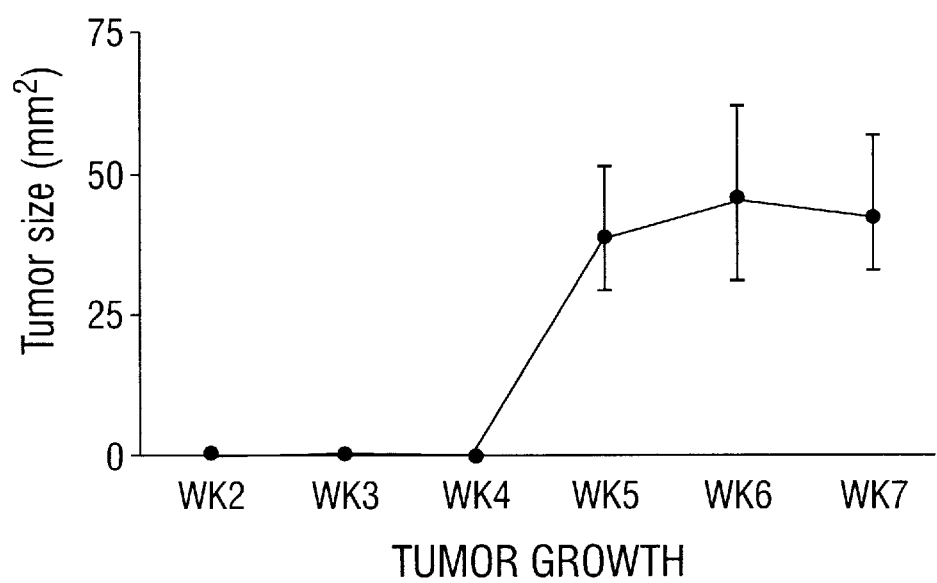
Figures 1, 40E:
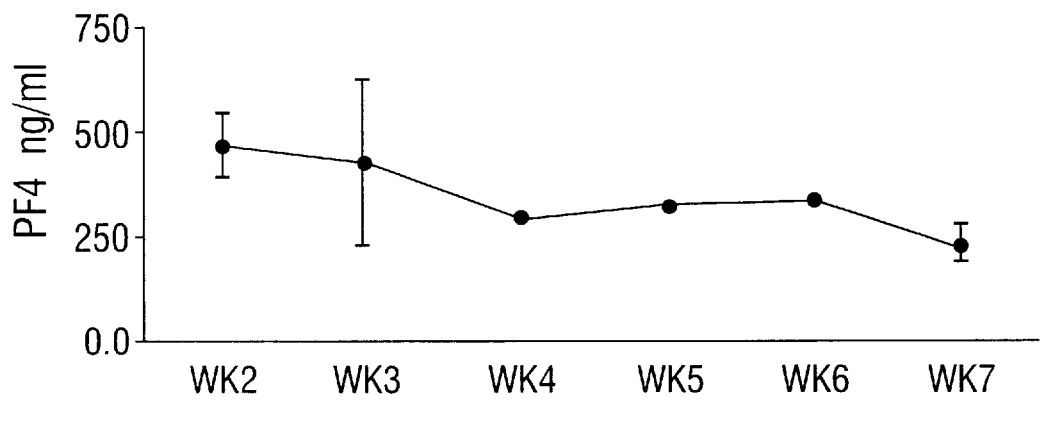
Figures 2, 40E:
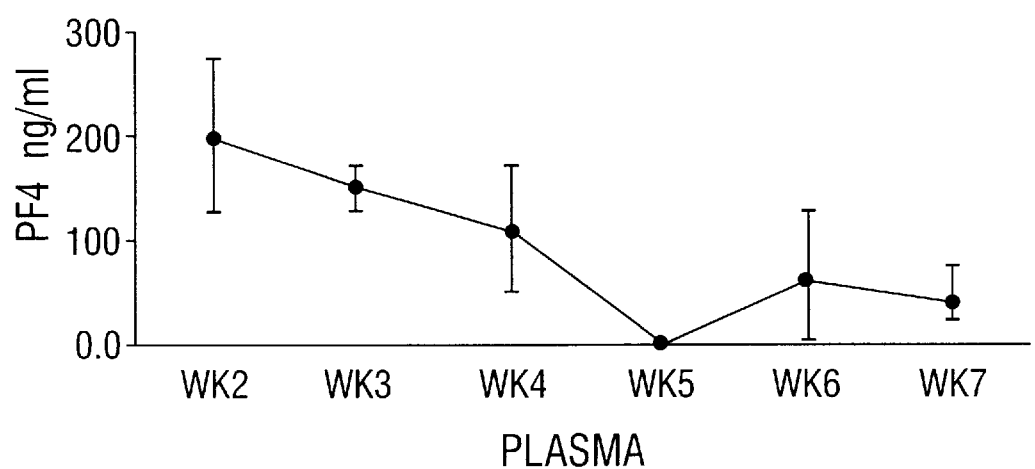
Figures 1, 40F:
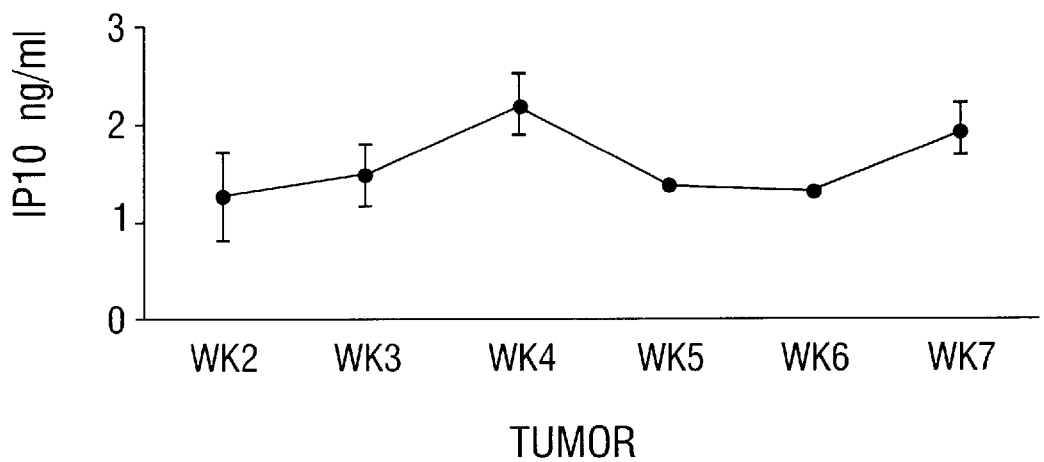
Figures 2, 40F:
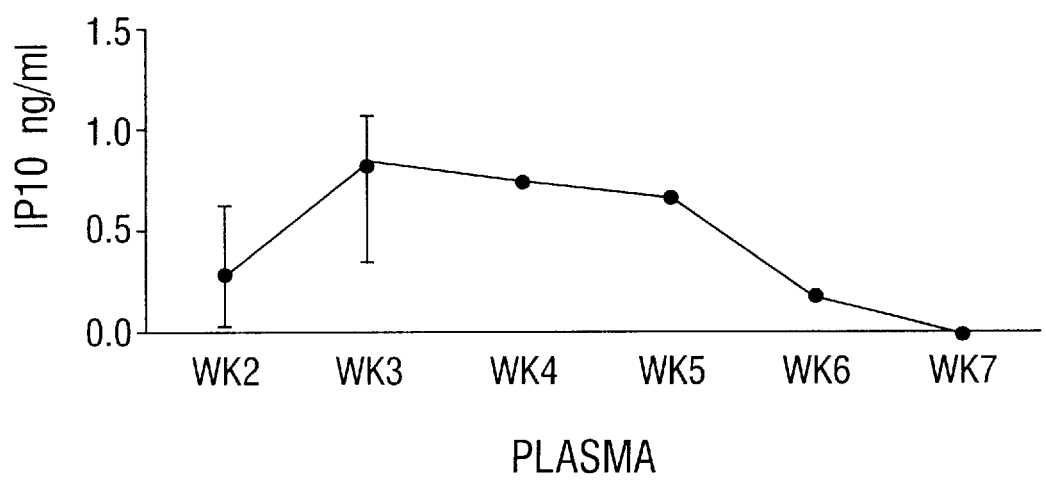
Figures 41A, 41B, 41C, 41D:
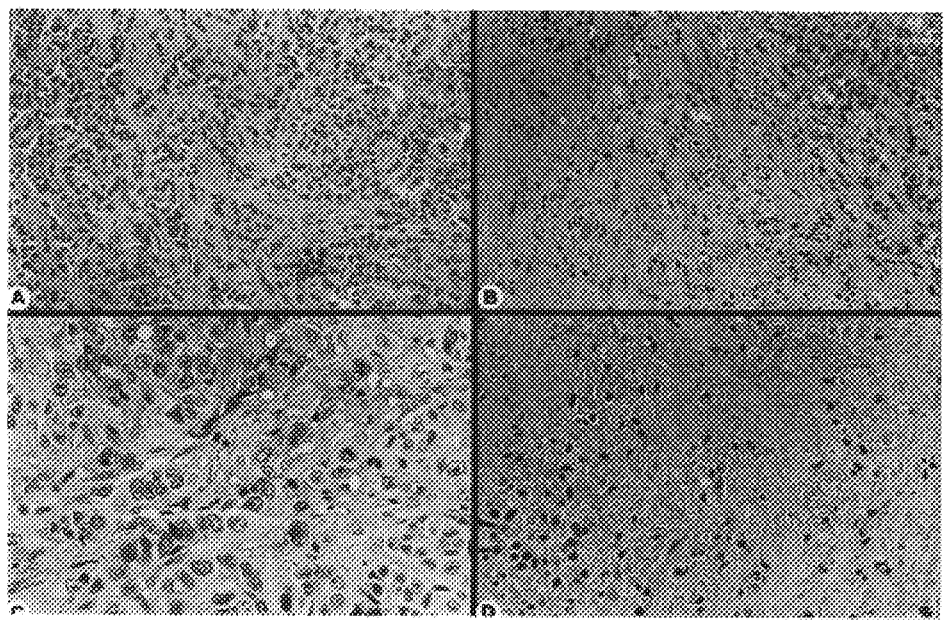
FIG. 41A, FIG. 41B, FIG. 41C and FIG. 41D. Tumorigenesis of A549 NSCLC cells in SCID mice in the presence of either control or neutralizing IL-8 antibodies.

When A549 tumors in SCID mice and plasma from these mice were analyzed for the presence of CXC chemokines, the inventors found a significant correlation of the temporal expression of angiogenic, as compared to angiostatic, CXC chemokines during tumorigenesis FIG. 40A-1, FIG. 40A-2, FIG. 40B-1, FIG. 40B-2, FIG. 40C-1, FIG. 40C-2, FIG. 40D, FIG. 40E-1, FIG. 40E-, FIG. 40F-1 and FIG. 40F-2. These studies substantiated that the production of angiogenic, as compared to angiostatic, CXC chemokines paralleled tumor growth and supported the proposal that an imbalance in angiogenic and angiostatic CXC chemokines exist during tumorigenesis. However, these studies did not demonstrate whether these angiogenic CXC chemokines directly contributed to an imbalance favoring net angiogenesis leading to tumor growth or tumor survival.

Figure 42:
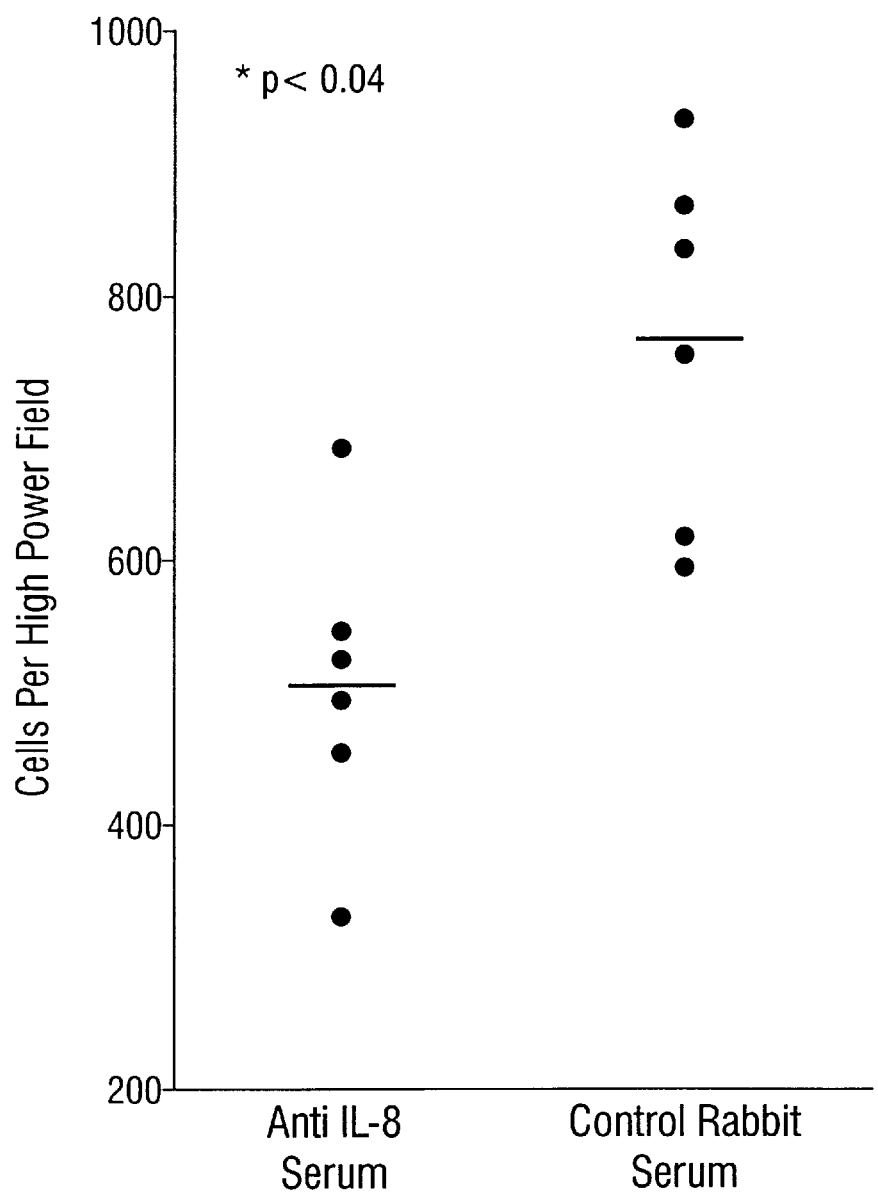
FIG. 42. Morphological analysis of the cellularity of tumors, threshold to NSCLC cell nuclear size.

To assess whether IL-8 directly contributed to tumor growth and survival, human NSCLC (A549) tumorigenesis was allowed to occur in SCID for a period of 4 weeks prior to the initiation of in vivo passive immunization with neutralizing antibodies to IL-8 (every other day during weeks 5, 6, and 7 of tumor growth). It was found that the tumors (at 8 weeks) demonstrated markedly more central necrosis in animals that had received neutralizing antibodies to IL-8, as compared to animals receiving control antibodies (FIG. 41A, FIG. 41B, FIG. 41C and FIG. 41D). In addition, morphological analysis, threshold to NSCLC cell nuclear size, showed a significant reduction in cellularity of the tumors that were exposed to neutralizing IL-8 antibodies (FIG. 42) in comparison to control antibodies.

Figure 46:
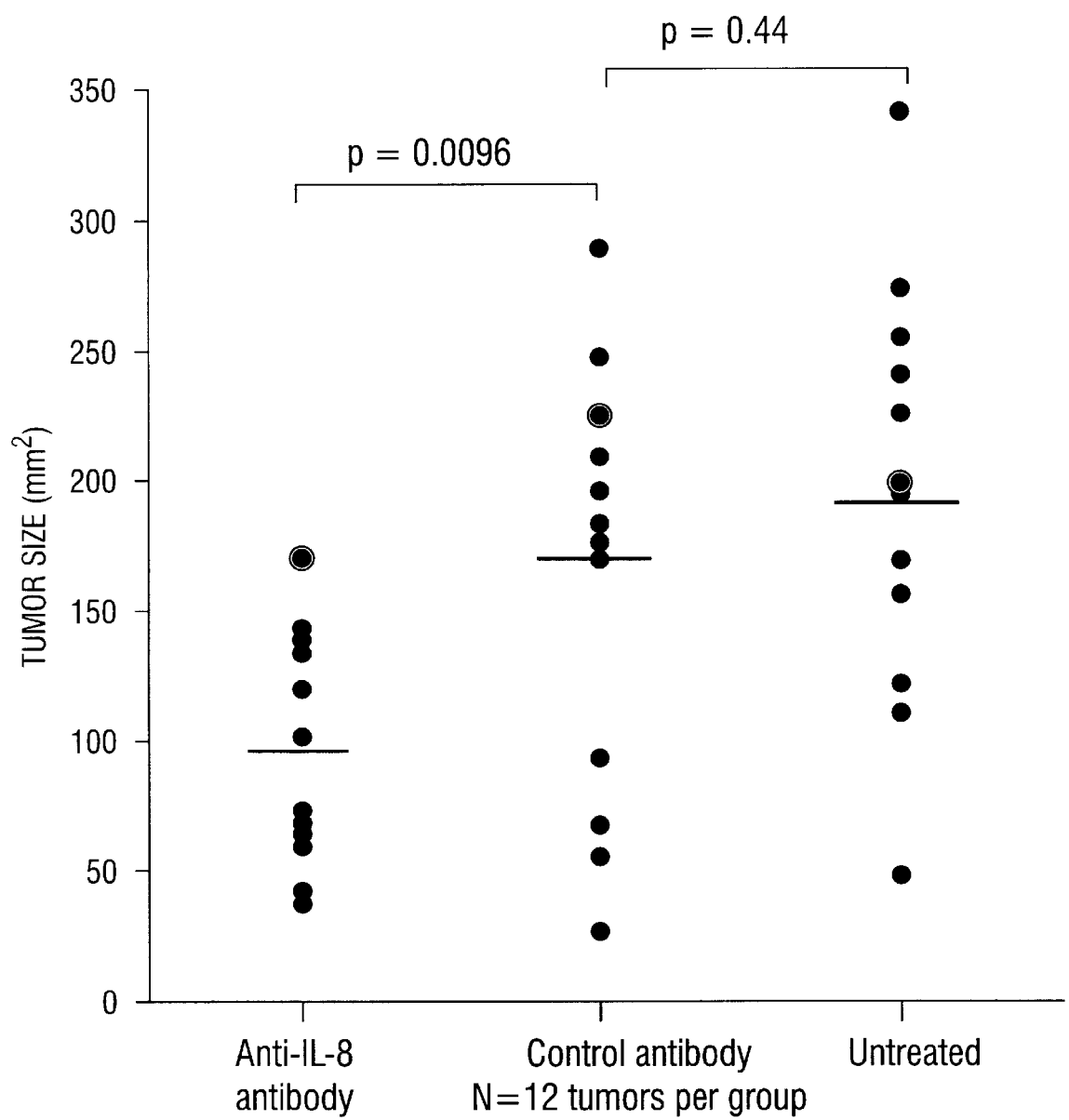
FIG. 46. The tumor size of A549 human tumors in SCID mice treated with anti-IL-8 or control antibodies for 6 weeks, as compared to the tumor size in untreated mice bearing the same tumors.
Figures 47A, 47B, 47C, 47D:
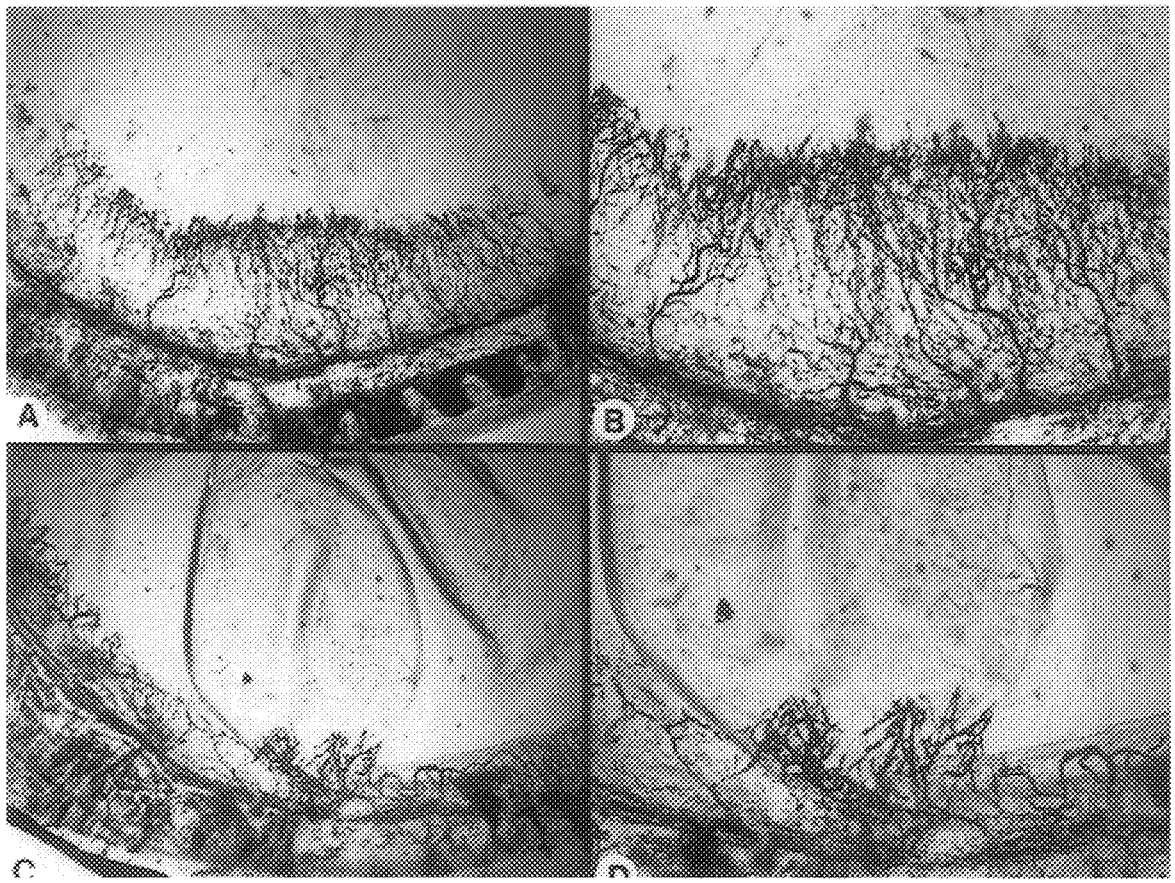
FIG. 47A, FIG. 47B, FIG. 47C and FIG. 47D. The effect of neutralizing IL-8 antibodies from A549/SCID mouse tumor homogenates on corneal neovascularization induced by IL-8.

Importantly, there was a 41% reduction in tumor size using upon anti-IL-8 treatment, as compared to animals receiving control antibodies (FIG. 46). This is due to inhibition of angiogenesis, as IL-8 was confirmed not to promote growth of A549 cells in vitro (Table 5). Anti-IL-8 treatment also showed evidence of reduced metastasis, as assessed by the numbers of human cancer cells in lung single cell suspensions of the treated mice (Table 6).

TABLE 5

IL-8 does not promote growth of A549 cells in vitro.
Anti-IL-8 is not growth inhibitory of A549 cells.

| | Cells/ml (±10⁴) | |
|---|---|---|
| | 24 h | 72 h |
| Control | 72 ± 11 | 135 ± 16.3 |
| IL-8 1 ng/ml | 58 ± 10 | 148 ± 10 |
| IL-8 10 ng/ml | 72 ± 15 | 116 ± 18 |
| anti IL-8 | 80 ± 11 | 144 ± 7 |

A549 cells were grown to 50% confluence, then serum starved for 24 hr. prior to adding either IL-8, or anti-IL-8. Cells were counted in a hemacytometer after 24 and 72 hr. to assess for proliferation.

TABLE 6

FACS analysis of lung homogenates from A549 tumor bearing anti-IL-8, control, and untreated mice demonstrating a trend towards reduced metastasis.

| | % human cells |
|---|---|
| Normal Lung (No tumor) | 1.3 ± 0.5 |
| Untreated (No serum) | 15.2 ± 8.9 |
| Control Serum | 11.6 ± 1.0 |
| Anti-IL-8 | 8.4 ± 4.4 |

FACS analysis was performed on lungs taken from all experimental groups to assess for lung metastasis. Identification of human cells was achieved with FITC-anti-human CD49b (rat).

When tumor homogenates from the A549/SCID mice were analyzed in the corneal neovascularization assay, it was found that neutralizing IL-8 antibodies inhibited the angiogenic effects of the homogenate (FIG. 47A, FIG. 47B, FIG. 47C and FIG. 47D).

The above findings provide evidence that further supports the proposal that the ELR motif containing CXC chemokines are important angiogenic molecules during tumorigenesis, and that an imbalance in their expression, as compared to angiostatic CXC chemokines, dictates their role in mediating net tumor-derived angiogenesis during tumorigenesis. Furthermore, the use of the human NSCLC/SCID mouse model will allow the use of CXC chemokines in tumor therapy to be developed to the completion of pre-clinical testing.

Following the data in Table 6, the inventors believe that the expression of angiogenic CXC chemokines will directly correlate with the tumorigenesis of both the intact NSCLC and NSCLC cell lines in the mice models. In addition, the NSCLC cell lines that are found to have a greater tendency to demonstrate both spontaneous metastasis and experimental lung colonization will show an imbalance in the expression of angiogenic and angiostatic CXC chemokines that favors the angiogenic CXC chemokines. Thus, tumorigenesis, spontaneous metastasis, and experimental lung colonization will all correlate to neovascularization of the evolving tumor.

Using freshly isolated specimens of NSCLC and normal lung tissue from human subjects, the inventors believe that the vascularity (not the leukocyte infiltration) of the NSCLC specimens will directly correlate with the expression of angiogenic CXC chemokines. The predominate cellular sources of these chemokines is expected to be neoplastic cells (a heterogeneous population), fibroblasts, resident macrophages, and endothelial cells. In addition, the magnitude of expression of the angiogenic CXC chemokines is expected to directly correlate with the post-operative staging of the NSCLC and with patient mortality.

EXAMPLE XVIII

Cytokine Networks of Angiogenic CXC Chemokines

The above data, coupled with what is known regarding the role of interferons in wound repair, suggest that the magnitude of IFN expression would be a pivotal event in locally regulating both angiogenic (through negative-feedback) and angiostatic (through positive-feedback) CXC chemokine production.

Interferons are pleiotropic cytokines that exert a broad range of immunomodulatory and inflammatory effects, however, they share a salient feature of cellular growth inhibition. IFNα and IFNβ are produced primarily by mononuclear phagocytes and fibroblasts, respectively, whereas IFNγ is produced by $CD4^+$ and $CD8^+$ T cells and NK cells (Stout et al., 1993; Demaeyer and Demaeyer-Guignard, 1988). These interferons are all known inhibitors of wound repair, specifically they appear to have a significant inhibitory influence on endothelial cell biology (Sidky and Borden, 1987; Zetter, 1988; McKay and Leigh, 1991; Symington, 1989; Yaar et al., 1985; Nickoloff et al., 1991; Shipley et al., 1986; Nickoloff and Mitra, 1989; Klagsbrun and D'Amore, 1991; Pober and Cotran, 1990; Stout et al., 1993; Demaeyer and Demaeyer-Guignard, 1988).

The present data support the idea that IFNs can modulate suppression of neovascularization through both direct and indirect pathways. While IFNα, IFNβ and IFNγ can inhibit the cellular expression of angiogenic CXC chemokines, these interferons are important for the induction of angiostatic CXC chemokines (IP-10 and MIG). The net effect of IFN stimulation would be to shift the biological balance in favor of angiostatic CXC chemokines. This potential mechanism could be operative during the later stages of normal wound repair, where new capillary blood vessel formation is rapid, under strict control, and undergoes marked regression to a physiologic steady-state level.

In contrast, angiogenesis during neoplastic transformation is exaggerated (Folkman and Cotran, 1976; Bouck, 1990). This perpetual neovascularizat-on during tumorigenesis suggests two possible pathologic mechanisms, neither of which are mutually exclusive: 1) tumorigenesis is associated with an increase in the synthesis and/or elaboration of angiogenic mediators; and 2) tumorigenesis is associated with reduced levels of substances which inhibit neovascularization. The inventors' data support the former, and also the fact that these neo-plasmas are often associated with reduced levels of IFNγ, as compared to normal lung tissue.

Figure 43:
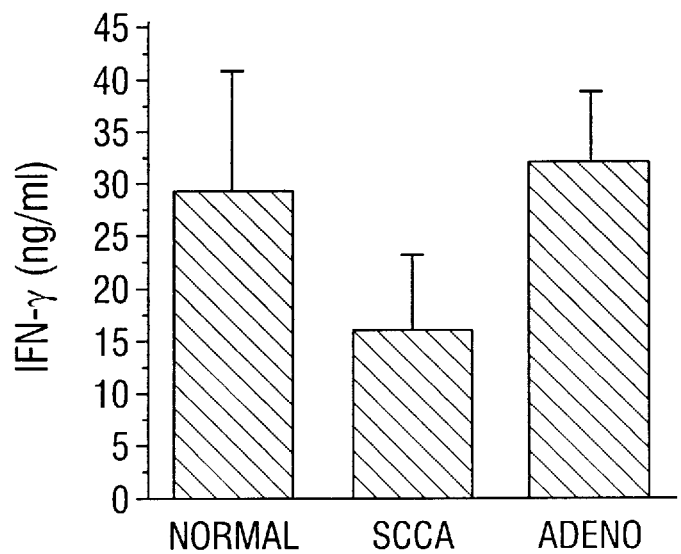
FIG. 43. The presence of IFNγ in NSCLC as compared to normal lung. Tumors represent squamous cell carcinoma (SCCA) and adenocarcinoma (adeno).

To test this hypothesis, the inventors analyzed human tissue homogenates of both normal and NSCLC for the presence of IFNγ using a IFNγ specific ELISA. As shown in FIG. 43, IFNγ concentrations from tumor samples were found to be similar to normal lung tissue. These findings corroborated the study by Vitolo and colleagues (Vitolo et al., 1992), which found while examining solid tumors that cytokine expression of mRNA (TH1 profile) by in situ hybridization from tumor infiltrating lymphocytes was unexpectedly reduced as compared to chronic inflammatory disorders. The above findings may reflect the reduced immunogenicity of tumor-associated antigens, however, an alternative explanation may be the ability of the tumor or host responding cells to produce immunosuppressive factors that may directly impact on the local production of IFNγ.

IL-10 is a recently characterized cytokine that demonstrates varied immunosuppressive bioactivity. Since its initial isolation by Mosmann and colleagues in 1986, investigations have elucidated many of the immunologic properties of this cytokine (Mosmann et al., 1986; Fiorentino et al., 1989). Originally identified as a product of CD4+ T cells, IL-10 is also produced by monocytes, macrophages, B cells, certain populations of CD8+ T cells, and EBV transformed lymphoblastoid cells lines (de Waal Malefyt et al., 1992; Howard et al., 1992; Yssel et al., 1992; Vieira et al., 1991; de Waal Malefyt et al., 1991a; O'Garra et al., 1992). Recent work has demonstrated that epidermal cells may also elaborate IL-10 (Rivas and Ullrich, 1992).

Functional studies reveal that IL-10 has profound effects on monocytes, resulting in alterations in cell morphology and cytotoxicity, down regulation of the expression of MHC class II antigens, and inhibition of proinflammatory cytokine production (Moore et al., 1990; Fiorentino et al., 1991; de Waal Malefyt et al., 1991b; Bogdan et al., 1991; Ralph et al., 1992; de Velde et al., 1992). Furthermore, IL-10 also exerts direct effects on the growth and function of T cells, B cells, and mast cell (de Waal Malefyt et al., 1992; Howard et al., 1992).

These specific actions result in the capacity for IL-10 to attenuate a wide range of effector immune responses, including T cell cytokine (i.e., IFNγ) production and antigen-specific proliferation, B cell immunoglobulin synthesis, and the elaboration of TNFα and IFNγ by NK cells (de Waal Malefyt et al., 1992; Howard et al., 1992). IL-10 may play an important role in homeostasis under normal circumstances, however, IL-10, in the context of tumorigenesis, may be a major immunosuppressive factor that attenuates the local generation of IFNγ.

Figure 44:
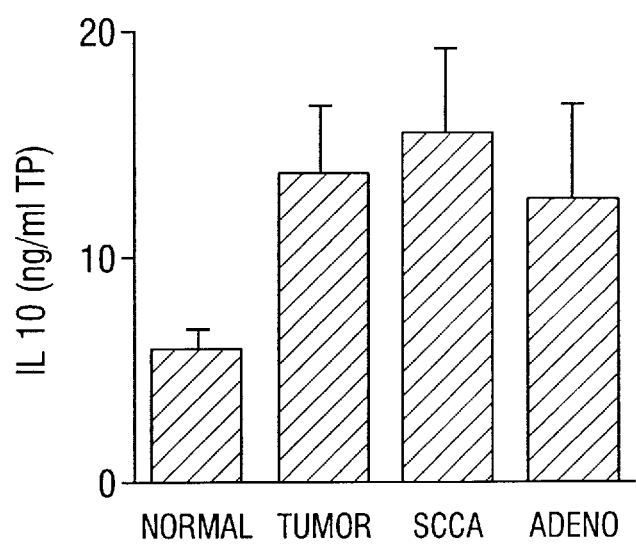
FIG. 44. The presence of IL-10 in NSCLC as compared to normal lung. Tumors represent squamous cell carcinoma (SCCA) and adenocarcinoma (adeno).

To test this premise, the inventors investigated the capacity of NSCLC to produce IL-10. The inventors found increased levels of antigenic IL-10 in tissue homogenates of NSCLC (13.7±2.8 ng/mg TP), as compared to normal lung tissue (5.8±0.8 ng/mg TP) (FIG. 44). No significant difference in IL-10 levels were seen between the squamous cell carcinoma (15.4±3.7 ng/mg TP) and adenocarcinoma (12.3±4.2 ng/mg TP).

To determine the celLular source of IL-10 in the NSCLCs, the inventors utilized immunohistochemical staining of NSCLC to show primary localization of antigenic IL-10 to individual NSCLC cells. In addition, immunostain utilizing HAM56, (Enzo Diagnostics, Inc., Farmingdale, N.Y.) a murine monoclonal antibody against human mononuclear cells, confirmed that tumor cells, rather than immune cells, were the primary cellular source of antigenic IL-10.

Since IL-10 had previously been demonstrated to be produced by epidermal cells (Rivas and Ullrich, 1992), the inventors analyzed the conditioned media of several unstimulated human NSCLC cell lines (A549, A427, and Calu-6) for the constitutive production of IL-10. These cells produced 6.3±1 ng/ml, 1.9±0.9 ng/ml, and 7.6±1.1 ng/ml of IL-10 after 24 hrs of culture, respectively. These findings demonstrate that NSCLC cell lines can elaborate IL-10. Thus, IL-10 may play a role in impairing immune cell effector function and enable the NSCLC to evade host immune defenses, however, IL-10 suppression of IFNγ may play an equally important role in perpetuating tumor-associated neovascularization.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abruzzo et al., "Cytokine-induced gene expression of interleukin-8 in human transitional cell carcinomas and renal cell carcinomas," *Am J Pathol*, 140: 365–373, 1992.

Adelman et al., *DNA*, 2: 183, 1983.

Anisowicz et al., "Constitutive overexpression of a growth-regulated gene in transformed Chinese hamster and human cells," *Proc. Natl. Acad. Sci. USA*, 84: 7188–92, 1987.

Anisowicz et al., "Functional diversity of gro gene expression in human fibroblasts and mammary epithelial cells," *Proc. Natl. Acad. Sci. USA*, 85: 9645–49, 1988.

Ansel et al., "Human keratinocytes are a major source of cutaneous platelet-derived growth factor," *J. Clin. Invest.*, 92: 671–78, 1993.

Antibodies: A Laboratory Manual, Cold Spring Harbor Laboratory, 1988.

Anttila et al., "Interleukin-8 immunoreactivity in the skin of healthy subjects and patients with palmoplantar pustulosis and psoriasis," *J. Invest. Dermtol.*, 98: 96–101, 1992.

Atherton, "Growth stimulation of endothelial cells by simultaneous culture with Sarcoma 180 cells in diffusion chambers," *Cancer Res.*, 37: 3619–3622, 1977.

Auerbach, "Angiogenesis-inducing factors: a review," *Lymphokines*, Vol. IV, 69–88, Academic Press, NY, 1981.

Bacon et al., "Potent and specific inhibition of IL-8. IL-1alpha, and IL-1beta-induced in vitro human lymphocyte migration by calcium channel antagonists," *Biochem. Biophy. Res. Comm.*, 165: 349–354, 1989.

Baggiolini et al., *Advances in Immunology*, 55: 97–179, 1994.

Baggiolini et al., "Neutrophil-activating peptide-1/interleukin 8, a novel cytokine that activates neutrophils," *J. Clin. Invest.*, 84: 1045–49, 1989.

Baggiolini et al., "Interleukin-8 and related chemotactic cytokines," In: Gallin JI, Goldstein IM, Snyderman R (eds.) Inflammation: Basic Principles and Clinical Correlates, Raven Press, Ltd., New York, N.Y., 1992.

Baker et al., "Epidemiology of chronic venous ulcers," *Br. J. Surg.*, 78: 864–67, 1991.

Baldwin et al., *Proc. Natl. Acad. Sci. USA*, 88: 502–506, 1991.

Bankert et al., "Human lung tumors, patient's peripheral blood lymphocytes and tumor infiltrating lymphocytes propagated in SCID mice," *Curr Top Micro. Immunol.*, 152: 201–10, 1989.

Barrondon and Gree, "Cell migration is essential for sustained growth of keratinocyte colonies: the role of transforming growth factor and epidermal growth factor," *Cell*, 50: 1131–37, 1987.

Beall et al., *The Journal of Biological Chemistry*, 267 (5): 3455–3459, 1992.

Bedard et al., *Am. J. Respir. Cell. Mol. Biol.*, 9: 455–462, 1993.

Begg et. al. Biochemistry 17: 1739, 1978.

Bittner et al., *Methods in Enzymol.*, 153: 516–544, 1987.

Bogdan et al., "Macrophage Deactivation by Interleukin 10," *J. Exp. Med.*, 174: 1549–55, 1991.

Bosma et al., *Nature*, 301: 527–30, 1983.

Bouck, "Tumor angiogenesis: the role of oncogenes and tumor suppressor genes," *Cancer Cells*, 2: 179–85, 1990.

Brandt et. al., *Mol. Immunol.*, 30 (11): 979–91, 1993.

Brem et al., "Inhibition of neovascularization by an extract derived from vitreous," *Am. J. Ophthalmol*, 84: 323–328, 1977.

Brem and Folkman, "Inhibition of tumor angiogenesis mediated by cartilage," *J Exp Med*, 141: 427–439, 1975.

Brennan et al., *Eur. J. Immunol.*, 20: 2141–2144, 1990.

Brenner et al., "Message amplification phenotyping (MAPPing): a technique to simultaneously measure multiple mRNAs from small numbers of cells," *Biotechniques*, 7: 1096–1103, 1989.

Brooks, P. C., Montgomery, A. M. P., Rosenfeld, M., Reisfeld, R. A., Hu, T., Klier, G., and Cheresh, D. A. (1994) *Cell* 79, 1157–1164

Brown et al., "Cytokine activated human mesangial cells generate the neutrophil chemoattractant—interleukin 8," *Kidney International*, 40: 86–90, 1991.

Brown et al., "Enhancement of epidermal regeneration by biosynthetic epidermal growth factor," *J. Exp Med.*, 163: 1319–24, 1986.

Browse and Burnand, "The cause of venous ulceration," *Lancet*, ii: 243–45, 1982.

Burdick M D, Polverini P J, Kunkel S L, Orringer M B, Whyte R I, Wilke C A, Strieter R M. FASEB J. 8 (4): A146. Abstract #849. 1994.

Burnand, "Etiology of venous ulceration," *Br. J. Surg.*, 77: 483–84, 1990.

Caamano et al., "Detection of p53 in primary lung tumors and nonsmall cell lung carcinoma cell lines," *Am J. Pathol.*, 139: 839–45, 1991.

Callam et al., "Chronic ulceration of the leg: extent of the problem and provision of care," *Br Med. J.*, 290: 1855–56, 1985.

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984.

Cerretti et al., *Molec. Immun.*, 30 (4): 359–367, 1993.

Chang et al., *J. Biol. Chem.*, 269 (41): 25277–82, 1994.

Clark et al., "Fibronectin and fibrin provide a provisional matrix for epidermal cell migration during wound re-epithelialization," *J. Invest. Dermatol.*, 79: 264–69, 1982.

Clark, "Basics of cutaneous wound repair," *J. Dermatol. Surg. Oncol.*, 19: 693–70, 1993.

Clark-Lewis et al., "Chemical synthesis, purification, and characterization of two inflammatory proteins, neutrophil activating peptide 1 (interleukin-8) and neutrophil activating peptide 2," *Biochemistry*, 30: 3128–35, 1991b.

Clark-Lewis et al., "Platelet factor 4 binds to interleukin 8 receptors and activates neutrophils when its N terminus is modified with Glu-Leu-Arg," *Proc. Natl. Acad. Sci. USA*, 90: 3574–3577, 1993.

Clark-Lewis et al., *The Journal of Biological Chemistry*, 266 (34): 23128–23134, 1991a.

Clore and Gronenborn, In Cytokines: Interleukin 8 (NAP-1) and Related Chemotactic Cytokines (Baggiolini, M. and Sorg, C., eds) pp. 18–40, Karger, Basel, 1992.

Clore et al., *Biochem.* 29: 1689–1696, 1990.

Cohen, "Naked DNA Points Way to Vaccines," *Science*, 259: 1691–1692, 1993.

Colberre-Garapin et al., *J. Mol. Biol.,* 150: 1, 1981.

Coon et al., "Venous thromboembolism and other venous disease in the Tecumseh community health study," *Circulation,* 143: 839–46, 1973.

Corbett et al., *Biochem. Biophys. Res. Comm.,* 205 (1): 612–17, 1994.

Cordts et al., *J. Vasc. Surg.,* 15: 480–486, 1992.

Cox et al., *J. Virol.* 67 (9): 5664–5667, 1993.

Crea et al. *Proc. Natl. Acad. Sci. U.S.A,* 75: 5765, 1978.

Crum et al., "A new class of steroids inhibits angiogenesis in the presence of heparin or a heparin fragment," *Science,* 230: 1375–78, 1985.

Davidson, "Wound repair," In: Gallin JI, Goldstein IM, and Snyderman R (eds.). Inflammation: Basic Principles and Clinical Correlates. Raven Press, Ltd., New York, N.Y., 1992.

de Waal Malefyt et al., "Interleukin-10 (IL-10) inhibits cytokine synthesis by human monocytes-an autoregulatory role of IL-10 produced by monocytes," *J. Exp. Med.,* 174: 1209–20, 1991a.

de Velde et al., "IL-10 stimulates monocyte Fc gamma R surface expression and cytotoxic activity: Distinct regulation of antibody-dependent cellular cytotoxicity by IFN-gamma, IL-4, and IL-10," *J. Immunol.,* 149: 4048–52, 1992.

de Boer et. al., *Invest. Ophthalmol. Vis. Sci.,* 34: 3376–3385, 1993.

de Waal Malefyt et al., "Interleukin-10 inhibits cytokine synthesis by human monocytes: an autoregulatory role of IL-10 produced by monocytes," *J. Exp. Med.,* 174: 1209–20, 1991b.

de Waal Malefyt et al., "Interleukin-10," *Curr Opin. Immunol.,* 4: 314–20, 1992.

Demaeyer and Demaeyer-Guignard, "Interferons and other regulatory cytokines," Wiley, N.Y., 1988.

Deutsch and Kain, "Studies on platelet factor 4," In: Jonson S A, Monto R W, Rebuck J W, Horn R C (eds), Blood Platelets, Little, Brown, Boston, 337, 1961.

Dewald, B., Moser, B., Barella, L., Schumacher, C., Baggiolini, M., and Clark-Lewis, I. (1992) *Immunol. Letts.* 32, 81–84

DiPietro and Polverini, "Angiogenic macrophages produce the angiogenic inhibitor thrombospondin 1," *Am J. Pathol.,* 143: 678–84, 1993.

Donnelly et al., *The Lancet,* 341: 643–647, 1993.

Donoff et al., "Preparation and properties of collagenases from epithelium and mesenchyme of healing mammalian wounds," *Biochem Biophys Acta,* 227: 639–653, 1971.

Eisenstein et al., "The resistance of certain tissues to invasion III. Cartilage extracts inhibit the growth of fibroblasts and endothelial cells in culture," *Am. J. Pathol.,* 81: 337–347, 1975.

Elner et al., "Neutrophil chemotactic factor (IL-8) gene expression by cytokine-treated retinal pigment epithelial cells," *Am. J. Path.,* 136: 745–750, 1990.

Engerman et al., "Cell turnover of capillaries," *Lab Invest.,* 17: 738–43, 1967.

Epstein, "[a1(III)3] human skin collagen: release by pepsin digestion and preponderance in fetal life," *J. Biol. Chem.,* 249: 3225–3231, 1974.

Evanoff et al., "A sensitive ELISA for the detection of human monocyte chemoattractant protein-1 (MCP-1)," *Immunol Invest,* 21 (1): 39–45, 1992.

Faber, "Lung cancer," In: Holleb A I, Fink D J, Murphy G P (eds.). American Cancer Society Textbook of Clinical Oncology. Atlanta: American Cancer Society, pp. 194–212, 1991.

Farber, "A macrophage mRNA selectively induced by γ-interferon encodes a member of the platelet factor-4 family of cytokines," *Proc. Natl. Acad. Sci. USA,* 87: 5238–42, 1990.

Farber, "HuMIG: a new member of the chemokine family of cytokines," *Biochem. Biophys. Res. Comm.,* 192: 223–30, 1993.

Ferrick et. al., *Invest. Ophthalmol. Vis. Sci.,* 32 (50): 1534–1539, 1991.

Fiorentino et al., "IL-10 inhibits cytokine production by activated macrophages," *J. Immunol.,* 147: 3815–22, 1991.

Fiorentino et al., "Two types of mouse helper T cell. IV. Th2 clones secrete a factor that inhibits cytokine production by Th1 clones," J. Exp. Med., 170: 2081–2095, 1989.

Folkman and Klagsbrun, "Angiogenic factors," *Science,* 235: 442–47, 1987.

Folkman, "Tumor Angiogenesis," In: Klein G, Weinhouse S, ed., *Advances in Cancer Research,* Orlando: Academic Press, Inc., 43: 175–203, 1985.

Folkman and Cotran, "Relation of vascular proliferation to tumor growth," *International Reviews of Experimental Pathology,* 16: 207–248, 1976.

Folkman et al., "Induction of angiogenesis during the transition from hyperplasia to neoplasia," *Nature,* 339: 58–61, 1989.

French-Constant et al., "Reappearance of an embryonic pattern of fibronectin splicing during wound healing in the adult rat," *J Cell Biol.,* 109: 90–14, 1989.

Fynan et al., "DNA vaccines: Protective immunizations by parenteral, mucosal, and gene-gun inoculations," *Proc. Natl. Acad. Sci. USA,* 90: 11478–11482, 1993.

Gal et. al., *Lab. Invest.,* 68 (1): 18-, 1993.

Garfinkel, "Cancer Statistics and Trends," In: Holleb A I, Fink D J, Murphy G P, ed., American Cancer Society Textbook of Clinical Oncology, Atlanta: American Cancer Society, 2–9, 1991.

Gefter et al., *Somatic Cell Genet.,* 3: 231–236, 1977.

Ghosh-Choudhury and Graham, *Biochem. Biophys. Res. Comm.,* 147: 964–973, 1987.

Gluzman et al., in *Eukaryotic Viral Vectors* (Gluzman, Y., ed) pp. 187–192, Cold Spring Harbor Press, Cold Spring Harbor, N.Y., 1982.

Goding, in Monoclonal Antibodies: Principles and Practice, 2d ed., Orlando, Fla., Academic Press, 1986, pp. 60–61, 65–66, 71–74, 1986.

Goldman et al., "Consensus paper on venous leg ulcer," *J. Dermatol. Surg. Oncol.,* 18: 592–602, 1992.

Good et al., "A tumor suppressor-dependent inhibitor of angiogenesis is immunologically and functionally indistinguishable from a fragment of thrombospondin," *Proc. Natl. Acad. Sci. USA,* 87: 6624–28, 1990.

Graham, F. L. and Prevec, L, "Manipulation of adenovirus vectors," In: Murray E. J. (ed.), *Methods in Molecular Biology, Gene Transfer and Expression Protocols,* pp. 109–128. New Jersey: The Humana Press Inc, 1991.

Graham, F. L., J. Smiley, W. C. Russell and R. Nairn, "Characteristics of a human cell line transformed by DNA from human adenovirus type 5," *J. Gen Virol,* 36: 59–72, 1977.

Graham, F. L. and A. J. van der Eb, "A new technique for the assay of infectivity of human adenovirus 5 DNA," *Virology,* 52: 456–467, 1973.

Greaves, "Lack of effect of topically applied epidermal growth factor (EGF) on epidermal growth in man in vivo," *Clin. Exp. Dermatol.,* 5: 101–3, 1980.

Griffiths et al., "Modulation of leukocyte adhesion molecules, a T-cell chemotaxin (IL-8) and a regulatory cytokine (TNF-a) in allergic contact dermatitis (rhus dermatitis)," Br. J. Dermtol., 124: 519–26, 1991.

Grotendorst et al., "Production of transforming growth factor beta by human peripheral blood monocytes and neutrophils," J. Cell Physiol., 140: 396–402, 1989.

Gusella et al., "IL-2 up-regulates but IFN-g suppresses IL-8 expression in human monocytes," J. Immunol., 151: 2725–32, 1993.

Han et al., J. Lab. Clin. Med., 120 (4): 645–660, 1992.

Harris, "Recent insights into the pathogenesis of the proliferative lesion in rheumatoid arthritis," Arthritis Rheum., 19: 68, 1976.

Haskill et al., Proc. Natl. Acad. Sci. USA, 87: 7732–7736, 1990.

Hébert et al., "Scanning mutagenesis of interleukin-8 identifies a cluster of residues required for receptor binding," J. Biol. Chem., 266 (28): 18989–94, 1991.

Hendrickson, "The SCID mouse: relevance as an animal model system for studying human disease," Am J. Pathol., 143: 1511–22, 1993.

Herlyn et al., "Biology of tumor progression in human melanocytes," Lab Invest., 56: 461–74, 1987.

Herrick et al., "Sequential changes in histologic pattern and extracellular matrix deposition during the healing of chronic venous ulcers," Am J. Pathol., 141: 1085–95, 1992.

Holmes, W. E., Lee, J., Kuang, W. J., Rice, G. C., and Wood, W. I. (1991) Science 253, –278–1280

Holmes et al., Science, 253: 1278, 1991.

Homandberg et al., "Heparin-binding fragments of fibronectin are potent inhibitors of endothelial cell growth: structure and function correlates," Biochem. Biophys. Acta., 874: 61, 1986.

Horuk, R. (1994) Immunol. Today 15, 169–174

Hotta et al., "Coding region structure of interleukin-8 gene of human lung giant cell carcinoma LU65C cells that produce LUCT/interleukin-8: homogeneity in interleukin-8 genes," Immunol. Letters, 24: 165–169, 1990.

Howard et al., "Biological properties of interleukin 10," J. Clin. Immunol., 12: 239–47, 1992.

Hu et al., "Interleukin-8 stimulates angiogenesis in rats," Inflammation, 17 (2): 135–43, 1993.

Iida and Grotendorst, Molecular and Cellular Biology, 10 (10): 5596–5599, 1990.

Ingber and Folkman, "Inhibition of angiogenesis through modulation of collagen metabolism," Lab. Invest., 59: 44–51, 1988.

Ingber et al., "A possible mechanism for inhibition of angiogenesis by angiostatic steroids: Induction of capillary basement membrane dissolution," Endocrinology, 119: 1768–75, 1986.

Inouye et al., Nucleic Acids Res., 13: 3101–3109, 1985.

Jaffe et al., Investigative Ophthalmology & Visual Science, 34 (9): 2776–2785, 1993.

Juhasz et al., Am. J. Pathol., 143: 1458–1469, 1993.

Kaashoek et al., "Cytokine production by the bladder carcinoma cell line 5637: rapid analysis of mRNA expression levels using a cDNA-PCR procedure," Lymphokine Cytokine Res, 10: 231–235, 1991.

Kaplan et al., "The expression of a interferon-induced protein (IP-10) in delayed immune responses in human skin," J. Exp. Med., 166: 1098–1108, 1987.

Karlsson et al., EMBO J., 5: 2377–2385, 1986.

Kasahara et al., "IL-1 and TNF-alpha induction of IL-8 and monocyte chemotactic and activating factor (MCAF) mRNA expression in a human astrocytoma cell line," Immunol., 74: 60–67, 1991.

Kasama et al., "Expression and regulation of human neutrophil-derived macrophage inflammatory protein-1a," J. Exp. Med., 178: 63–72, 1993.

Kawahara and Deuel, J. Biol. Chem., 264: 679–682, 1989.

Klagsbrun and D'Amore, "Regulators of angiogenesis," Annu. Rev. Physiol., 53: 217–39, 1991.

Koch et al., "Enhanced production of the chemotactic cytokines interleukin-8 (IL-8) and monocyte chemoattractant protein-1 (MCP-1) in human abdominal aortic aneurysms," Am J. Pathol., 142: 1423–31, 1993.

Koch et al., "Decreased monocyte-mediated angiogenesis in scleroderma," Clin. Immunol. Immunopath., 64: 153–60, 1992a.

Koch et al., "Stimulation of neovascularization by human rheumatoid synovial tissue macrophages," Arthritis Rheum, 29 (4): 471–9, 1986.

Koch et al., "Interleukin-8 (IL-8) as a macrophage-derived mediator of angiogenesis," Science, 258: 1798–1801, 1992b.

Koch et al., "The synovial tissue macrophage as a source of the chemotactic cytokine interleukin-8," J Immunol, 147: 2187–95, 1991a.

Koch et al., "Thiol-containing compounds inhibit the production of monocyte/macrophage-derived angiogenic activity," Agents Actions, 34 (3–4): 350–7, 1991b.

Kohler and Milstein, Nature, 256: 495–497, 1975.

Kohler and Milstein, Eur. J. Immunol., 6: 511–519, 1976.

Kotin, Human Gene Therapy, 5: 793: 801, 1994.

Kunkel et al., Methods Enzymol., 154: 367–382, 1987.

Kurkinen et al., "Sequential appearance of fibronectin and collagen in experimental granulation tissue," Lab Invest., 43: 47–51, 1980.

Laemmli, Nature, 227: 680–685, 1970.

Langer et al., "Control of tumor growth in animals by infusion of an antiangiogenesis inhibitor," Proc Natl Acad Sci USA, 77: 4331–4335, 1980.

LaRosa et al., J. Biol. Chem., 267: 25402–25406, 1992.

Larsen et al., "Neutrophil activating protein (NAP-1) is also chemotactic fro T lymphocytes," Science, 243: 1164–1167, 1989.

Lee and Langer, "Shark cartilage contains inhibitors of tumor angiogenesis," Science 221: 1185–1187, 1983.

Lee et al., "Efficacy of antitumor chemotherapy in C3H mice enhanced by the antiangiogenesis steroid, cortisone acetate," Cancer Res., 47: 5021, 1987.

Lee, J., Horuk, R., Rice, G. C., Bennett, G. L., Camerato, T., and Wood, W. I. (1992) J. Biol. Chem., 267 16283–16287

Leibovich and Weisman, "Macrophages, wound repair and angiogenesis," Prog. Clin. Biol. Res., 266: 131–145, 1988.

Leung et al., "Expression of endothelial-leukocyte adhesion molecule-1 in elicited late phase allergic reactions," J. Clin. Invest., 87: 1805–09, 1991.

Li et. al., "Angiostatic steroids potentiated by sulfated cyclodextrins inhibit corneal neovascularization," Invest. Ophthalmol. Vis. Sci., 32 (11): 2898–905, 1991.

Lindley et al., Proc. Natl. Acad. Sci. USA, 85: 9199–9203, 1988.

Lowy et al., Cell, 22: 817, 1980.

Lukacs et al., "The role of MIP-1a in S. Mansoni egg-induced granulomatous inflammation," J. Exp. Med., 177: 1551–1559, 1993.

Luster and Ravetch, "Genomic characterization of a gamma-interferon-inducible gene (IP-10) and identification of an interferon-inducible hypersensitive site," Mol. Cell. Biol., 7: 3723–31, 1987b.

Luster and Ravetch, J. Exp. Med., 166: 1084–1097, 1987a.

Luster and Leder, *J. Exp. Med.,* 178: 1057–1065, 1993.

Luster et al., *Nature,* 315: 672–676, 1985.

Luster et. al., *Proc. Natl. Acad. Sci. USA,* 84: 2868–2871, 1987.

Lutty et al., "Vitreous: an inhibitor of retinal extract-induced neovascularization," *Inv. Opthalmol Vis. Sci.,* 24: 52–56, 1983.

Macchiarini et al., "Relation of neovascularization to metastasis of non-small cell lung cancer," *Lancet,* 340: 145–46, 1992.

Madri et al., "Phenotypic modulation of endothelial cells by transforming growth factor-beta depends upon the composition and organization of the extracellular matrix," *J Cell Biol,* 106: 1375–1384, 1988.

Maione et al., "Inhibition of angiogenesis by recombinant human platelet factor-4," *Science,* 247: 77–79, 1990.

Maione et al., "Inhibition of tumor growth in mice by an analogue of platelet factor 4 that lacks affinity for heparin and retains potent angiostatic activity," *Cancer Res.,* 51: 2077–83, 1991.

Maiorana and Gullino, "Acquisition of angiogenic capacity and neoplastic transformation in the rat mammary gland," *Cancer Res.,* 38: 4409–4414, 1978.

Maragoudakis et al., "Inhibition of basement membrane biosynthesis prevents angiogenesis," *J. Pharmacol. Exp. Therapy,* 244: 729–33, 1988.

Martins-Green and Bissell, *The Journal of Cell Biology,* 110: 581–595, 1990.

Martins-Green et al., *Cell Regulation,* 2: 739–752, 1991.

Matsushima and Oppenheim, "Interleukin 8 and MCAF: Novel inflammatory cytokines inducible by IL-1 and TNF," *Cytokine,* 1: 2–13, 1989.

Matsushima et al., "Molecular cloning of a human monocyte-derived neutrophil chemotactic factor (MDNCF) and the induction of MDNCF mRNA by interleukin-1 and tumor necrosis factor," *J. Exp. Med.,* 167: 1883–93, 1988.

McElvaney et al., *J. Clin. Invest.,* 90: 1296–1301, 1992.

McGrory, W. J. et al., "A simple technique for the rescue of early region I mutations into infectious human adenovirus type 5," *Virology,* 163: 614–617, 1988.

McKay and Leigh, "Epidermal cytokines and their role in cutaneous wound healing," *Br. J. Dermatol.,* 124: 513–18, 1991.

McLemore et al., "Comparison of intrapulmonary, percutaneous intrathoracic, and subcutaneous models for the propagation of human pulmonary and nonpulmonary cancer cell lines in athymic nude mice," *Cancer Res.,* 48: 2880–86, 1988.

Messing et al., Third Cleveland Symposium on Macromoleculesand Recombinant DNA, Editor A. Walton, Elsevier, Amsterdam, 1981.

Messing, *Methods Enzymol.,* 101: 20–78, 1983.

Mette et al., "Distribution of integrin cell adhesion receptors on normal bronchial epithelial cells and lung cancer cells in vitro and in vivo," *Am. J. Respir. Cell Mol. Biol.,* 8: 562–72, 1993.

Michel et al., "Interleukin-8 receptor-mediated chemotaxis of normal human epidermal cells," *FEBS,* 305: 241–43, 1992.

Miller and Krangel, "Biology and biochemistry of the chemokines: a family of chemotactic and inflammatory cytokines," *Crit. Rev. Immunol.,* 12: 17–46, 1992.

Miller, *Curr. Top. Microbiol. Immunol.,* 158: 1, 1992.

Miller et. al., "Vascular endothelial growth factor/vascular permeability factor is temporally and spatially correlated with ocular angiogenesis in a primate model," *Am. J. Pathol.,* 145 (3): p574–84, 1994.

Miller et al., *Am. Rev. Respir. Dis.,* 146: 427–432, 1992.

Miller and Brelsford, *J. Rheumatol.,* 20: 1250–1252, 1993.

Modi et. al., *Hu. Genet,* 84: 185–187, 1990.

Moore et al., "Homology of cytokine synthesis inhibitory factor (IL-10) to the Epstein-Barr Virus gene BCRFI," *Science,* 248: 1230–34, 1990.

Moser et al., *J. Biol. Chem.,* 268: 7125–7128, 1993.

Moser et al., The Journal of Biological Chemistry, 266(16): 10666–10671, 1991.

Mosmann et al., "Two types of murine helper T cell clone. I. Definition according to profiles of lymphokine activities and secreted proteins," *J. Immunol.,* 136: 2348–57, 1986.

Mourad et al., "Changes in endothelial cell mass, luminal volume and capillary number in the gravitational syndrome," *Br J. Dermatol.,* 121: 447–61, 1989.

Mueller and Reisfeld, "Potential of the SCID mouse as a host for human tumors," *Cancer and Metastasis Rev.,* 10: 193–200, 1991.

Mukaida et. al., *J. Immunol,* 143: 1366–1371, 1989.

Mulligan et al., *Proc. Natl. Acad. Sci. USA,* 78: 2072, 1981.

Mulliken and Glowacki, "Hemangiomas and vascular malformations in infants and children: a classification based on endothelial characteristics," *Plast. Reconstr Surg.,* 69: 412–20, 1982.

Murphy and Tiffany, *Science,* 253: 1280–1283, 1991.

Murphy, P. M., and Tiffany, H. L. (1991) *Science,* 253: 1280–1283

Murphy, P. M. (994) *Annu. Rev. Immunol.,* 12: 593–633

Nakamura et al., *J. Clin. Invest.,* 89: 1478–1484, 1992.

Nickoloff and Turka, "Keratinocytes: key immunocytes of the integument," *Am. J. Pathol.,* 143: 325–31, 1993.

Nickoloff, "The cytokine network in psoriasis," *Arch Dermatol.,* 127: 871–84, 1991.

Nickoloff et al., "Modulation of keratinocyte motility: correlation with production of extracellular matrix molecules in response to growth promoting and anti-proliferative factors," *Am. J. Pathol.* 132: 543–551, 1988.

Nickoloff and Mitra, "Inhibition of 125I-epidermal growth factor binding to cultured keratinocytes by antiproliferative molecules gamma interferon, cyclosporine A, and transforming growth factor-beta," *J. Invest. Dermatol.,* 93: 799–803, 1989.

O'Garra et al., "Ly-1 B (B-1) cells are the main source of B cell-derived interleukin 10," *Eur. J. Immunol.,* 22: 711–17, 1992.

O'Hare et al., *Proc. Natl. Acad. Sci. USA,* 78: 1527, 1981.

Oppenheim et al., "Properties of the novel proinflammatory supergene "intercrine" cytokine family," *Annu. Rev. Immunol.,* 9: 617–48, 1991.

O'Reilly, M. S., Holmgren, L., Shing, Y., Chen, C., Rosenthal, R. A., Moses, M., Lane, W. S., Cao, Y., Sage, E. H., and Folkman, J. (1994) *Cell,* 79, 315–328

Petersen et. al., *J. Immunol.,* 152(5): 2467–78, 1994.

Peterson, "Tumor angiogenesis inhibition by prostaglandin synthetase inhibitors," *Anticancer Res.,* 6: 251–54, 1986.

Peveri et al., *J. Exp. Med.,* 167: 1547–1559, 1988.

Phillips et al., "Growth of human tumors in immune-deficient SCID and nude mice," *Curr Top. Micro. Immunol.,* 152: 260–63, 1989.

Pober and Cotran, "Cytokines and endothelial cell biology," *Pathol Rev.,* 70: 427–51, 1990.

Polverini et al., "Activated macrophages induce vascular proliferation," *Nature(London),* 269 (5631): 804–6, 1977.

Polverini, "Macrophage-induced angiogenesis: a review," *Cytokines,* 1: 54–73, S. Karger, Bazel, 1989.

Polverini and Novak, "Inhibition of angiogenesis by the antineoplastic agents mitoxantrone and bisantrene," *Biochem. Biophys. Res. Comm.,* 140: 901–7, 1986.

Poncz et al., "Cloning and characterization of platelet factor 4 cDNA derived from a human erythroleukemia cell line," *Blood*, 69: 219–23, 1987.

Power et. al., "Cloning of a full-length cDNA encoding the neutrophil-activating peptide ENA-78 from human platelets," *Gene*, 151 (1–2): 333–334, 1994.

Proost et al., "Identification of a novel granulocyte chemotactic protein (GCP-1) from human tumor cells: in vitro and in vivo comparison with natural forms of GROβ, IP-10, and IL-8," *J Immunol.*, 150: 1000–10, 1993a.

Proost et al., "Human and bovine granulocyte chemotactic protein-2: complete amino acid sequence and functional characterization as chemokines," *Biochemistry*, 32 (38): 10170–7, 1993b.

Ralph et al., "IL-10, T lymphocyte inhibitor of human blood cell production of IL-1 and tumor necrosis factor," *J. Immunol.*, 148: 808–14, 1992.

Rastinejad et al., "Regulation of the activity of a new inhibitor of angiogenesis by a cancer suppressor gene," *Cell*, 56: 345–55, 1989.

Remington's Pharmaceutical Sciences, 18th Edition, Mack Publishing Co., Easton, Pa.

Rendt et al., "Engraftment of human synovium into severe combined immune deficient mice," *J. Immunol.*, 151: 7324: 36, 1993.

Richmond et al., *EMBO J.*, 7: 2025–2033, 1988.

Richmond and Thomas, "Melanoma growth stimulatory activity: isolation from human melanoma tumors and characterization of tissue distribution," *J. Cell Biochem.*, 36: 185–98, 1988.

Rivas and Ullrich, "Keratinocyte-derived IL-10," *J. Invest. Dermatol.*, 98: 578–81, 1992.

Rolfe et al., "Pulmonary fibroblast expression of interleukin-8: a model for alveolar macrophage-derived cytokine networking," *Am. J. Respir. Cell Mol. Biol.*, 5: 493–501, 1991.

Rosenfeld et al., *Science*, 252: 431–434, 1991.

Rosenfeld et al., *Cell*, 68: 143–155, 1992.

Sambrook, J., Fritsch, E. F., and Maniatis, T. *Molecular Cloning, A Laboratory Manual.* Cold Spring Harbor Laboratory Press, 1989.

Sanger et al., *Proc. Natl. Acad. Sci. USA*, 74: 5463–5467, 1977.

Santerre et al., *Gene*, 30: 147, 1984.

Sato et al., "Tumor necrosis factor inhibits angiogenesis in vitro," *JNCI*, 79: 1383, 1987.

Schmid and Weissmann, *The Journal of Immunology*, 139 (1): 250–256, 1987.

Schonbeck, U., Brandt, E., Peterson, F., Flad, H-D., and Loppnow, H. (1995) *J. Immunol.*, 154, 2375–2383

Schroder et al., *J. Immunol.*, 140: 3534–3540, 1988.

Schulz et al., "Increased expression of epidermal IL-8 receptor in psoriasis," *J. Immunol.*, 151: 4399–4406, 1993.

Schwigerer, "Basic fibroblast growth factor and its relation to angiogenesis in normal and neoplastic tissue," *Klin Wochenschr*, 66: 340–45, 1988.

Seitz et al., *J. Clin. Invest.*, 87: 463–469, 1991.

Shapiro and Vallee, "Human placental ribonuclease inhibitor abolishes both angiogenic and ribonucleolytic activities of angiogenin," *Proc. Natl. Acad. Sci. USA*, 84: 2238, 1987.

Sharpe et al., "Growth inhibition of murine melanoma and human colon carcinoma by recombinant human platelet factor 4," *J. Natl. Cancer Inst.*, 82: 848–53, 1990.

Shields and Harris, "Genetic predisposition to cancer," In: Roth J A, Cox J D, Hong W K (eds.), Lung Cancer, Blackwell Scientific Pub., Boston, Mass., pp. 3–19, 1993.

Shipley et al., "Reversible inhibition of human prokeratinocyte proliferation by type beta transforming growth factor inhibitor in serum free medium," *Cancer Res.*, 46: 2068–71, 1986.

Sibille and Reynolds, "Macrophages and polymorphonuclear neutrophils in lung defense and injury," *Am. Rev. Respir. Dis.*, 141: 471–501, 1990.

Sidky and Borden, "Inhibition of angiogenesis by interferons: effects on tumor- and lymphocyte-induced vascular responses," *Cancer Res.*, 47: 5155–61, 1987.

Smith et al., "The production of interleukin-1 receptor antagonist protein by human bronchogenic carcinoma," *Am. J. Path.*, 143 (3): 794–803, 1993.

Smith et al., *J. Exp. Med.*, 179: 1409–1415, 1994.

Sorgente et al., "The resistance of certain tissues to invasion. II. Evidence for extractable factors in cartilage which inhibit invasion by vascularized mesenchyme," *Lab Invest*, 32: 217–222, 1975.

St. Charles et al., *The Journal of Biological Chemistry*, 264 (4): 2092–2099, 1989.

Standiford et al., "Interleukin-8 gene expression by a pulmonary epithelial cell line: A model for cytokine networks in the lung," *J. Clin. Invest.*, 86: 1945–1953, 1990.

Sticherling et al., "Localization of neutrophil-activating peptide-1/interleukin-8-immunoreactivity in normal and psoriatic skin," *J. Invest. Dermatol.*, 96: 26–30, 1991.

Stout et al., "Inhibition of wound healing in mice by local interferona/b injection," *Int. J. Exp. Path.*, 74: 79–85, 1993.

Stratford-Perricaudet et al., *Hum. Gene Ther.*, 1: 241–256, 1990.

Stratford-Perricaudet et al., *J. Clin. Invest.*, 90: 626–630, 1992.

Strieter et al., "Monokine-induced neutrophil chemotactic factor gene expression in human fibroblasts," *J. Biol. Chem.*, 264: 10621–10626, 1989a.

Strieter et al., "Interleukin-8: A corneal factor that induces neovascularization," *Am J. Pathol.*, 141 (6): 1279–84, 1992a.

Strieter et al., "Monokine-induced gene expression of human endothelial cell-derived neutrophil chemotactic factor," *Biochem. Biophys. Res. Commun.*, 156: 1340–1345, 1988.

Strieter et al., "The detection of novel neutrophil-activating peptide (ENA-78) using a sensitive ELISA," *Immunol Invest*, 21: 589–596, 1992b.

Strieter et al., "Cytokines and lung inflammation," *Thorax*, 48: 765–69, 1993.

Strieter et al., "Human alveolar macrophage gene expression of interleukin-8 by tumor necrosis factor-a, lipopolysaccharide, and interleukin-1b," *Am. J. Respir. Cell Mol. Biol.*, 2: 321–326, 1990a.

Strieter et al., "Human neutrophils exhibit disparate chemotactic factor gene expression," *Biochem. Biophys. Res. Comm.*, 173 (2): 725–730, 1990b.

Strieter et al., "Cytokine-induced neutrophil-derived interleukin-8," *Am. J. Pathol.*, 141: 397–407, 1992c.

Strieter et al., "Endothelial cell gene expression of a neutrophil chemotactic factor by TNF-a, LPS, and IL-1b," *Science*, 243: 1467–1469, 1989b.

Sugano et al., *Cell*, 49: 321–328, 1987.

Symington, "Lymphotoxin, tumor necrosis factor and gamma interferon are cytostatic for normal human keratinocytes," *J. Invest. Dermatol.*, 92: 798–805, 1989.

Szybalska et al., *Proc. Natl. Acad. Sci. USA*, 48: 2026, 1962.

Tang et al., *Nature*, 356: 152–154, 1992.

Tannock and Hayashi, "The proliferation of capillary and endothelial cells," *Cancer Res.*, 32: 77–82, 1972.

Taylor and Folkman, "Protamine is an inhibitor of angiogenesis," *Nature,* 297: 307–12, 1982.

Thomsen, D. R., Stenberg et al., *Proc. Natl. Acad. Sci. USA,* 81: 659–663, 1984.

Thornton et al., "Cytokine-induced gene expression of a neutrophil chemotactic factor/interleukin-8 by human hepatocytes," *J Immuol,* 144: 2609–2613, 1990.

Tokunaga et al., "Nucleotide sequence of a full-length cDNA for mouse cytoskeletal beta-actin mRNA," *Nucleic Acids Res.,* 14: 229–39, 1986.

Tolsma et al., "Peptides derives from two separate domains of the matrix protein thrombospondin-1 have antiangiogenic activity," *J. Cell Biol.,* 122: 497–511, 1993.

Ulmer et al., "Heterologous Protection Against Influenza by Injection of DNA Encoding a Viral Protein," *Science,* 259: 1745–1749, 1993.

Valyi-Nagy et al., "Cytokine-induced expression of transforming growth factor-a and the epidermal growth factor receptor in neonatal skin explants," *J. Invest. Dermatol.,* 99: 350–56, 1992.

Vanguri and Farber, "Identification of CRG-2. An interferon-inducible mRNA predicted to encode a murine monokine," *J. Biol. Chem.,* 265: 15049–57, 1990.

VanMeir et al., "Interleukin-8 is produced in neoplastic and infectious diseases of the human central nervous system," *Cancer Res.,* 52: 4297–4305, 1992.

Vanscheidt et al., "Pericapillary fibrin cuff: a histological sign of venous ulceration," *J. Cutan. Pathol.,* 17: 266–68, 1990.

Vanscheidt et al., "Immunohistochemical investigation of dermal capillaries in chronic venous insufficiency," *Acta Derm Vener,* 71: 17–29, 1991.

Vieira et al., "Isolation and expression of human cytokine synthesis inhibitory factor cDNA clones: Homology to Epstein-Barr virus open reading frame BCRFI," *Proc. Natl. Acad. Sci. USA,* 88: 1172–1176, 1991.

Vitolo et al., "Expression of mRNA for cytokines in tumor-infiltrating mononuclear cells in ovarian adenocarcinoma and invasive breast cancer," *Int. J. Cancer,* 51: 573–80, 1992.

Wagner, R. W., Matteucci, M. D., Lewis, J. G., Gutierrez, A. J., Moulds, C. and Froehler, B. C. *Science,* 260: 1510–1513, 1993.

Wakefield and Lloyd, *Cytokine,* 4 (1): 1–5, 1992.

Walz et al., *J. Exp. Med.,* 170: 1745–1750, 1989.

Walz et al., "Structure arid neutrophil-activating properties of a novel inflammatory peptide (ENA-78) with homology to interleukin-8," *J. Exp. Med.,* 174: 1355–62, 1991.

Walz and Baggiolini, "Generation of the neutrophil-activating peptide NAP-2 from platelet basic protein or connective tissue-activating peptide III through monocyte proteases," *J. Exp. Med.,* 171: 449–54, 1990.

Wang et al., *Proc. Natl. Acad. Sci. USA,* 90: 4156–4160, 1993.

Wang et al., "A new patient-like metastatic model of human lung cancer constructed orthotopically with intact tissue via thoracotomy in immunodeficient mice," *Int. J. Cancer,* 51: 992–95, 1992.

Weidner et al., "Tumor angiogenesis and metastasis-correlation in invasive breast carcinoma," *N Eng. J. Med.,* 324: 1–8, 1991.

Weidner et al., "Tumor angiogenesis correlates with metastasis in invasive prostate carcinoma," *Am J. Pathol.,* 143: 401–09, 1993.

Wenger et. al.., *Blood,* 73: 1498-, 1989.

Wenner et al., "Ultrastructural changes of capillaries in chronic venous insufficiency," *Exp. Cell Biol.,* 48: 1–14, 1980.

Wertheim et al., "Regulation of neutrophil-derived interleukin-8: The role of prostaglandin E2, dexamethasone, and interleukin-4," *J. Immunol.* 151: 2166–2175, 1993.

Whalen, "Solid tumors and wounds: transformed cells misunderstood as injured tissue?" *Lancet,* 336: 1489–92, 1990.

Whitton et al., *J. Virol.* 67: (1) 348–352, 1993.

Wigler et al., *Proc. Natl. Acad. Sci. USA,* 77: 3567, 1980.

Wigler et al., *Cell,* 11: 223, 1977.

Wolpe et al., *J. Exp. Med.,* 167: 570–581, 1988.

Woodley et al., "Cutaneous wound healing: a model for cell-matrix interactions," *J. Am. Acad. Dermatol.,* 12: 420–33, 1986.

Wu et al., *Science,* 261: 101–103, 1993.

Yaar et al., "Effect of alpha and beta interferon on cultured human keratinocytes," *J. Invest. Dermatol.,* 85: 70–74, 1985.

Yan et al., "Human/severe combined immunodeficient mouse chimeras: an experimental in vivo model system to study the regulation of human endothelial cell-leukocyte adhesion molecules," *J. Clin. Invest.,* 91: 986–96, 1993.

Yoshimura et al., "Neutrophil chemotactic factor produced by LPS-stimulated human blood mononuclear leukocytes: Partial characterization and separation from interleukin-1," *J. Immunol.,* 139: 788–794, 1987b.

Yoshimura et al., *Molec. Immun.,* 26: 87–93, 1989.

Yoshimura et al., *Proc. Natl. Acad. Sci. USA.,* 84: 9233–9237, 1987a.

Yssel et al., "Interleukin-10 is produced by subsets of human CD4+ T cell clones and peripheral blood T cells," *J. Immunol.,* 149: 2378–2384, 1992.

Zetter, "Migration of capillary endothelial cells is stimulated by tumor-derived factors," *Nature (London),* 285: 41–43, 1980.

Zetter, "Angiogenesis: state of the art," *Chest,* 93: 159S–66S, 1988.

Zucker et al., "Secretion of gelatinases and tissue inhibitors of metalloproteinases by human lung cancer cell lines and revertant cell lines: not an invariant correlation with metastasis," *Int. J. Cancer,* 52: 366–71, 1992.

---

What is claimed is:

1. A method for inhibiting angiogenesis, comprising administering to an animal a biologically effective amount of a pharmaceutically acceptable CXC chemokine composition that comprises a non-ELR CXC chemokine other than PF4, the non-ELR CXC chemokine lacking the amino acid sequence ELR (Glu Leu Arg).

2. The method of claim 1, wherein said CXC chemokine composition comprises IP-10.

3. The method of claim 1, wherein said CXC chemokine composition comprises MIG.

4. The method of claim 1, wherein said CXC chemokine composition comprises an ELR-CXC chemokine modified to remove or replace the amino acid sequence ELR.

5. The method of claim 4, wherein said CXC chemokine composition comprises an ELR-CXC chemokine in which the amino acid sequence ELR has been replaced with the amino acid sequence TVR.

6. The method of claim 4, wherein said CXC chemokine composition comprises an ELR-CXC chemokine in which the amino acid sequence ELR has been replaced with the amino acid sequence DLQ.

7. The method of claim 4, wherein said CXC chemokine composition comprises an ELR-CXC chemokine in which the amino acid sequence ELR has been replaced with the amino acid sequence KGR.

8. The method of claim 4, wherein said CXC chemokine composition comprises an IL-8 polypeptide modified to remove or replace the amino acid sequence ELR.

9. The method of claim 8, wherein said CXC chemokine composition comprises an IL-8 polypeptide in which the amino acid sequence ELR has been replaced with the amino acid sequence TVR.

10. The method of claim 8, wherein said CXC chemokine composition comprises an IL-8 polypeptide in which the amino acid sequence ELR has been replaced with the amino acid sequence DLQ.

11. The method of claim 8, wherein said CXC chemokine composition comprises an IL-8 polypeptide in which the amino acid sequence ELR has been replaced with the amino acid sequence KGR.

12. The method of claim 1, wherein said CXC chemokine composition comprises a non-ELR CXC chemokine prepared by expressing a CXC chemokine gene in a recombinant host cell and collecting the expressed CXC chemokine protein.

13. The method of claim 1, wherein said CXC chemokine composition comprises a non-ELR CXC chemokine prepared by automated peptide synthesis.

14. The method of claim 1, wherein two non-ELR CXC chemokines are administered to said animal.

15. The method of claim 1, wherein said CXC chemokine composition is administered to said animal parenterally.

16. The method of claim 1, wherein said animal has a tumor.

17. The method of claim 1, wherein said animal is a human subject.

18. A method for inducing angiostasis, comprising administering to an animal a biologically effective amount of a pharmaceutically acceptable CXC chemokine composition that comprises a non-ELR CXC chemokine other than PF4, the non-ELR CXC chemokine lacking the amino acid sequence ELR.

19. The method of claim 18, wherein said CXC chemokine composition comprises IP-10.

20. The method of claim 18, wherein said CXC chemokine composition comprises MIG.

21. The method of claim 18, wherein said CXC chemokine composition comprises an ELR-CXC chemokine modified to remove or replace the amino acid sequence ELR.

22. The method of claim 18, wherein two non-ELR CXC chemokines are administered to said animal.

23. The method of claim 18, wherein said CXC chemokine composition is administered to said animal parenterally.

24. The method of claim 18, wherein said animal has a tumor.

25. The method of claim 18, wherein said animal is a human subject.

26. A method for inhibiting angiogenesis, comprising administering to an animal a pharmaceutically acceptable composition comprising a biologically effective amount of IP-10, MIG or an ELR-CXC chemokine modified to remove or replace the amino acid sequence ELR.

27. A method for inhibiting angiogenesis, comprising administering to an animal a pharmaceutically acceptable composition comprising a biologically effective amount of IP-10 or MIG.

28. A method for inducing angiostasis, comprising administering to an animal a pharmaceutically acceptable composition comprising a biologically effective amount of IP-10, MIG or an ELR-CXC chemokine modified to remove or replace the amino acid sequence ELR.

29. A method for inducing angiostasis, comprising administering to an animal a pharmaceutically acceptable composition comprising a biologically effective amount of IP-10 or MIG.

* * * * *

UNITED STATES PATENT AND TRADEMARK OFFICE
CERTIFICATE OF CORRECTION

PATENT NO.   : 5,871,723
DATED        : February 16, 1999
INVENTOR(S)  : Strieter et al.

Page 1 of 7

It is certified that error appears in the above-identified patent and that said Letters Patent is hereby corrected as shown below:

Title page,
Item [56], References Cited, U.S. PATENT DOCUMENTS, and the two references listed thereon, please insert the following:
-- OTHER PUBLICATIONS Angiolillo et al., "Human Interferon-Inducible Protein 10 is a Potent Inhibitor of Angiogenesis In Vivo," *The Journal of Experimental Medicine*, 182:155-162, Jul. 1995.

Anisowicz et al., "Constitutive Overexpression of a Growth-Regulated Gene in Transformed Chinese Hamster and Human Cells," *Proc. Natl. Acad. Sci. USA*, 84:7188-7192, Oct. 1987.

Anisowicz et al., "Functional Diversity of gro Gene Expression in Human Fibroblasts and Mammary Epithelial Cells," *Proc. Natl. Acad. Sci. USA*, 85:9645-9649, Dec. 1988.

Arenberg et al., "C-X-C Chemokines Display Disparate Angiogenic Activity," *FASEB J.*, 9:A587, 1995.

Arenberg et al., "The Role of C-X-C Chemokines in Tumor Derived Angiogenesis," *Am. J. Respir. Crit. Care Med.*, 151:A211, 1995.

Baggiolini et al., "Interleukin-8 and Related Chemotactic Cytokines—CXC and CC Chemokines," *Advances in Immunology*, 55:97-179, Jun., 1993.

Beall et al., "Conversion of Monocyte Chemoattractant Protein-1 into a Neutrophil Attractant by Substitution of Two Amino Acids," *The Journal of Biological Chemistry*, 267(5):3455-3459, 1992.

Brandt et al., "A Novel Molecular Variant of the Neutrophil-Activating Peptide NAP-2 with Enhanced Biological Activity is Truncated at the C-Terminus: Identification by Antibodies with Defined Epitope Specificity," *Molecular Immunology*, 30(11):979-991 1993.

Burdick et al., "Human Bronchogenic Carcinoma Angiogenesis is Mediated by Tumor-Derived Interleukin-8," *FASEB J.*, 8(4), Mar. 1994, Abstract 849.

Cerretti et al., "Molecular Characterization of Receptors for Human Interleukin-8, GRO/Melanoma Growth-Stimulatory Activity and Neutrophil Activating Peptide-2," *Molecular Immunology*, 30(4):359-367, 1993.

Chomarat et al., "Interferon γ Inhibits Interleukin 10 Production by Monocytes," *J. Exp. Med.*, 177:523-527, Feb. 1993.

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),

Clark–Lewis et al., "Platelet Factor 4 Binds to Interleukin 8 Receptors and Activates Neutrophils When its N Terminus is Modified with Glu–Leu–Arg," *Proc. Natl. Acad. Sci. USA*, 90:3574–3577, 1993.

Clark–Lewis et al., "Structure–Activity Relationships of Interleukin–8 Determined Using Chemically Synthesized Analogs," *The Journal of Biological Chemistry*, 266(34):23128–23134, 1991.

Clore et al., "Three–Dimensional Structure of Interleukin 8 in Solution," *Biochemistry*, 29:1689–1696, 1990.

D'Andrea et al., "Interleukin 10 (IL–10) Inhibits Human Lymphocyte Interferon γ–Production by Suppressing Natural Killer Cell Stimulatory Factor/IL–12 Synthesis in Accessory Cells," *J. Exp. Med.*, 178:1041–1048, Sep. 1993.

Dewald et al., "IP–10, a γ–Interferon–Inducible Protein Related to Interleukin–8, Lacks Neutrophil Activating Properties," *Immunology Letters*, 32:81–84, 1992.

Farber, "A Macrophage mRNA Selectivley Induced by γ–Interferon Encodes a Member of the Platelet Factor 4 Family of Cytokines," *Proc. Natl. Acad. Sci. USA*, 87:5238–5242. 1990.

Farber, "HuMIG; A New Human Member of the Chemokine Family of Cytokines," *Biochemical and Biophysical Research Communications*, 192(1):223–230, Apr. 1993.

Fivenson et al., "Biological Wound Dressings Function as a Reservoir for C–X–C Chemokines in Chronic Venous Ulcer Therapy," *Clin. Res.*, 42:232A, 1994.

Gastl et al., "Interleukin–10 Production by Human Carcinoma Cell Lines and its Relationship to Interleukin–6 Expression," *Int. J. Cancer*, 55:96–101, 1003.

Gronenborn and Clore, "Modeling the Three–Dimensional Structure of the Monocyte Chemo–Attractant and Activating Protein MCAF/MCP–1 on the Basis of the Solution Structure of Interleukin–8," *Protein Engineering*, 4(3):263–269, 1991.

Han et al., "Inhibitory Effect of Platelet Factor 4 (PF4) on the Growth of Human Erythroleukemia Cells: Proposed Mechanism of Action of PF4," *J. Lab. Clin. Med.*, 120(4):645–660, Oct. 1992.

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),

Haskill et al., "Identification of Three Related Human GRO Genes Encoding Cytokine Functions," *Proc. natl. Acad. Sci. USA*, 87:7732–7736, Oct. 1990.

Hébert et al., "Scanning Mutagenesis of Interleukin–8 a Cluster of Residues Required for Receptor Binding," *The Journal of Biological Chemistry*, 266(28):18989–18994, 1991.

Hu et al., "Interleukin–8 Stimulates Angiogenesis in Rats," *Inflammation*, 17(2):135–143, 1993.

Iida and Grotendorst, "Cloning and Sequencing of a New gro Transcript from Activated Human Monocytes: Expression in Leukocytes and Wound Tissue," *Molecular and Cellular Biology*, 10(10):5596–5599, Oct. 1990.

Jaffe et al., "Expression of Three Forms of Melanoma Growth Stimulating Activity (MGSA)/gro in Human Retinal Pigment Epithelial Cells," *Investigative Ophthalmology & Visual Science*, 34(9):2776–2785, 1993.

Koch et al., "Interleukin–8 as a Macrophage–Derived Mediator of Angiogenesis," *Science*, 258:1798–1801, Dec. 1992.

LaRosa et al., "Amino Terminus of the Interleukin–8 Receptor is a Major Determinant of Receptor Subtype Specificity," *The Journal of Biological Chemistry*, 267(35):25402–25406, 1992.

Lindley et al., "Synthesis and Expression in *Escherichia coli* of the Gene Encoding Monocyte–Derived Neutrophil–Activating Factor: Biological Equivalence Between Natural and Recombinant Neutrophil–Activating Factor," *Proc. Natl. Acad. Sci. USA*, 85:9199–9203, Dec. 1988.

Luster and Ravetch, "Genomic Characterization of a Gamma–Interferon–Inducible Gene (IP–10) and Identification of an Interferon–Inducible Hypersensitive Site," *Molecular and Cellular Biology*, 7(10):3723–3731, Oct. 1987.

Luster et al., "γ–Interferon Transcriptionally Regulates an Early–Response Gene Containing Homology to Platelet Proteins," *Nature*, 315:672–676, Jun. 1985.

Luster and Ravetch, "Biochemical Characterization of a γ Interferon–Inducible Cytokine (IP–10)," *J. Exp. Med.*, 166:1084–1097, Oct. 1987.

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),

Luster and Leder, "IP–10, a –C–X–C– Chemokine, Elicits a Potent Thymus–Dependent Antitumor Response In Vivo," *J. Exp. Med.*, 178:1057–1065, Sep. 1993.

Luster et al., "The IP–10 Chemokine Binds to a Specific Cell Surface Heparan Sulfate Site Shared with Platelet Factor 4 Inhibits Endothelial Cell Proliferation," *J. Exp. Med.*, 182:219–231, Jul. 1995.

Maione et al., "Inhibition of Angiogenesis by Recombinant Human Platelet Factor–4 and Related Peptides," *Science*, 247:77–79, Jan. 1990.

Maione et al., "Inhibition of Tumor Growth in Mice by an Analogue of Platelet Factor 4 That Lacks Affinity for Heparin and Retains Potent Angiostatic Activity," *Cancer Research*, 51:2077–2083, Apr. 1991.

Martins–Green and Bissell, "Localization of 9E3/CEF–4 in Avian Tissues: Expression is Absent in Rous Sarcoma Virus–Induced Tumors but is Stimulated by Injury," *The Journal of Cell Biology*, 110:581–595, Mar. 1990.

Martins–Green et al., "Wound–Factor–Induced and Cell Cycle Phase–Dependent Expression of 9E3/CEF4, the Avian gro Gene," *Cell Regulation*, 2:739–752, 1991.

Matsushima et al., "Molecular Cloning of a Human Monocyte–Derived Neutrophil Chemotactic Factor (MDNCF) and the Induction of MdNCF mRNA by Interleukin 1 and Tumor Necrosis Factor," *J. Exp. Med.*, 167: 1883–1893, Jun. 1988.

Moser et al., "Interleukin–8 Antagonists Generated by N–Terminal Modification," *The Journal of Biological Chemistry*, 268(10):7125–7128, Apr. 1993.

Moser et al., "Neutrophil–Activating Peptide 2 and gro/Melanoma Growth–Stimulatory Activity Interact with Neutrophil–Activating Peptide 1/Interleukin 8 Receptors on Human Neutrophils," *The Journal of Biological Chemistry*, 266(16):10666–10671, Jun. 1991.

Petersen, "Reply to the letter of Dr. Besemer", *The Journal of Immunology*, 154(2):972–973, Jan. 1995.

Petersen et al., "Neutrophil–Activating Peptides NAP–2 and IL–8 Bind to the Same Sites on Neutrophils but Interact in Different Ways," *Journal of Immunology*, 2467–2478, 1994.

Proost et al., "Human and Bovine Granulocyte Chemotactic Protein–2: Complete Amino Acid Sequence and Functional Characterization as Chemokines," *Biochemistry*, 32:10170–10177, 1993.

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),

Proost et al., "Identification of a Novel Granulocyte Chemotactic Protein (GCP-2) From Human Tumor Cells," *The Journal of Immunology*, 150(3):1000–1010, Feb. 1993.

Richter et al., "Interleukin 10 Transfected into Chinese Hamster Ovary Cells Prevents Tumor Growth and Macrophage Infiltration," *Cancer Research*, 53:4134–4137, Sep. 1993.

Schmid and Weissmann, "Induction of mRNA for a Serine Protease and a β–Thromboglobulin–like Protein in Mitogen–Stimulated Human Leukoyctes," *The Journal of Immunology*, 139(1):250–256, Jul. 1987.

Sharpe et al., "Growth Inhibition of Murine Melanoma and Human Colon Carcinoma by Recombinant Human Platelet Factor 4," *Journal of the National Cancer Institute*, 82(10):848–853, May 1990.

Smith et al., "The Role of Interleukin–8 in Human Bronchogenic Carcinoma Angiogenesis," *Am. Respir. Crit. Care Med.*, 149:A171, 1994.

Smith et al., "Interleukin–8: A Primary Mediator of Angiogenesis in Human Bronchogenic Carcinoma," *Clinical Research*, 41(3):688A, 1993.

Smith et al., "Inhibition of Interleukin 8 Attenuates Angiogenesis in Bronchogenic Carcinoma," *J. Exp. Med.*, 179:1409–1415, 1994.

St., Charles et al., "The Three–Dimensional Structure of Bovine Platelet Factor 4 at 3.0–Å Resolution," *The Journal of Biological Chemistry*, 264(4):2092–2099, 1989.

Strieter et al., "Interferon γ–Inducible Protein in (IP–10) A Member of the C–X–C Chemokine Family is an Inhibitor of Angiogenesis," *Biochem. Biophys. Res. Comm.*, 210:51–57, May 1995.

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),

Strieter et al., "Interferon–α and interferon–γ down–regulate the production of interleukin–8 and ENA–78 in human monocytes," *J. Leukocyte Biology,* 57:929–935, Jun. 1995.
Strieter et al., "Role of C–X–C Chemokines as Regulators of Angiogenesis in Lung Cancer," *J. Leukocyte Biology,* 57(5):752–62, May 1995.
Strieter et al., "A Corneal Factor that Induces Neovascularization," *American Journal of Pathology,* 141(6):1279–1283, Dec. 1992.

Walz et al., "Structure and Neutrophil–Activating Properties of a Novel Inflammatory Peptide (ENA–78) with Homology to Interleukin 8," *J. Exp. Med.,* 174:1355–1362, Dec. 1991.

Walz et al., "Effects of the Neutrophil–Activating Peptide NAP–2, Platelet Basic Protein, Connective Tissue–Activating Peptide III, and Platelet Factor 4 on Human Neutrophils," *J. Exp. Med.,* 170:1745–1750, Nov. 1989.

Walz and Baggiolini, "Generation of the Neutrophil–Activating Peptide NAP–2 from Platelet Basic Protein or Connective Tissue–Activating Peptide III Through Monocyte Proteases," *J. Exp. Med.,* 171:449–454, Feb. 1990.

Streiter *et al.*, "The Functional Role of the ELR Motif in CXC Chemokine-Mediated Angiogenesis," *J. Biol. Chem.*, 270(45):27348-27357, 1995.*
Baggiolini *et al.*, "Human Chemokines: An Update," *Annu. Rev. Immunol.*, 15:675-705, 1997.*
Cao *et al.*, "gro-β, a –C-X-C- Chemokine, Is An Angiogenesis Inhibitor That Suppresses the Growth of Lewis Lung Carcinoma in Mice," *J. Exp. Med.*, 182:2069-2077, 1995.*
Fivenson *et al.*, "CXC Chemokine Efflux During Chronic Wound Healing: Critical Role of the ELR Motif in Angiogenesis," *J. Invest. Dermatol.*,104(4):625, 1995.*
Park *et al.*, "*In Vitro* Studies of Recombinant Human Platelet Factor 4: Inhibition of Megakaryocytopoiesis and Angiogenesis," *Korean J. Biochem.*, 27(3):157-163, 1995.*
Strieter *et al.*, "The Role of CXC Chemokines as Regulators of Angiogenesis," *Shock*, 4(3):155-160, 1995.*

UNITED STATES PATENT AND TRADEMARK OFFICE
CERTIFICATE OF CORRECTION

PATENT NO. : 5,871,723
DATED : February 16, 1999
INVENTOR(S) : Strieter et al.

It is certified that error appears in the above-identified patent and that said Letters Patent is hereby corrected as shown below:

Title page (cont'd),
Howard et al., "Chemokines: Progress Toward Identifying Molecular Targets for Therapeutic Agents," *TibTech*, 14:46-51, 1996.*
Lusti-Narasimhan et al., "Mutations in Leu$^{25}$ and Val$^{27}$ Introduces CC Chemokine Activity Into Interleukin-8," *J. Biol. Chem*, 270(6):2716-2721, 1995.*

\* cited by examiner--

Signed and Sealed this

Sixteenth Day of March, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 98 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

| Met | Asn | Gln | Thr | Ala | Ile | Leu | Ile | Cys | Cys | Leu | Ile | Phe | Leu | Thr | Leu |
|---|---|---|---|---|---|---|---|---|---|---|---|---|---|---|---|
| 1 | | | | 5 | | | | | 10 | | | | | 15 | |
| Ser | Gly | Ile | Gln | Gly | Val | Pro | Leu | Ser | Arg | Thr | Val | Arg | Cys | Thr | Cys |
| | | | 20 | | | | | 25 | | | | | 30 | | |
| Ile | Ser | Ile | Ser | Asn | Gln | Pro | Val | Asn | Pro | Arg | Ser | Leu | Glu | Lys | Leu |
| | | | 35 | | | | | 40 | | | | | 45 | | |
| Glu | Ile | Ile | Pro | Ala | Ser | Gln | Phe | Cys | Pro | Arg | Val | Glu | Ile | Ile | Ala |
| | | 50 | | | | | 55 | | | | | 60 | | | |
| Thr | Met | Lys | Lys | Lys | Gly | Glu | Lys | Arg | Cys | Leu | Asn | Pro | Glu | Ser | Lys |
| 65 | | | | | 70 | | | | | 75 | | | | | 80 |
| Ala | Ile | Lys | Asn | Leu | Leu | Lys | Ala | Val | Ser | Lys | Glu | Met | Ser | Lys | Arg |
| | | | | 85 | | | | | 90 | | | | | 95 | |
| Ser | Pro | | | | | | | | | | | | | | |

(2) INFORMATION FOR SEQ ID NO:2:

(i) SEQUENCE CHARACTERISTICS:
(A) LENGTH: 125 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

| Met | Lys | Lys | Ser | Gly | Val | Leu | Phe | Leu | Leu | Gly | Ile | Ile | Leu | Leu | Val |
|---|---|---|---|---|---|---|---|---|---|---|---|---|---|---|---|
| 1 | | | | 5 | | | | | 10 | | | | | 15 | |
| Leu | Ile | Gly | Val | Gln | Gly | Thr | Pro | Val | Val | Arg | Lys | Gly | Arg | Cys | Ser |
| | | | 20 | | | | | 25 | | | | | 30 | | |
| Cys | Ile | Ser | Thr | Asn | Gln | Gly | Thr | Ile | His | Leu | Gln | Ser | Leu | Lys | Asp |
| | | | 35 | | | | | 40 | | | | | 45 | | |
| Leu | Lys | Gln | Phe | Ala | Pro | Ser | Pro | Ser | Cys | Glu | Lys | Ile | Glu | Ile | Ile |
| | | 50 | | | | | 55 | | | | | 60 | | | |
| Ala | Thr | Leu | Lys | Asn | Gly | Val | Gln | Thr | Cys | Leu | Asn | Pro | Asp | Ser | Ala |
| 65 | | | | | 70 | | | | | 75 | | | | | 80 |
| Asp | Val | Lys | Glu | Leu | Ile | Lys | Lys | Trp | Glu | Lys | Gln | Val | Ser | Gln | Lys |
| | | | | 85 | | | | | 90 | | | | | 95 | |
| Lys | Lys | Gln | Lys | Asn | Gly | Lys | Lys | His | Gln | Lys | Lys | Lys | Val | Leu | Lys |
| | | | 100 | | | | | 105 | | | | | 110 | | |
| Val | Arg | Lys | Ser | Gln | Arg | Ser | Arg | Gln | Lys | Lys | Thr | Thr | | | |
| | | 115 | | | | | 120 | | | | | 125 | | | |

(2) INFORMATION FOR SEQ ID NO:3:

(i) SEQUENCE CHARACTERISTICS:
(A) LENGTH: 99 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

| Met | Thr | Ser | Lys | Leu | Ala | Val | Ala | Leu | Leu | Ala | Ala | Phe | Leu | Ile | Ser |
|---|---|---|---|---|---|---|---|---|---|---|---|---|---|---|---|
| 1 | | | | 5 | | | | | 10 | | | | | 15 | |

```
Ala  Ala  Leu  Cys  Glu  Gly  Ala  Val  Leu  Pro  Arg  Ser  Ala  Lys  Glu  Leu
               20                       25                      30

Arg  Cys  Gln  Cys  Ile  Lys  Thr  Tyr  Ser  Lys  Pro  Phe  His  Pro  Lys  Phe
          35                       40                      45

Ile  Lys  Glu  Leu  Arg  Val  Ile  Glu  Ser  Gly  Pro  His  Cys  Ala  Asn  Thr
     50                       55                      60

Glu  Ile  Ile  Val  Lys  Leu  Ser  Asp  Gly  Arg  Glu  Leu  Cys  Leu  Asp  Pro
65                       70                      75                           80

Lys  Glu  Asn  Trp  Val  Gln  Arg  Val  Val  Glu  Lys  Phe  Leu  Lys  Arg  Ala
               85                       90                           95

Glu  Asn  Ser
```

(2) INFORMATION FOR SEQ ID NO:4:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met  Ser  Leu  Leu  Ser  Ser  Arg  Ala  Ala  Arg  Val  Pro  Gly  Pro  Ser  Ser
1                   5                       10                      15

Ser  Leu  Cys  Ala  Leu  Leu  Val  Leu  Leu  Leu  Leu  Thr  Gln  Pro  Gly
               20                       25                      30

Pro  Ile  Ala  Ser  Ala  Gly  Pro  Ala  Ala  Ala  Val  Leu  Arg  Glu  Leu  Arg
          35                       40                      45

Cys  Val  Cys  Leu  Gln  Thr  Thr  Gln  Gly  Val  His  Pro  Lys  Met  Ile  Ser
     50                       55                      60

Asn  Leu  Gln  Val  Phe  Ala  Ile  Gly  Pro  Gln  Cys  Ser  Lys  Val  Glu  Val
65                       70                      75                           80

Val  Ala  Ser  Leu  Lys  Asn  Gly  Lys  Glu  Ile  Cys  Leu  Asp  Pro  Glu  Ala
               85                       90                           95

Pro  Phe  Leu  Lys  Lys  Val  Ile  Gln  Lys  Ile  Leu  Asp  Gly  Gly  Asn  Lys
               100                      105                         110

Glu  Asn
```

(2) INFORMATION FOR SEQ ID NO:5:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met  Ala  Arg  Ala  Ala  Leu  Ser  Ala  Ala  Pro  Ser  Asn  Pro  Arg  Leu  Leu
1                   5                       10                      15

Arg  Val  Ala  Leu  Leu  Leu  Leu  Leu  Leu  Val  Ala  Ala  Gly  Arg  Arg  Ala
               20                       25                      30

Ala  Gly  Ala  Ser  Val  Ala  Thr  Glu  Leu  Arg  Cys  Gln  Cys  Leu  Gln  Thr
          35                       40                      45

Leu  Gln  Gly  Ile  His  Pro  Lys  Asn  Ile  Gln  Ser  Val  Asn  Val  Lys  Ser
     50                       55                      60

Pro  Gly  Pro  His  Cys  Ala  Gln  Thr  Glu  Val  Ile  Ala  Thr  Leu  Lys  Asn
```

-continued

```
                65                  70                  75                  80
        Gly Arg Lys Ala Cys Leu Asn Pro Ala Ser Pro Ile Val Lys Lys Ile
                        85                  90                  95
        Ile Glu Lys Met Leu Asn Ser Asp Lys Ser Asn
                        100                 105
```

( 2 ) INFORMATION FOR SEQ ID NO:6:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
        Met Ala Arg Ala Thr Leu Ser Ala Ala Pro Ser Asn Pro Arg Leu Leu
        1               5                   10                  15
        Arg Val Ala Leu Leu Leu Leu Leu Leu Val Ala Ala Ser Arg Arg Ala
                        20                  25                  30
        Ala Gly Ala Pro Leu Ala Thr Glu Leu Arg Cys Gln Cys Leu Gln Thr
                        35                  40                  45
        Leu Gln Gly Ile His Leu Lys Asn Ile Gln Ser Val Lys Val Lys Ser
                50                  55                  60
        Pro Gly Pro His Cys Ala Gln Thr Glu Val Ile Ala Thr Leu Lys Asn
        65                  70                  75                  80
        Gly Gln Lys Ala Cys Leu Asn Pro Ala Ser Pro Met Val Lys Lys Ile
                        85                  90                  95
        Ile Glu Lys Met Leu Lys Asn Gly Lys Ser Asn
                        100                 105
```

( 2 ) INFORMATION FOR SEQ ID NO:7:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
        Met Ala His Ala Thr Leu Ser Ala Ala Pro Ser Asn Pro Arg Leu Leu
        1               5                   10                  15
        Arg Val Ala Leu Leu Leu Leu Leu Leu Val Gly Ser Arg Arg Ala Ala
                        20                  25                  30
        Gly Ala Ser Val Val Thr Glu Leu Arg Cys Gln Cys Leu Gln Thr Leu
                        35                  40                  45
        Gln Gly Ile His Leu Lys Asn Ile Gln Ser Val Asn Val Arg Ser Pro
                50                  55                  60
        Gly Pro His Cys Ala Gln Thr Glu Val Ile Ala Thr Leu Lys Asn Gly
        65                  70                  75                  80
        Lys Lys Ala Cys Leu Asn Pro Ala Ser Pro Met Val Gln Lys Ile Ile
                        85                  90                  95
        Glu Lys Ile Leu Asn Lys Gly Ser Thr Asn
                        100                 105
```

( 2 ) INFORMATION FOR SEQ ID NO:8:

( i ) SEQUENCE CHARACTERISTICS:

(A) LENGTH: 128 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

| Met | Ser | Leu | Arg | Leu | Asp | Thr | Thr | Pro | Ser | Cys | Asn | Ser | Ala | Arg | Pro |
|---|---|---|---|---|---|---|---|---|---|---|---|---|---|---|---|
| 1 | | | | 5 | | | | | 10 | | | | | 15 | |
| Leu | His | Ala | Leu | Gln | Val | Leu | Leu | Leu | Ser | Leu | Leu | Leu | Thr | Ala | |
| | | | 20 | | | | 25 | | | | | 30 | | | |
| Leu | Ala | Ser | Ser | Thr | Lys | Gly | Gln | Thr | Lys | Arg | Asn | Leu | Ala | Lys | Gly |
| | | 35 | | | | | 40 | | | | | 45 | | | |
| Lys | Glu | Glu | Ser | Leu | Asp | Ser | Asp | Leu | Tyr | Ala | Glu | Leu | Arg | Cys | Met |
| | 50 | | | | | 55 | | | | | 60 | | | | |
| Cys | Ile | Lys | Thr | Thr | Ser | Gly | Ile | His | Pro | Lys | Asn | Ile | Gln | Ser | Leu |
| 65 | | | | | 70 | | | | | 75 | | | | | 80 |
| Glu | Val | Ile | Gly | Lys | Gly | Thr | His | Cys | Asn | Gln | Val | Glu | Val | Ile | Ala |
| | | | | 85 | | | | | 90 | | | | | 95 | |
| Thr | Leu | Lys | Asp | Gly | Arg | Lys | Ile | Cys | Leu | Asp | Pro | Asp | Ala | Pro | Arg |
| | | | 100 | | | | | 105 | | | | 110 | | | |
| Ile | Lys | Lys | Ile | Val | Gln | Lys | Lys | Leu | Ala | Gly | Asp | Glu | Ser | Ala | Asp |
| | | 115 | | | | | 120 | | | | | 125 | | | |

(2) INFORMATION FOR SEQ ID NO:9:

(i) SEQUENCE CHARACTERISTICS:
(A) LENGTH: 85 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

| Asn | Leu | Ala | Lys | Gly | Lys | Glu | Glu | Ser | Leu | Asp | Ser | Asp | Leu | Tyr | Ala |
|---|---|---|---|---|---|---|---|---|---|---|---|---|---|---|---|
| 1 | | | | 5 | | | | | 10 | | | | | 15 | |
| Glu | Leu | Arg | Cys | Met | Cys | Ile | Lys | Thr | Thr | Ser | Gly | Ile | His | Pro | Lys |
| | | | 20 | | | | | 25 | | | | | 30 | | |
| Asn | Ile | Gln | Ser | Leu | Glu | Val | Ile | Gly | Lys | Gly | Thr | His | Cys | Asn | Gln |
| | | 35 | | | | | 40 | | | | | 45 | | | |
| Val | Glu | Val | Ile | Ala | Thr | Leu | Lys | Asp | Gly | Arg | Lys | Ile | Cys | Leu | Asp |
| | 50 | | | | | 55 | | | | | 60 | | | | |
| Pro | Asp | Ala | Pro | Arg | Ile | Lys | Lys | Ile | Val | Gln | Lys | Lys | Leu | Ala | Gly |
| 65 | | | | | 70 | | | | | 75 | | | | | 80 |
| Asp | Glu | Ser | Ala | Asp | | | | | | | | | | | |
| | | | | 85 | | | | | | | | | | | |

(2) INFORMATION FOR SEQ ID NO:10:

(i) SEQUENCE CHARACTERISTICS:
(A) LENGTH: 81 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

| Gly | Lys | Glu | Glu | Ser | Leu | Asp | Ser | Asp | Leu | Tyr | Ala | Glu | Leu | Arg | Cys |
|---|---|---|---|---|---|---|---|---|---|---|---|---|---|---|---|
| 1 | | | | 5 | | | | | 10 | | | | | 15 | |

```
Met  Cys  Ile  Lys  Thr  Thr  Ser  Gly  Ile  His  Pro  Lys  Asn  Ile  Gln  Ser
               20                      25                      30

Leu  Glu  Val  Ile  Gly  Lys  Gly  Thr  His  Cys  Asn  Gln  Val  Glu  Val  Ile
               35                      40                      45

Ala  Thr  Leu  Lys  Asp  Gly  Arg  Lys  Ile  Cys  Leu  Asp  Pro  Asp  Ala  Pro
          50                      55                      60

Arg  Ile  Lys  Lys  Ile  Val  Gln  Lys  Lys  Leu  Ala  Gly  Asp  Glu  Ser  Ala
65                       70                      75                           80

Asp
```

( 2 ) INFORMATION FOR SEQ ID NO:11:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ala  Glu  Leu  Arg  Cys  Met  Cys  Ile  Lys  Thr  Thr  Ser  Gly  Ile  His  Pro
1                   5                      10                      15

Lys  Asn  Ile  Gln  Ser  Leu  Glu  Val  Ile  Gly  Lys  Gly  Thr  His  Cys  Asn
               20                      25                      30

Gln  Val  Glu  Val  Ile  Ala  Thr  Leu  Lys  Asp  Gly  Arg  Lys  Ile  Cys  Leu
               35                      40                      45

Asp  Pro  Asp  Ala  Pro  Arg  Ile  Lys  Lys  Ile  Val  Gln  Lys  Lys  Leu  Ala
          50                      55                      60

Gly  Asp  Glu  Ser  Ala  Asp
65                       70
```

( 2 ) INFORMATION FOR SEQ ID NO:12:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Gly  Pro  Val  Ser  Ala  Val  Leu  Thr  Glu  Leu  Arg  Cys  Thr  Cys  Leu  Arg
1                   5                      10                      15

Val  Thr  Leu  Arg  Val  Asn  Pro  Lys  Thr  Ile  Gly  Lys  Leu  Gln  Val  Phe
               20                      25                      30

Pro  Ala  Gly  Pro  Gln  Cys  Ser  Lys  Val  Glu  Val  Val  Ala  Ser  Leu  Lys
               35                      40                      45

Asn  Gly  Lys  Gln  Val  Cys  Leu  Asp  Pro  Glu  Ala  Pro  Phe  Leu  Lys  Lys
          50                      55                      60

Val  Ile  Gln  Lys  Ile  Leu  Asp  Ser  Gly  Asn  Lys
65                       70                      75
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Val Pro Leu Ser Arg Thr Val Arg Cys Thr Cys
1               5                   10

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Thr Pro Val Val Arg Lys Gly Arg Cys Ser Cys
1               5                   10

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Glu Ala Glu Glu Asp Gly Asp Leu Gln Cys Leu Cys
1               5                   10

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Val Pro Leu Ser Arg Glu Leu Arg Cys Thr Cys
1               5                   10

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Thr Pro Val Val Arg Glu Leu Arg Cys Ser Cys
1               5                   10

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Glu Ala Glu Glu Asp Gly Glu Leu Arg Cys Leu Cys
1               5                   10

( 2 ) INFORMATION FOR SEQ ID NO:19:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:19:

Ser Ala Lys Glu Leu Arg Cys Gln Cys
1               5

( 2 ) INFORMATION FOR SEQ ID NO:20:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:20:

Ala Gly Pro Ala Ala Ala Val Leu Arg Glu Leu Arg Cys Val Cys
1               5                   10                  15

( 2 ) INFORMATION FOR SEQ ID NO:21:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Asp Ser Asp Leu Tyr Ala Glu Leu Arg Cys Met Cys
1               5                   10

( 2 ) INFORMATION FOR SEQ ID NO:22:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Ala Glu Leu Arg Cys Met Cys Ile Lys Thr Thr Ser
1               5                   10

( 2 ) INFORMATION FOR SEQ ID NO:23:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide (x i) SEQUENCE DESCRIPTION: SEQ ID NO:23:

Glu Ser Leu Asp Ser Asp Leu Tyr Ala Glu Leu Arg Cys Met Cys
1               5                   10                  15

(2) INFORMATION FOR SEQ ID NO:24:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:24:

Ala Ser Val Ala Thr Glu Leu Arg Cys Gln Cys
1               5                   10

(2) INFORMATION FOR SEQ ID NO:25:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (i i) MOLECULE TYPE: peptide (x i) SEQUENCE DESCRIPTION: SEQ ID NO:25:

AATRCC      6

(2) INFORMATION FOR SEQ ID NO:26:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:26:

Ala Ser Val Val Thr Glu Leu Arg Cys Gln Cys
1               5                   10

(2) INFORMATION FOR SEQ ID NO:27:

(i) SEQUENCE CHARACTERISTICS:
      (A) LENGTH: 20 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:27:

Gly Pro Val Ser Ala Val Leu Thr Glu Leu Arg Cys Thr Cys Leu Val
1               5                   10                  15

Arg Thr Leu Arg
                20

(2) INFORMATION FOR SEQ ID NO:28:

(i) SEQUENCE CHARACTERISTICS:
      (A) LENGTH: 21 base pairs
      (B) TYPE: nucleic acid
      (C) STRANDEDNESS: single
      (D) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:28:

AGCCCTCTTC AAAAACTTCT C                                                                 21

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:29:

CTTTGTTGCC GCCGTCGAGG                                                                   20

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:30:

TTCAGTAAAT TCTTGATGGC C                                                                 21

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:31:

CAGCGGGGCT TGCAGGTCCA A                                                                 21

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:32:

AAGAGCTGGC GAGGAGGTGC C                                                                 21

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i  i  ) MOLECULE TYPE: other nucleic acid
              ( A ) DESCRIPTION: /desc = "DNA"

( x i ) SEQUENCE DESCRIPTION: SEQ ID NO:33:

GTGGCTCTCC GAGAACGGCG A                                                                                    21

( 2 ) INFORMATION FOR SEQ ID NO:34:

(  i  ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear (  i  i  ) MOLECULE TYPE: other nucleic acid
              ( A ) DESCRIPTION: /desc = "DNA"

( x i ) SEQUENCE DESCRIPTION: SEQ ID NO:34:

TTATGCATGG TTGAGACTGG A                                                                                    21

( 2 ) INFORMATION FOR SEQ ID NO:35:

(  i  ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear (  i  i  ) MOLECULE TYPE: other nucleic acid
              ( A ) DESCRIPTION: /desc = "DNA"

( x i ) SEQUENCE DESCRIPTION: SEQ ID NO:35:

CTAGGCAGGT TTGATCTCCG T                                                                                    21

( 2 ) INFORMATION FOR SEQ ID NO:36:

(  i  ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear (  i  i  ) MOLECULE TYPE: other nucleic acid
              ( A ) DESCRIPTION: /desc = "DNA"

( x i ) SEQUENCE DESCRIPTION: SEQ ID NO:36:

CAGATACTCT CTGGAGGCTG C                                                                                    21

( 2 ) INFORMATION FOR SEQ ID NO:37:

(  i  ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear (  i  i  ) MOLECULE TYPE: other nucleic acid
              ( A ) DESCRIPTION: /desc = "DNA"

( x i ) SEQUENCE DESCRIPTION: SEQ ID NO:37:

AGCGAGGCAC ATCAGGTACG                                                                                      20

( 2 ) INFORMATION FOR SEQ ID NO:38:

(  i  ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:38:

AGATCCGATT TTGGAGACCT C                                              21

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:39:

GCCTGGGGCA TCACTTCTAC                                                20

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:40:

TTACTGGGAT GCTCTTTCGA C                                              21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:41:

GCTCGGCCGT GGTGGTGAAG C                                              21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:42:

AAGCTGGGGG TGGCTCTGTT G                                              21

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: other nucleic acid
    (A) DESCRIPTION: /desc = "DNA"

(x i) SEQUENCE DESCRIPTION: SEQ ID NO:43:

AGCCCTCTTC AAAAACTTCT C                                                         21

(2) INFORMATION FOR SEQ ID NO:44:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (i i) MOLECULE TYPE: other nucleic acid
       (A) DESCRIPTION: /desc = "DNA"

(x i) SEQUENCE DESCRIPTION: SEQ ID NO:44:

GAACTGCGGT GCGTGTGTTT                                                           20

(2) INFORMATION FOR SEQ ID NO:45:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (i i) MOLECULE TYPE: other nucleic acid
       (A) DESCRIPTION: /desc = "DNA"

(x i) SEQUENCE DESCRIPTION: SEQ ID NO:45:

CTTTGTTGCC GCCGTCGAGG                                                           20

(2) INFORMATION FOR SEQ ID NO:46:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (i i) MOLECULE TYPE: other nucleic acid
       (A) DESCRIPTION: /desc = "DNA"

(x i) SEQUENCE DESCRIPTION: SEQ ID NO:46:

GATTTGCTGC CTTATCTTTC T                                                         21

(2) INFORMATION FOR SEQ ID NO:47:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (i i) MOLECULE TYPE: other nucleic acid
       (A) DESCRIPTION: /desc = "DNA"

(x i) SEQUENCE DESCRIPTION: SEQ ID NO:47:

TTCAGTAAAT TCTTGATGGC C                                                         21

(2) INFORMATION FOR SEQ ID NO:48:

(i) SEQUENCE CHARACTERISTICS:
       (A) LENGTH: 21 base pairs
       (B) TYPE: nucleic acid
       (C) STRANDEDNESS: single
       (D) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:48:

CTGGGGTTGC TGCTCCTGCC A 21

( 2 ) INFORMATION FOR SEQ ID NO:49:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:49:

CAGCGGGGCT TGCAGGTCCA A 21

( 2 ) INFORMATION FOR SEQ ID NO:50:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:50:

GTGGGGCGCC CCAGGCACCA 20

( 2 ) INFORMATION FOR SEQ ID NO:51:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:51:

GCTCGGCCGT GGTGGTGAAG C 21

( 2 ) INFORMATION FOR SEQ ID NO:52:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:52:

CAGGTGGTAT CTTCAGCGCA G 21

( 2 ) INFORMATION FOR SEQ ID NO:53:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear (  i i  ) MOLECULE TYPE: other nucleic acid
  ( A ) DESCRIPTION: /desc = "DNA"

( x i ) SEQUENCE DESCRIPTION: SEQ ID NO:53:

AAGAGCTGGC GAGGAGGTGC C                                              21

( 2 ) INFORMATION FOR SEQ ID NO:54:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:54:

AAGAGCTGGC GAGGAGGTGC C                                              21

( 2 ) INFORMATION FOR SEQ ID NO:55:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:55:

GTGGCTCTCC GAGAACGGCG A                                              21

( 2 ) INFORMATION FOR SEQ ID NO:56:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:56:

AGGCTGTATC TTCAGCGAGG T                                              21

( 2 ) INFORMATION FOR SEQ ID NO:57:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:57:

TTATGCATGG TTGAGACTGG A                                              21

( 2 ) INFORMATION FOR SEQ ID NO:58:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
              ( A ) DESCRIPTION: /desc = "DNA"

( x i ) SEQUENCE DESCRIPTION: SEQ ID NO:58:

ACATTCTCGG ACTTCACTCC A                                                                 21

( 2 ) INFORMATION FOR SEQ ID NO:59:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA"

( x i ) SEQUENCE DESCRIPTION: SEQ ID NO:59:

CTAGGCAGGT TTGATCTCCG T                                                                 21

( 2 ) INFORMATION FOR SEQ ID NO:60:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA"

( x i ) SEQUENCE DESCRIPTION: SEQ ID NO:60:

TCCACCTACA ATCCTTGAAA G                                                                 21

( 2 ) INFORMATION FOR SEQ ID NO:61:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA"

( x i ) SEQUENCE DESCRIPTION: SEQ ID NO:61:

CAGATACTCT CTGGAGGCTG C                                                                 21

( 2 ) INFORMATION FOR SEQ ID NO:62:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA"

( x i ) SEQUENCE DESCRIPTION: SEQ ID NO:62:

AAGCGCTTCA TCCACCG                                                                      17

( 2 ) INFORMATION FOR SEQ ID NO:63:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: other nucleic acid
   ( A ) DESCRIPTION: /desc = "DNA"

( x i ) SEQUENCE DESCRIPTION: SEQ ID NO:63:

GCGTGGCTTC TCTCCAG                                                                    17

( 2 ) INFORMATION FOR SEQ ID NO:64:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:64:

GCTGGCCACC AACCACCAGG                                                                 20

( 2 ) INFORMATION FOR SEQ ID NO:65:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:65:

AGCGAGGCAC ATCAGGTACG                                                                 20

( 2 ) INFORMATION FOR SEQ ID NO:66:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:66:

CAGTCTGAGA ACAGCTGCAC C                                                               21

( 2 ) INFORMATION FOR SEQ ID NO:67:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:67:

AGATCCGATT TTGGAGACCT C                                                               21

( 2 ) INFORMATION FOR SEQ ID NO:68:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:68:

GCTATGTTGC CTGCTCTTAC                                                                               20

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:69:

GCCTGGGGCA TCACTTCTAC                                                                               20

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:70:

ATGAAATATA CAAGTTATAT C                                                                             21

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:71:

TTACTGGGAT GCTCTTTCGA C                                                                             21

( 2 ) INFORMATION FOR SEQ ID NO:72:

( i ) SEQUENCE CHARACTERISTICS:
        ( A ) LENGTH: 2545 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:72:

ATCCAATACA GGAGTGACTT GGAACTCCAT TCTATCACTA TGAAGAAAAG TGGTGTTCTT      60

TTCCTCTTGG GCATCATCTT GCTGGTTCTG ATTGGAGTGC AAGGAACCCC AGTAGTGAGA     120

AAGGGTCGCT GTTCCTGCAT CAGCACCAAC CAAGGGACTA TCCACCTACA ATCCTTGAAA     180

GACCTTAAAC AATTTGCCCC AAGCCCTTCC TGCGAGAAAA TTGAAATCAT TGCTACACTG     240

AAGAATGGAG TTCAAACATG TCTAAACCCA GATTCAGCAG ATGTGAAGGA ACTGATTAAA     300

| | | | | | | |
|---|---|---|---|---|---|---|
| AAGTGGGAGA | AACAGGTCAG | CCAAAAGAAA | AAGCAAAAGA | ATGGGAAAAA | ACATCAAAAA | 360 |
| AAGAAAGTTC | TGAAAGTTCG | AAAATCTCAA | CGTTCTCGTC | AAAAGAAGAC | TACATAAGAG | 420 |
| ACCACTTCAC | CAATAAGTAT | TCTGTGTTAA | AAATGTTCTA | TTTTAATTAT | ACCGCTATCA | 480 |
| TTCCAAAGGA | GGATGGCATA | TAATACAAAG | GCTTATTAAT | TTGACTAGAA | AATTTAAAAC | 540 |
| ATTACTCTGA | AATTGTAACT | AAAGTTAGAA | AGTTGATTTT | AAGAATCCAA | ACGTTAAGAA | 600 |
| TTGTTAAAGG | CTATGATTGT | CTTTGTTCTT | CTACCACCCA | CCAGTTGAAT | TTCATCATGC | 660 |
| TTAAGGCCAT | GATTTTAGCA | ATACCATGT | CTACACAGAT | GTTCACCCAA | CCACATCCCA | 720 |
| CTCACAACAG | CTGCCTGGAA | GAGCAGCCCT | AGGCTTCCAC | GTACTGCAGC | CTCCAGAGAG | 780 |
| TATCTGAGGC | ACATGTCAGC | AAGTCCTAAG | CCTGTTAGCA | TGCTGGTGAG | CCAAGCAGTT | 840 |
| TGAAATTGAG | CTGGACCTCA | CCAAGCTGCT | GTGGCCATCA | ACCTCTGTAT | TGAATCAGC | 900 |
| CTACAGGCCT | CACACACAAT | GTGTCTGAGA | GATTCATGCT | GATTGTTATT | GGGTATCACC | 960 |
| ACTGGAGATC | ACCAGTGTGT | GGCTTTCAGA | GCCTCCTTTC | TGGCTTTGGA | AGCCATGTGA | 1020 |
| TTCCATCTTG | CCCGCTCAGG | CTGACCACTT | TATTTCTTTT | TGTTCCCCTT | TGCTTCATTC | 1080 |
| AAGTCAGCTC | TTCTCCATCC | TACCACAATG | CAGTGCCTTT | CTTCTCTCCA | GTGCACCTGT | 1140 |
| CATATGCTCT | GATTTATCTG | AGTCAACTCC | TTTCTCATCT | TGTCCCCAAC | ACCCCACAGA | 1200 |
| AGTGCTTTCT | TCTCCCAATT | CATCCTCACT | CAGTCCAGCT | TAGTTCAAGT | CCTGCCTCTT | 1260 |
| AAATAAACCT | TTTTGGACAC | ACAAATTATC | TTAAAACTCC | TGTTTCACTT | GGTTCAGTAC | 1320 |
| CACATGGGTG | AACACTCAAT | GGTTAACTAA | TTCTTGGGTG | TTTATCCTAT | CTCTCCAACC | 1380 |
| AGATTGTCAG | CTCCTTGAGG | GCAAGAGCCA | CAGTATATTT | CCCTGTTTCT | TCCACAGTGC | 1440 |
| CTAATAATAC | TGTGGAACTA | GGTTTTAATA | ATTTTTTAAT | TGATGTTGTT | ATGGGCAGGA | 1500 |
| TGGCAACCAG | ACCATTGTCT | CAGAGCAGGT | GCTGGCTCTT | TCCTGGCTAC | TCCATGTTGG | 1560 |
| CTAGCCTCTG | GTAACCTCTT | ACTTATTATC | TTCAGGACAC | TCACTACAGG | GACCAGGGAT | 1620 |
| GATGCAACAT | CCTTGTCTTT | TTATGACAGG | ATGTTTGCTC | AGCTTCTCCA | ACAATAAGAA | 1680 |
| GCACGTGGTA | AAACACTTGC | GGATATTCTG | GACTGTTTTT | AAAAAATATA | CAGTTTACCG | 1740 |
| AAAATCATAT | AATCTTACAA | TGAAAAGGAC | TTTATAGATC | AGCCAGTGAC | CAACCTTTTC | 1800 |
| CCAACCATAC | AAAAATTCCT | TTTCCCGAAG | GAAAAGGGCT | TTCTCAATAA | GCCTCAGCTT | 1860 |
| TCTAAGATCT | AACAAGATAG | CCACCGAGAT | CCTTATCGAA | ACTCATTTTA | GGCAAATATG | 1920 |
| AGTTTTATTG | TCCGTTTACT | TGTTTCAGAG | TTTGTATTGT | GATTATCAAT | TACCACACCA | 1980 |
| TCTCCCATGA | AGAAAGGGAA | CGGTGAAGTA | CTAAGCGCTA | GAGGAAGCAG | CCAAGTCGGT | 2040 |
| TAGTGGAAGC | ATGATTGGTG | CCCAGTTAGC | CTCTGCAGGA | TGTGGAAACC | TCCTTCCAGG | 2100 |
| GGAGGTTCAG | TGAATTGTGT | AGGAGAGGTT | GTCTGTGGCC | AGAATTTAAA | CCTATACTCA | 2160 |
| CTTTCCCAAA | TTGAATCACT | GCTCACACTG | CTGATGATTT | AGAGTGCTGT | CCGGTGGAGA | 2220 |
| TCCCACCCGA | ACGTCTTATC | TAATCATGAA | ACTCCCTAGT | TCCTTCATGT | AACTTCCCTG | 2280 |
| AAAAATCTAA | GTGTTTCATA | AATTTGAGAG | TCTGTGACCC | ACTTACCTTG | CATCTCACAG | 2340 |
| GTAGACAGTA | TATAACTAAC | AACCAAAGAC | TACATATTGT | CACTGACACA | CACGTTATAA | 2400 |
| TCATTTATCA | TATATATACA | TACATGCATA | CACTCTCAAA | GCAAATAATT | TTTCACTTCA | 2460 |
| AAACAGTATT | GACTTGTATA | CCTTGTAATT | TGAAATATTT | TCTTTGTTAA | AATAGAATGG | 2520 |
| TATCAATAAA | TAGACCATTA | ATCAG | | | | 2545 |

( 2 ) INFORMATION FOR SEQ ID NO:73:

( i ) SEQUENCE CHARACTERISTICS:

(A) LENGTH: 654 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:73:

| | | | | | | |
|---|---|---|---|---|---|---|
| CTGGTTCCGC | GTGGATCTCC | AGTAGTGAGA | AAGGGTCGCT | GTTCCTGCAT | CAGCACCAAC | 60 |
| GACCAAGGCG | CACCTAGAGG | TCATCACTCT | TTCCCAGCGA | CAAGGACGTA | GTCGTGGTTG | 120 |
| CAAGGGACTA | TCCACCTACA | ATCCTTGAAA | GACCTTAAAC | AATTTGCCCC | AAGCCCTTCC | 180 |
| GTTCCCTGAT | AGGTGGATGT | TAGGAACTTT | CTGGAATTTG | TTAAACGGGG | TTCGGGAAGG | 240 |
| TGCGAGAAAA | TTGAAATCAT | TGCTACACTG | AAGAATGGAG | TTCAAACATG | TCTAAACCCA | 300 |
| ACGCTCTTTT | AACTTTAGTA | ACGATGTGAC | TTCTTACCTC | AAGTTTGTAC | AGATTTGGGT | 360 |
| GATTCAGCAG | ATGTGAAGGA | ACTGATTAAA | AAGTGGGAGA | AACAGGTCAG | CCAAAAGAAA | 420 |
| CTAAGTCGTC | TACACTTCCT | TGACTAATTT | TTCACCCTCT | TTGTCCAGTC | GGTTTTCTTT | 480 |
| AAGCAAAAGA | ATGGGAAAAA | ACATCAAAAA | AAGAAAGTTC | TGAAAGTTCG | AAAATCTCAA | 540 |
| TTCGTTTTCT | TACCCTTTTT | TGTAGTTTTT | TTCTTTCAAG | ACTTTCAAGC | TTTTAGAGTT | 600 |
| CGTTCTCGTC | AAAAGAAGAC | TACATAAGCA | AGAGCAGTTT | TCTTCTGATG | TATT | 654 |

(2) INFORMATION FOR SEQ ID NO:74:

(i) SEQUENCE CHARACTERISTICS:
(A) LENGTH: 108 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:74:

| Leu | Val | Pro | Arg | Gly | Ser | Pro | Val | Val | Arg | Lys | Gly | Arg | Cys | Ser | Cys |
|---|---|---|---|---|---|---|---|---|---|---|---|---|---|---|---|
| 1 | | | | 5 | | | | | 10 | | | | | 15 | |
| Ile | Ser | Thr | Asn | Gln | Gly | Thr | Ile | His | Leu | Gln | Ser | Leu | Lys | Asp | Leu |
| | | | 20 | | | | | 25 | | | | | 30 | | |
| Lys | Gln | Phe | Ala | Pro | Ser | Pro | Ser | Cys | Glu | Lys | Ile | Glu | Ile | Ile | Ala |
| | | | 35 | | | | | 40 | | | | | 45 | | |
| Thr | Leu | Lys | Asn | Gly | Val | Gln | Thr | Cys | Leu | Asn | Pro | Asp | Ser | Ala | Asp |
| | | 50 | | | | | 55 | | | | | 60 | | | |
| Val | Lys | Glu | Leu | Ile | Lys | Lys | Trp | Glu | Lys | Gln | Val | Ser | Gln | Lys | Lys |
| 65 | | | | | 70 | | | | | 75 | | | | | 80 |
| Lys | Gln | Lys | Asn | Gly | Lys | Lys | His | Gln | Lys | Lys | Val | Leu | Lys | Val | |
| | | | | 85 | | | | | 90 | | | | | 95 | |
| Arg | Lys | Ser | Gln | Arg | Ser | Arg | Gln | Lys | Lys | Thr | Thr | | | | |
| | | | | 100 | | | | | 105 | | | | | | |

(2) INFORMATION FOR SEQ ID NO:75:

(i) SEQUENCE CHARACTERISTICS:
(A) LENGTH: 654 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:75:

-continued

| CTGGTTCCGC | GTGGATCTCC | AGTAGTGAGA | GAGCTTCGCT | GTTCCTGCAT | CAGCACCAAC | 60 |
| GACCAAGGCG | CACCTAGAGG | TCATCACTCT | CTCGAAGCGA | CAAGGACGTA | GTCGTGGTTG | 120 |
| CAAGGGACTA | TCCACCTACA | ATCCTTGAAA | GACCTTAAAC | AATTTGCCCC | AAGCCCTTCC | 180 |
| GTTCCCTGAT | AGGTGGATGT | TAGGAACTTT | CTGGAATTTG | TTAAACGGGG | TTCGGGAAGG | 240 |
| TGCGAGAAAA | TTGAAATCAT | TGCTACACTG | AAGAATGGAG | TTCAAACATG | TCTAAACCCA | 300 |
| ACGCTCTTTT | AACTTTAGTA | ACGATGTGAC | TTCTTACCTC | AAGTTTGTAC | AGATTTGGGT | 360 |
| GATTCAGCAG | ATGTGAAGGA | ACTGATTAAA | AAGTGGGAGA | AACAGGTCAG | CCAAAAGAAA | 420 |
| CTAAGTCGTC | TACACTTCCT | TGACTAATTT | TTCACCCTCT | TTGTCCAGTC | GGTTTTCTTT | 480 |
| AAGCAAAAGA | ATGGGAAAAA | ACATCAAAAA | AAGAAAGTTC | TGAAAGTTCG | AAAATCTCAA | 540 |
| TTCGTTTTCT | TACCCTTTTT | TGTAGTTTTT | TTCTTTCAAG | ACTTTCAAGC | TTTTAGAGTT | 600 |
| CGTTCTCGTC | AAAAGAAGAC | TACATAAGCA | AGAGCAGTTT | TCTTCTGATG | TATT | 654 |

(2) INFORMATION FOR SEQ ID NO:76:

(i) SEQUENCE CHARACTERISTICS:
    (A) LENGTH: 108 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:76:

```
Leu Val Pro Arg Gly Ser Pro Val Val Arg Glu Leu Arg Cys Ser Cys
1               5                   10                  15

Ile Ser Thr Asn Gln Gly Thr Ile His Leu Gln Ser Leu Lys Asp Leu
                20                  25                  30

Lys Gln Phe Ala Pro Ser Pro Ser Cys Glu Lys Ile Glu Ile Ile Ala
            35                  40                  45

Thr Leu Lys Asn Gly Val Gln Thr Cys Leu Asn Pro Asp Ser Ala Asp
        50                  55                  60

Val Lys Glu Leu Ile Lys Lys Trp Glu Lys Gln Val Ser Gln Lys Lys
65                  70                  75                  80

Lys Gln Lys Asn Gly Lys Lys His Gln Lys Lys Val Leu Lys Val
                85                  90                  95

Arg Lys Ser Gln Arg Ser Arg Gln Lys Lys Thr Thr
                100                 105
```

(2) INFORMATION FOR SEQ ID NO:77:

(i) SEQUENCE CHARACTERISTICS:
    (A) LENGTH: 1639 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA"

(xi) SEQUENCE DESCRIPTION: SEQ ID NO:77:

| ACAAACTTTC | AGAGACAGCA | GAGCACACAA | GCTTCTAGGA | CAAGAGCCAG | GAAGAAACCA | 60 |
| CCGGAAGGAA | CCATCTCACT | GTGTGTAAAC | ATGACTTCCA | AGCTGGCCGT | GGCTCTCTTG | 120 |
| GCAGCCTTCC | TGATTTCTGC | AGCTCTGTGT | GAAGGTGCAG | TTTTGCCAAG | GAGTGCTAAA | 180 |
| GAACTTAGAT | GTCAGTGCAT | AAAGACATAC | TCCAAACCTT | TCCACCCCAA | ATTTATCAAA | 240 |
| GAACTGAGAG | TGATTGAGAG | TGGACCACAC | TGCGCCAACA | CAGAAATTAT | TGTAAAGCTT | 300 |

| | | | | | | |
|---|---|---|---|---|---|---|
|TCTGATGGAA|GAGAGCTCTG|TCTGGACCCC|AAGGAAAACT|GGGTGCAGAG|GGTTGTGGAG|360|
|AAGTTTTTGA|AGAGGGCTGA|GAATTCATAA|AAAAATTCAT|TCTCTGTGGT|ATCCAAGAAT|420|
|CAGTGAAGAT|GCCAGTGAAA|CTTCAAGCAA|ATCTACTTCA|ACACTTCATG|TATTGTGTGG|480|
|GTCTGTTGTA|GGGTTGCCAG|ATGCAATACA|AGATTCCTGG|TTAAATTTGA|ATTTCAGTAA|540|
|ACAATGAATA|GTTTTCATT|GTACCATGAA|ATATCCAGAA|CATACTTATA|TGTAAAGTAT|600|
|TATTTATTTG|AATCTACAAA|AAACAACAAA|TAATTTTTGA|ATATAAGGAT|TTTCCTAGAT|660|
|ATTGCACGGG|AGAATATACA|AATAGCAAAA|TTGGGCCAAG|GGCCAAGAGA|ATATCCGAAC|720|
|TTTAATTTCA|GGAATTGAAT|GGGTTTGCTA|GAATGTGATA|TTTGAAGCAT|CACATAAAAA|780|
|TGATGGACA|ATAAATTTTG|CCATAAAGTC|AAATTTAGCT|GGAAATCCTG|GATTTTTTC|840|
|TGTTAAATCT|GGCAACCCTA|GTCTGCTAGC|CAGGATCCAC|AAGTCCTTGT|TCCACTGTGC|900|
|CTTGGTTTCT|CCTTTATTTC|TAAGTGGAAA|AAGTATTAGC|CACCATCTTA|CCTCACAGTG|960|
|ATGTTGTGAG|GACATGTGGA|AGCACTTTAA|GTTTTTCAT|CATAACATAA|ATTATTTCA|1020|
|AGTGTAACTT|ATTAACCTAT|TTATTATTTA|TGTATTTATT|TAAGCATCAA|ATATTTGTGC|1080|
|AAGAATTTGG|AAAAATAGAA|GATGAATCAT|TGATTGAATA|GTTATAAAGA|TGTTATAGTA|1140|
|AATTTATTTT|ATTTTAGATA|TTAAATGATG|TTTTATTAGA|TAAATTTCAA|TCAGGGTTTT|1200|
|TAGATTAAAC|AAACAAACAA|TTGGGTACCC|AGTTAAATTT|TCATTTCAGA|TAAACAACAA|1260|
|ATAATTTTTT|AGTATAAGTA|CATTATTGTT|TATCTGAAAT|TTTAATTGAA|CTAACAATCC|1320|
|TAGTTTGATA|CTCCCAGTCT|TGTCATTGCC|AGCTGTGTTG|GTAGTGCTGT|GTTGAATTAC|1380|
|GGAATAATGA|GTTAGAACTA|TTAAAACAGC|CAAAACTCCA|CAGTCAATAT|TAGTAATTTC|1440|
|TTGCTGGTTG|AAACTTGTTT|ATTATGTACA|AATAGATTCT|TATAATATTA|TTTAAATGAC|1500|
|TGCATTTTTA|AATACAAGGC|TTTATATTTT|TAACTTTAAG|ATGTTTTTAT|GTGCTCTCCA|1560|
|AATTTTTTTT|ACTGTTTCTG|ATTGTATGGA|AATATAAAAG|TAAATATGAA|ACATTTAAAA|1620|
|TATAATTTGT|TGTCAAAGT| | | | |1639|

(2) INFORMATION FOR SEQ ID NO:78:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:78:

| | | | | | | |
|---|---|---|---|---|---|---|
|ATCGAGGGAA|GGAGTGCTAA|AGAACTTAGA|TGTCAGTGCA|TAAAGACATA|CTCCAAACCT|60|
|TAGCTCCCTT|CCTCACGATT|TCTTGAATCT|ACAGTCACGT|ATTTCTGTAT|GAGGTTTGGA|120|
|TTCCACCCCA|AATTTATCAA|AGAACTGAGA|GTGATTGAGA|GTGGACCACA|CTGCGCCAAC|180|
|AAGGTGGGGT|TTAAATAGTT|TCTTGACTCT|CACTAACTCT|CACCTGGTGT|GACGCGGTTG|240|
|ACAGAAATTA|TTGTAAAGCT|TTCTGATGGA|AGAGAGCTCT|GTCTGGACCC|CAAGGAAAAC|300|
|TGTCTTTAAT|AACATTTCGA|AAGACTACCT|TCTCTCGAGA|CAGACCTGGG|GTTCCTTTTG|360|
|TGGGTGCAGA|GGGTTGTGGA|GAAGTTTTTG|AAGAGGGCTG|AGAATTCATA|AACCCACGTC|420|
|TCCCAACACC|TCTTCAAAAA|CTTCTCCCGA|CTCTTAAGTA|TT| |462|

(2) INFORMATION FOR SEQ ID NO:79:

(i) SEQUENCE CHARACTERISTICS:

( A ) LENGTH: 76 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:79:

```
Ile Glu Gly Arg Ser Ala Lys Glu Leu Arg Cys Gln Cys Ile Lys Thr
 1               5                  10                  15
Tyr Ser Lys Pro Phe His Pro Lys Phe Ile Lys Glu Leu Arg Val Ile
            20                  25                  30
Glu Ser Gly Pro His Cys Ala Asn Thr Glu Ile Ile Val Lys Leu Ser
         35                  40                  45
Asp Gly Arg Glu Leu Cys Leu Asp Pro Lys Glu Asn Trp Val Gln Arg
         50                  55                  60
Val Val Glu Lys Phe Leu Lys Arg Ala Glu Asn Ser
 65              70                  75
```

( 2 ) INFORMATION FOR SEQ ID NO:80:

( i ) SEQUENCE CHARACTERISTICS:
( A ) LENGTH: 462 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:80:

```
ATCGAGGGAA GGAGTGCTAA AACAGTTAGA TGTCAGTGCA TAAAGACATA CTCCAAACCT      60
TAGCTCCCTT CCTCACGATT TTGTCAATCT ACAGTCACGT ATTTCTGTAT GAGGTTTGGA     120
TTCCACCCCA AATTTATCAA AGAACTGAGA GTGATTGAGA GTGGACCACA CTGCGCCAAC     180
AAGGTGGGGT TTAAATAGTT TCTTGACTCT CACTAACTCT CACCTGGTGT GACGCGGTTG     240
ACAGAAATTA TTGTAAAGCT TTCTGATGGA AGAGAGCTCT GTCTGGACCC CAAGGAAAAC     300
TGTCTTTAAT AACATTTCGA AAGACTACCT TCTCTCGAGA CAGACCTGGG GTTCCTTTTG     360
TGGGTGCAGA GGGTTGTGGA GAAGTTTTTG AAGAGGGCTG AGAATTCATA AACCCACGTC     420
TCCCAACACC TCTTCAAAAA CTTCTCCCGA CTCTTAAGTA TT                        462
```

( 2 ) INFORMATION FOR SEQ ID NO:81:

( i ) SEQUENCE CHARACTERISTICS:
( A ) LENGTH: 76 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:81:

```
Ile Glu Gly Arg Ser Ala Lys Thr Val Arg Cys Gln Cys Ile Lys Thr
 1               5                  10                  15
Tyr Ser Lys Pro Phe His Pro Lys Phe Ile Lys Glu Leu Arg Val Ile
            20                  25                  30
Glu Ser Gly Pro His Cys Ala Asn Thr Glu Ile Ile Val Lys Leu Ser
         35                  40                  45
Asp Gly Arg Glu Leu Cys Leu Asp Pro Lys Glu Asn Trp Val Gln Arg
         50                  55                  60
Val Val Glu Lys Phe Leu Lys Arg Ala Glu Asn Ser
```

( 2 ) INFORMATION FOR SEQ ID NO:82:

( i ) SEQUENCE CHARACTERISTICS:
        ( A ) LENGTH: 411 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:82:

```
ATCGAGGGAA  GGAGTGCTAA  AGATCTTCAA  TGTCAGTGCA  TAAAGACATA  CTCCAAACCT    60
TAGCTCCCTT  CCTCACGATT  TCTAGAAGTT  ACAGTCACGT  ATTTCTGTAT  GAGGTTTGGA   120
TTCCACCCCA  AATTTATCAA  AGAACTGAGA  GTGATTGAGA  GTGGACCACA  CTGCGCCAAC   180
AAGGTGGGGT  TTAAATAGTT  TCTTGACTCT  CACTAACTCT  CACCTGGTGT  GACGCGGTTG   240
ACAGAAATTA  TTGTAAAGCT  TTCTGATGGA  AGAGAGCTCT  GTCTGGACCC  CAAGGAAAAC   300
TGTCTTTAAT  AACATTTCGA  AAGACTACCT  TCTCTCGAGA  CAGACCTGGG  GTTCCTTTTG   360
TGGGTGCAGA  GGGTTGTGGA  GAAGTTTTTG  AAGAGGGCTG  AGAATTCATA  A            411
```

( 2 ) INFORMATION FOR SEQ ID NO:83:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

```
Ile Glu Gly Arg Ser Ala Lys Asp Leu Gln Cys Gln Cys Ile Lys Thr
  1               5                  10                  15
Tyr Ser Lys Pro Phe His Pro Lys Phe Ile Lys Glu Leu Arg Val Ile
             20                  25                  30
Glu Ser Gly Pro His Cys Ala Asn Thr Glu Ile Ile Val Lys Leu Ser
             35                  40                  45
Asp Gly Arg Glu Leu Cys Leu Asp Pro Lys Glu Asn Trp Val Gln Arg
        50                  55                  60
Val Val Glu Lys Phe Leu Lys Arg Ala Glu Asn Ser
 65                  70                  75
```

( 2 ) INFORMATION FOR SEQ ID NO:84:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:84:

```
CAAGGTGGAT  CCATGAAGAA  AAGTGGTGTT  C                                     31
```

( 2 ) INFORMATION FOR SEQ ID NO:85:

( i ) SEQUENCE CHARACTERISTICS:
        ( A ) LENGTH: 39 base pairs
        ( B ) TYPE: nucleic acid ( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:85:

| GCAAGCTCTA | GATTATGTAG | TCTTCTTTTG | ACGAGAACG | | 39 |
|---|---|---|---|---|---|

( 2 ) INFORMATION FOR SEQ ID NO:86:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:86:

| AGTGCTAAAG | AACTTAGATG | | | | 20 |
|---|---|---|---|---|---|

( 2 ) INFORMATION FOR SEQ ID NO:87:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:87:

| GGGATCCTCA | TGAATTCTC | | | | 19 |
|---|---|---|---|---|---|

( 2 ) INFORMATION FOR SEQ ID NO:88:

( i ) SEQUENCE CHARACTERISTICS:
( A ) LENGTH: 1173 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:88:

| CGGCACGAGC | ACAGTGCTCC | GGATCCTCCA | ATCTTCGCTC | CTCCAATCTC | CGCTCCTCCA | 60 |
|---|---|---|---|---|---|---|
| CCCAGTTCAG | GAACCCGCGA | CCGCTCGCAG | CGCTCTCTTG | ACCACTATGA | GCCTCCTGTC | 120 |
| CAGCCGCGCG | GCCCGTGTCC | CCGGTCCTTC | GAGCTCCTTG | TGCGCGCTGT | TGGTGCTGCT | 180 |
| GCTGCTGCTG | ACGCAGCCAG | GGCCCATCGC | CAGCGCTGGT | CCTGCCGCTG | CTGTGTTGAG | 240 |
| AGAGCTGCGT | TGCGTTTGTT | TACAGACCAC | GCAGGGAGTT | CATCCCAAAA | TGATCAGTAA | 300 |
| TCTGCAAGTG | TTCGCCATAG | GCCCACAGTG | CTCCAAGGTG | GAAGTGGTAG | CCTCCCTGAA | 360 |
| GAACGGGAAG | GAAATTTGTC | TTGATCCAGA | AGCCCCTTTT | CTAAAGAAAG | TCATCCAGAA | 420 |
| AATTTTGGAC | GGTGGAAACA | AGGAAAACTG | ATTAAGAGAA | ATGAGCACGC | ATGGAAAAGT | 480 |
| TTCCCAGTCT | ACAGCAGAGA | AGTTTTCTGG | AGGTCTCTGA | ACCCAGGGAA | GACAAGAAGG | 540 |
| AAAGATTTTG | TTGTTGTTTG | TTTATTTGGT | TCCCCAGTA | GTTAGCTTTC | TTCCCTGGAT | 600 |
| TCCTCACTTT | TGAAGAGTGT | GAGGAAAACC | TATGTTTGGC | GCTTAAGCTT | TCAGCTCAGC | 660 |
| TTAATGAAGT | GTTTAGCATA | GTACCTCTGC | TATTTGCTGT | TATTTTATCT | GCTATGCTAT | 720 |

| | | | | | |
|---|---|---|---|---|---|
| TGAAGTTTTG | GCAATTGACT | ATAGTGTGAG | CCAGGAATCA | CTGGCTGTTA | ATCTTACAAA | 780
| GTGTCTTGGA | ATTGTAGGTG | ACTATTATTT | TTCCAAGAAA | TATCCCTTAA | GATATTAACT | 840
| GAGAAGGCTG | GGGGTTTAAT | GTGGAAATGA | TGTTTCAAAA | GGAATCCTGT | GATGGAAATA | 900
| CAACTGGTAT | CTTCACTTTT | TTAGGAATTG | GGAAATATTT | TAATGTTTCT | TGGGGAATAT | 960
| GTTAGAGAAT | TCCCTTACTC | TTGATTGTGG | GATACTATTT | AATTATTTCA | CTTTAGAAAG | 1020
| CTGAGTGTTT | CACACCTTAT | CTATGTAGAA | TATATTTCCT | TATTCAGAAT | TTCTAAAAGT | 1080
| TTAAGTTCTA | TGAGGGCTAA | TATCTTATCT | TCCTATAATT | TTAGACATTG | CTTTAACTTT | 1140
| TTAGTAAAAA | AAAAAAAAAA | AAAAAAAAAA | AAA | | | 1173

( 2 ) INFORMATION FOR SEQ ID NO:89:

( i ) SEQUENCE CHARACTERISTICS:
        ( A ) LENGTH: 297 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:89:

| | | | | | |
|---|---|---|---|---|---|
| ATGAATCAAA | CTGCGATTCT | GATTTGCTGC | CTTATCTTTC | TGACTCTAAG | TGGCATTCAA | 60
| GGAGTACCTC | TCTCTAGAAC | CGTACGCTGT | ACCTGCATCA | GCATTAGTAA | TCAACCTGTT | 120
| AATCCAAGGT | CTTTAGAAAA | ACTTGAAATT | ATTCCTGCAA | GCCAATTTTG | TCCACGTGTT | 180
| GAGATCATTG | CTACAATGAA | AAAGAAGGGT | GAGAAGAGAT | GTCTGAATCC | AGAATCGAAG | 240
| GCCATCAAGA | ATTTACTGAA | AGCAGTTAGC | AAGGAAATGT | CTAAAGATC | TCCTTAA | 297

( 2 ) INFORMATION FOR SEQ ID NO:90:

( i ) SEQUENCE CHARACTERISTICS:
        ( A ) LENGTH: 1050 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:90:

| | | | | | |
|---|---|---|---|---|---|
| CTCGCCAGCT | CTTCCGCTCC | TCTCACAGCC | GCCAGACCCG | CCTGCTGAGC | CCCATGGCCC | 60
| GCGCTGCTCT | CTCCGCCGCC | CCCAGCAATC | CCCGGCTCCT | GCGAGTGGCA | CTGCTGCTCC | 120
| TGCTCCTGGT | AGCCGCTGGC | CGGCGCGCAG | CAGGAGCGTC | CGTGGCCACT | GAACTGCGCT | 180
| GCCAGTGCTT | GCAGACCCTG | CAGGGAATTC | ACCCCAAGAA | CATCCAAAGT | GTGAACGTGA | 240
| AGTCCCCCGG | ACCCCACTGC | GCCCAAACCG | AAGTCATAGC | CACACTCAAG | AATGGGCGGA | 300
| AAGCTTGCCT | CAATCCTGCA | TCCCCCATAG | TTAAGAAAAT | CATCGAAAAG | ATGCTGAACA | 360
| GTGACAAATC | CAACTGACCA | GAAGGGAGGA | GGAAGCTCAC | TGGTGGCTGT | TCCTGAAGGA | 420
| GGCCCTGCCC | TTATAGGAAC | AGAAGAGGAA | AGAGAGACAC | AGCTGCAGAG | GCCACCTGGA | 480
| TTGTGCCTAA | TGTGTTTGAG | CATCGCTTAG | GAGAAGTCTT | CTATTTATTT | ATTTATTCAT | 540
| TAGTTTTGAA | GATTCTATGT | TAATATTTTA | GGTGTAAAAT | AATTAAGGGT | ATGATTAACT | 600
| CTACCTGCAC | ACTGTCCTAT | TATATTCATT | CTTTTTGAAA | TGTCAACCCC | AAGTTAGTTC | 660
| AATCTGGATT | CATATTTAAT | TTGAAGGTAG | AATGTTTTCA | AATGTTCTCC | AGTCATTATG | 720
| TTAATATTTC | TGAGGAGCCT | GCAACATGCC | AGCCACTGTG | ATAGAGGCTG | GCGGATCCAA | 780

| | | | | | | |
|---|---|---|---|---|---|---|
| GCAAATGGCC | AATGAGATCA | TTGTGAAGGC | AGGGGAATGT | ATGTGCACAT | CTGTTTTGTA | 840 |
| ACTGTTTAGA | TGAATGTCAG | TTGTTATTTA | TTGAAATGAT | TTCACAGTGT | GTGGTCAACA | 900 |
| TTTCTCATGT | TGAAACTTTA | AGAACTAAAA | TGTTCTAAAT | ATCCTTGGA | CATTTTATGT | 960 |
| CTTTCTTGTA | AGGCATACTG | CCTTGTTTAA | TGGTAGTTTT | ACAGTGTTTC | TGGCTTAGAA | 1020 |
| CAAAGGGGCT | TAATTATTGA | TGTTTTCGGA | | | | 1050 |

( 2 ) INFORMATION FOR SEQ ID NO:91:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:91:

| | | | | | | |
|---|---|---|---|---|---|---|
| GACAGAGCCC | GGGCCACGGA | GCTCCTTGCC | AGCTCTCCTC | CTCGCACAGC | CGCTCGAACC | 60 |
| GCCTGCTGAG | CCCCATGGCC | CGCGCCACGC | TCTCCGCCGC | CCCCAGCAAT | CCCCGGCTCC | 120 |
| TGCGGGTGGC | GCTGCTGCTC | CTGCTCCTGG | TGGCCGCCAG | CCGGCGCGCA | GCAGGAGCGC | 180 |
| CCCTGGCCAC | TGAACTGCGC | TGCCAGTGCT | TGCAGACCCT | GCAGGGAATT | CACCTCAAGA | 240 |
| ACATCCAAAG | TGTGAAGGTG | AAGTCCCCCG | GACCCCACTG | CGCCCAAACC | GAAGTCATAG | 300 |
| CCACACTCAA | GAATGGGCAG | AAAGCTTGTC | TCAACCCCGC | ATCGCCCATG | GTTAAGAAAA | 360 |
| TCATCGAAAA | GATGCTGAAA | AATGGCAAAT | CCAACTGACC | AGAAGGAAGG | AGGAAGCTTA | 420 |
| TTGGTGGCTG | TTCCTGAAGG | AGGCCCTGCC | TTACAGGAAC | AGAAGAGGAA | AGAGAGACAC | 480 |
| AGCTGCAGAG | GCCACCTGGC | TTGCGCCTAA | TGTGTTTGAG | CATACTTAGG | AGAAGTCTTC | 540 |
| TATTTATTTA | TTTATTTATT | TATTTGTTTG | TTTTAGAAGA | TTCTATGTTA | ATATTTTATG | 600 |
| TGTAAAATAA | GGTTATGATT | GAATCTACTT | GCACACTCTC | CCATTATATT | TATTGTTTAT | 660 |
| TTTAGGTCAA | ACCCAAGTTA | GTTCAATCCT | GATTCATATT | TAATTTGAAG | ATAGAAGGTT | 720 |
| TGCAGATATT | CTCTAGTCAT | TTGTTAATAT | TTCTTCGTGA | TGACATATCA | CATGTCAGCC | 780 |
| ACTGTGATAG | AGGCTGAGGA | ATCCAAGAAA | ATGGCCAGTA | AGATCAATGT | GACGGCAGGG | 840 |
| AAATGTATGT | GTGTCTATTT | TGTAACTGTA | AAGATGAATG | TCAGTTGTTA | TTTATTGAAA | 900 |
| TGATTTCACA | GTGTGTGGTC | AACATTTCTC | ATGTTGAAGC | TTTAAGAACT | AAAATGTTCT | 960 |
| AAATATCCCT | TGGCATTTTA | TGTCTTTCTT | GTAAGATACT | GCCTTGTTTA | ATGTTAATTA | 1020 |
| TGCAGTGTTT | CCCTCTGTGT | TAGAGCAGAG | AGGTTTCGAT | ATTTATTGAT | GTTTTCACAA | 1080 |
| AGAACAGGAA | AATAAAATAT | TTAAAAATAT | | | | 1110 |

( 2 ) INFORMATION FOR SEQ ID NO:92:

( i ) SEQUENCE CHARACTERISTICS:
        ( A ) LENGTH: 1062 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:92:

| | | | | | | |
|---|---|---|---|---|---|---|
| CACAGCCGGG | TCGCAGGCAC | CTCCCCGCCA | GCTCTCCCGC | ATTCTGCACA | GCTTCCCGAC | 60 |
| GCGTCTGCTG | AGCCCCATGG | CCCACGCCAC | GCTCTCCGCC | GCCCCCAGCA | ATCCCCGGCT | 120 |

-continued

| | | | | | | |
|---|---|---|---|---|---|---|
| CCTGCGGGTG | GCGCTGCTGC | TCCTGCTCCT | GGTGGGCAGC | CGGCGCGCAG | CAGGAGCGTC | 180 |
| CGTGGTCACT | GAACTGCGCT | GCCAGTGCTT | GCAGACACTG | CAGGGAATTC | ACCTCAAGAA | 240 |
| CATCCAAAGT | GTGAATGTAA | GGTCCCCCGG | ACCCCACTGC | GCCCAAACCG | AAGTCATAGC | 300 |
| CACACTCAAG | AATGGGAAGA | AAGCTTGTCT | CAACCCCGCA | TCCCCCATGG | TTCAGAAAAT | 360 |
| CATCGAAAAG | ATACTGAACA | AGGGGAGCAC | CAACTGACAG | GAGAGAAGTA | AGAAGCTTAT | 420 |
| CAGCGTATCA | TTGACACTTC | CTGCAGGGTG | GTCCCTGCCC | TTACCAGAGC | TGAAAATGAA | 480 |
| AAAGAGAACA | GCAGCTTTCT | AGGGACAGCT | GGAAAGGGAC | TTAATGTGTT | TGACTATTTC | 540 |
| TTACGAGGGT | TCTACTTATT | TATGTATTTA | TTTTTGAAAG | CTTGTATTTT | AATATTTTAC | 600 |
| ATGCTGTTAT | TTAAAGATGT | GAGTGTGTTT | CATCAAACAT | AGCTCAGTCC | TGATTATTTA | 660 |
| ATTGGAATAT | GATGGGTTTT | AAATGTGTCA | TTAAACTAAT | ATTTAGTGGG | AGACCATAAT | 720 |
| GTGTCAGCCA | CCTTGATAAA | TGACAGGGTG | GGGAACTGGA | GGGTGGGGGA | TTGAAATGCA | 780 |
| AGCAATTAGT | GGATCACTGT | TAGGGTAAGG | GAATGTATGT | ACACATCTAT | TTTTTATACT | 840 |
| TTTTTTTTA | AAAAGAATG | TCAGTTGTTA | TTTATTCAAA | TTATCTCACA | TTATGTGTTC | 900 |
| AACATTTTTA | TGCTGAAGTT | TCCCTTAGAC | ATTTTATGTC | TTGCTTGTAG | GGCATAATGC | 960 |
| CTTGTTTAAT | GTCCATTCTG | CAGCGTTTCT | CTTTCCCTTG | GAAAAGAGAA | TTTATCATTA | 1020 |
| CTGTTACATT | TGTACAAATG | ACATGATAAT | AAAAGTTTTA | TG | | 1062 |

( 2 ) INFORMATION FOR SEQ ID NO:93:

( i ) SEQUENCE CHARACTERISTICS:
        ( A ) LENGTH: 387 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:93:

| | | | | | | |
|---|---|---|---|---|---|---|
| ATGAGCCTCA | GACTTGATAC | CACCCCTTCC | TGTAACAGTG | CGAGACCACT | TCATGCCTTG | 60 |
| CAGGTGCTGC | TGCTTCTGTC | ATTGCTGCTG | ACTGCTCTGG | CTTCCTCCAC | CAAAGGACAA | 120 |
| ACTAAGAGAA | ACTTGGCGAA | AGGCAAAGAG | GAAAGTCTAG | ACAGTGACTT | GTATGCTGAA | 180 |
| CTCCGCTGCA | TGTGTATAAA | GACAACCTCT | GGAATTCATC | CCAAAAACAT | CCAAAGTTTG | 240 |
| GAAGTGATCG | GGAAAGGAAC | CCATTGCAAC | CAAGTCGAAG | TGATAGCCAC | ACTGAAGGAT | 300 |
| GGGAGGAAAA | TCTGCCTGGA | CCCAGATGCT | CCCAGAATCA | AGAAAATTGT | ACAGAAAAA | 360 |
| TTGGCAGGTG | ATGAATCTGC | TGATTAA | | | | 387 |